(12) United States Patent
Morita et al.

(10) Patent No.: US 8,334,314 B2
(45) Date of Patent: Dec. 18, 2012

(54) PHENYLPROPIONIC ACID DERIVATIVE AND USE THEREOF

(75) Inventors: Kohei Morita, Tokyo (JP); Hiroshi Kuriyama, Tokyo (JP); Kosuke Tanaka, Tokyo (JP)

(73) Assignee: Asahi Kasei Pharma Corporation, Tokyo (JP)

( * ) Notice: Subject to any disclaimer, the term of this patent is extended or adjusted under 35 U.S.C. 154(b) by 36 days.

(21) Appl. No.: 12/430,575

(22) Filed: Apr. 27, 2009

(65) Prior Publication Data

US 2010/0093819 A1 Apr. 15, 2010

Related U.S. Application Data

(60) Provisional application No. 61/048,346, filed on Apr. 28, 2008.

(51) Int. Cl.
*A01N 43/38* (2006.01)
*A61K 31/415* (2006.01)
(52) U.S. Cl. .................................. 514/406; 548/361.1
(58) Field of Classification Search .................. 514/406; 548/361.1
See application file for complete search history.

(56) References Cited

U.S. PATENT DOCUMENTS

| | | | |
|---|---|---|---|
| 3,816,443 A | 6/1974 | Dorn, Jr. | |
| 3,940,434 A | 2/1976 | Haas et al. | |
| 5,391,817 A | 2/1995 | Springer et al. | |
| 5,468,898 A | 11/1995 | Huang et al. | |
| 5,482,941 A | 1/1996 | Terrett | |
| 6,376,546 B1 | 4/2002 | Shoda et al. | |
| 6,867,320 B2 | 3/2005 | Shoda et al. | |
| 2004/0044258 A1 | 3/2004 | Shoda et al. | |
| 2004/0102437 A1 | 5/2004 | Takami et al. | |
| 2004/0138286 A1 | 7/2004 | Imazaki et al. | |
| 2005/0032787 A1 | 2/2005 | Giannessi et al. | |
| 2005/0032858 A1 | 2/2005 | Takagi et al. | |
| 2006/0122221 A1 | 6/2006 | Angell et al. | |
| 2007/0213333 A1 | 9/2007 | Shoda et al. | |
| 2007/0232620 A1 | 10/2007 | Dorsch et al. | |
| 2008/0070967 A1 | 3/2008 | Arimoto et al. | |
| 2009/0054401 A1 | 2/2009 | Matsumoto et al. | |

FOREIGN PATENT DOCUMENTS

| | | |
|---|---|---|
| CN | 101031539 A | 9/2007 |
| DE | 2 046 992 A1 | 3/1972 |
| EP | 0 279 263 A2 | 8/1988 |
| EP | 1 614 683 A1 | 1/2006 |
| JP | 52-93755 | 8/1977 |
| JP | 2007-528362 A | 10/2007 |
| WO | WO-96/26921 A1 | 9/1996 |
| WO | WO-97/28146 A1 | 8/1997 |
| WO | WO-99/43654 A2 | 9/1999 |
| WO | WO-00/35886 A2 | 6/2000 |
| WO | WO 0064436 A1 * | 11/2000 |
| WO | WO-01/53268 A2 | 7/2001 |
| WO | WO-03/011842 A1 | 2/2003 |
| WO | WO-03/048122 A2 | 6/2003 |
| WO | WO-2004/011446 A1 | 2/2004 |
| WO | WO-2005/016862 A1 | 2/2005 |

OTHER PUBLICATIONS

Wolff, Manfred E., Ed. Burger's Medicinal Chemistry and Drug Discovery—Fifth Edition, New York: John Wiley & Sons, 1995, vol. 1, pp. 975-977).*
Merck manuals online medical library (review/revision Aug. 2006.*
Patani et al "Bioisosterism: A rational approach in drug design", Chem. Rev. 1996, 96 (8) 3147-3176.*
Extended European Search Report for European Application No. 09738768.2 mailed Aug. 4, 2011.
International Preliminary Report on Patentability and Written Opinion (with English language translation) issued in PCT/JP2009/058240.
International Search Report issued in PCT/JP2009/058240.
Aono et al., "1-Indancarboxylic Acids. I. Electrophilic Substitution Reactions of 1-Indancarboxylic Acid and Synthesis of 6-Substituted 1-Indancarboxylic Acids as Potential Antiinflammatory Agents", Chem. Pharm. Bull., vol. 25, No. 12, 1977, pp. 3198-3209.
Kuzuna et al., "Biological Activities of Metabolites of 6-Chloro-5-Cyclohexylindan-1-Carboxylic Acid (TAI-284: Anti-Inflammatory Agent)", Japanese Journal of Pharmacology, vol. 24, No. 5, 1974, pp. 687-693.
Juby et al., "Antiinflammatory Activity of Some Indan-1-carboxylic Acids and Related Compounds", Journal of Medicinal Chemistry, 1972, vol. 15, No. 12, pp. 1297-1306.
Australian Office Action dated May 31, 2011 issued in Australian patent application No. 2009241038.
Canadian Office Action dated Mar. 1, 2012 issued in Canadian patent application No. 2,722,102.
Chinese Office Action dated Dec. 23, 2011 issued in Chinese patent application No. 2009/80114964.6.
Russian Office Action dated Jan. 21, 2011 issued in Russian patent application No. 2010148387.
Russian Office Action dated Mar. 21, 2012 issued in Russian patent application No. 2010148387.
Chinese Office Action of Chinese Patent Application No. 200980114964.6 dated Jun. 11, 2012.

* cited by examiner

*Primary Examiner* — Timothy Thomas
*Assistant Examiner* — Jean Cornet
(74) *Attorney, Agent, or Firm* — Birch, Stewart, Kolasch & Birch, LLP.

(57) ABSTRACT

A compound represented by the following general formula (1) or a salt thereof, which has superior inhibitory activity against type 4 $PLA_2$, and thus has prostaglandin and/or leucotriene production suppressing action [X represents a halogen atom, an alkyl group which may be substituted, or the like, Y represents hydrogen atom or an alkyl group which may be substituted, and Z represents hydrogen atom or an alkyl group which may be substituted].

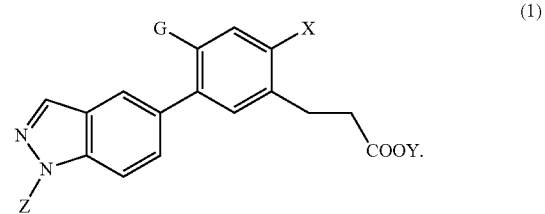

(1)

27 Claims, No Drawings

PHENYLPROPIONIC ACID DERIVATIVE AND USE THEREOF

TECHNICAL FIELD

The present invention relates to a novel phenylpropionic acid derivative, and a medicament comprising the phenylpropionic acid derivative as an active ingredient.

BACKGROUND ART

In living bodies of mammals, various prostaglandins and various leukotrienes are produced by various stimulations such as inflammatory and physical stimulations. Both of prostaglandins and leukotrienes are metabolites of arachidonic acid, and they are physiologically active substances called lipid mediators. They trigger various kinds of physiological reactions of mammals by binding to their respective receptors expressed on cell surfaces or expressed intracellularly.

Arachidonic acid is produced from phospholipids such as phosphatidylcholine as substrates, which are components of cell membranes, with the aid of the enzymatic activity of phospholipase $A_2$ ($PLA_2$). In particular, type 4 $PLA_2$ is activated by inflammatory stimulation, and plays an important role in the arachidonic acid production. Arachidonic acid produced by $PLA_2$ is converted into prostaglandin (PG) $H_2$ by an enzymatic activity of constitutive-type cyclooxygenase (COX) 1 or inducible-type COX-2 and further converted into $PGE_2$, $PGD_2$, $PGF_2\alpha$, $PGI_2$, thromboxane (TX) $A_2$ and the like by each synthetic enzyme. Further, arachidonic acid is also metabolized by 5-lipoxygenase (5-LO) to give leukotriene (LT) $A_4$, and further converted into $LTB_4$, $LTC_4$, $LTD_4$, $LTE_4$ and the like by enzymatic activities of $LTA_4$ hydrolase, $LTC_4$ synthase, and glutathione-5-transferase [Goodman and Gilman's the Pharmacological Basis of Therapeutics, 11th edition (Hirokawa Shoten), 2007, p. 814; C. D. Funk, SCIENCE, 2001, vol. 294, p. 1871].

Each of the prostaglandins binds with a specific receptor to cause, for example, inflammatory reactions such as fervescence, increase of blood vessel permeability, vasodilation, swelling, and pain, bronchial smooth muscle contraction, platelet aggregation, tumor cell proliferation, bone resorption promotion, nerve cell degeneration and the like, and plays an important role in expression of symptoms or formation of pathological states in various diseases. Leukotrienes are physiological substances, each of which binds with a specific receptor to cause, for example, inflammatory reactions such as excessive accumulation of leucocytes and increase of blood vessel permeability, smooth muscle contraction, mucus secretion, tumor cell proliferation and the like, and also play an important role in expression of symptoms or formation of pathological states in various diseases.

Although inflammatory reactions, per se, are essential reactions in order that living bodies can survive when they face a pathogenic substance or affection, inflammatory reactions sometimes occur in excess levels in certain conditions or diseases, or they may sometimes continue without any reason for bringing evident benefits [Goodman and Gilman's the Pharmacological Basis of Therapeutics, 11th edition (Hirokawa Shoten), 2007, p. 837]. Conditions of living bodies exhibiting acute or chronic inflammatory reactions referred to in the present specification mean conditions where excess or non-profitable inflammatory reactions are generated acutely and transiently or chronically and continuously. Further, inflammatory reactions are a series of events caused by stimulations including physical hazards such as those caused by heat, infectious substance, ischemia, antigen-antibody reaction and the like, and they are accompanied by flare, swelling, algesia, and pain generation as well-known macroscopic clinical symptoms. As histological mechanisms of these symptoms, it is known that vasodilation, increase of blood vessel permeability, invasion of leucocytes and phagocytes, decomposition or fibrosis of tissues and the like are caused [Goodman and Gilman's the Pharmacological Basis of Therapeutics, 11th edition (Hirokawa Shoten), 2007, p. 837]. It is known that many of these histological reactions are triggered by prostaglandins and/or leukotrienes, and prostaglandins and/or leukotrienes have important roles in the inflammatory reactions.

For example, in a pathological tissue of rheumatoid arthritis, which is an autoimmune disease and is one of chronic inflammatory diseases, expression of COX-2 and production of $PGE_2$ or $TXA_2$ as well as expression of 5-LO and production of $LTB_4$ are observed [Bonnet et al., Prostaglandins, 1995, vol. 50, p. 127]. In a mouse deficient in FLAP which is a protein required for activation of 5-LO, symptoms of collagen-induced arthritis, as a disease model of chronic rheumatoid arthritis, are reported to be milder compared with those in a wild-type mouse [Griffiths et al., J. Exp. Med, 1997, vol. 185, p. 1123]. Thus, prostaglandins and leukotrienes are demonstrated to be responsible for important roles in the formation of pathologies of chronic rheumatoid arthritis.

In a pathological tissue of bronchial asthma, which is one of chronic allergic diseases, overproduction of $PGD_2$ and $TXA_2$ as well as overproduction of $LTC_4$ and $LTD_4$ are observed [Wenzel et al., Am. Rev. Respir. Dis, 1990, vol. 142, p. 112], and airway hypersensitivity, which is a disease model of bronchial asthma, is reported to unlikely occur in a $PGD_2$ receptor deficient mouse [Matsuoka et al., SCIENCE, 2000, vol. 287, p. 2013]. Accordingly, roles of prostaglandins and leukotrienes are demonstrated to be important in bronchial asthma.

In a cerebral tissue after ischemia and reperfusion, expression of COX-2 is increased to increase $PGE_2$ and $TXA_2$ concentrations, whereas activity of 5-LO is increased to increase production of $LTC_4$ [Ohtsuki et al., Am. J. Physiol., 1995, vol. 268, p. 1249]. Thus, it is known that prostaglandins and leukotrienes are responsible for important roles in the formation of infarct, which is recognized as a disorder from ischemia and reperfusion. In a pathological tissue of Alzheimer's disease, which is one of diseases accompanied by neurodegeneration, it is demonstrated that COX activity and 5-LO activity are increased, and prostaglandins and leukotrienes cause formation of β-amyloid proteins which constitute one class of pathogenic substances of Alzheimer's disease to induce degeneration of nerve cells [Sugaya et al., Jpn. J. Pharmacol., 2000, vol. 82, p. 85]. Thus, it is considered that prostaglandins and leukotrienes are responsible for important roles in formation of neurodegenerative diseases such as Alzheimer's disease.

In a pathological tissue of colon cancer, for example, COX and 5-LO are expressed, and the production of prostaglandins and leukotrienes are increased [Dreyling et al., Biochim. Biophys. Acta, 1986, vol. 878, p. 184]. Further, leukotrienes are reported to cause proliferation of colon cancer cells [Qiao et al., Biochim. Biophys. Acta, 1995, vol. 1258, p. 215; Hong et al., Cancer Res., 1999, vol. 59, p. 2223]. Thus, it is considered that prostaglandins and leukotrienes also play important roles in tissues of colon cancer.

Involvements of prostaglandins and/or leukotrienes in diseases and pathological conditions are not limited to the diseases exemplified above. It has been demonstrated that prostaglandins and/or leukotrienes are involved in various conditions, diseases, and pathological states accompanied by acute or chronic inflammatory reactions, and that their roles are important. From the above facts, various kinds of inhibitors against prostaglandin production or against leukotriene production have been used as agents for prophylactic or therapeutic treatment of conditions, diseases, and pathological conditions with acute or chronic inflammatory reactions.

Drugs having suppressing actions on prostaglandin production include various kinds of non-steroidal anti-inflammatory drugs (NSAIDS), and they have been used as agents for therapeutic treatment of chronic rheumatoid arthritis and osteoarthritis, anti-inflammatory analgesics for external injury and the like, agents for prophylactic treatment of cerebral infarction or myocardial infarction, agents for prophylactic treatment of colorectal polyposis and the like. However, various kinds of NSAIDS inhibit only the production of prostaglandins, and as a result, they increase production of leukotrienes to cause side effects such as asthmatic attack and gastrointestinal injury, and in addition, exhibit side effects of nephropathy and the like. Further, differences in an effective dose and a dose inducing the side effects are small in these NSAIDS, and no satisfactory drug is available also from a viewpoint of a therapeutic effect. For example, it has been reported that inhibition of COX by the above drug leads to suppression of biosynthesis of PG required for maintaining homeostatic functions in the upper gastrointestinal tract such as stomach and duodenum, kidney, and the like, and as a result, for example, they induce side effects such as upper gastrointestinal injury and/or renal dysfunction [Goodman and Gilman's the Pharmacological Basis of Therapeutics, 11th edition (Hirokawa Shoten), 2007, Chapter 26].

5-LO inhibitors described in EP279263 are available as drugs having suppressing action on leukotriene production and are known as prophylactic agents for asthma. However, their doses are limited because of induction of side effects such as hepatotoxicity, which results in unsatisfactoriness from a viewpoint of a therapeutic effect. Steroids inhibit productions of both of prostaglandins and leukotrienes, and accordingly, they are used as prophylactic or therapeutic agents for treatment of conditions of living bodies, various diseases, or pathological states with various acute or chronic inflammatory reactions. However, their actions are not limited to the suppressing action on lipid mediator production, but they have severe side effects such as induction and exacerbation of infection due to immune suppressing effects, growth delay and dermatrophy due to suppressing action on normal cell proliferation, digestive ulcer and the like. Therefore, their use has been limited.

Under the circumstances as explained above, a compound which suppresses production of both of prostaglandins and leukotrienes and shows less side effects is considered to be effective as a therapeutic or prophylactic agent for the conditions, diseases or pathological states of living bodies in mammals as described above, and a method of using such compound and an existing medicament in combination is considered to be a further effective method for therapeutic treatment or prophylactic treatment. Therefore, it is desired to create a compound which suppresses production of both of prostaglandins and leukotrienes and to develop the compound as a medicament.

Although the compounds disclosed in Patent documents 1 to 3, for example, are known as compounds exhibiting the same affect as that of the compounds of the present invention, all of these compounds are structurally different from the compounds of the present invention.

Patent document 1: International Patent Publication WO99/19291
Patent document 2: International Patent Publication WO03/07686
Patent document 3: International Patent Publication WO05/016862

DISCLOSURE OF THE INVENTION

Object to be Achieved by the Invention

An object of the present invention is to provide a compound that solves the aforementioned problems. Specifically, the object of the present invention is to provide a compound that has superior inhibitory activity against type 4 $PLA_2$ enzyme, and hence has prostaglandin production suppressing action and/or leukotriene production suppressing action.

Another object of the present invention is to provide a compound for prophylactic treatment and/or therapeutic treatment of various kinds of inflammatory diseases, autoimmune diseases, allergic diseases, pains, and fibroses in mammals induced by lipid mediators.

Another object of the present invention is to provide a pharmaceutical composition comprising such a compound as mentioned above.

Means for Achieving the Object

In order to achieve the aforementioned object, the inventors of the present invention conducted various researches, and as a result, they found that compounds represented by the general formula (1) mentioned below had superior inhibitory activity against type 4 $PLA_2$, and accomplished the present invention described below.

<1> A compound represented by the following general formula (I) or a salt thereof:

[Formula 1]

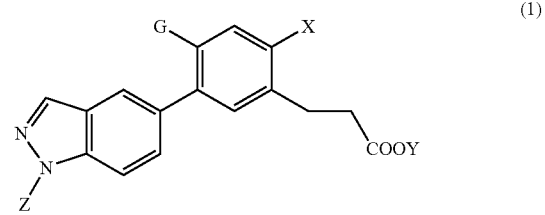

wherein, in the general formula (1),
X represents a halogen atom, cyano group, an alkyl group which may be substituted,
an alkenyl group which may be substituted, an alkynyl group which may be substituted, an alkoxy group which may be substituted, hydroxy group, —N($R^1$)($R^2$), or —C(O)NH$R^8$;
$R^1$ and $R^2$ both or independently represent hydrogen atom or an alkyl group;
$R^3$ represents hydrogen atom or an alkyl group;
Y represents hydrogen atom or an alkyl group which may be substituted;
Z represents hydrogen atom or an alkyl group which may be substituted; and
G represents a group represented by any one of the following general formulas ($G^1$) to ($G^7$):

[Formula 2]

$$R^4-A^2- \quad (G^1)$$

-continued

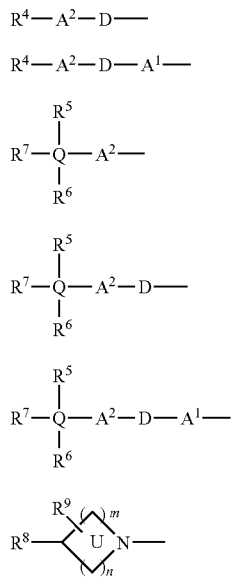

$$R^4-A^2-D- \quad (G^2)$$

$$R^4-A^2-D-A^1- \quad (G^3)$$

$$\begin{array}{c} R^5 \\ | \\ R^7-Q-A^2- \\ | \\ R^6 \end{array} \quad (G^4)$$

$$\begin{array}{c} R^5 \\ | \\ R^7-Q-A^2-D- \\ | \\ R^6 \end{array} \quad (G^5)$$

$$\begin{array}{c} R^5 \\ | \\ R^7-Q-A^2-D-A^1- \\ | \\ R^6 \end{array} \quad (G^6)$$

$$(G^7)$$

wherein, in the general formulas $(G^1)$, $(G^2)$, $(G^3)$, $(G^4)$, $(G^5)$, $(G^6)$, and $(G^7)$, $R^4$ represents hydrogen atom or an alkyl group which may be substituted;

D represents oxygen atom, $-NR^{10}C(O)-$, $-C(O)NR^{10}-$, $-S(O)_2NR^{10}-$, or $-N(R^{11})-$;

$R^{10}$ represents hydrogen atom or an alkyl group which may be substituted;

$R^{11}$ represents hydrogen atom or an alkyl group which may be substituted;

$A^1$ represents an alkylene group which may be substituted;

$A^2$ represents a single bond, an alkylene which may be substituted, an alkenylene which may be substituted, or an alkynylene which may be substituted;

Q represents an aryl group which may be substituted;

$R^5$, $R^6$, and $R^7$ all or independently represent hydrogen atom, a halogen atom, an alkyl group which may be substituted, an alkoxy group which may be substituted, $-N(R^{12})(R^{13})$ group, an aryl group which may be substituted, an aryloxy group which may be substituted, or an aralkyl group which may be substituted;

$R^{12}$ and $R^{13}$ both or independently represent hydrogen atom, or an alkyl group, or $R^{12}$ and $R^{13}$ bind to each other to form a saturated cyclic substituent together with the nitrogen atom;

m represents an integer of 0, 1, or 2;

n represents an integer of 1, 2, 3, or 4;

$R^8$ is a substituent on a ring constituting carbon atom constituting a nitrogen-containing saturated ring represented by U, and represents hydrogen atom or an alkyl group which may be substituted; and $R^9$ represents hydrogen atom, an alkyl group which may be substituted, or hydroxy group;

<2> The compound or a salt thereof according to <1>, wherein X is a halogen atom, an alkyl group which may be substituted, an alkenyl group which may be substituted, an alkoxy group which may be substituted, hydroxy group, or $-N(R^1)(R^2)$ ($R^1$ and $R^2$ have the same meanings as those explained above);

<3> The compound or a salt thereof according to <1> or <2>, wherein Y is hydrogen atom;

<4> The compound or a salt thereof according to any one of <1> to <3>, wherein Z is an alkyl group which may be substituted;

<5> The compound or a salt thereof according to any one of <1> to <4>, wherein G is a group represented by the general formula $(G^2)$, $(G^3)$, $(G^5)$, or $(G^6)$ (the groups represented by the general formulas $(G^2)$, $(G^3)$, $(G^5)$ and $(G^6)$ have the same meanings as those explained above, provided that in the general formulas $(G^2)$, $(G^3)$, $(G^5)$ and $(G^6)$, D represents $-NR^{10}C(O)-$, $-C(O)NR^{10}-$, or $-S(O)_2NR^{10}-$);

<6> The compound or a salt thereof according to any one of <1> to <4>, wherein G is a group represented by the general formula $(G^2)$ or $(G^5)$ (the groups represented by the general formulas $(G^2)$ and $(G^5)$ have the same meanings as those explained above, provided that in the general formulas $(G^2)$ and $(G^5)$, D represents $-NR^{10}C(O)-$, $-C(O)NR^{10}-$, or $-S(O)_2NR^{10}-$);

<6-2> The compound or a salt thereof according to any one of <1> to <4>, wherein G is a group represented by the general formula $(G^3)$ or $(G^6)$ (the groups represented by the general formulas $(G^3)$ and $(G^6)$ have the same meanings as those explained above, provided that in the general formulas $(G^3)$ and $(G^6)$, D represents $-NR^{10}C(O)-$, $-C(O)NR^{10}-$, or $-S(O)_2NR^{10}-$);

<7> The compound or a salt thereof according to any one of <1> to <4>, wherein G is a group represented by the general formula $(G^1)$ or $(G^4)$ (the groups represented by the general formulas $(G^1)$ and $(G^4)$ have the same meanings as those explained above);

<8> The compound or a salt thereof according to any one of <1> to <4>, wherein G is a group represented by the general formula $(G^7)$ (the group represented by the general formula $(G^7)$ has the same meaning as that explained above);

<9> The compound or a salt thereof according to any one of <1> to <4>, wherein G is a group represented by the general formula $(G^2)$, $(G^3)$, $(G^5)$, or $(G^6)$ (the groups represented by the general formulas $(G^2)$, $(G^3)$, $(G^5)$ and $(G^6)$ have the same meanings as those explained above, provided that in the general formulas $(G^2)$, $(G^3)$, $(G^5)$ and $(G^6)$, D represents $-N(R^{11})-$);

<10> The compound or a salt thereof according to any one of <1> to <4>, wherein G is a group represented by the general formula $(G^2)$ or $(G^5)$ (the groups represented by the general formulas $(G^2)$ and $(G^5)$ have the same meanings as those explained above, provided that in the general formula $(G^2)$ and $(G^5)$, D represents $-N(R^{11})-$);

<10-2> The compound or a salt thereof according to any one of <1> to <4>, wherein G is a group represented by the general formula $(G^3)$ or $(G^6)$ (the groups represented by the general formulas $(G^3)$ and $(G^6)$ have the same meanings as those explained above, provided that in the general formulas $(G^3)$ and $(G^6)$, D represents $-N(R^{11})-$);

<11> The compound or a salt thereof according to any one of <1> to <4>, wherein G is a group represented by the general formula $(G^2)$, $(G^3)$, $(G^5)$ or $(G^6)$ (the groups represented by the general formulas $(G^2)$, $(G^3)$, $(G^5)$ and $(G^6)$ have the same meanings as those explained above, provided that in the general formulas $(G^2)$, $(G^3)$, $(G^5)$ and $(G^6)$, D represents oxygen atom);

<12> The compound or a salt thereof according to any one of <1> to <4>, wherein G is a group represented by the general formula $(G^2)$ or $(G^5)$ (the groups represented by the general formulas $(G^2)$ and $(G^5)$ have the same meanings as those explained above, provided that in the general formulas $(G^2)$ and $(G^5)$, D represents oxygen atom);

<12-2> The compound or a salt thereof according to any one of <1> to <4>, wherein G is a group represented by the general formula (G³) or (G⁶) (the groups represented by the general formulas (G³) and (G⁶) have the same meanings as those explained above, provided that in the general formulas (G³) and (G⁶), D represents oxygen atom);

<12-3> The compound or a salt thereof according to any one of <1> to <4>, wherein G is a group represented by the general formula (G²) (the group represented by the general formula (G²) has the same meaning as that explained above, provided that in the general formula (G²), D represents —NH—), and X is methyl group or chlorine atom;

<12-4> The compound or a salt thereof according to any one of <1> to <4>, wherein G is a group represented by the general formula (G²) (the group represented by the general formula (G²) has the same meaning as that explained above, provided that in the general formula (G²), D represents —NH—), and X is methyl group;

<12-5> The compound or a salt thereof according to any one of <1> to <4>, wherein G is a group represented by the general formula (G²) (the group represented by the general formula (G²) has the same meaning as that explained above, provided that in the general formula (G²), D represents —NH—), and X is chlorine atom;

<13> A prodrug of the compound or a salt thereof according to any one of <1> to <12-5>;

When the item numbers are indicated with a range like "<1> to <12-5>" as mentioned above, and the range include an item indicated with a number having a subnumber like <6-2> or the like, it is meant that the item indicated with the number having a subnumber like <6-2> or the like is also cited. The same shall apply to the following definitions.

<14> A medicament comprising the compound according to any one of <1> to <12-5> or a pharmaceutically acceptable thereof, or a prodrug thereof as an active ingredient;

<15> A prostaglandin and/or leucotriene production suppressing agent comprising the compound according to any one of <1> to <12-5> or a pharmaceutically acceptable thereof, or a prodrug thereof as an active ingredient;

<16> The medicament according to <14>, which is for prophylactic and/or therapeutic treatment of a disease for which suppression of prostaglandin and/or leucotriene production is effective;

<17> An inhibitor against type 4 phospholipase $A_2$ enzyme activity comprising the compound according to any one of <1> to <12-5> or a pharmaceutically acceptable thereof, or a prodrug thereof as an active ingredient;

<18> The medicament according to <14>, which is for prophylactic and/or therapeutic treatment of a disease induced by expression of type 4 phospholipase $A_2$ enzyme activity;

<19> The medicament according to <14>, which is for prophylactic and/or therapeutic treatment of an inflammatory disease of a mammal;

<20> The medicament according to <14>, which is for prophylactic and/or therapeutic treatment of an autoimmune disease of a mammal;

<21> The medicament according to <14>, which is for prophylactic and/or therapeutic treatment of an allergic disease of a mammal;

<22> The medicament according to <14>, which is for defervescence and/or analgesia of a mammal;

<23> A pharmaceutical composition for prophylactic and/or therapeutic treatment of a condition in living body of a mammal in which an acute or chronic inflammatory reaction is observed, which comprises the compound according to any one of <1> to <12-5> or a pharmaceutically acceptable thereof, or a prodrug thereof in an amount effective for the aforementioned prophylactic and/or therapeutic treatment, and a pharmaceutically acceptable carrier;

<24> A method for prophylactic and/or therapeutic treatment of a condition in living body of a mammal in which an acute or chronic inflammatory reaction is observed, which comprises the step of administering the compound according to any one of <1> to <12-5> or a pharmaceutically acceptable thereof, or a prodrug thereof to the mammal in an amount effective for the aforementioned prophylactic and/or therapeutic treatment.

From another aspect, the present invention provides a medicament comprising a substance selected from the group consisting of the compound according to any one of <1> to <12-5>, a pharmaceutically acceptable salt thereof, and a prodrug thereof as an active ingredient. This medicament can be used for mammals including human as a prostaglandin and/or leucotriene production suppressing agent, a prophylactic and/or therapeutic agent for a disease induced by production of prostaglandin and/or leucotriene, a prophylactic and/or therapeutic agent for an inflammatory disease, a prophylactic and/or therapeutic agent for an autoimmune disease, a prophylactic and/or therapeutic agent for an allergic disease, antipyretic and/or analgesic, a prophylactic and/or therapeutic agent for a fibrosis, and a prophylactic and/or therapeutic agent for a condition of living body in which an acute or chronic inflammatory reaction is observed.

The present invention also provides use of a substance selected from the group consisting of the compound according to any one of <1> to <12-5>, a pharmaceutically acceptable salt thereof, and a prodrug thereof for manufacture of the aforementioned medicament.

From a further aspect, the present invention provides a method for prophylactic and/or therapeutic treatment of a disease induced by production of prostaglandin and/or leucotriene, which comprises the step of administering an effective amount of a substance selected from the group consisting of the compound according to any one of <1> to <12-5>, a pharmaceutically acceptable salt thereof, and a prodrug thereof to a mammal.

Examples of the method for prophylactic and/or therapeutic treatment of a disease induced by production of prostaglandin and/or leucotriene include, for example, for mammals including human, a method for prophylactic and/or therapeutic treatment of an inflammatory disease, a method for prophylactic and/or therapeutic treatment of an autoimmune disease, a method for prophylactic and/or therapeutic treatment of an allergic disease, a method for defervescence and/or analgesia, a method for prophylactic and/or therapeutic treatment of a fibrosis, a method for prophylactic and/or therapeutic treatment of a condition in a living body in which an acute or chronic inflammatory reaction is observed, and the like.

Diseases and pathological conditions as object of application of the medicament or method for prophylactic and/or therapeutic treatment of the present invention include, for example, diseases diagnosed as arthritis, chronic rheumatoid arthritis, malignant rheumatoid arthritis, juvenile rheumatoid arthritis, Felty's syndrome, adult Still's disease, osteoarthritis, synovitis, gout, slack of artificial joint implant, fervescence, common cold, algesia, burn, thermal injury, keloplasty, menstrual pain, dysmenorrhea, menstrual cramp, allergic reaction, allergic contact hypersensitivity, allergic rhinitis, pollinosis, allergic conjunctivitis, hypersensitivity pneumonitis, allergic bronchopulmonary mycosis, emphysema, acute respiratory distress syndrome, asthma, bronchitis, chronic obstructive pulmonary disease, chronic bronchitis, pulmonary emphysema, diffuse panbronchiolitis, respiratory obstruction, graft versus host syndrome, urticaria, ultraviolet radiation dermatitis, atopic dermatitis, cancer, myelogenous leukemia, sarcomata, brain tumor, cachexia, tissue ulcer, digestive ulcer, gastritis, acute and chronic pancreatitis, regional enteritis, ulcerative colitis, diverticulitis, recurrent gastroenteric disorder, gastroenteric bleeding, inflammatory bowel disease, Crohn's disease, intestinal tract type Behcet's disease, infectious enteritis, ischemic enteritis, radiation enteritis, drug-induced enteritis, irritable bowel syndrome, hepatic diseases (hepatopathies, liver failures) such as acute hepatitis, fulminant hepatitis, chronic hepatitis, hepatic cirrhosis, fatty liver, alcoholic liver injury, drug liver injury (drug-induced hepatitis), congestive hepatitis, autoimmune hepatitis, primary biliary cirrhosis and hepatic porphyria, coagulation, anemia, ankylosing spondilitis, restenosis, periodontosis, epidermolysis bullosa, atherosclerosis, aortic aneurysm, periarteritis nodosa, congestive cardiac failure, arrhythmia, myocardial infarction, cerebral infarction, attack, cerebral ischemia, head injury, spinal cord injury, myelopathic muscular atrophy, neuralgia, neurodegenerative disease, Alzheimer's disease, Lewy body disease, Shy-Drager syndrome, Reye's syndrome, progressive supranuclear palsy, progressive multifocal leukoencephalopathy, normal pressure hydrocephalus, subacute sclerosing panencephalitis, frontal lobe type dementia, acute anterior poliomyelitis (poliomyelitis), poliomyelitis neurosis, viral encephalitis, Creutzfeldt-Jakob disease, Kuru disease, bovine spongiform encephalopathy (mad cow disease), scrapie, epilepsy, cerebral amyloid angiopathy, autoimmune disease, Huntington's disease, Parkinson's disease, migraine, depression, mania, manic-depressive psychosis, hereditary cerebellar ataxia, peripheral neuropathy, glaucoma, pain, gingivitis, postoperative pain, amyotrophic lateral sclerosis, osteoporosis, multiple sclerosis, ocular angiogenesis, cornea damage, macular degeneration, conjunctivitis, abnormal wound healing, sprain or strain of muscle or joint, tendinitis, skin disease, psoriasis vulgaris, pustular psoriasis, erythroderma psoriaticum, arthritic psoriasis, myasthenia gravis, multiple myositis, myositis, bursitis, diabetes mellitus, tumor invasion, tumor growth, tumor metastasis, cornea scar, scleritis, immunodeficiency disease, pachydermia, eosinophilic fasciitis, sepsis, endotoxin shock, premature delivery, hypoprothrombinemia, hemophilia, thyroiditis, sarcoidosis, Behcet's syndrome, hypersensitivity, renal disease, rickettsial infectious disease, protozoal disease, reproduction disease, sepsis shock, toothache, pain after tooth extraction, back or low back pain, periarthritis humeroscapularis, cervico-omo-brachial syndrome, tenosynovitis, acute upper respiratory inflammation, herpes zoster, fibrosis, pulmonary fibrosis, drug-induced pulmonary fibrosis, pneumoconiosis, chronic interstitial pneumonia, granulomatous interstitial pneumonia, fibrosing interstitial pneumonia, renal fibrosis, nephropyelitis, various types of secondary contracted kidney, glomerular nephritis, chronic nephritis, glomerulosclerosis, hepatic fibrosis, cardiac fibrosis after myocardial infarction, idiopathic cardiomyopathy, pancreatic sclerosis, pancreatic fibrosis, pancreatolithiasis, Takayasu's arteritis, chronic thyroiditis, dermatomyositis, multiple myositis, myelofibrosis, Banti disease, retroperitoneal fibrosis, various radiation injuries and the like, as well as pathological conditions suspected to be those diseases.

Biphenyl-5-alkanoic acid derivatives and use thereof are reported in Patent document 1. However, the moieties of these compounds corresponding to the indazole group in the compounds represented by the aforementioned general formula (1) of the present invention are phenyl groups, and therefore they are structurally different. Further, the moieties of these compounds corresponding to X in the aforementioned general formula (1) are hydrogen atoms, and therefore they are structurally different.

Moreover, substituted phenylalkanoic acid derivatives and use thereof are reported in Patent document 2. However, the moieties of these compounds corresponding to X in the compounds represented by the aforementioned general formula (1) of the present invention are limited to hydrogen atom, and therefore they are structurally different.

Substituted arylalkanoic acid derivatives and use thereof are reported in Patent document 3. However, the moieties of these compounds corresponding to X in the compounds represented by the aforementioned general formula (1) of the present invention are hydrogen atoms, or the benzene ring to which the group X in the general formula (1) binds is limited to pyridine ring in the Patent document 3. Therefore, they are structurally different.

Effect of the Invention

The compounds represented by the aforementioned general formula (1) and pharmaceutically acceptable salts thereof of the present invention have superior inhibitory activity against type 4 $PLA_2$. As a result, they have suppression actions for both of prostaglandin production and/or leucotriene production, and they have characteristics that when they are administered to human or animals, they show superior prophylactic and/or therapeutic effect for diseases or pathological conditions in which prostaglandin and/or leucotriene is involved, and they are highly safe.

BEST MODE FOR CARRYING OUT THE INVENTION

Hereafter, the present invention will be specifically explained.

In the specification, unless particularly indicated, examples of the halogen atom include fluorine atom, chlorine atom, bromine atom, and iodine atom. Preferred examples of the halogen atom include chlorine atom, bromine atom, and iodine atom, and chlorine atom and bromine atom are more preferred. Particularly preferred is chlorine atom. There is also another embodiment in which fluorine atom is preferred.

Examples of the alkyl group include, for example, a straight, branched, or cyclic saturated hydrocarbon group, and a saturated hydrocarbon group consisting a combination thereof, and a lower alkyl group is preferred. In the specification, the term "lower" means that number of carbon atoms constituting a certain functional group is, for example, 1 to 6. As the lower alkyl group, for example, an alkyl group having 1 to 6 carbon atoms is preferred, and an alkyl group having 1 to 3 carbon atoms is particularly preferred. The same shall apply to an alkyl moiety of other substituents having the alkyl moiety (for example, an alkoxy group and the like).

Preferred examples of the alkyl group having 1 to 3 carbon atoms include, for example, methyl group, ethyl group, n-propyl group, isopropyl group, cyclopropyl group and the like, and preferred examples of the alkyl group having 4 to 6 carbon atoms include, for example, n-butyl group, isobutyl group, s-butyl group, t-butyl group, cyclobutyl group, cyclopropylmethyl group, n-pentyl group, cyclopentyl group, cyclopropylethyl group, cyclobutylmethyl group, n-hexyl group, cyclohexyl group, cyclopropylpropyl group, cyclobutylethyl group, cyclopentylmethyl group and the like. As the alkyl group, for example, methyl group, ethyl group, n-propyl group, and isopropyl group are particularly preferred.

Examples of the alkenyl group include, for example, a lower alkenyl group containing one or more double bonds and the like, and a lower alkenyl group containing one double bond is preferred. As the lower alkenyl group, for example, an alkenyl group having 2 to 5 carbon atoms is preferred, and an alkenyl group having 2 to 4 carbon atoms is particularly preferred. Preferred examples of the alkenyl group having 2 to 4 carbon atoms include, for example, vinyl group, allyl group, propenyl group, butylidene group, but-1-enyl group, but-2-enyl group, but-3-enyl group, and the like, and preferred examples of the alkenyl group having 5 carbon atoms include, for example, pentylidene group, pent-1-enyl group, pent-2-enyl group, pent-3-enyl group, pent-4-enyl group, and the like. As the alkenyl group, for example, vinyl group, allyl group, and propenyl group are more preferred, vinyl group, and allyl group are still more preferred, and allyl group is particularly preferred. There is also another embodiment in which vinyl group is particularly preferred.

Examples of the alkynyl group include, for example, a lower alkynyl group containing one or more triple bonds, and the like, and a lower alkynyl group containing one triple bond is preferred. As the lower alkynyl group, for example, an alkynyl group having 2 to 5 carbon atoms is preferred. Specifically, preferred examples include ethynyl group, prop-1-ynyl group, prop-2-ynyl group, but-1-ynyl group, but-2-ynyl group, but-3-ynyl group, pent-1-ynyl group, pent-2-ynyl group, pent-3-ynyl group, pent-4-ynyl group and the like. Ethynyl group, prop-2-ynyl group, and but-3-ynyl group are more preferred, ethynyl group, and prop-1-ynyl group are still more preferred, and ethynyl group is particularly preferred.

Examples of the alkoxy group include, for example, a straight, branched, or cyclic saturated alkyloxy group, and a saturated alkyloxy group consisting a combination thereof, and a lower alkoxy group is preferred. Examples of the lower alkoxy group include, for example, an alkoxy group having 1 to 6 carbon atoms, and an alkoxy group having 1 to 4 carbon atoms is preferred. Preferred examples of the alkoxy group having 1 to 4 carbon atoms include, for example, methoxy group, ethoxy group, n-propoxy group, isopropoxy group, cyclopropoxy group, n-butoxy group, isobutoxy group, s-butoxy group, t-butoxy group, cyclobutoxy group, cyclopropylmethoxy group, and the like, and preferred examples of the alkoxy group having 5 or 6 carbon atoms include, for example, n-pentyloxy group, cyclopentyloxy group, cyclopropylethyloxy group, cyclobutylmethyloxy group, n-hexyloxy group, cyclohexyloxy group, cyclopropylpropyloxy group, cyclobutylethyloxy group, cyclopentylmethyloxy group, and the like.

Examples of the aryl ring include, for example, a monocyclic aromatic ring, a condensed polycyclic aromatic ring, and the like. The monocyclic aromatic ring or condensed polycyclic aromatic ring defined here includes a partially unsaturated monocyclic or condensed bicyclic carbon ring, hetero ring, and the like. Although the aryl ring may be a hydrocarbon ring, it may contain one or more, for example, 1 to 3, of one or more kinds of heteroatoms selected from the group consisting of nitrogen atom, sulfur atom, and oxygen atom as ring-constituting atoms other than carbon atom.

Examples of the monocyclic aromatic ring include, for example, a monocyclic aromatic hydrocarbon, a monocyclic aromatic heterocyclic ring containing one or more heteroatoms, and the like. Examples include, for example, benzene ring, and a 5- or 6-membered aromatic heterocyclic ring containing one or more heteroatoms. Specifically, preferred examples of the 5- or 6-membered aromatic heterocyclic ring include thiophene, pyridine, furan, thiazole, oxazole, pyrazole, pyrazine, pyrimidine, pyrrole, imidazole, pyridazine, isothiazole, isoxazole, 1,2,4-oxadiazole, 1,3,4-oxadiazole, 1,2,4-thiadiazole, 1,3,4-thiadiazole, furazan, and the like.

Examples of the condensed polycyclic aromatic ring include, for example, a condensed polycyclic aromatic hydrocarbon, a condensed polycyclic aromatic heterocyclic ring containing one or more heteroatoms, and the like. Examples of the condensed polycyclic aromatic hydrocarbon include, for example, a condensed polycyclic aromatic hydrocarbon having 9 to 14 carbon atoms, i.e., bi- or tricyclic aromatic hydrocarbon, and specific preferred examples include, for example, naphthalene, 1,2,3,4-tetrahydronaphthalene, indene, 2,3-dihydroindene (indane), fluorene, phenanthrene, 9,10-dihydrophenanthrene, anthracene, and the like. Examples of the condensed polycyclic aromatic heterocyclic ring include, for example, a 9- to 14-membered, preferably 9- or 10-membered, condensed polycyclic aromatic heterocyclic ring containing one or more, for example, 1 to 4, heteroatoms, and the like, and preferred specific examples include, for example, benzofuran, 2,3-dihydrobenzofuran, benzothiophene, 2,3-dihydrobenzothiophene, benzimidazole, benzoxazole, benzisoxazole, benzothiazole, benzisothiazole, naphtho[2,3-b]thiophene, quinoline, isoquinoline, 1,2-dihydroisoquinoline, 3,4-dihydroisoquinoline, 1,2-dihydroquinoline, 3,4-dihydroquinoline, 1,2,3,4-tetrahydroisoquinoline, 1,2,3,4-tetrahydroquinoline, indole, indoline, quinoxaline, phenanthoridine, phenothiazine, phenoxazine, phthalazine, naphthylidine, quinazoline, cinnoline, carbazole, β-carboline, acridine, phenazine, phthalimide, thioxanthene, and the like.

Examples of the aryl group include, for example, a monocyclic aromatic group, a condensed polycyclic aromatic group, and the like, and a monovalent residue obtained by removing arbitrary one hydrogen atom from the aryl ring explained above can be exemplified.

Examples of the substituent of the aryl group which may be substituted are similar to, for example, the preferred examples of the substituent of the alkyl group which may be substituted described later.

Examples of the monocyclic aromatic group include, for example, a monovalent residue obtained by removing arbitrary one hydrogen atom from a monocyclic aromatic ring. Preferred specific examples of the monocyclic aromatic group include, phenyl group, thienyl group (2- or 3-thienyl group), pyridyl group (2-, 3- or 4-pyridyl group), furyl group (2- or 3-furyl group), thiazolyl group (2-, 4- or 5-thiazolyl group), oxazolyl group (2-, 4- or 5-oxazolyl group), pyrazolyl group (1-, 3- or 4-pyrazolyl group), 2-pyrazinyl group, pyrimidinyl group (2-, 4- or 5-pyrimidinyl group), pyrrolyl group (1-, 2- or 3-pyrrolyl group), imidazolyl group (1-, 2- or 4-imidazolyl group), pyridazinyl group (3- or 4-pyridazinyl group), 3-isothiazolyl group, 3-isoxazolyl group, 1,2,4-oxadiazol-5-yl group, 1,2,4-oxadiazol-3-yl group, and the like.

Examples of the condensed polycyclic aromatic group include, for example, a monovalent residue obtained by removing arbitrary one hydrogen atom from a bi- to tetracyclic, preferably, bi- or tricyclic, condensed polycyclic aromatic ring.

Preferred specific examples of the condensed polycyclic aromatic group include, for example, 1-naphthyl group, 2-naphthyl group, 1-indenyl group, 2-indenyl group, 2,3-dihydroinden-1-yl group, 2,3-dihydroinden-2-yl group, 2-anthryl group, quinolyl group (2-, 3-, 4-, 5-, 6-, 7- or 8-quinolyl group), isoquinolyl group (1-, 3-, 4-, 5-, 6-, 7- or 8-isoquinolyl group), 1,2-dihydroisoquinolyl group or 1,2,3,4-tetrahydroisoquinolyl group (substitution positions are the same as those of isoquinolyl group), indolyl group (1-, 2-, 3-, 4-, 5-, 6- or 7-indolyl group), isoindolyl group (1-, 2-, 4- or 5-isoindolyl group), phthalazinyl group (1-, 5- or 6-phthalazinyl group), quinoxalinyl group (2-, 3- or 5-quinoxalinyl group), benzofuranyl group (2-, 3-, 4-, 5- or 6-benzofuranyl group), 2,3-dihydrobenzofuran-1-yl group, 2,3-dihydrobenzofuran- 2-yl group, 2,3-dihydrobenzothiophen-1-yl group, 2,3-dihydrobenzothiophen-2-yl group, benzothiazolyl group (2-, 4-, 5- or 6-benzothiazolyl group), benzimidazolyl group (1-, 2-, 4-, 5- or 6-benzimidazolyl group), fluorenyl group (1-, 2-, 3- or 4-fluorenyl group), or thioxanthenyl group, and the like.

The aryloxy group refers to, for example, a group consisting of an aryl group binding via oxygen atom, and the aryl moiety of the aryloxy group is similar to the aryl described above. The aryl moiety of the aryloxy is preferably a monocyclic aromatic group, and preferred as the aryloxy group are, for example, phenoxy group, 2-thienyloxy group, 3-thienyloxy group, 2-pyridyloxy group, 3-pyridyloxy group, 4-pyridyloxy group, 2-furyloxy group, 3-furyloxy group, 2-thiazolyloxy group, 4-thiazolyloxy group, 5-thiazolyloxy group, 2-oxazolyloxy group, 4-oxazolyloxy group, 5-oxazolyloxy group, 1-pyrazolyloxy group, 3-pyrazolyloxy group, 4-pyrazolyloxy group, 2-pyrazinyloxy group, 2-pyrimidinyloxy group, 4-pyrimidinyloxy group, 5-pyrimidinyloxy group, 1-pyrrolyloxy group, 2-pyrrolyloxy group, 3-pyrrolyloxy group, 1-imidazolyloxy group, 2-imidazolyloxy group, 4-imidazolyloxy group, 3-pyridazinyloxy group, 4-pyridazinyloxy group, 3-isothiazolyloxy group, 3-isooxazolyloxy group, 1,2,4-oxadiazol-5-yloxy group, 1,2,4-oxadiazol-3-yloxy group, and the like. Phenoxy group, 2-thienyloxy group, 3-thienyloxy group, 2-furyloxy group, 3-furyloxy group, 2-pyrrolyloxy group, 3-pyrrolyloxy group, and the like are preferred, and phenoxy group and 2-furyloxy group are particularly preferred.

Examples of the substituent of the aryloxy group which may be substituted are similar to, for example, the preferred examples of the substituent of the alkyl group which may be substituted described later.

The aralkyl group refers to, for example, an alkyl group substituted with an aryl group (arylalkyl group). The alkyl moiety of the arylalkyl group is similar to the alkyl group described above, and the aryl moiety of the arylalkyl group is similar to the aryl described above. The aryl moiety of the arylalkyl is preferably a monocyclic aromatic group, and examples of the arylalkyl group include, for example, benzyl group, 2-thienylmethyl group, 3-thienylmethyl group, 2-pyridylmethyl group, 3-pyridylmethyl group, 4-pyridylmethyl group, 2-furylmethyl group, 3-furylmethyl group, 2-thiazolylmethyl group, 4-thiazolylmethyl group, 5-thiazolylmethyl group, 2-oxazolylmethyl group, 4-oxazolylmethyl group, 5-oxazolylmethyl group, 1-pyrazolylmethyl group, 3-pyrazolylmethyl group, 4-pyrazolylmethyl group, 2-pyrazinylmethyl group, 2-pyrimidinylmethyl group, 4-pyrimidinylmethyl group, 5-pyrimidinylmethyl group, 1-pyrrolylmethyl group, 2-pyrrolylmethyl group, 3-pyrrolylmethyl group, imidazolylmethyl group, 2-imidazolylmethyl group, 4-imidazolylmethyl group, 3-pyridazinylmethyl group, 4-pyridazinylmethyl group, 3-isothiazolylmethyl group, 3-isooxazolylmethyl group, 1,2,4-oxadiazol-5-ylmethyl group, 1,2,4-oxadiazol-3-ylmethyl group, and the like. Preferred are benzyl group, 2-thienylmethyl group, 3-thienylmethyl group, 2-furylmethyl group, 3-furylmethyl group, 2-pyrrolylmethyl group, 3-pyrrolylmethyl group, 2,3-dihydroinden-1-ylmethyl group, 2,3-dihydroinden-2-ylmethyl group, and the like, and 2-furylmethyl group is particularly preferred.

Examples of the arylalkyl group include, for example, 2-phenylethyl group, 2-(2-thienyl)ethyl group, 2-(3-thienyl)ethyl group, 2-(2-pyridyl)ethyl group, 2-(3-pyridyl)ethyl group, 2-(4-pyridyl)ethyl group, 2-(2-furyl)ethyl group, 2-(3-furyl)ethyl group, 2-(2-thiazolyl)ethyl group, 2-(4-thiazolyl)ethyl group, 2-(5-thiazolyl)ethyl group, 2-(2-oxazolyl)ethyl group, 2-(4-oxazolyl)ethyl group, 2-(5-oxazolyl)ethyl group, 2-(1-pyrazolyl)ethyl group, 2-(3-pyrazolyl)ethyl group, 2-(4-pyrazolyl)ethyl group, 2-(2-pyrazinyl)ethyl group, 2-(2-pyrimidinyl)ethyl group, 2-(4-pyrimidinyl)ethyl group, 2-(5-pyrimidinyl)ethyl group, 2-(1-pyrrolyl)ethyl group, 2-(2-pyrrolyl)ethyl group, 2-(3-pyrrolyl)ethyl group, 2-(1-imidazolyl)ethyl group, 2-(2-imidazolyl)ethyl group, 2-(4-imidazolyl)ethyl group, 2-(3-pyridazinyl)ethyl group, 2-(4-pyridazinyl)ethyl group, 2-(3-isothiazolyl)ethyl group, 2-(3-isoxazolyl)ethyl group, 2-(1,2,4-oxadiazol-5-yl)ethyl group, 2-(1,2,4-oxadiazol-3-yl)ethyl group, and the like. Preferred are 2-phenylethyl group, 2-(2-thienyl)ethyl group, 2-(3-thienyl)ethyl group, 2-(2-furyl)ethyl group, 2-(3-furyl)ethyl group, 2-(2-pyrrolyl)ethyl group, and 2-(3-pyrrolyl)ethyl group, and 2-(2-furyl)ethyl group is particularly preferred.

Examples of the arylalkyl group further include, for example, 1-phenylethyl group, 1-(2-thienyl)ethyl group, 1-(3-thienyl)ethyl group, 1-(2-pyridyl)ethyl group, 1-(3-pyridyl)ethyl group, 1-(4-pyridyl)ethyl group, 1-(2-furyl)ethyl group, 1-(3-furyl)ethyl group, 1-(2-thiazolyl)ethyl group, 1-(4-thiazolyl)ethyl group, 1-(5-thiazolyl)ethyl group, 1-(2-oxazolyl)ethyl group, 1-(4-oxazolyl)ethyl group, 1-(5-oxazolyl)ethyl group, 1-(1-pyrazolyl)ethyl group, 1-(3-pyrazolyl)ethyl group, 1-(4-pyrazolyl)ethyl group, 1-(2-pyrazinyl)ethyl group, 1-(2-pyrimidinyl)ethyl group, 1-(4-pyrimidinyl)ethyl group, 1-(5-pyrimidinyl)ethyl group, 1-(1-pyrrolyl)ethyl group, 1-(2-pyrrolyl)ethyl group, 1-(3-pyrrolyl)ethyl group, 1-(1-imidazolyl)ethyl group, 1-(2-imidazolyl)ethyl group, 1-(4-imidazolyl)ethyl group, 1-(3-pyridazinyl)ethyl group, 1-(4-pyridazinyl)ethyl group, 1-(3-isothiazolyl)ethyl group, 1-(3-isoxazolyl)ethyl group, 1-(1,2,4-oxadiazol-5-yl)ethyl group, 1-(1,2,4-oxadiazol-3-yl)ethyl group, and the like. Preferred are 1-phenylethyl group, 1-(2-thienyl)ethyl group, 1-(3-thienyl)ethyl group, 1-(2-furyl)ethyl group, 1-(3-furyl)ethyl group, 1-(2-pyrrolyl)ethyl group, and 1-(3-pyrrolyl)ethyl group, and 1-(2-furyl)ethyl group is particularly preferred.

Examples of the substituent of the aralkyl group which may be substituted are similar to, for example, the preferred examples of the substituent of the alkyl group which may be substituted described later.

Examples of the saturated heterocyclic group include, for example, a monocyclic saturated heterocyclic group, and the ring thereof is, for example, a 3- to 7-membered ring, most preferably 5- or 6-membered ring, containing one or two, preferably one, heteroatom. Specifically, preferred examples include tetrahydropyranyl group (3- or 4-tetrahydropyranyl group), 3-tetrahydrofuryl group, piperidyl group (3- or 4-piperidyl group), 3-pyrrolidyl group, tetrahydrothiopyranyl group (3- or 4-tetrahydrothiopyranyl group), 3-tetrahydrothiofuryl group, and the like. A particularly preferred example includes tetrahydropyranyl group.

Preferred examples of the substituent of the alkyl group which may be substituted include, for example, hydroxyl group, a halogen atom, carboxy group, cyano group, a saturated heterocyclic group, an alkylsulfonylamino group, aminocarbonylamino group, and the like. Hydroxyl group, and a halogen atom are more preferred, hydroxyl group and fluorine atom are still more preferred, and hydroxyl group is particularly preferred. There is also another embodiment in which fluorine atom is particularly preferred.

As the alkyl group which may be substituted, one group selected from the group consisting of the preferred examples mentioned above for the alkyl group, trifluoromethyl group, difluoromethyl group, hydroxymethyl group, and 2-hydroxyethyl group is preferred. Methyl group, ethyl group, n-propyl group, isopropyl group, cyclopropyl group, trifluoromethyl group, difluoromethyl group, hydroxymethyl group, and 2-hydroxyethyl group are more preferred, and methyl group is particularly preferred.

The substituents of the alkenyl group which may be substituted and the alkynyl group which may be substituted are similar to the substituent of the aforementioned alkyl group which may be substituted.

As the alkenyl group which may be substituted, for example, the preferred examples mentioned above for the alkenyl group are preferred, and as the alkynyl group which may be substituted, for example, the preferred examples mentioned above for the alkynyl group are preferred.

The substituent of the alkoxy group which may be substituted is similar to, for example, the substituent of the aforementioned alkyl group which may be substituted, and one or more halogen atoms are particularly preferred.

As the substituted alkoxy group, for example, an alkoxy group optionally substituted with one or more halogen atoms is preferred, and an alkoxy group optionally substituted with one or more halogen atoms and having 1 to 4 carbon atoms is preferred. When the alkoxy group is substituted with two or more halogen atoms, the halogen atoms may be the same or different.

As the alkoxy group which may be substituted, a group selected from the group consisting of, for example, the preferred examples of the alkoxy group having 1 to 6 carbon atoms mentioned above, monofluoromethoxy group, difluoromethoxy group, trifluoromethoxy group, and 2,2,2-trifluoroethoxy group is preferred, and a group selected from the group consisting of the preferred examples of the alkoxy group having 1 to 6 carbon atoms mentioned above, trifluoromethoxy group, and 2,2,2-trifluoroethoxy group is particularly preferred.

As the aralkyl group which may be substituted, for example, the preferred examples of the aforementioned aralkyl group are preferred. There is also another embodiment in which examples in which a carbon atom among the constituent elements forming the aryl ring of the aralkyl group is substituted with an alkyl group, an alkoxy group, amino group, hydroxyl group, or a halogen atom are preferred. Specifically, examples include 4-methylphenylmethyl group, 4-methoxyphenylmethyl group, 4-aminophenylmethyl group, 4-hydroxyphenylmethyl group, 4-fluorophenylmethyl group, 5-methyl-2-furylmethyl group, 4-methyl-2-furylmethyl group, 5-methyl-3-furylmethyl group, 5-methyl-2-pyrrolylmethyl group, 4-methyl-2-pyrrolylmethyl group, 5-methyl-3-pyrrolylmethyl group, 5-methyl-2-thienylmethyl group, 4-methyl-2-thienylmethyl group, 5-methyl-3-thienylmethyl group, and the like. Further, there is another embodiment in which examples in which a nitrogen atom among the constituent elements forming the aryl ring of the aralkyl group is substituted with an alkyl group, or an alkoxy group are preferred. Specifically, examples include 1-methyl-2-pyrrolylmethyl group, 1-ethyl-2-pyrrolylmethyl group, 1-methyl-3-pyrrolylmethyl group, and the like.

As the saturated heterocyclic group which may be substituted, for example, the preferred examples of the aforementioned saturated heterocyclic group are preferred.

The alkylene is, for example, a divalent group consisting of a straight, branched, or cyclic saturated hydrocarbon having 1 to 6 carbon atoms, or a saturated hydrocarbon having 1 to 6 carbon atoms consisting a combination thereof. An alkylene having 1 to 3 carbon atoms is preferred, and there is also another embodiment in which alkylene having 4 to 6 carbon atoms is preferred. A straight alkylene or branched alkylene is preferred, and a straight alkylene is particularly preferred. Specific examples include methylene, ethylene, trimethylene, tetramethylene, pentamethylene, hexamethylene, and the like, and preferred examples include methylene, ethylene, and trimethylene.

As the substituent of the alkylene which may be substituted, for example, one group selected from the group consisting of the preferred examples mentioned above for the alkyl group, trifluoromethyl group, difluoromethyl group, hydroxymethyl group, and 2-hydroxyethyl group is preferred. Methyl group, ethyl group, n-propyl group, isopropyl group, cyclopropyl group, trifluoromethyl group, difluoromethyl group, hydroxymethyl group, and 2-hydroxyethyl group are more preferred, and methyl group is particularly preferred.

The alkenylene is a divalent group consisting of the aforementioned alkylene containing, for example, one or more double bonds, and a lower alkenylene containing one double bond is preferred. As the lower alkenylene, for example, an alkenylene having 2 to 5 carbon atoms is preferred, and an alkenylene having 2 to 4 carbon atoms is particularly preferred. Preferred examples of the alkenylene having 2 to 4 carbon atoms include, for example, vinylene, allylene, propenylene, butylidenylene, and the like. Specific examples include vinylene, 1-propenylene, 2-propenylene, 1-butenylene, 2-butenylene, 3-butenylene, 1-pentenylene, 2-pentenylene, 3-pentenylene, 4-pentenylene, 2,4-pentadienylene, and the like. As for the stereochemistry of the double bond, the steric configuration may be either cis- or trans-configuration. Preferred steric configuration is, for example, trans-configuration.

The substituent of the alkenylene which may be substituted is similar to, for example, the substituent of the aforementioned alkylene which may be substituted. Methyl group and trifluoromethyl group are preferred, and methyl group is particularly preferred. There is also another embodiment in which trifluoromethyl group is preferred.

The alkynylene is a divalent group consisting of the aforementioned alkylene containing, for example, one or more triple bonds, and a lower alkynylene containing one triple bond is preferred. As the lower alkynylene, for example, an alkynylene having 2 to 4 carbon atoms is preferred, and an alkynylene having 2 carbon atoms is particularly preferred. Specific examples include ethynylene, 2-propynylene, 2-butynylene, 3-butynylene, 2-pentynylene, 3-pentynylene, and the like.

Examples of the substituent of the alkynylene which may be substituted include, for example, an alkyl group, and the like, and it may independently have one or two substituents.

X is defined as a halogen atom, cyano group, an alkyl group which may be substituted, an alkenyl group which may be substituted, an alkynyl group which may be substituted, an alkoxy group which may be substituted, hydroxy group, —N($R^1$)($R^2$), or —C(O)NH$R^3$. A halogen atom, an alkyl group which may be substituted, and hydroxy group are preferred, a halogen atom and an alkyl group which may be substituted are preferred, and a halogen atom is particularly preferred. Further, there is also another embodiment in which an alkyl group which may be substituted is particularly preferred. Furthermore, there is also another embodiment in which hydroxy group is preferred.

As the halogen atom as X, for example, chlorine atom, bromine atom, and the like are preferred, and chlorine atom is particularly preferred.

Examples of the alkyl group which may be substituted as X include the preferred examples of the alkyl group which may be substituted mentioned above. For example, methyl group, ethyl group, n-propyl group, isopropyl group, trifluoromethyl group, and the like are preferred, and methyl group is more preferred. Further, there is also another embodiment in which trifluoromethyl group is more preferred. In a further embodiment, as X, chlorine atom, methyl group, and trifluoromethyl group are preferred, and chlorine atom and methyl group are most preferred.

$R^1$ and $R^2$ are both or independently defined as hydrogen atom or an alkyl group, and it is preferred that both $R^1$ and $R^2$ are hydrogen atoms. There is also another embodiment in which it is preferred that one of $R^1$ and $R^2$ is hydrogen atom, and the other is an alkyl group. Examples of the alkyl group as $R^1$ and $R^2$ include the preferred examples of the alkyl group mentioned above, an alkyl group having 1 to 3 carbon atoms is preferred, and methyl group and ethyl group are more preferred. It is more preferred that one of $R^1$ and $R^2$ is hydrogen atom, and the other is methyl group or ethyl group, and it is particularly preferred that one of $R^1$ and $R^2$ is hydrogen atom, and the other is methyl group. There is also another embodiment in which it is preferred that $R^1$ and $R^2$ are both alkyl groups. The alkyl group as $R^1$, for example, an alkyl group having 1 to 3 carbon atoms is preferred, and as the alkyl group as $R^2$, for example, an alkyl group having 1 to 3 carbon atoms is preferred.

$R^3$ is defined as hydrogen atom or an alkyl group, and it is preferably hydrogen atom. There is also another embodiment in which it is preferably an alkyl group. As the alkyl group as $R^3$, for example, an alkyl group having 1 to 3 carbon atoms is preferred.

Y is defined as hydrogen atom or an alkyl group which may be substituted, and it is preferably hydrogen atom. There is also another embodiment in which it is preferably an alkyl group which may be substituted. As the alkyl group which may be substituted as Y, for example, an alkyl group having 1 to 6 carbon atoms which may be substituted is preferred. An alkyl group having 1 to 3 carbon atoms which may be substituted is particularly preferred.

Z is defined as hydrogen atom or an alkyl group which may be substituted, and it is preferably an alkyl group. There is also another embodiment in which hydrogen atom is preferred. Examples of the alkyl group include methyl group, ethyl group, n-propyl group, isopropyl group, and the like, methyl group and ethyl group are more preferred, and methyl group is particularly preferred. Further, ethyl group may be particularly preferred. Further, there is also another embodiment in which n-propyl group and isopropyl group are preferred.

[Formula 3]

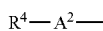  (G¹)

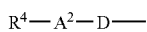  (G²)

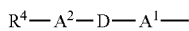  (G³)

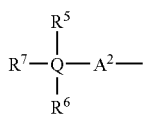  (G⁴)

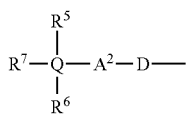  (G⁵)

  (G⁶)

  (G⁷)

G is defined as a group represented by any one of the general formulas ($G^1$) to ($G^7$). It is preferably a group represented by the general formula ($G^1$), ($G^2$), or ($G^3$), more preferably a group represented by the general formula ($G^1$) or ($G^2$), most preferably a group represented by the general formula ($G^2$). Further, it is preferably a group represented by the general formula ($G^4$), ($G^5$), or ($G^6$), more preferably a group represented by the general formula ($G^4$) or ($G^5$), most preferably a group represented by the general formula ($G^5$). There is also another embodiment in which a group represented by the general formula ($G^2$) or ($G^5$) is particularly preferred. There is also another embodiment in which a group represented by the general formula ($G^7$) is preferred.

Apart form the above, G is preferably a group represented by the general formula ($G^2$), ($G^3$), ($G^5$), or ($G^6$), more preferably a group represented by the general formula ($G^2$) or ($G^5$). There is also another embodiment in which a group represented by the general formula ($G^3$) or ($G^6$) is more preferred.

There is also another embodiment in which a group represented by the general formula ($G^1$) or ($G^4$) is preferred as G.

D is defined as oxygen atom, —NR¹⁰C(O)—, —C(O)NR¹⁰—, —S(O)₂NR¹⁰—, or —N(R¹¹)—. Oxygen atom, —C(O)NR¹⁰—, —S(O)₂NR¹⁰—, and —N(R¹¹)— are preferred, oxygen atom, —C(O)NR¹⁰—, and —N(R¹¹)— are particularly preferred, and —N(R¹¹)— is most preferred. There is also another embodiment in which oxygen atom is preferred, and there is also another embodiment in which —C(O)NR¹⁰— is most preferred. There is also another embodiment in which —NR¹⁰C(O)—, —C(O)NR¹⁰—, and —S(O)₂NR¹⁰— are preferred.

$R^4$ is defined as hydrogen atom or an alkyl group which may be substituted, and hydrogen atom and an alkyl group which may be substituted are preferred. There is also another embodiment in which an alkyl group which may be substituted is most preferred. Examples of the alkyl group which may be substituted include the preferred examples of the alkyl group which may be substituted mentioned above.

$R^{10}$ is defined as hydrogen atom or an alkyl group which may be substituted, and it is preferably hydrogen atom. It is also preferably an alkyl group. As the alkyl group as $R^{10}$, for example, an alkyl group having 1 to 3 carbon atoms is preferred.

$R^{11}$ is defined as hydrogen atom or an alkyl group which may be substituted, and it is preferably hydrogen atom. It is also preferably an alkyl group which may be substituted. As the alkyl group which may be substituted, for example, methyl group, ethyl group, n-propyl group, isopropyl group, trifluoromethyl group, and the like are preferred, and methyl group is more preferred. There is also another embodiment in which trifluoromethyl group is more preferred.

$A^1$ is defined as an alkylene which may be substituted, and the alkylene is preferably an alkylene having 2 to 6 carbon atoms. An alkylene having 2 or 3 carbon atoms is more preferred, and an alkylene having 2 carbon atoms is particularly preferred.

$A^2$ is defined as a single bond, an alkylene which may be substituted, an alkenylene which may be substituted, or an alkynylene which may be substituted. It is preferably a single bond or an alkylene which may be substituted, more preferably a single bond. There is also another embodiment in which an alkylene which may be substituted is more preferred. There is also another embodiment in which an alkenylene which may be substituted or an alkynylene which may be substituted is more preferred.

When G represents a group represented by the general formula ($G^5$), and $A^2$ represents an alkylene which may be substituted, as the substituent, one group selected from the group consisting of the preferred examples of the alkyl group mentioned above, trifluoromethyl group, difluoromethyl group, and an aryl group is preferred. An alkyl group or an aryl group is more preferred. The aryl group referred to here has the same definition as that of the aforementioned aryl group, and it is preferably a monocyclic aromatic group, more preferably phenyl group. There is also another embodiment in which a monocyclic and heterocyclic aromatic group such as thiazolyl group is preferred.

When $A^2$ represents an alkenylene which may be substituted or an alkynylene which may be substituted, G is preferably a group represented by the general formula ($G^1$) or ($G^4$), most preferably a group represented by the general formula ($G^4$). There is also another embodiment in which it is preferably a group represented by the general formula ($G^1$).

When D represents —$NR^{10}C(O)$—, —$C(O)NR^{10}$—, or —$S(O)_2NR^{10}$—, G is preferably a group represented by the general formula ($G^2$), ($G^3$), ($G^5$), or ($G^6$), more preferably a group represented by the general formula ($G^5$) or ($G^6$), most preferably a group represented by the general formula ($G^5$). There is also another embodiment in which it is preferably a group represented by the general formula ($G^2$). In such a case, $A^2$ is defined as a single bond, an alkylene which may be substituted, an alkenylene which may be substituted, or an alkynylene which may be substituted, and it is preferably a single bond or an alkylene which may be substituted, most preferably a single bond.

When G represents a group represented by the general formula ($G^3$) or ($G^6$), D is preferably oxygen atom or most preferably —$N(R^{11})$—. There is also another embodiment in which —$C(O)NR^{10}$— or —$S(O)_2NR^{10}$— is preferred.

When D represents —$N(R^{11})$—, G is preferably a group represented by the general formula ($G^2$), ($G^3$), ($G^5$), or ($G^6$), more preferably a group represented by the general formula ($G^2$) or ($G^5$), most preferably a group represented by the general formula ($G^2$). There is also another embodiment in which a group represented by the general formula ($G^5$) is particularly preferred. $R^{11}$ is defined as an alkyl group which may be substituted or hydrogen atom, and it is preferably an alkyl group which may be substituted. As the alkyl group which may be substituted, a lower alkyl group having 1 to 3 carbon atoms is more preferred. There is also another embodiment in which hydrogen atom is preferred.

When D represents and G represents a group represented by the general formula ($G^2$), preferred examples of the substituent of D formed by $R^4$ and $A^2$ include an alkyl group which may be substituted. Specific examples of the alkyl group and the substituent thereof are similar to those mentioned above. $R^{11}$ is defined as an alkyl group which may be substituted or hydrogen atom, and it is preferably an alkyl group which may be substituted. As the alkyl group which may be substituted, a lower alkyl group having 1 to 3 carbon atoms is more preferred. There is also another embodiment in which hydrogen atom is preferred.

When D represents —$N(R^{11})$—, and G represents a group represented by the general formula ($G^5$), the substituent of D formed by Q and $A^2$ is preferably the aforementioned aralkyl group which may be substituted or aryl group which may be substituted, more preferably the aralkyl group which may be substituted. Specific examples of the aralkyl group which may be substituted include the preferred examples of the aralkyl group which may be substituted mentioned above. $R^{11}$ is defined as an alkyl group which may be substituted or hydrogen atom, and it is preferably an alkyl group which may be substituted. As the alkyl group which may be substituted, a lower alkyl group having 1 to 3 carbon atoms is more preferred. There is also another embodiment in which hydrogen atom is preferred as $R^{11}$.

When G is a group represented by the general formula ($G^5$) or ($G^6$), and D is —$C(O)NR^{10}$—, Q is defined as an aryl group which may be substituted, and it is preferably a monocyclic aromatic group, more preferably phenyl group. $R^{10}$ is defined as hydrogen atom or an alkyl group which may be substituted, and it is preferably hydrogen atom. There is also another embodiment in which an alkyl group which may be substituted is preferred. As the alkyl group which may be substituted, a lower alkyl group having 1 to 3 carbon atoms is preferred. $R^5$, $R^6$, and $R^7$ represent a substituent of Q, and preferred examples of these substituents are similar to the preferred examples of $R^5$, $R^6$, and $R^7$ described later.

Q is defined as an aryl group which may be substituted, examples of the aryl group include, for example, a monocyclic aromatic group, a condensed polycyclic aromatic group, and the like, and it is preferably a monocyclic aromatic group. There is also another embodiment in which a condensed polycyclic aromatic group is preferred.

Examples of the monocyclic aromatic group include, for example, a monovalent residue obtained by removing arbitrary one hydrogen atom from a monocyclic aromatic ring, and the like. As specific examples of the monocyclic aromatic group, phenyl group, thienyl group (2- or 3-thienyl group), pyridyl group (2-, 3- or 4-pyridyl group), furyl group (2- or 3-furyl group), thiazolyl group (2-, 4- or 5-thiazolyl group), oxazolyl group (2-, 4- or 5-oxazolyl group), pyrazolyl group (1-, 3- or 4-pyrazolyl group), 2-pyrazinyl group, pyrimidinyl group (2-, 4- or 5-pyrimidinyl group), pyrrolyl group (1-, 2- or 3-pyrrolyl group), imidazolyl group (1-, 2- or 4-imidazolyl group), pyridazinyl group (3- or 4-pyridazinyl group), 3-isothiazolyl group, 3-isooxazolyl group, 1,2,4-oxadiazol-5-yl group, 1,2,4-oxadiazol-3-yl group, and the like are preferred, phenyl group, pyridyl group (2-, 3- or 4-pyridyl group), furyl group (2- or 3-furyl group), thiazolyl group (2-, 4- or 5-thiazolyl group), oxazolyl group (2-, 4- or 5-oxazolyl group), and the like are more preferred, and phenyl group is particularly preferred.

Examples of the condensed polycyclic aromatic group include, for example, a monovalent residue obtained by removing arbitrary one hydrogen atom from a condensed polycyclic aromatic ring consisting of 2 to 4 rings, preferably 2 or 3 rings. Specific preferred examples of the condensed polycyclic aromatic group include, for example, 1-naphthyl group, 2-naphthyl group, 1-indenyl group, 2-indenyl group, 2,3-dihydroinden-1-yl group, 2,3-dihydroinden-2-yl group, 2-anthryl group, quinolyl group (2-, 3-, 4-, 5-, 6-, 7- or 8-quinolyl group), isoquinolyl group (1-, 3-, 4-, 5-, 6-, 7- or 8-isoquinolyl group), 1,2-dihydroisoquinolyl group or 1,2,3,4-tetrahydroisoquinolyl group (substitution positions are the same as those of isoquinolyl group), indolyl group (1-, 2-, 3-, 4-, 5-, 6- or 7-indolyl group), isoindolyl group (1-, 2-, 4- or 5-isoindolyl group), phthalazinyl group (1-, 5- or 6-phthalazinyl group), quinoxalinyl group (2-, 3- or 5-quinoxalinyl group), benzofuranyl group (2-, 3-, 4-, 5- or 6-benzofuranyl group), 2,3-dihydrobenzofuran-1-yl group, 2,3-dihydrobenzofuran-2-yl group, 2,3-dihydrobenzothiophen-1-yl group, 2,3-dihydrobenzothiophen-2-yl group, benzothiazolyl group (2-, 4-, 5- or 6-benzothiazolyl group), benzimidazolyl group (1-, 2-, 4-, 5- or 6-benzimidazolyl group), fluorenyl group (1-, 2-, 3- or 4-fluorenyl group), thioxanthenyl group, and the like.

Q is defined as an aryl group which may be substituted. The substituent of the aryl group which may be substituted means $R^5$, $R^6$, and $R^7$. $R^5$, $R^6$, and $R^7$ are all or independently defined as hydrogen atom, a halogen atom, an alkyl group which may be substituted, an alkoxy group which may be substituted, an —$N(R^{12})(R^{13})$ group, an aryl group which may be substituted, an aryloxy group which may be substituted, or an aralkyl group which may be substituted, and they preferably represent hydrogen atom, a halogen atom, an alkyl group which may be substituted, or an alkoxy group which may be substituted. There is also another embodiment in which an aryl group which may be substituted, an aryloxy group which may be substituted, and an aralkyl group which may be substituted are preferred. When Q has only one position for binding a substituent, $R^5$ is the substituent of Q, and when Q has two positions for binding a substituent, $R^5$ and $R^6$ are the substituents of Q.

When $R^5$, $R^6$, or $R^7$ represents an aryl group which may be substituted, preferred examples thereof are similar to the preferred examples of the monocyclic aromatic group mentioned above.

When $R^5$, $R^6$, or $R^7$ represents an aryloxy group which may be substituted, preferred examples thereof are similar to the preferred examples of the aryloxy group which may be substituted mentioned above.

When Q represents phenyl group, it is preferred that any one or two of $R^5$, $R^6$, and $R^7$ are hydrogen atoms, and it is particularly preferred that any two of them are hydrogen atoms. There is also another embodiment in which it is particularly preferred that any one of them is hydrogen atom. As for combination of substitution positions of $R^5$, $R^6$ and $R^7$, the combinations represented by the following general formulas ($Q^1$) to ($Q^5$) are preferred (* represents the binding position to $A^2$):

[Formula 4]

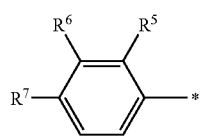

(Q$^1$)

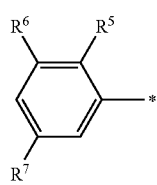

(Q$^2$)

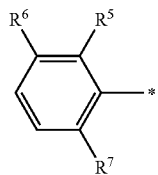

(Q$^3$)

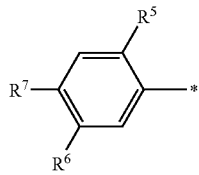

(Q$^4$)

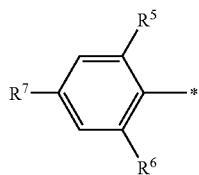

(Q$^5$)

Q is preferably a group represented by the general formula ($Q^1$), ($Q^4$), or ($Q^5$), more preferably a group represented by the general formula ($Q^1$) or ($Q^4$). There is also another embodiment in which a group represented by the general formula ($Q^2$) or ($Q^3$) is preferred.

When Q represents a phenyl group, preferred examples thereof include the following groups: 2-, 3-, or 4-fluorophenyl group, 2,3-difluorophenyl group, 2,4-difluorophenyl group, 3,4-difluorophenyl group, 2-fluoro-3-chlorophenyl group, 2-fluoro-4-chlorophenyl group, 2-fluoro-5-chlorophenyl group, 2-fluoro-6-chlorophenyl group, 3-fluoro-4-chlorophenyl group, 3-fluoro-5-chlorophenyl group, 3-fluoro-6-chlorophenyl group, 2-, 3-, or 4-(trifluoromethyl)phenyl group, 2-, 3-, or 4-methoxyphenyl group, 2-, 3-, or 4-ethoxyphenyl group, 2-, 3-, or 4-propoxyphenyl group, 2-, 3-, or 4-butoxyphenyl group, 2-fluoro-4-butoxyphenyl group, 2-, 3-, or 4-phenoxyphenyl group, 2-fluoro-4-(trifluoromethyl)phenyl group, 2-fluoro-5-(trifluoromethyl)phenyl group, 2-fluoro-6-(trifluoromethyl)phenyl group, 3-fluoro-4-(trifluoromethyl)phenyl group, and 2-(biphenyl-4-yl) group.

When Q represents a condensed bicyclic aromatic group, it is preferred that any one or two of $R^5$, $R^6$, and $R^7$ are hydrogen atoms, and it is more preferred that any two of them are hydrogen atoms.

$R^{12}$ and $R^{13}$ both or independently represent hydrogen atom or an alkyl group, or $R^{12}$ and $R^{13}$ are defined as groups which bind to each other to form a saturated cyclic substituent together with the nitrogen atom, and it is preferred that both $R^1$ and $R^2$ are hydrogen atoms. There is also another embodiment in which it is preferred that one of $R^1$ and $R^2$ is hydrogen atom, and the other is an alkyl group. Further, it is preferred that one of $R^1$ and $R^2$ is hydrogen atom, and the other is methyl group or ethyl group, and it is particularly preferred that one of $R^1$ and $R^2$ is hydrogen atom, and the other is methyl group. It is also preferred that $R^{12}$ and $R^{13}$ are hydrogen atoms. There is also another embodiment in which it is preferred that they are alkyl groups. As the saturated cyclic substituent formed by $R^{12}$ and $R^{13}$ binding to each other together with the nitrogen atom, for example, azetidine, pyrrolidine, piperidine, homopiperidine, and the like are preferred.

In $G^7$ in the aforementioned general formula (1), U represents a nitrogen-containing saturated ring. Examples of the nitrogen-containing saturated ring include, for example, a 3- to 8-membered, preferably 4- to 7-membered, monocyclic saturated heterocyclic ring containing one nitrogen atom as a ring-constituting atom. Specifically, azetidine, pyrrolidine, piperidine, homopiperidine, and the like are preferred examples. Further, m represents an integer of 0, 1 or 2, preferably 1 or 2, most preferably 1. Furthermore, when m is 1 or 2, n preferably represents an integer of 1, 2 or 3, most preferably 2 or 3.

$R^8$ is a substituent on a ring-constituting carbon atom constituting the nitrogen-containing saturated ring represented by U, and is defined as hydrogen atom or an alkyl group which may be substituted, and it is preferably hydrogen atom. An alkyl group which may be substituted is also preferred. Examples of the alkyl group which may be substituted include methyl group, ethyl group, n-propyl group, fluoromethyl group, difluoromethyl group, and trifluoromethyl group, and methyl group is particularly preferred.

$R^9$ is defined as hydrogen atom, an alkyl group which may be substituted, or hydroxy group, and it is preferably hydrogen atom. An alkyl group which may be substituted is also preferred. There is also another embodiment in which hydroxy group is preferred. Examples of the alkyl group which may be substituted include methyl group, ethyl group, n-propyl group, fluoromethyl group, difluoromethyl group, and trifluoromethyl group, and methyl group is particularly preferred.

The compounds of the present invention represented by the formula (1) may exist as geometrical isomers based on the cycloalkyl ring structure, and any geometrical isomers in pure forms and any mixtures of geometrical isomers fall within the scope of the present invention.

The compounds of the present invention represented by the formula (1) may have one or more asymmetric carbons, and stereoisomers based on such asymmetric carbons such as optical antipodes and diastereoisomer may exist. The stereoisomers in pure forms, arbitrary mixtures, racemates and the like of the stereoisomers all fall within the scope of the present invention. There is also another embodiment in which mixtures such as racemates are preferred from a view point of easiness for preparation. Further, when the compounds of the present invention have an olefinic double bond or a cyclic structure, two or more kinds of stereoisomers may exist, and arbitrary such stereoisomers in pure forms, and arbitrary mixtures of such stereoisomers all fall within the scope of the present invention. Furthermore, the compounds of the present invention represented by the formula (1) may exist as tautomers. Existence of such tautomers is apparent to those skilled in the art, and any of the tautomers fall within the scope of the present invention.

The prodrug refers to a substance which is chemically or biochemically hydrolyzed to regenerate the compound of the present invention. For example, when the compound of the present invention has carboxyl group, examples of the prodrug include a compound corresponding to the compound of the present invention of which carboxyl group is converted into an appropriate ester. Specific examples of such ester include pivaloyloxymethyl ester, acetyloxymethyl ester, cyclohexylacetyloxymethyl ester, 1-methylcyclohexylcarbonyloxymethyl ester, ethyloxycarbonyloxy-1-ethyl ester, cyclohexyloxycarbonyloxy-1-ethyl ester, and the like. Prodrugs of the compounds represented by the general formula (1) or salts thereof also fall within the scope of the present invention.

The compounds of the present invention may also exist as salts, and they also fall within the scope of the present invention. Forms of the salts are not particularly limited. Acid addition salts are generally formed, or base addition salts may be formed depending on the types of substituents. As the salts, pharmaceutically acceptable salts are preferred. Types of acids and bases that form pharmaceutically acceptable salts are well known to those skilled in the art, and examples include, for example, those described by Berge et al. in J. Pharm. Sci., 1-19 (1977). Examples of the acid addition salts include, for example, mineral acid salts such as hydrochlorides, hydrobromides, hydroiodides, nitrates, sulfates, hydrogensulfates, phosphates, and hydrogenphosphates, organic acid salts such as acetates, trifluoroacetates, gluconates, lactates, salicylates, citrates, tartrates, ascorbates, succinates, maleates, fumarates, formates, benzoates, methanesulfonates, ethanesulfonates, and p-toluenesulfonates. Where one or more substituents contain an acidic moiety, examples of base addition salts include, for example, alkali metal salts such as sodium salts and potassium salts, alkaline earth metal salts such as magnesium salts and calcium salts, salts of organic amines such as triethylamine salts, pyridine salts, procaine salts, picoline salts, dicyclohexylamine salts, diethanolamine salts, triethanolamine salts and tris(hydroxymethyl)aminomethane salts, amino acid addition salts such as arginine salts, lysine salts, ornithine salts, serine salts, glycine salts, aspartic acid salts, and glutamic acid salts, and the like.

Although the combination of substituents in the compounds of the present invention represented by the general formula (1) is not particularly limited, for example, compounds having the following combinations are preferred:

[A1] the compounds wherein X is a lower alkyl group having 1 to 3 carbon atom;
[A2] the compounds wherein X is a halogen atom;
[B1] the compounds wherein Y is hydrogen atom;
[B2] the compounds wherein Y is a lower alkyl group having 1 to 3 carbon atom;
[B3] the compounds wherein Y is ethyl group;
[C1] the compounds of [A1] or [A2] which have the characteristic of [B1];
[C2] the compounds of [A1] or [A2] which have the characteristic of [B2];
[C3] the compounds of [A1] or [A2] which have the characteristic of [B3];
[D1] the compounds wherein Z is a lower alkyl group having 1 to 3 carbon atom;
[D2] the compounds wherein Z is methyl group;
[D3] the compounds wherein Z is hydrogen atom;
[E1] the compounds of any one of [A1] to [C3] which have the characteristic of [D1];
[E2] the compounds of any one of [A1] to [C3] which have the characteristic of [D2];
[E3] the compounds of any one of [A1] to [C3] which have the characteristic of [D3];
[F1] the compounds wherein G is a group represented by the general formula ($G^1$);
[F2] the compounds wherein G is a group represented by the general formula ($G^2$);
[F3] the compounds wherein G is a group represented by the general formula ($G^3$);
[F4] the compounds wherein G is a group represented by the general formula ($G^4$);
[F5] the compounds wherein G is a group represented by the general formula ($G^5$);
[F6] the compounds wherein G is a group represented by the general formula ($G^6$);

[F7] the compounds wherein G is a group represented by the general formula (G⁷);
[G1] the compounds of any one of [A1] to [E3] which have the characteristic of [F1];
[G2] the compounds of any one of [A1] to [E3] which have the characteristic of [F2];
[G3] the compounds of any one of [A1] to [E3] which have the characteristic of [F3];
[G4] the compounds of any one of [A1] to [E3] which have the characteristic of [F4];
[G5] the compounds of any one of [A1] to [E3] which have the characteristic of [F5];
[G6] the compounds of any one of [A1] to [E3] which have the characteristic of [F6];
[G7] the compounds of any one of [A1] to [E3] which have the characteristic of [F7];
[H1] the compounds wherein D is —C(O)NR¹⁰—;
[H2] the compounds wherein D is —N(R¹¹)—;
[H3] the compounds wherein D is oxygen atom;
[H4] the compounds wherein D is —S(O)₂NR¹⁰—;
[H5] the compounds wherein D is —NR¹⁰C(O)—;
[I1] the compounds of any one of [A1] to [G7] which have the characteristic of [H1];
[I2] the compounds of any one of [A1] to [G7] which have the characteristic of [H2];
[I3] the compounds of any one of [A1] to [G7] which have the characteristic of [H3];
[I4] the compounds of any one of [A1] to [G7] which have the characteristic of [H4];
[I5] the compounds of any one of [A1] to [G7] which have the characteristic of [H5];
[J1] the compounds wherein R⁴ is a lower alkyl group having 1 to 6 carbon atoms;
[J2] the compounds wherein R⁴ is hydrogen atom;
[K1] the compounds of any one of [A1] to [I5] which have the characteristic of [J1];
[K2] the compounds of any one of [A1] to [I5] which have the characteristic of [J2];
[L1] the compounds wherein R¹⁰ is a lower alkyl group having 1 to 6 carbon atoms;
[L2] the compounds wherein R¹⁰ is hydrogen atom;
[M1] the compounds of any one of [A1] to [K2] which have the characteristic of [L1];
[M2] the compounds of any one of [A1] to [K2] which have the characteristic of [L2];
[N1] the compounds wherein R¹¹ is hydrogen atom;
[N2] the compounds wherein R¹¹ is an alkyl group having 1 to 3 carbon atoms;
[O1] the compounds of any one of [A1] to [M2] which have the characteristic of [N1];
[O2] the compounds of any one of [A1] to [M2] which have the characteristic of [N2];
[P1] the compounds wherein A² is a single bond;
[Q1] the compounds of any one of [A1] to [O2] which have the characteristic of [P1];
[R1] the compounds wherein A² is an alkylene which may be substituted;
[R2] the compounds wherein A² is an alkenylene which may be substituted;
[S1] the compounds of any one of [A1] to [Q1] which have the characteristic of [R1];
[S2] the compounds of any one of [A1] to [Q1] which have the characteristic of [R2];
[T1] the compounds wherein Q is a monocyclic aromatic group which may be substituted;
[T2] the compounds wherein Q is a polycyclic aromatic group which may be substituted;
[T3] the compounds wherein Q is a phenyl group;
[U1] the compounds of any one of [A1] to [S2] which have the characteristic of [T1];
[U2] the compounds of any one of [A1] to [S2] which have the characteristic of [T2];
[U3] the compounds of any one of [A1] to [S2] which have the characteristic of [T3];
[V1] the compounds wherein any one of R⁵, R⁶, and R⁷ is hydrogen atom;
[V2] the compounds wherein any two of R⁵, R⁶, and R⁷ are hydrogen atoms;
[V3] the compounds wherein any one of R⁵, R⁶, and R⁷ is an alkyl group which may be substituted;
[V4] the compounds wherein any one of R⁵, R⁶, and R⁷ is an alkoxy group which may be substituted;
[V5] the compounds wherein any one of R⁵, R⁶, and R⁷ is a halogen atom;
[V6] the compounds wherein any one of R⁵, R⁶, and R⁷ is an aryl group;
[V7] the compounds wherein any one of R⁵, R⁶, and R⁷ is an aryloxy group;
[V8] the compounds wherein any one of R⁵, R⁶, and R⁷ is an aralkyl group;
[W1] the compounds of any one of [A1] to [U3] which have the characteristic of [V1];
[W2] the compounds of any one of [A1] to [U3] which have the characteristic of [V2];
[W3] the compounds of any one of [A1] to [U3] which have the characteristic of [V3];
[W4] the compounds of any one of [A1] to [U3] which have the characteristic of [V4];
[W5] the compounds of any one of [A1] to [U3] which have the characteristic of [V5];
[W6] the compounds of any one of [A1] to [U3] which have the characteristic of [V6];
[W7] the compounds of any one of [A1] to [U3] which have the characteristic of [V7]; and
[W8] the compounds of any one of [A1] to [U3] which have the characteristic of [V8].

As preferred embodiments of the compounds of the present invention falling within the scope of the general formula (1), for example, the following compounds can be exemplified. However, the scope of the present invention is not limited to these compounds.

[Formula 5]

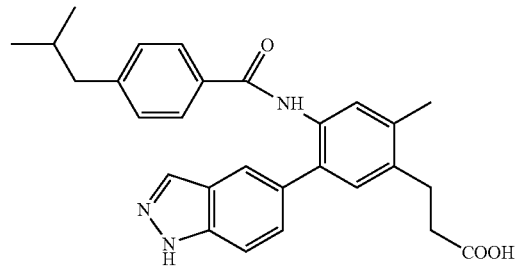

EX-1

EX-2
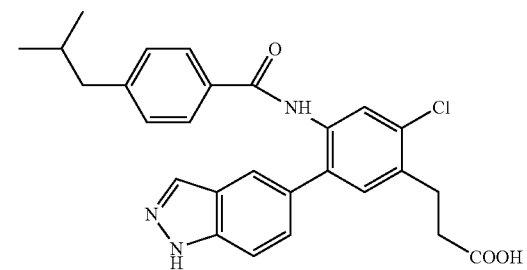
EX-3
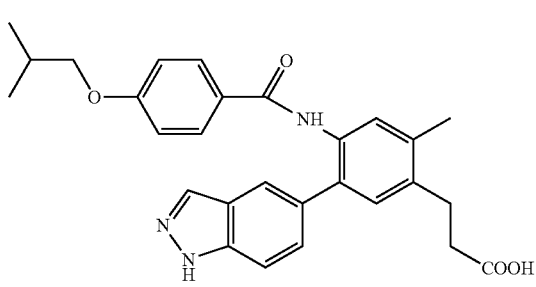
EX-4
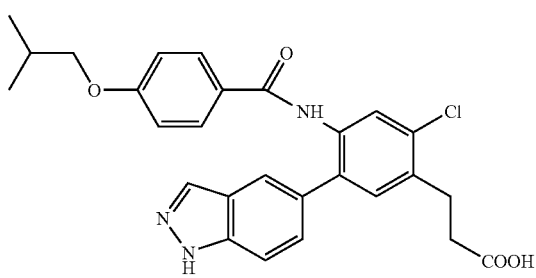
EX-5
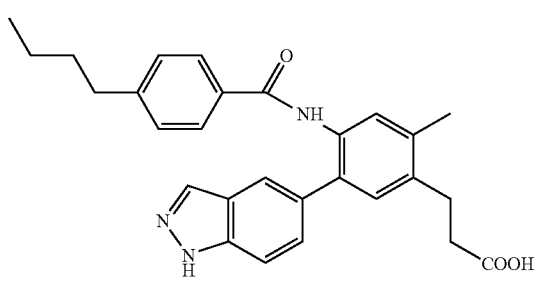
EX-6
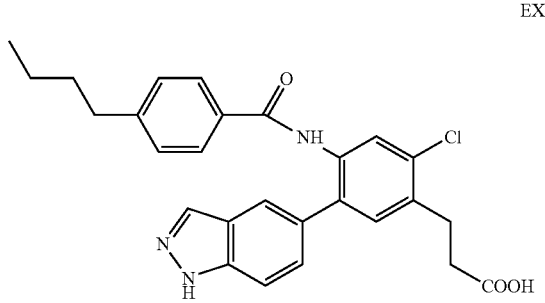
EX-7
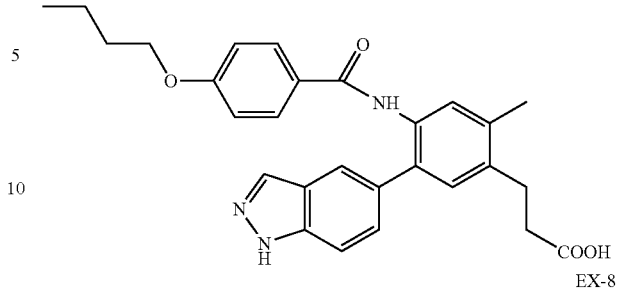
EX-8
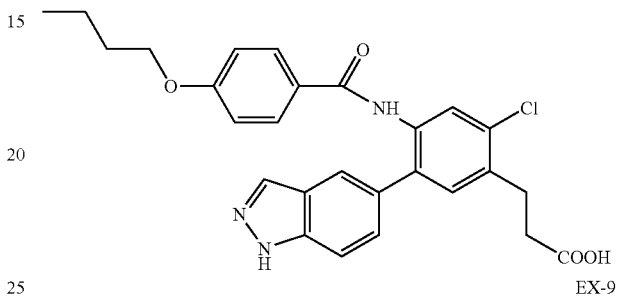
EX-9
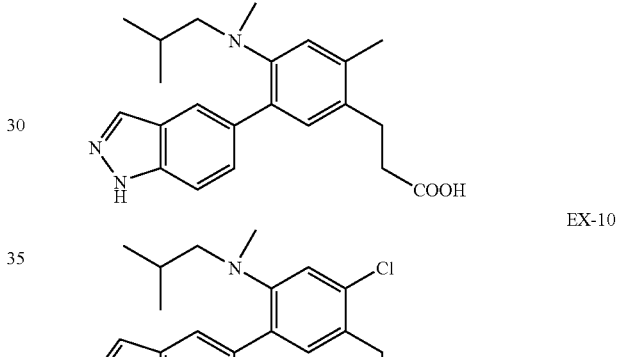
EX-10
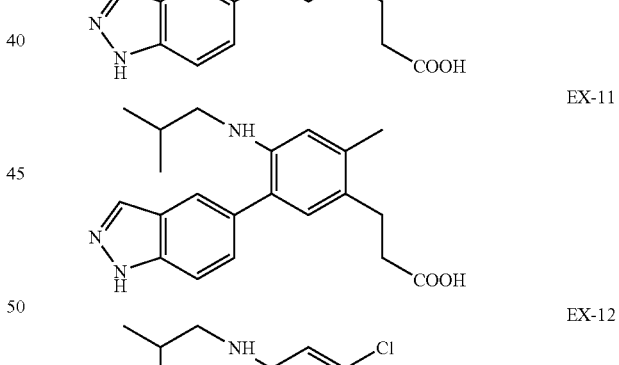
EX-11
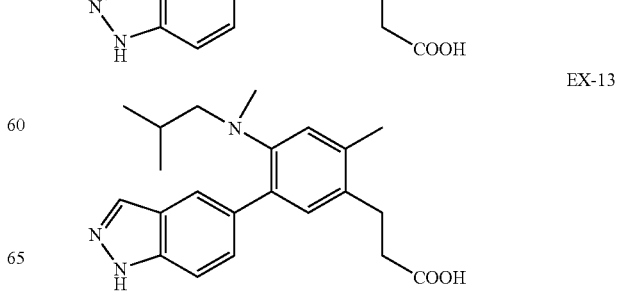

-continued

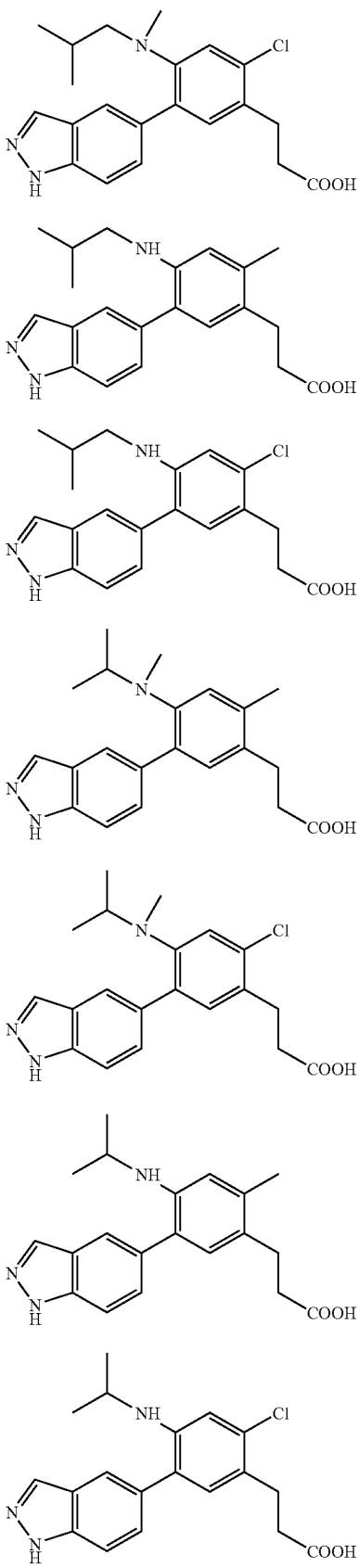

EX-14
EX-15
EX-16
EX-17
EX-18
EX-19
EX-20

<Preparation Method>

The compounds of the present invention represented by the general formula (1) are novel compounds not described in literature. Although the compounds of the present invention can be prepared by, for example, the following methods, the preparation method of the compounds of the present invention is not limited to the following methods.

Although reaction time in each of the reactions is not particularly limited, progress of the reactions can be easily monitored by analysis methods described later, and therefore the reactions may be terminated when the maximum yield of objective substance is obtained. Each of the reactions can be performed in an inert gas atmosphere, for example, under a nitrogen flow or an argon flow, as required. When protection with a protective group and subsequent deprotection are needed in each of the reactions, the reactions can be appropriately performed by utilizing the methods described below. For performing the following preparation methods, the literatures [International Patent Publications WO03/07686 and WO05/016862] can be referred to as main references.

Examples of the protective group used in the present invention include the following groups: protective groups for carboxyl group (—COOH), protective groups for hydroxy group (—OH), protective groups for formyl group (—CHO), protective groups for amino group (—NH$_2$), and the like.

Examples of the protective group for carboxyl group include, for example, an alkyl group having 1 to 4 carbon atoms, an alkenyl group having 2 to 4 carbon atoms, an alkyl group having 1 to 4 carbon atoms substituted with an alkoxy group having 1 to 4 carbon atoms, an alkyl group having 1 to 4 carbon atoms substituted with 1 to 3 halogen atoms, and the like. Specific examples include methyl group, ethyl group, t-butyl group, allyl group, methoxyethyl group, trichloroethyl group, and the like.

Examples of the protective groups for hydroxy group include, for example, an alkyl group having 1 to 4 carbon atoms, an alkenyl group having 2 to 4 carbon atoms, an alkyl group having 1 to 4 carbon atoms substituted with an alkoxy group having 1 to 4 carbon atoms, an alkyl group having 1 to 4 carbon atoms substituted with 1 to 3 halogen atoms, a silyl group substituted with three of the same or different alkyl groups having 1 to 4 carbon atoms or phenyl groups, tetrahydropyranyl group, tetrahydrofuryl group, propargyl group, trimethylsilylethyl group, and the like. Specific examples include methyl group, ethyl group, t-butyl group, allyl group, methoxymethyl (MOM) group, methoxyethyl (MEM) group, trichloroethyl group, phenyl group, methylphenyl group, chlorophenyl group, benzyl group, methylbenzyl group, chlorobenzyl group, dichlorobenzyl group, fluorobenzyl group, trifluoromethylbenzyl group, nitrobenzyl group, methoxyphenyl group, N-methylaminobenzyl group, N,N-dimethylaminobenzyl group, phenacyl group, trityl group, 1-ethoxyethyl (EE) group, tetrahydropyranyl (THP) group, tetrahydrofuryl group, propargyl group, trimethylsilyl (TMS) group, triethylsilyl (TES) group, t-butyldimethylsilyl (TB-DMS) group, t-butyldiphenylsilyl (TBDPS) group, acetyl (Ac) group, pivaloyl group, benzoyl group, allyloxycarbonyl (Alloc) group, 2,2,2-trichloroethoxycarbonyl (Troc) group, and the like.

Examples of the protective groups for formyl group include, for example, an acetal group, or the like, and specific examples include dimethylacetal, and the like.

Examples of the protective groups for amino group include, for example, benzyl group, methylbenzyl group, chlorobenzyl group, dichlorobenzyl group, fluorobenzyl group, trifluoromethylbenzyl group, nitrobenzyl group, methoxyphenyl group, N-methylaminobenzyl group, N,N-dimethylaminobenzyl group, phenacyl group, acetyl group, trifluoroacetyl group, pivaloyl group, benzoyl group, allyloxycarbonyl group, 2,2,2-trichloroethoxycarbonyl group, benzyloxycarbonyl group, t-butoxycarbonyl (Boc) group, 1-methyl-1-(4-biphenyl)ethoxycarbonyl (Bpoc) group, 9-fluorenylmethoxycarbonyl group, benzyloxymethyl (BOM) group, 2-(trimethylsilyl)ethoxymethyl (SEM) group, and the like.

By removing these protective groups simultaneously with the preparation or stepwise during the preparation process or at the final step, protected compounds can be converted into objective compounds. The protection and deprotection reactions can be performed according to known methods such as the methods described in, for example, Protective Groups in Organic Synthesis, published by John Wiley and Sons (2007), and the like, and they can be performed by, for example, the methods of (1) to (6) mentioned below, and the like.

(1) The deprotection reaction by alkali hydrolysis is performed by, for example, reacting a protected compound with a base in a polar solvent. Examples of the base used in this reaction include, for example, alkali metal bases such as sodium hydroxide, potassium hydroxide, lithium hydroxide, barium hydroxide, calcium hydroxide, sodium carbonate, potassium carbonate, sodium methoxide, and potassium t-butoxide, and organic bases such as triethylamine. For example, they are usually used in an amount of 1 to 20 fold moles, preferably 1 to 10 fold moles, based on the reactant, when an alkali metal base is used, or 1 fold mole to a large excess amount, when an organic base is used. As for the reaction solvent, it is usually preferred that the reaction is performed in an inactive medium that does not inhibit the reaction, preferably a polar solvent. Examples of the polar solvent include water, methanol, ethanol, tetrahydrofuran, dioxane, and the like, and these can be used as a mixture as required. As the reaction temperature, a suitable temperature, for example, from −10° C. to the reflux temperature of the solvent, is chosen. The reaction time is, for example, usually 0.5 to 72 hours, preferably 1 to 48 hours, when an alkali metal base is used, or 5 hours to 14 days, when an organic base is used. However, since the progress of the reaction can be monitored by thin layer chromatography (TLC), high performance liquid chromatography (HPLC), or the like, the reaction may usually be terminated when the maximum yield of the objective compound is obtained.

(2) The deprotection reaction under an acidic condition is performed, for example, in an organic solvent (dichloromethane, chloroform, dioxane, ethyl acetate, anisole and the like) in the presence of an organic acid (acetic acid, trifluoroacetic acid, methanesulfonic acid, p-toluenesulfonic acid and the like), a Lewis acid (boron tribromide, boron trifluoride, aluminum bromide, aluminum chloride and the like), or an inorganic acid (hydrochloric acid, sulfuric acid and the like), or a mixture thereof (hydrogen bromide/acetic acid and the like) at a temperature of −10 to 100° C. There is also a method of adding ethanethiol, 1,2-ethanedithiol, or the like as an additive.

(3) The deprotection reaction by hydrogenolysis is performed, for example, in a solvent [ether type solvents (tetrahydrofuran, dioxane, dimethoxyethane, diethyl ether and the like), alcohol type solvents (methanol, ethanol and the like), benzene type solvents (benzene, toluene and the like), ketone type solvents (acetone, methyl ethyl ketone and the like), nitrile type solvents (acetonitrile and the like), amide type solvents (dimethylformamide and the like), ester type solvents (ethyl acetate and the like), water, acetic acid, mixtures of two or more types of those solvents, and the like] in the presence of a catalyst (palladium/carbon powder, platinum oxide ($PtO_2$), activated nickel and the like) and a hydrogen source such as hydrogen gas of ordinary pressure or under pressurization, ammonium formate, or hydrazine hydrate at a temperature of −10 to 60° C.

(4) The deprotection reaction of silyl group is performed, for example, by using tetra-n-butylammonium fluoride or the like in a water-miscible organic solvent (tetrahydrofuran, acetonitrile and the like) at a temperature of −10 to 60° C.

(5) The deprotection reaction using a metal is performed, for example, in an acidic solvent (acetic acid, buffer of pH 4.2 to 7.2, a mixture of such a solution and an organic solvent such as tetrahydrofuran) in the presence of zinc powder with or without ultrasonication at a temperature of −10 to 60° C.

(6) The deprotection reaction using a metal complex is performed, for example, in an organic solvent (dichloromethane, dimethylformamide, tetrahydrofuran, ethyl acetate, acetonitrile, dioxane, ethanol and the like), water, or a mixture thereof in the presence of a trap reagent (tributyltin hydride, triethylsilane, dimedone, morpholine, diethylamine, pyrrolidine and the like), an organic acid (acetic acid, formic acid, 2-ethylhexanoic acid and the like) and/or an organic acid salt (sodium 2-ethylhexanoate, potassium 2-ethylhexanoate and the like) in the presence or absence of a phosphine type regent (triphenylphosphine and the like) by using a metal complex [tetrakistriphenylphosphine palladium(0), bis(triphenylphosphine) palladium(II) dichloride, palladium(II)acetate, tris(triphenylphosphine) rhodium(I) chloride and the like] at a temperature of −10 to 60° C.

(Preparation Method 1)

The compounds represented by the general formula (1) [in the general formula (1), Y, Z, and G have the same meanings as those explained above, and X represents cyano group, an alkyl group which may be substituted, an alkenyl group which may be substituted, an alkynyl group which may be substituted, an alkoxy group which may be substituted, hydroxy group, —N($R^1$)($R^2$), or —C(O)NH$R^3$—] can be prepared according to the following reaction route. In the following scheme, "STEP" means a process step, and for example, "STEP1-1" means Step 1-1.

[Formula 6]
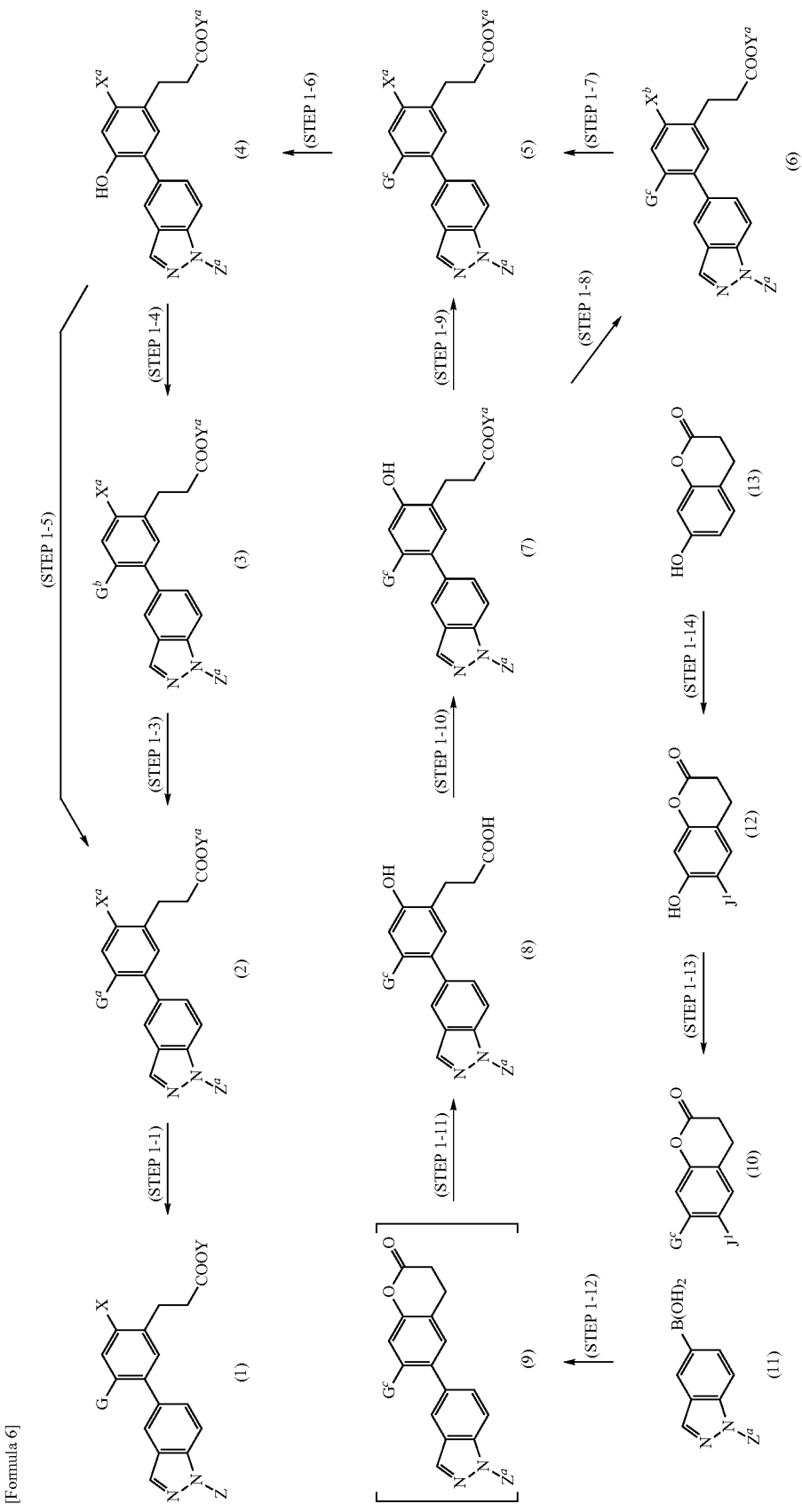

For example, the compounds represented by the general formula (1), wherein Y is hydrogen atom can be prepared by performing a deprotection reaction of a compound represented by the general formula (2) [in the general formula (2), X, Y, Z and G have the same meanings as those explained above, $X^a$, $Y^a$, and $Z^a$ have the same meanings as those of X, Y, and Z, or one or more of these group may be protected, and $G^a$ has the same meaning as that of, G (G may be protected), or represents cyano group or carboxyl group] (Step 1-1).

The deprotection reaction may be performed according to known methods, for example, the methods described in Protective Groups in Organic Synthesis, published by John Wiley and Sons (2007), and the like. When $X^a$, $Y^a$, $Z^a$, and $G^a$ are the same groups as X, Y, Z, and G, respectively, the compounds represented by the general formula (2) constitute a part of the compounds represented by the general formula (1), and Step 1-1 mentioned above is not required.

When a hydrolysis reaction is performed as a reaction for converting the compound represented by the general formula (2) into the compound represented by the general formula (1), it is usually preferable to perform the hydrolysis reaction under a basic condition, and it is more preferable to perform the hydrolysis with an alkali metal base. The reaction of converting the compound represented by the general formula (2) into the compound represented by the general formula (1) is preferably performed in a polar solvent.

Examples of the base include, for example, alkali metal bases such as sodium hydroxide, potassium hydroxide, sodium carbonate, potassium carbonate, sodium methoxide, and potassium t-butoxide, and organic bases such as triethylamine. Amount of the bases is preferably 1 to 20 fold moles, more preferably 1 to 10 fold moles, for alkali metal bases, or 1 fold mole to a large excess amount for organic bases, based on the compound represented by the general formula (2).

Examples of the polar solvent include water, methanol, ethanol, tetrahydrofuran, dioxane, and the like, and these solvents may be used as a mixture as required. As the reaction temperature, an appropriate temperature of, for example, from room temperature to the reflux temperature of the solvent is chosen. The reaction time is, for example, generally 0.5 to 72 hours, preferably 1 to 48 hours, when an alkali metal base is used, or generally 5 hours to 14 days when an organic base is used.

When the compound represented by the general formula (1) become solid after the reaction by forming a salt with the base used, by isolating and purifying it in a conventional manner, a salt of the compound represented by the general formula (1) can be obtained.

The compounds represented by the aforementioned the general formula (1), wherein Y is an alkyl group which may be substituted can be prepared by, for example, by performing esterification of a compound represented by the general formula (1), wherein Y represents hydrogen atom with a compound of the following general formula (V): $Y^1$—OH (in the formula, $Y^1$ represents an alkyl group which may be substituted) (Step 1-2).

Examples of the method for the esterification include a method of allowing the compound represented by the general formula (1) to react with an inorganic halide without solvent or in an inert solvent to convert the compound into an acid halide and then reacting the acid halide per se without solvent or the acid halide dissolved in an inert solvent in the solution with an excess amount of hydroxide. Examples of the inorganic halide include, for example, thionyl chloride, phosphoryl chloride, phosphorus pentachloride, phosphorus trichloride and the like, and thionyl chloride is a preferred example. Examples of an amount used include generally an equimolar to a large excess amount, preferably 1.5 to 5 fold moles, based on the compound represented by the general formula (1). Examples of the inert solvent include, for example, halogenated hydrocarbons such as dichloromethane, chloroform and 1,2-dichloroethane, ethers such as tetrahydrofuran and dioxane, and benzene compounds such as benzene, toluene, xylene and chlorobenzene. These solvents can be used, for example, each alone or as a mixed solvent. In order to promote the reaction, a catalytic amount of N,N-dimethylformamide may be added. As the reaction temperature, an appropriate temperature of from room temperature to the reflux temperature of the solvent is generally chosen. The reaction time is, for example, generally 0.5 to 24 hours, preferably 1 to 6 hours.

It is also possible to perform the reaction by using an excess amount of the compound represented by the general formula (V) without using solvent. As the reaction temperature, an appropriate temperature from −10° C. to room temperature is chosen. The reaction time is, for example, usually 0.5 to 24 hours, preferably 0.5 to 6 hours. When protection with a protective group and following deprotection are required, the reactions can be appropriately performed by utilizing the aforementioned methods described by Greene and Wuts, and Kocienski.

For performing the esterification, for example, "Esterification using an alcohol" described in Shin Jikken Kagaku Koza (edited by the Chemical Society of Japan, published by Maruzen Co., Ltd.), vol. 14, p. 1002, "Esterification using an O-alkylating agent", ibid, the same volume, p. 1002, "Esterification using an alkyl halide", ibid, the same volume, p. 1008, "Esterification reaction using a dehydrating agent", ibid, vol. 22, p. 45, and the like can be referred to.

The compounds represented by the general formula (2), wherein $G^a$ is a group represented by the general formula ($G^2$) or ($G^5$), and D in the group represented by the general formulas ($G^2$) or ($G^5$) is —$NR^{10}C(O)$— can be prepared by performing an amidation reaction of a compound represented by the general formula (2), wherein $G^a$ is carboxyl group (—COOH) [in the general formula (2), $X^a$, $Y^a$, and $Z^a$ have the same meanings as those explained above, and the group represented by the general formula ($G^2$) or ($G^5$) may be protected] according to the method described in the literature ["Acid amides and acid imides" described in Shin Jikken Kagaku Koza (edited by the Chemical Society of Japan, published by Maruzen Co., Ltd.), vol. 22, p. 137], and references cited in the literature.

The compounds represented by the general formula (2), wherein $G^a$ is a group represented by the general formula ($G^3$) or ($G^6$), $A^1$ in the group represented by the general formula ($G^3$) or ($G^6$) is an alkylene having one carbon atom, and D in the same represents —$N(R^{11})$— can be synthesized from a compound represented by the general formula (2), wherein $G^a$ is carboxyl group, or wherein $G^a$ is cyano group. Specifically, it is well known to those skilled in the art that the objective compound can be synthesized by converting the carboxyl group into an aldehyde group by hydrogenation reduction, and then subjecting the resultant to the reductive amination described later or the like.

The compounds represented by the general formula (2), wherein $G^a$ is carboxyl group can be prepared from a compound represented by the general formula (2), wherein $G^a$ is cyano group by performing a hydrolysis reaction according to the method of Step 1-1.

The compounds represented by the general formula (2), wherein $G^a$ is a group represented by the general formula ($G^3$) or ($G^6$), $A^1$ in the group represented by the general formula ($G^3$) or ($G^6$) is an alkylene having 2 to 6 carbon atoms which may be substituted, and D in the same is —N(R$^{11}$)— can be prepared from a compound represented by the general formula (2), wherein G$^a$ is a group represented by the general formula (G$^1$), A$^2$ in the group represented by the general formula (G$^1$) is an alkenylene having one double bond in the moiety binding to D, and R$^4$ in the group represented by the general formula (G$^1$) is hydrogen atom [in the general formula (2), X$^a$, Y$^a$, and Z$^a$ have the same meanings as those explained above, respectively, A$^2$, R$^4$, R$^5$, R$^6$, R$^7$, R$^{11}$, and Q in the group represented by the general formula (G$^3$) or (G$^6$) have the same meanings as those explained above, respectively].

For example, the method includes a method of amination of a compound represented by the general formula (2), wherein G$^a$ is vinyl group in an inert solvent according to the methods described in the literatures ["Amines" described in Shin Jikken Kagaku Koza (edited by the Chemical Society of Japan, published by Maruzen Co., Ltd.), vol. 20, p. 279; "Synthesis by addition reaction", ibid, the same volume, p. 292; V. Snieckus, Chemical Review], 1990, vol. 90, p. 879], or the references cited in the literatures, and the like. The amination referred to herein include not only conversion into unsubstituted —NH$_2$, but also conversion into an amino group which may have one or two substituents. Examples of the inert solvent include, for example, ether solvents such as tetrahydrofuran, 1,4-dioxane and 1,2-dimethoxyethane, N,N-dimethylformamide, N-methylpyrrolidone, dimethyl sulfoxide, sulfolane, alcohol solvents such as methanol and ethanol, water, and mixed solvents of these. Examples of the amination regent include, for example, ammonia, primary amines such as methylamine, and secondary amines such as dimethylamine. The amination regent is preferably used in an amount of 1 fold mole to a large excess amount based on the compound represented by the general formula (2) mentioned above. The reaction is preferably performed at room temperature or under a heated condition up to about 200° C., and the reaction time is, for example, 0.5 to 72 hours.

The compounds represented by the general formula (2), wherein G$^a$ is a group represented by the general formula (G$^3$) or a group represented by the general formula (G$^6$), A$^1$ in the group represented by the general formula (G$^3$) or (G$^6$) is an alkylene having 2 to 6 carbon atoms which may be substituted, and D in the same is oxygen atom can be prepared from a compound represented by the general formula (2), wherein G$^a$ is a group represented by the general formula (G$^1$), A$^2$ in the group represented by the general formula (G$^1$) is an alkenylene having one double bond in the moiety binding to D, and R$^4$ in the same is hydrogen atom. Examples of the method include for example, a method of etherifying a compound represented by the general formula (2), wherein G$^a$ is vinyl group in an inert solvent according to the method of Step 1-3 (iii) mentioned later, and the like.

The compounds represented by the general formula (2), wherein G$^a$ is a group represented by the general formula (G$^1$), (G$^2$), (G$^4$), (G$^5$), or (G$^7$), and D in the group represented by the general formula (G$^2$) or (G$^5$) is oxygen atom or —N(R$^{11}$)— can be prepared from a compound represented by the general formula (3) [in the general formula (3), X$^a$, Y$^a$, and Z$^a$ have the same meanings as those explained above, G$^b$ is p-toluenesulfonyloxy group (TsO—), methanesulfonyloxy group (MsO—), or trifluoromethanesulfonyloxy group (TfO—), and the group represented by the general formula (G$^1$), (G$^2$), (G$^3$), (G$^5$), or (G$^7$) may be protected] (Step 1-3). When Step 1-3 is performed, G$^b$ in the general formula (3) represents TsO—, MsO—, or TfO—, and G$^b$ is preferably TfO or MsO—, most preferably TfO—. When G$^b$ and G$^a$ are the same groups, the compounds represented by the general formula (3) constitute a part of the compounds represented by the general formula (2), and Step 1-3 mentioned above is not required.

Step 1-3 can be performed by any one of the methods of (i) to (iv) mentioned below.

(i) The compounds represented by the general formula (2), wherein G$^a$ is a group represented by the general formula (G$^1$) or (G$^4$) [the group represented by the general formula (G$^1$) or (G$^4$) may be protected] can be prepared from a compound represented by the general formula (3) according to, for example, the methods described in Jikken Kagaku Koza, 4th edition (edited by the Chemical Society of Japan, published by Maruzen Co., Ltd.), vol. 25, p. 403, the methods described in the literatures [J. Tsuji, Journal of Synthetic Organic Chemistry, Japan, 2001, vol. 59, No. 6, p. 609; Miyaura, N., Suzuki, A., Chemical Review, 1995, vol. 95, p. 2457; Snieckus, V., Chemical Review, 1990, vol. 90, p. 879]. Specifically, it is preferable to alkylate, alkenylate, alkynylate, or arylate a compound represented by the general formula (3) in an inert solvent. Examples of the inert solvent include, for example, ether solvents such as diethyl ether, tetrahydrofuran, and 1,2-dimethoxyethane, acetonitrile, N,N-dimethylformamide, water, and mixed solvents thereof. The alkylation, alkenylation, alkynylation, and arylation can be preferably performed, for example, by reacting an alkylating reagent, an alkenylating reagent, an alkynylating reagent, or an arylating reagent in the presence of a nickel catalyst or a palladium catalyst. As an alternative method, the compounds represented by the general formula (2), wherein G$^a$ is a group represented by the general formula (G$^1$) or (G$^4$) can be prepared by deriving a compound represented by the general formula (3) into an organic boronic acid compound according to the methods described in the literature [Miyaura et al., Journal of Organometallic Chemistry, 2000, vol. 611, p. 392], or the references cited in the literature, and then performing a coupling reaction of the organic boronic acid compound and an organic halide (aryl halide, alkyl halide, alkenyl halide, alkynyl halide, etc), an organic sulfonyl compound (aryl triflate, alkenyl triflate, and the like), an organic phosphorous reagent comprising a dialkoxyphosphate (benzyl dialkylphosphate, and the like), or the like in the presence of a palladium catalyst.

Examples of the nickel catalyst include, for example, dichloro(1,1'-bis(diphenylphosphino)ferrocene)nickel(II), dichloro(1,3-bis(diphenylphosphino)-propane)nickel(II), and bis(acetylacetonato)nickel(II).

As the palladium catalyst, for example, a commercially available catalyst such as tetrakis(triphenylphosphine)palladium, tetrakis(methyldiphenylphosphine)palladium, dichlorobis(triphenylphosphine)palladium, dichlorobis(tri-o-tolylphosphine)palladium, dichlorobis(tricyclohexylphosphine)palladium, dichlorobis(triethylphosphine)palladium, palladium acetate, palladium chloride, bis(acetonitrile)palladium chloride, tris(dibenzylideneacetone)dipalladium and bis(diphenylphosphinoferrocene)palladium chloride may be purchased and added to the reaction system, per se, or a catalyst may be added which is separately prepared from palladium acetate, tris(dibenzylideneacetone)dipalladium or the like and arbitrary ligands and isolated. Further, a catalyst considered to actually participate in the reaction may also be prepared by mixing palladium acetate, tris(dibenzylideneacetone)dipalladium or the like and arbitrary ligands in the reaction system. The valence of palladium may be 0 or may be +2. Examples of the ligand include phosphine ligands such as trifurylphosphine, tri(o-tolyl)phosphine, tri(cyclohexyl)phosphine, tri(t-butyl)phosphine, dicyclohexylphenylphosphine, 1,1'-bis(di-t-butylphosphino)ferrocene, 2-dicyclohexylphosphino-2'-dimethylamino-1,1'-biphenyl and 2-(di-t-butylphosphino) biphenyl, phosphine mimic ligands such as imidazol-2-ylidenecarbenes, and the like. Examples also include 2-dicyclohexylphosphino-2',6'-dimethoxybiphenyl, 2-dicyclohexyl-2',4',6'-triisopropylbiphenyl, 1,2,3,4,5-pentamethyl-1'-(di-t-butylphosphino)ferrocene), and the like. Chemical equivalents of the palladium catalyst used may be one equivalent or a catalytic amount, and the amount may preferably be 0.01 to 20.0 mol %, more preferably 0.10 to 10.0 mol %.

Examples of the base include sodium carbonate, potassium carbonate, cesium carbonate, cesium fluoride, potassium fluoride, potassium phosphate, potassium acetate, triethylamine, potassium hydroxide, sodium hydroxide, sodium methoxide, lithium methoxide and the like. The reaction temperature is, for example, preferably 20° C. to 150° C., and particularly preferable examples include 20° C. to 120° C.

The reaction system may be either a two-phase system of water and an organic solvent, or a homogeneous system of a water-containing organic solvent or an organic solvent, and an appropriate system can be chosen as required, with considering properties of the reagents used for the reaction. As for the organic solvent, examples include uses of hydrocarbon-type solvents such as toluene, xylene and hexane, halogen-type solvents such as methylene chloride, sulfoxide-type solvents such as dimethyl sulfoxide, amide-type solvents such as dimethylformamide, ether-type solvents such as tetrahydrofuran, dioxane and diglyme, alcohol-type solvents such as methanol and ethanol, nitrile-type solvents such as acetonitrile, ketone-type solvents such as acetone and cyclohexanone, ester-type solvents such as ethyl acetate, heterocyclic-type solvents such as pyridine and the like. Two or more kinds of organic solvents may be mixed and used.

Examples of the alkylating reagent, alkenylating reagent, alkynylating reagent, and arylating reagent include, for example, Grignard reagents such as magnesium methyl iodide and magnesium methyl bromide, organic zinc reagents such as (ethoxycarbonylethyl)zinc bromide and (ethoxycarbonylmethyl)zinc bromide, organic tin reagents such as allyltributyltin and vinyltributyltin, organic aluminum reagents such as vinyldiisobutylaluminum, organic boron reagents such as an alkylboronic acid, an alkenylboronic acid, and an arylboronic acid, organic lithium reagents such as methyllithium and vinyllithium, organic copper reagents such as an alkylcopper and an alkenylcopper, organic silicon reagents such as vinyltrimethylsilane and trimethylsylilacetylene, and the like. The alkylating reagent, alkenylating reagent, alkynylating reagent, and arylating reagent are preferably used in an amount of 1 to 20 fold moles, and the catalyst is preferably used in an amount of 0.0001 to 1 fold mole, based on the compound represented by the general formula (3).

The reaction is performed, for example, at 0 to 150° C., preferably at room temperature to 120° C., and the reaction time is preferably 0.1 to 48 hours. For example, by using tetramethyltin as the aforementioned alkylating reagent, the compounds represented by the general formula (2) wherein $G^a$ is methyl group can be prepared. By using allyltributyltin, the compounds wherein $G^a$ is allyl group can be prepared. By using (ethoxycarbonylethyl)zinc bromide, the compounds wherein $G^a$ is ethoxycarbonylethyl group can be prepared. By using (ethoxycarbonylmethyl)zinc bromide, the compounds wherein $G^a$ is ethoxycarbonylmethyl group can be prepared. By using vinyltributyltin, the compounds wherein $G^a$ is vinyl group can be prepared. Further, by using an arylboronic acid, the compounds wherein $G^a$ is a corresponding aryl group can be prepared.

Further, the objective compounds can also be prepared by reacting an alkenyl compound or alkynyl compound including acrylic acid esters, acrylonitrile, propargyl alcohol derivatives, end acetylene derivatives, and the like in the presence of a palladium catalyst, base, copper(I) iodide, or the like. As for these reactions, Heck R. F. et al., J. Org. Chem., 2947 (1978); Sonogashira, K. et al., Tetrahedron, 2303 (1984), and the like can be referred to. Examples of the palladium catalyst include tetrakis(triphenylphosphine)palladium(0), dichlorobis(triphenylphosphine)palladium(II), those of palladium(II) acetate/triphenylphosphine type, tris(dibenzylideneacetone)dipalladium(0)/tri(tert-butyl)phosphine type, dichlorobis (benzonitrile)palladium(0)/tri(tert-butyl)phosphine type, and the like. Examples of the base include triethylamine, diethylamine, diisopropylamine, sodium acetate, sodium hydroxide, lithium hydroxide, potassium fluoride, potassium carbonate, cesium carbonate, cesium fluoride, sodium tert-butoxide, and the like. When protection with a protective group and following deprotection are required in the aforementioned synthesis, the reaction can be appropriately carried out by utilizing the aforementioned methods of Greene and Wuts, and Kocienski.

(ii) The compounds represented by the general formula (2), wherein $G^a$ is a group represented by the general formula $(G^2)$, $(G^5)$, or $(G^7)$, and D in the group represented by the general formula $(G^2)$ or $(G^5)$ is $—N(R^{11})—$ [the group represented by the general formula $(G^2)$, $(G^5)$, or $(G^7)$ may be protected] can be prepared by performing coupling of a compound represented by the general formula (3) and an aminating agent in an inert solvent in the presence of a palladium catalyst, phosphorus compound, and base (according to, for example, Buchwald, S. L., J. Org. Chem., 1158 (2000); Buchwald, S. L., Organic Letters, 1101 (2000)). Examples of the inert solvent include ether solvents such as tetrahydrofuran, 1,4-dioxane and 1,2-dimethoxyethane, toluene, and N,N-dimethylformamide, and examples of the palladium catalyst include, for example, tris(dibenzylideneacetone)dipalladium (0), palladium(II)acetate, and the like. Examples of the phosphorus compound include, for example, 2-(di-tert-butylphosphino)biphenyl, 2-(dicyclohexylphosphino)biphenyl, 2,2'-bis(diphenylphosphino)-1,1'-binaphthyl, xanthophos, and tri (tert-butyl)phosphine. Examples of the base include, for example, sodium tert-butoxide, cesium carbonate, potassium phosphate, and the like. Examples of the aminating agent include, for example, lithium hexamethyldisilazide, primary amines such as methylamine, secondary amines such as dimethylamine, and the like. By using lithium hexamethyldisilazide, the compounds represented by the general formula (2) wherein amino group is introduced as $G^a$ can be prepared. Further, by using methylamine, methylamino group can be introduced, and by using dimethylamine, dimethylamino group can be introduced. A substituent having an amino group corresponding to $G^a$ can also be introduced according to this method.

(iii) The compounds represented by the general formula (2), wherein $G^a$ is a group represented by the general formula $(G^2)$ or $(G^5)$, and D in the group represented by the general formula $(G^2)$ or $(G^5)$ is oxygen atom [the group represented by the general formula $(G^2)$ or $(G^5)$ may be protected] can be prepared from a compound represented by the general formula (3). Preferred examples of the method include a method of etherifying a compound represented by the general formula (3) in an inert solvent. Examples of the inert solvent include, for example, ether solvents such as tetrahydrofuran, 1,4-dioxane, and 1,2-dimethoxyethane, solvents such as N,N-dimethylformamide, N-methylpyrrolidone, dimethyl sulfoxide, and sulfolane, water, and mixed solvents thereof. Examples of the etherifying reagent include, for example, metal alcoholates such as those of lithium, sodium, and potassium (including, for example, $C_{1-6}$ alkoxides such as methylate, and ethylate, 2-hydroxyethylate, 2-methoxyethylate, 2-methanesulfonylethylate, and the like). The reaction is preferably carried out in the presence of a copper catalyst, and the reaction temperature is room temperature to about 180° C. The etherifying agent is preferably used in an amount of 1 to 20 fold moles. For example, if a methylate is used as the metal alcoholate, the compounds represented by the general formula (2) wherein methoxy group is introduced as $G^a$ can be obtained. By using an ethylate, ethoxy group can be introduced, by using 2-hydroxyethylate, 2-hydroxyethoxy group can be introduced, by using 2-methoxyethylate, 2-methoxyethoxy group can be introduced, and by using 2-methanesulfonylethylate, 2-methanesulfonylethoxy group can be introduced. The reaction time is preferably 0.1 to 72 hours.

As an alternative method, the compounds represented by the general formula (2), wherein $G^a$ is a group represented by the general formula ($G^2$) or ($G^5$), and D in the group represented by the general formula ($G^2$) or ($G^5$) is oxygen atom [the group represented by the general formula ($G^2$) or ($G^5$) may be protected] can be prepared by reacting a compound represented by the general formula (3) with an etherifying agent in an inert solvent in the presence of a palladium catalyst, phosphorus compound, and base (according to, for example, Buchwald, S. L., J. Org. Chem., 1158 (2000); Buchwald, S. L., Organic Letters, 1101 (2000)). Examples of the inert solvent include, for example, ether solvents such as tetrahydrofuran, 1,4-dioxane, and 1,2-dimethoxyethane, and toluene. Examples of the palladium catalyst include, for example, palladium(II)acetate, tris(dibenzylideneacetone)dipalladium(0), palladium(II)acetate and the like. Examples of the phosphorus compound include, for example, 2-(di-tert-butylphosphino)biphenyl, 2-(di-tert-butylphosphino)-1,1'-binaphthyl, and 2-(di-tert-butylphosphino)-2'-dimethylamino-1,1'-binaphthyl. Examples of the base include, for example, sodium tert-butoxide, potassium tert-butoxide, cesium carbonate, potassium phosphate, and the like. Examples of the etherifying agent include, for example, alcohols including methanol, ethanol, ethylene glycol, methanesulfonylethanol, and the like. Depending on the type of the alcohol used, the compounds represented by the formula (2) wherein $G^a$ is converted into a corresponding alkoxy group are obtained. Further, when the alkyl moiety of the alkoxy group is a protective group, the compounds can be converted into the compounds wherein $G^a$ is hydroxyl group by performing a deprotection reaction. When protection with a protective group and following deprotection are required, the reactions can be appropriately performed by utilizing the aforementioned methods described by Greene and Wuts, and Kocienski.

(iv) The compounds represented by the general formula (2) wherein $G^a$ is cyano group can be prepared from a compound represented by the general formula (3). Preferred examples of the method include a method of cyanating a compound represented by the formula (3) in an inert solvent by using a suitable cyanating agent (according to, for example, Newman, M. S. et al., J. Org. Chem., 2525 (1961)). Examples of the inert solvent include, for example, solvents such as tetrahydrofuran, 1,4-dioxane, 1,2-dimethoxyethane, N,N-dimethylformamide, N-methylpyrrolidone, dimethyl sulfoxide, sulfolane, methanol, ethanol, and propanol, water, and mixed solvents thereof. Examples of the cyanating agent include, for example, copper(I) cyanide, sodium cyanide, potassium cyanide, zinc cyanide, silver cyanide, potassium ferrocyanide, and the like. The cyanating agent is preferably used in an amount of 1 to 20 fold moles, and the reaction is preferably carried out at room temperature to about 180° C.

As an alternative method, the coupling of a compound represented by the general formula (3) and the aforementioned cyanating agent can be performed in an inert solvent in the presence of a catalyst and a phosphorus compound (according to, for example, Weissman, S. A. et al., J. Org. Chem., 2005, 70, 1508). Examples of the catalyst include dichloro(1,1'-bis(diphenylphosphino)ferrocene)palladium(II), tetrakis (triphenylphosphine)palladium(0), dichloro(bistriphenylphosphine)palladium(II), dichloro(bis(benzonitrile) palladium(II), tris(dibenzylideneacetone)dipalladium(0), palladium(II)acetate, dichloro(1,1'-bis(diphenylphosphino) ferrocene)nickel(II), dichloro(1,3-bis(diphenylphosphino) propane)nickel(II), dibromo(bis(triphenylphosphine))nickel (II), bis(acetylacetonato)nickel(II), and the like. Examples of the phosphorus compound include, for example, 2-(di-tert-butylphosphino)biphenyl, 2-(dicyclohexylphosphino)biphenyl, 2,2'-bis(diphenylphosphino)-1,1'-binaphthyl, 1,1'-bis (diphenylphosphino)ferrocene, xanthophos, and tri(tert-butyl)phosphine. When protection with a protective group and following deprotection are required in the aforementioned synthesis, the reactions can be appropriately carried out by utilizing the aforementioned methods described by Greene and Wuts, and Kocienski.

The compounds represented by the general formula (3) can be prepared from a compound represented by the general formula (4) [in the formula, $X^a$, $Y^a$, and $Z^a$ have the same meanings as those explained above, respectively] (Step 1-4). Specifically, preferred examples of the method include known methods such as a method of reacting the compound represented by the general formula (4) with p-toluenesulfonyl chloride, methanesulfonyl chloride, trifluoromethanesulfonyl chloride, methanesulfonic anhydride, trifluoromethanesulfonic anhydride, or the like in the presence of an appropriate base such as triethylamine, N,N-diisopropylethylamine, pyridine, sodium carbonate, potassium carbonate, or sodium hydrogencarbonate.

The compounds represented by the general formula (2), wherein $G^a$ is a group represented by the general formula ($G^2$) or ($G^5$), and D in the group represented by the general formula ($G^2$) or ($G^5$) is oxygen atom [the group represented by the general formula ($G^2$) or ($G^5$) may be protected] can be prepared by alkylating a compound represented by the general formula (4) (Step 1-5).

Examples of the method for the alkylation include, for example, a method of using a halide of $G^a$ (chloride, bromide, iodide, and the like). The reaction can usually be performed in the presence of a base. As the base, for example, an inorganic base is preferred, and for example, an alkali metal compound such as potassium carbonate, sodium carbonate, cesium carbonate, sodium hydrogencarbonate, potassium hydroxide, sodium hydroxide sodium methoxide, and potassium t-butoxide, pyridine, 4-dimethylaminopyridine, 1,8-diazabicyclo [5,4,0]undecene, or an organic tertiary amine such as trimethylamine or triethylamine is used in an amount of 1 to 10 fold moles, preferably 1 to 5 fold moles. It is particularly preferable to use potassium carbonate. The halide of $G^a$ is preferably used in an amount of 1 fold mole or more, most preferably 2 to 10 fold moles, based on the compound represented by the general formula (4). Examples of the reaction solvent include, for example, water, alcohol solvents such as methanol, and ethanol, inert solvents such as N,N-dimethylformamide, tetrahydrofuran, 1,4-dioxane, acetone, 2-butanone, dimethyl sulfoxide, and acetonitrile, and the like, which can be used independently or as a mixed solvent thereof, and water, N,N-dimethylformamide, and acetone can be preferably used. The reaction temperature is, for example, −10° C. or higher, preferably 0 to 80° C. The reaction time is, for example, usually 0.5 hour or longer, preferably 2 to 20 hours. When the reaction progresses slowly, a catalyst such as potassium iodide and copper powder may be added as required in an amount of 0.1 to 1.5 fold moles based on the starting material.

An example of an alternative method of the alkylation of Step 1-5 mentioned above includes alkylation by the Mitsunobu reaction. Specifically, compounds represented by the general formula (2), wherein $G^a$ is a group represented by the general formula ($G^2$) or ($G^5$), and D in the group represented by the general formula ($G^2$) or ($G^5$) is oxygen atom can also be prepared from a compound represented by the general formula (4) by the Mitsunobu reaction described in the literature [Mitsunobu, O., SYNTHESIS, 1981, p. 1]. For example, the aforementioned compounds can be prepared by reacting a compound represented by the general formula (4) and a hydroxide of $G^a$, which provides the substituent $G^a$ and is commercially available or can be synthesized by a known method or a similar method thereto, in an organic solvent in the presence of a phosphine such as triphenylphosphine and tributylphosphine and an azo compound such as diethyl azodicarboxylate, diisopropyl azodicarboxylate, N,N,N',N'-tetramethylazodicarboxamide, (azodicarbonyl)dipiperidine, and N,N,N',N'-tetraisopropylcarboxamide. Examples of the solvent include ethers such as diethyl ether, tetrahydrofuran and dimethoxyethane, halogen-type solvents such as methylene chloride, and benzene compounds such as benzene, toluene, and xylene, and these solvents may be used as a mixture as required. The phosphine is used in an amount of, for example, generally 1 to 10 fold moles, preferably 1.5 to 5 fold moles based on the compound represented by the general formula (4). The azo compound is used in an amount of, for example, generally 1 to 10 fold moles, preferably 1.5 to 5 fold moles, based on the compound represented by the general formula (4). The alcohol is used in an amount of, for example, generally 1 to 10 fold moles, preferably 1.5 to 5 fold moles, based on the compound represented by the general formula (4). As the reaction temperature, an appropriate temperature of from −20° C. to 60° C. is generally chosen. Preferred examples include a temperature of from 0° C. to room temperature. The reaction time may generally be 1 hour to 3 days, preferably 3 to 24 hours.

The compounds represented by the general formula (2), wherein $G^a$ is a group represented by the general formula ($G^2$) or ($G^5$), and D in the group represented by the general formula ($G^2$) or ($G^5$) is oxygen atom can be prepared from a compound represented by the general formula (4) by adding an alkene, which is commercially available or can be synthesized by a known method or a similar method thereto, in the presence of an acid catalyst as described in Jikken Kagaku Koza, 4th edition (edited by the Chemical Society of Japan, published by Maruzen Co., Ltd.), vol. 20, p. 200. Examples of the alkene used in this reaction include, for example, isobutylene, cyclopentene, cyclohexene, cycloheptene, alkenes having an aromatic ring such as substituted or unsubstituted styrene and α-methylstyrene, and the like. The alkene is used in an amount of, for example, generally 1 fold mole to a large excess amount, preferably 1.5 to 10 fold moles, based on the compound represented by the general formula (4). Examples of the acid catalyst used include mineral acids such as hydrochloric acid and sulfuric acid, boron trifluoride (including solvent complex thereof), tetrafluoroboric acid, trifluorosulfonic acid and the like. The amount of the acid catalyst used is generally 0.05 to 5 moles, preferably 0.1 to 2 moles, based on the compound represented by the general formula (4).

Examples of the solvent include ethers such as diethyl ether, tetrahydrofuran and dimethoxyethane, halogen-type solvents such as methylene chloride and benzene compounds such as benzene, toluene and xylene, and these solvents can be used as a mixture as required. Further, the alkene to be reacted may be used as a solvent. As the reaction temperature, an appropriate temperature of from −20° C. to 60° C. is generally chosen, and preferred examples include a temperature of from 0° C. to 50° C. The reaction time is generally 1 hour to 3 days, preferably 3 to 24 hours.

The compounds represented by the general formula (2), wherein $G^a$ is a group represented by the general formula ($G^5$), D in the group represented by the general formula ($G^5$) is oxygen atom, and $A^2$ in the same is a single bond can be prepared from a compound represented by the general formula (4) by reacting the compound represented by the general formula (4) with an aryl halide under a basic condition, according to the example described in Jikken Kagaku Koza, 4th Edition (edited by Chemical Society of Japan, published by Maruzen Co., Ltd.), vol. 20, p. 191. The aryl halide may be an unsubstituted or substituted aryl halide, examples of the aryl halide include chlorides, bromides, or iodides of a substituted or unsubstituted aryl, which are commercially available or can be synthesized by a known method or a method similar thereto, and bromides and iodides are preferred. Alternatively, an aryl triflate may also be used instead of the aryl halide. The aryl halide is used in an amount of, for example, generally 1 fold mole to a large excess amount, preferably 2 to 10 fold moles, based on the compound represented by the general formula (4). Examples of the base include, for example, alkali metal compounds such as sodium hydroxide, potassium hydroxide, sodium carbonate, potassium carbonate, sodium hydride, sodium methoxide and potassium t-butoxide and organic tertiary amines such as pyridine, 4-dimethylaminopyridine, 1,8-diazabicyclo[5,4,0]undecene, trimethylamine, and triethylamine. These bases are used in an amount of, for example, generally 1 to 10 fold moles, preferably 1 to 5 fold moles, based on the compound represented by the general formula (4). To the reaction system, copper powder, cuprous halide, or copper alkoxide may be added as a catalyst. Further, for example, a phase transfer catalyst or crown ether may also be added. The amount of these additives is generally about 0.05 to 3 fold moles, preferably about 0.1 to 1 fold mole, based on the compound represented by the general formula (4). As the reaction solvent, hydrocarbon-type solvents such as toluene, xylene, chlorobenzene, dichlorobenzene and nitrobenzene, sulfoxide-type solvents such as dimethyl sulfoxide, amide-type solvents such as dimethylformamide, ether-type solvents such as dioxane and diglyme, heterocyclic-type solvents such as pyridine and the like may be used. Further, two or more kinds of organic solvents may be used as a mixture. As the reaction temperature, an appropriate temperature of from room temperature to the 300° C. is generally chosen, and preferred examples include a temperature of from room temperature to 200° C. The reaction time is generally 1 hour to 7 days, preferably 16 hours to 3 days.

The compounds represented by the general formula (4) can be prepared from a compound represented by the general formula (5) [in the formula, $X^a$, $Y^a$, and $Z^a$ have the same meanings as those explained above, and $G^c$ represents a protective group of hydroxy group] (Step 1-6). Specifically, said compound can be prepared by removing $G^c$ in the compound represented by the general formula (5) according to the methods described in Protective Groups in Organic Synthesis, published by John Wiley and Sons (2007) mentioned above, or the like.

When $G^c$ in the compound of the general formula (5) is the same as $G^a$ in the compound of the general formula (2), Step 1-6 and Steps 1-3 to 1-5 mentioned above are not required.

Examples of $G^c$ in the general formula (5) include an alkyl group, and the like, and specific examples include methyl group, and the like. Examples of Step 1-6 mentioned above include demethylation, and the like, and examples of the method for the demethylation include a method of performing the reaction in pyridine/hydrochloric acid complex at about 180° C., a method of using boron tribromide, and the like. When an ester group is simultaneously converted into carboxyl group at the time of the conversion of methoxy group into hydroxy group by a conventional demethylation reaction, the compound can then be prepared by performing an esterification reaction of the carboxyl group according to Step 1-2.

The compounds represented by the general formula (5), wherein $X^a$ is cyano group, an alkyl group which may be substituted, an alkenyl group which may be substituted, an alkynyl group which may be substituted, or —N($R^1$)($R^2$) [in the formula, $R^1$ and $R^2$ have the same meanings as those explained above, respectively] can be prepared from a compound represented by the general formula (6) [in the general formula (6), $G^c$, $Y^a$, and $Z^a$ have the same meanings as those explained above, and $X^b$ is p-toluenesulfonyloxy group (TsO—), methanesulfonyloxy group (MsO—), or trifluoromethanesulfonyloxy group (TfO—)] in the same manner as that of Step 1-3 (Step 1-7). For performing Step 1-7, $X^b$ in the general formula (6) represents TsO—, MsO—, or TfO—, preferably TfO or MsO—, most preferably TfO—. When the group $X^b$ is the same as the group $X^a$, the compounds represented by the general formula (6) constitute a part of the compounds represented by the general formula (7), and Step 1-7 mentioned above is not required.

The compounds represented by the aforementioned general formula (6) can be prepared from a compound represented by the aforementioned general formula (7) [in the general formula (7), $G^c$, $Y^a$, and $Z^a$ have the same meanings as those explained above, respectively] in the same manner as that of Step 1-4 (Step 1-8).

The compounds represented by the aforementioned general formula (5), wherein $X^a$ is an alkoxy group which may be substituted can be prepared from a compound represented by the aforementioned general formula (7) in the same manner as that of Step 1-5 (Step 1-9).

When the compounds represented by the general formula (7) are the same as the compounds represented by the general formula (2), Steps 1-2 to 1-9 mentioned above are not required.

The compounds represented by the aforementioned general formula (7) can be prepared by esterifying a compound represented by the aforementioned general formula (8) [in the general formula (8), $G^c$ and $Z^a$ have the same meanings as those explained above, respectively] in the same manner as that of Step 1-2 (Step 1-10). However, when the compound represented by the general formula (8) is the same as the compound represented by the general formula (7), Step 1-10 is not required.

The compounds represented by the aforementioned general formula (8) can be prepared by hydrolyzing a compound represented by the aforementioned general formula (9) [in the general formula (9), $G^c$ and $Z^a$ have the same meanings as those explained above, respectively] in the same manner as that of Step 1-1 (Step 1-11). When the hydrolysis reaction advances in the reaction system simultaneously with the coupling reaction in Step 1-12 mentioned later, this step is not required. In such a case, the compounds represented by the aforementioned general formula (8) can be synthesized from a compound represented by the general formula (10).

The compounds represented by the aforementioned general formula (9) can be prepared by coupling a compound represented by the general formula (10) [in the general formula (10), $G^c$ and $Z^a$ have the same meanings as those explained above, and $J^1$ is iodine, bromine, or chlorine] and a compound represented by the general formula (11) [in the general formula (11), $G^c$ and $Z^a$ have the same meanings as those explained above, respectively] in the same manner as that of Step 1-3, (i) (Step 1-12). $J^1$ in the general formula (10) represents iodine, bromine, or chlorine, preferably iodine or bromine, most preferably bromine. There are also another embodiment in which iodine is preferred, and another embodiment in which chlorine is preferred. The compounds represented by the general formula (11) are known from the literature (International Patent Publication WO03/1078686) as arylboronic acids.

The compounds represented by the aforementioned general formula (10) can be prepared from a compound represented by the general formula (12) [in the general formula (12), $J^1$ has the same meaning as that explained above] (Step 1-13). Specifically, said compounds can be prepared by introducing a protective group into hydroxy group according to a known method, for example, the methods described in Protective Groups in Organic Synthesis, published by John Wiley and Sons (2007), and the like.

Examples of the protective group of hydroxy group include, for example, methyl group, and the like. Examples of the method for the methylation include, for example, a method based on the alkylation reaction mentioned above, a method of using methyl iodide, and the like.

The compounds represented by the aforementioned general formula (12) can be prepared by halogenating a compound represented by the general formula (13) by a method described in ordinary publications in the filed of chemistry, for example, Shin Jikken Kagaku Koza (edited by Chemical Society of Japan, published by Maruzen Co., Ltd.), vol. 14, p. 354. (Step 1-14). The compounds wherein $J^1$ is bromine can be prepared by, for example, a method of using bromine ($Br_2$), a method of using N-bromosuccinimide, and the like.

The compounds represented by the aforementioned general formula (13) are commercially available compounds or compounds described in literatures [for example, G. Carmela et al., Journal of Medicinal Chemistry, 2000, vol. 43, p. 4747], and thus they are obtainable.

(Preparation Method 2)

Among the compounds represented by the general formula (1) [in the general formula (1), X, Y, Z, and G have the same meanings as those explained above], the compounds wherein G is a group represented by the general formula ($G^2$), ($G^5$), or ($G^7$), and D in the group represented by the general formula ($G^2$) or ($G^5$) is —N($R^{11}$)— can be prepared by following the reaction route mentioned below.

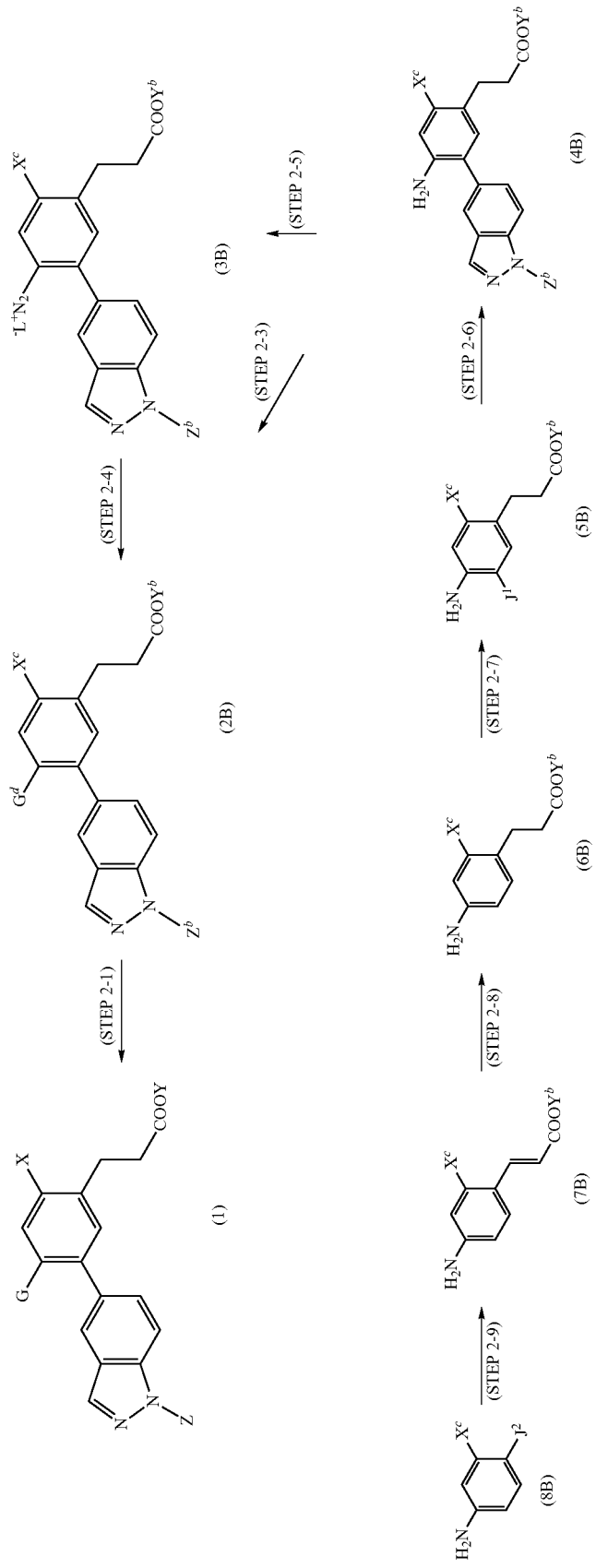

The compounds represented by the aforementioned the general formula (1), wherein Y is hydrogen atom can be prepared by performing deprotection of a compound represented by the aforementioned general formula (2B) [in the general formula (2B), $X^c$, $Y^b$, $Z^b$, and $G^d$ have the same meanings as those of X, Y, Z, and G explained above, or one or more of these groups may be protected] in the same manner as that of Step 1-1 (Step 2-1).

The compounds represented by the aforementioned general formula (1), wherein Y is an alkyl group which may be substituted can be prepared by esterifying a compound represented by the general formula (1), wherein Y is hydrogen atom in the same manner as that of Step 1-2 (Step 2-2).

The compounds represented by the general formula (2B), wherein $G^d$ is a group represented by the general formula ($G^2$) or ($G^5$), D in the group represented by the general formula ($G^2$) or ($G^5$) is —N($R^{11}$)—, and $R^{11}$ represents an alkyl group which may be substituted can be prepared from a compound represented by the general formula by (2B), wherein $G^d$ is a group represented by the general formula ($G^2$) or a group represented by the general formula ($G^5$), D in the group represented by the general formula ($G^2$) or ($G^5$) is —N($R^{11}$)—, and $R^{11}$ is hydrogen atom (Step 2-3-1). The aforementioned compounds can be prepared by performing alkylation, or reductive amination of the compound represented by the general formula (2B), wherein $R^{11}$ is hydrogen atom. When $G^d$ is —$NH_2$, this step is not required.

The compounds represented by the general formula (2B), wherein $G^d$ is a group represented by the general formula ($G^2$) or ($G^5$), D in the group represented by the general formula ($G^2$) or ($G^5$) is —N($R^{11}$)—, and $R^{11}$ represents hydrogen atom can be prepared from a compound represented by the general formula (4B) [in the general formula (4B), $X^c$, $Y^b$, and $Z^b$ have the same meanings as those explained above, respectively] (Step 2-3-2). The aforementioned compounds can be prepared by performing alkylation, or reductive amination of the compound represented by the general formula (4B). When $G^d$ is —$NH_2$, this step is not required.

The compounds represented by the general formula (2B), wherein $G^d$ is a group represented by the general formula ($G^7$) can be prepared from a compound represented by the general formula (4B) (Step 2-3-3). Specifically, the preparation can be attained by performing alkylation, reductive amination, or both in combination of the compound represented by the general formula (4B) according to the methods described in the literatures [U. Sameer et al., Journal of Organic Chemistry, 2003, vol. 68, p. 452; J. P. Donald et al., Bioorganic & Medicinal Chemistry Letters, 1999, vol. 9, p. 919; J. Magnus et al., Tetrahedron Asymmetry, 2004, vol. 15, p. 3531: and "Acid amides and acid imides" described in Shin Jikken Kagaku Koza (edited by the Chemical Society of Japan, published by Maruzen Co., Ltd.), vol. 22, p. 137].

Examples of the method for the alkylation include, for example, a method of using an alkyl halide (chloride, bromide, iodide, and the like). The reaction can usually be performed in the presence of a base. As the base, for example, an inorganic base is preferred, and examples include potassium carbonate, sodium carbonate, cesium carbonate, sodium hydrogencarbonate, potassium hydroxide, and sodium hydroxide. Particularly preferred is potassium carbonate. The halide is preferably used in an amount of 1 fold mole or more, most preferably 2 to 10 fold moles, based on the compound represented by the general formula (2B), wherein $G^d$ is a group represented by the general formula ($G^2$) or ($G^5$), D in the group represented by the general formula ($G^2$) or ($G^5$) is —N($R^{11}$)—, and $R^{11}$ represents hydrogen atom. Preferred amount of the halide relative to the compound represented by the general formula (4B) is the same as mentioned above. Examples of the reaction solvent include, for example, water, alcohol solvents such as methanol and ethanol, inert solvents such as N,N-dimethylformamide, tetrahydrofuran, 1,4-dioxane, acetone, 2-butanone, dimethyl sulfoxide, and acetonitrile, and the like, which can be used independently or as a mixed solvent thereof, and preferred are water, N,N-dimethylformamide, and acetone. The reaction temperature is, for example, −10° C. or higher, preferably 0 to 80° C. The reaction time is, for example, usually 0.5 hour or longer, preferably 2 to 20 hours.

Examples of the method for the reductive amination include, for example, the methods described in the literature ["Reductive amination reaction" described in Shin Jikken Kagaku Koza (edited by the Chemical Society of Japan, published by Maruzen Co., Ltd.), vol. 20, p. 300], or the references cited in the literature. Specifically, the compounds can be prepared by coupling an aldehyde or ketone corresponding to a substituent to be introduced and a compound represented by the general formula (4B) or a compound represented by the general formula (2B), wherein $G^d$ is a group represented by the general formula ($G^2$) or ($G^5$), D in the group represented by the general formula ($G^2$) or ($G^5$) is —N($R^{11}$)—, and $R^{11}$ represents hydrogen atom by reductive amination. A method of performing the coupling by allowing a reducing agent to act on the compound in a solvent is preferred. Examples of the reducing agent include, for example, metal hydride reducing agents such as sodium borohydride, zinc borohydride, sodium triacetoxyborohydride, borane/dimethyl sulfide complex, borane/pyridine complex, borane/triethylamine complex, borane/tetrahydrofuran complex, and lithium triethylborohydride, and preferred examples include sodium borohydride and sodium triacetoxyborohydride. The reducing agent is used in an amount of, for example, 0.1 fold mole or more, preferably 1 to 20 fold moles, based on the compound represented by the formula (2B) or (4B). Examples of the solvent include, for example, alcohols such as methanol, ethanol, and isopropanol, ethers such as tetrahydrofuran, 1,2-dimethoxyethane, and 1,4-dioxane, halogenated hydrocarbons such as dichloromethane, chloroform, and 1,2-dichloroethane, N,N-dimethylformamide and the like, and preferred examples include methanol, tetrahydrofuran, and 1,2-dichloroethane. The reaction temperature is, for example, 0° C. or higher, preferably 10° C. to the reflux temperature of the solvent. The reaction time is, for example, 0.1 hour or longer, preferably 0.5 to 30 hours.

The compounds represented by the aforementioned general formula (2B), wherein $G^d$ is a group represented by the general formula ($G^2$) or ($G^5$), and D is —C(O)N$R^{10}$— or —S(O)$_2$N$R^{10}$— [the group represented by the general formula ($G^2$) or ($G^5$) may be protected] can be prepared by coupling a compound represented by the general formula (4B) and a corresponding carbonyl chloride or sulfonyl chloride in an inert solvent in the presence of a base according to the method described in the literature ["Acid amides and acid imides" described in Shin Jikken Kagaku Koza (edited by the Chemical Society of Japan, published by Maruzen Co., Ltd.), vol. 22, p. 137] (Step 2-3-4). Examples of the inert solvent include, for example, halogenated hydrocarbons such as dichloromethane, chloroform, and 1,2-dichloroethane, and acetonitrile. Examples of the base include, for example, organic bases such as triethylamine, N,N-diisopropylethylamine, and pyridine, and inorganic bases such as potassium carbonate, and sodium hydrogencarbonate. The base and the carbonyl chloride or sulfonyl chloride are usually used in an amount of 1 to 6 fold moles, preferably 1.1 to 3.3 fold moles, based on the compound represented by the formula (4B), and the reaction temperature is about −10 to 40° C., preferably about 0 to 30° C. The reaction time is preferably 0.1 to 48 hours.

The compounds represented by the aforementioned the general formula (2B), wherein $G^d$ is a group represented by the general formula ($G^1$) or ($G^4$) can be prepared from a compound represented by the general formula (3B) [in the general formula (3B), $X^c$, $Y^b$, and $Z^b$ have the same meanings as those explained above, respectively, $R^4$, $R^5$, $R^6$, $R^7$, $A^2$, and Q in the group represented by the general formula ($G^1$) or ($G^4$) have the same meanings as those explained above, L-represents a counter anion of the diazonium salt, and the group represented by the general formula ($G^1$) or ($G^4$) may be protected] according to the methods described in the literature [S. Darses et al., European Journal of Chemistry, 1999, p. 1875], or the references cited in the literature (Step 2-4). As for the metal catalyst, ligand, solvent, reaction condition, and the like used for the coupling reaction, the examples mentioned in (Step 1-3) described above can be referred to. Examples of the counter anion of diazonium salt include $SO_4^{2-}$, $HSO_4^-$, $F^-$, $Cl^-$, $Br^-$, $I^-$, $NO_3^-$, $ClO_4^-$, $BF_4^-$, $PF_6^-$, $PtCl_6^{2-}$, and the like, and $BF_4^-$, $ClO_4^-$, $PF_6^-$, and $SO_4^{2-}$ are preferred. Further, $BF_4^-$ is particularly preferred. There is also another embodiment in which $PF_6^-$ is preferred.

The compounds represented by the aforementioned the general formula (3B) can be prepared from a compound represented by the aforementioned general formula (4B) (Step 2-5). This reaction can be performed according to the methods described in the literatures [S. Darses et al., European Journal of Chemistry, 1999, p. 1875; "Synthesis from aromatic amines" described in Shin Jikken Kagaku Koza (edited by the Chemical Society of Japan, published by Maruzen Co., Ltd.), vol. 20, p. 112; and "Diazo compound" ibid, the same volume, p. 425], and the like, or and references cited in the literatures. Examples of the method include, for example, a method of reacting a diazonium salt and an aromatic amine in an inert solvent in the presence of a catalyst such as palladium and a ligand such as phosphine.

The compounds represented by the aforementioned general formula (4B) can be prepared by coupling a compound represented by the general formula (5B) [in the general formula (5B), $X^c$, $Y^b$, and $Z^b$ have the same meanings as those explained above, respectively, and $J^2$ is iodine, bromine, or chlorine] and a compound represented by the aforementioned general formula (11) in the same manner as that of Step 1-12 (Step 2-6). $J^2$ represents iodine, bromine, or chlorine, and is preferably iodine or bromine. Further, $J^2$ is most preferably bromine. There is also another embodiment in which iodine is preferred, and there is also another embodiment in which chlorine is preferred.

The compounds represented by the aforementioned general formula (5B) can be prepared in the same manner as that of Step 1-14 by using a compound represented by the aforementioned general formula (6B) [in the general formula (6B), $X^c$, $Y^b$, and $J^2$ have the same meanings as those explained above, respectively] (Step 2-7).

The compounds represented by the aforementioned general formula (6B) can be prepared by reducing the double bond of a compound represented by the general formula (7B) [in the general formula (7B), $X^c$, and $Y^b$ have the same meanings as those explained above] using a reduction reaction described in the ordinary literature in the filed of chemistry (Step 2-8). Examples of the reaction include a method of converting the double bond of the compound represented by the general formula (7B) into a single bond by hydrogenation using a hydrogen source such as hydrogen gas, ammonium formate, and hydrazine hydrate in a single solvent or a mixed solvent of alcoholic-type solvents such as methanol, or ester-type solvents such as ethyl acetate in the presence of a catalyst such as palladium/carbon powder.

The compounds represented by the aforementioned general formula (7B) can be prepared by performing coupling in the same manner as that of Step 1-3 by using a compound represented by the aforementioned general formula (8B) [in the general formula (8B), $X^c$, and $Y^b$ have the same meanings as those explained above] (Step 2-9).

The compounds represented by the general formula (8B) are commercially available or known compounds, and thus obtainable. For example, 4-bromo-3-methylaniline is available from Tokyo Kasei Kogyo Co., Ltd. 3-Chloro-4-iodoaniline is available from Wako Pure Chemical Industries, Ltd. 4-Bromo-3-(trifluoromethyl)aniline is available from Aldrich Co. 4-Bromo-3-fluoroaniline is available from Aldrich Co. Further, 5-amino-2-bromophenol is known from the literature [P. Vincent, Tetrahedron Letters, 1994, vol. 35, p. 7055].

Examples of the preparation method for the compounds of the present invention represented by the general formula (1) which contains an asymmetric carbon in the substituent G include a method of using, as a reagent for alkylation in the aforementioned preparation methods, an alkylating agent in which a moiety corresponding to the asymmetric carbon in the substituent G is already optically active, which is commercially available (or can be prepared by a known method or a method similar thereto). A method is also available in which the compound of the present invention or a precursor thereof is separated as an optically active isomer by a conventional method. Examples of such method include, for example, a method utilizing high performance liquid chromatography (HPLC) using a chiral column, a method comprising condensation with an optically active regent to form a diastereomer, successive separation and purification, followed by decomposition, and the like. When a precursor is separated to obtain an optical isomer, an optically active compound represented by the general formula (1) can then be prepared by performing the aforementioned preparation methods.

When the compounds of the present invention represented by the general formula (1) contain an acidic functional group such as carboxyl group or phenolic hydroxyl group, the compounds can be converted into pharmaceutically acceptable salts (e.g., inorganic salts with sodium, ammonia and the like, or organic salts with triethylamine and the like) by a known means. For example, when an inorganic salt is to be obtained, it is preferable to dissolve the compounds of the present invention represented by the general formula (1) in water containing at least 1 equivalence of hydroxide, carbonate, bicarbonate or the like corresponding to a desired inorganic salt. For the reaction, an inactive water-miscible organic solvent such as methanol, ethanol, acetone, and dioxane may be mixed. For example, it is well known to those skilled in the art that by using sodium hydroxide, sodium carbonate, or sodium bicarbonate, a solution of sodium salt can be obtained.

When the compounds of the present invention represented by the general formula (1) contain a basic functional group such as amino group, the compounds can be converted into pharmaceutically acceptable salts (e.g., salt with inorganic acids such as hydrochloric acid and sulfuric acid, or salts with organic acids such as acetic acid and citric acid) by a known means. For example, when an inorganic salt is to be obtained, it is preferable to dissolve the compounds of the present invention represented by the general formula (1) in water containing at least 1 equivalence of a desired inorganic acid. For the reaction, an inactive water-miscible organic solvent such as methanol, ethanol, acetone, and dioxane may be mixed. For example, it is well known to those skilled in the art that by using hydrochloric acid, a solution of hydrochloride can be obtained.

If a solid salt is desired, a solution may be evaporated, or a water-miscible organic solvent having polarity to some extent, such as butanol or ethyl methyl ketone, can be added to obtain a solid salt thereof.

The various compounds disclosed by the present invention can be purified by known methods such as recrystallization, and variety of chromatography techniques (column chromatography, flash column chromatography, thin layer chromatography, high performance liquid chromatography).

<Pharmacological Action>

The compounds of the present invention represented by the general formula (1) and pharmacologically acceptable salts thereof have a superior inhibitory activity against type 4 $PLA_2$, as well as an action of suppressing the production of both of prostaglandins and leukotrienes. The inhibitory activity against type 4 $PLA_2$ herein referred to includes, for example, an activity of inhibiting the type 4 $PLA_2$ activity for decomposing γ-linolenoyl ester of 7-hydroxycoumarin (GLU) dispersed on liposome membranes of 1,2-dioleoyl-sn-glycero-3-phospho-L-serine (DOPS) by 10% or more, preferably 30% or more, most preferably 50% or more, for example, at a concentration of the compound at which the compound does not exhibit cytotoxicity. The action of suppressing the production of prostaglandins and/or leukotrienes herein referred to includes, for example, an action of suppressing $PGE_2$ production, observed when cultured cells of MG-63 which is a human osteosarcoma cell line are stimulated with IL-1β and/or $PGD_2$ and $LTB_4$ production observed when cultured cells of RBL-2H3 which is a rat mastocytoma cell line are stimulated with IgE, by 10% or more, preferably 30% or more, most preferably 50% or more, at a concentration of the compound at which the compound does not show cytotoxicity. As for a mode of action at a molecular level, it is considered that the compounds of the present invention inhibit both of COX-1 and/or COX-2, which produce prostaglandins, and 5-LO, which produces leukotrienes. It is also considered that the compounds of the present invention inhibit enzymatic activity of type 2A, 4, or 5 $PLA_2$ involved in prostaglandin and leukotriene production and thereby suppress the production of arachidonic acid.

For example, as for the enzymatic inhibitory action against COX-1, methods for measuring the enzymatic activity are described in the published literature [Yokoyama and Tanabe, Biochemical and Biophysical Research Communications (Biochem. Biophys. Res. Commun.), 1989, vol. 165, p. 888; Funk et al., FASEB Journal (FASEB. J), 1992, vol. 5, p. 2304; Kraemer et al., Archive of Biochemistry and Biophysics (Arch. Biochem. Biophys), 1992, vol. 293, p. 391 and the like], and the COX-1 inhibitory action of the compounds of the present invention will be elucidated by employing these methods. As for the enzyme inhibitory action against COX-2, methods for measuring the enzymatic activity are described in the published literature [Xie et al., Proceeding of National Academy of Science USA (Proc. Natl. Acad. Sci. USA), 1991, vol. 88, p. 2692; Kujubu et al., Journal of Biological Chemistry (J. Biol. Chem.), 1991, vol. 266, p. 12866; O'Banion et al., Journal of Biological Chemistry (J. Biol. Chem.), 1991, vol. 266, p. 23261; Hla et al., Proceeding of National Academy of Science USA (Proc. Natl. Acad. Sci. USA), 1992, vol. 89, p. 7384; Jones et al., Journal of Biological Chemistry (J. Biol. Chem.), vol. 268, p. 9049 and the like], and the COX-2 inhibitory action of the compounds of the present invention will be elucidated by employing these methods.

As for the enzyme inhibitory action against 5-LO, methods for measuring the enzymatic activity are described in the published literature [Dixon et al., Proceeding of National Academy of Science USA (Proc. Natl. Acad. Sci. USA), 1988, vol. 85, p. 416; Rouzer et al., Journal of Biological Chemistry (J. Biol. Chem.), 1989, vol. 263, p. 10135; Chen et al., Journal of Biological Chemistry (J. Biol. Chem.), 1995, vol. 270, p. 17993 and the like], and the 5-LO inhibitory action of the compounds of the present invention will be elucidated by employing these methods. As for the enzyme inhibitory action against type 2A $PLA_2$, methods for measuring the enzymatic activity are described in the published literature [Seilhamer et al., Journal of Biological Chemistry (J. Biol. Chem.), 1989, vol. 264, p. 5335; Kramer et al., Journal of Biological Chemistry (J. Biol. Chem.), 1989, vol. 264, p. 5768; Johansen et al., Biochemical and Biophysical Research Communications (Biochem. Biophys. Res. Commun.), 1992, vol. 187, p. 544 and the like], and the type 2A $PLA_2$ inhibitory action of the compounds of the present invention will be elucidated by employing these methods. As for the enzyme inhibitory action against type 4 $PLA_2$, methods for measuring the enzymatic activity are described in the published literature [Clark et al., Proceeding of National Academy of Science USA (Proc. Natl. Acad. Sci. USA), 1990, vol. 87, p. 7708; Gronich et al., Biochemical Journal (Biochem. J.), 1990, vol. 271, p. 37; Clark et al., Cell, 1991, vol. 65, p. 1043; Kramer et al., Journal of Biological Chemistry (J. Biol. Chem.), 1991, vol. 266, p. 5268; Bayburt et al., Biochemistry, 1997, vol. 36, p. 3216, and the like], and the type 4 $PLA_2$ inhibitory action of the compounds of the present invention can be elucidated by employing these methods. As for the enzyme inhibitory action against type 5 $PLA_2$, methods for measuring the enzymatic activity are described in the published literature [Chen et al., Journal of Biological Chemistry (J. Biol. Chem.), 1994, vol. 269, p. 2365; Chen et al., Biochimica Biophysica Acta (Biochim. Biophys. Acta), 1994, vol. 1215, p. 115 and the like], and the type 5 $PLA_2$ inhibitory action of the compounds of the present invention will be elucidated by employing these methods.

Safety of the compounds of the present invention represented by the general formula (1) and pharmaceutically acceptable salts thereof can be confirmed by the fact that they inhibit mouse inflammatory edema, allergic edema, acetic acid writhing reaction, and rat adjuvant arthritis by oral administration at a dose of 0.1 to 500 mg/kg, or by orally administering the compounds to mice at a dose of 500 mg/kg/day for 3 days. The edema in the rat adjuvant arthritis may be called swelling. More specifically, it can be demonstrated that they are safe compounds as drugs for mammals, preferably humans, pets or companion animals such as dogs and cats, and farm animals, and they are useful substances as active ingredients of medicaments. Preferred examples of the medicaments for mammals, preferably humans, pets or companion animals such as dogs and cats, and farm animals include agents for prophylactic and/or therapeutic treatment of various conditions, various diseases, and pathological conditions in which an acute or chronic inflammatory reaction resulted from production of prostaglandin and/or leukotriene is observed, specifically inflammatory diseases, allergic diseases, autoimmune diseases, and pain.

More specifically, the conditions or diseases include, for example, arthritis, chronic rheumatoid arthritis, malignant rheumatoid arthritis, juvenile rheumatoid arthritis, Felty's syndrome, adult Still's disease, osteoarthritis, synovitis, gout, slack of artificial joint implant, fervescence, common cold, algesia, burn, thermal injury, keloplasty, menstrual pain, dysmenorrhea, menstrual cramp, allergic reaction, allergic contact hypersensitivity, allergic rhinitis, pollinosis, allergic conjunctivitis, hypersensitivity pneumonitis, allergic bronchopulmonary mycosis, emphysema, acute respiratory distress syndrome, asthma, bronchitis, chronic obstructive pulmonary disease, chronic bronchitis, pulmonary emphysema, diffuse panbronchiolitis, respiratory obstruction, graft versus host syndrome, urticaria, ultraviolet radiation dermatitis, atopic dermatitis, cancer, myelogenous leukemia, sarcomata, brain tumor, cachexia, tissue ulcer, digestive ulcer, gastritis, acute and chronic pancreatitis, regional enteritis, ulcerative colitis, diverticulitis, recurrent gastroenteric disorder, gastroenteric bleeding, inflammatory bowel disease, Crohn's disease, intestinal tract type Behcet's disease, infectious enteritis, ischemic enteritis, radiation enteritis, drug-induced enteritis, irritable bowel syndrome, hepatic diseases (hepatopathies, liver failures) such as acute hepatitis, fulminant hepatitis, chronic hepatitis, hepatic cirrhosis, fatty liver, alcoholic liver injury, drug liver injury (drug-induced hepatitis), congestive hepatitis, autoimmune hepatitis, primary biliary cirrhosis and hepatic porphyria, coagulation, anemia, ankylosing spondilitis, restenosis, periodontosis, epidermolysis bullosa, atherosclerosis, aortic aneurysm, periarteritis nodosa, congestive cardiac failure, arrhythmia, myocardial infarction, cerebral infarction, attack, cerebral ischemia, head injury, spinal cord injury, myelopathic muscular atrophy, neuralgia, neurodegenerative disease, Alzheimer's disease, Lewy body disease, Shy-Drager syndrome, Reye's syndrome, progressive supranuclear palsy, progressive multifocal leukoencephalopathy, normal pressure hydrocephalus, subacute sclerosing panencephalitis, frontal lobe type dementia, acute anterior poliomyelitis (poliomyelitis), poliomyelitis neurosis, viral encephalitis, Creutzfeldt-Jakob disease, Kuru disease, bovine spongiform encephalopathy (mad cow disease), scrapie, epilepsy, cerebral amyloid angiopathy, autoimmune disease, Huntington's disease, Parkinson's disease, migraine, depression, mania, manic-depressive psychosis, hereditary cerebellar ataxia, peripheral neuropathy, glaucoma, pain, gingivitis, postoperative pain, amyotrophic lateral sclerosis, osteoporosis, multiple sclerosis, ocular angiogenesis, cornea damage, macular degeneration, conjunctivitis, abnormal wound healing, sprain or strain of muscle or joint, tendinitis, skin disease, psoriasis vulgaris, pustular psoriasis, erythroderma psoriaticum, arthritic psoriasis, myasthenia gravis, multiple myositis, myositis, bursitis, diabetes mellitus, tumor growth, tumor invasion, tumor metastasis, cornea scar, scleritis, immunodeficiency disease, pachydermia, eosinophilic fasciitis, sepsis, endotoxin shock, premature delivery, hypoprothrombinemia, hemophilia, thyroiditis, sarcoidosis, Behcet's syndrome, hypersensitivity, renal disease, rickettsial infectious disease, protozoal disease, reproduction disease, sepsis shock and the like. Other specific conditions and diseases include toothache, pain after tooth extraction, back or low back pain, periarthritis humeroscapularis, cervico-omo-brachial syndrome, tenosynovitis, acute upper respiratory inflammation, herpes zoster, fibrosis, pulmonary fibrosis, pneumoconiosis, chronic interstitial pneumonia, granulomatous interstitial pneumonia, fibrosing interstitial pneumonia, renal fibrosis, nephropyelitis, various types of secondary contracted kidney, glomerular nephritis, chronic nephritis, glomerulosclerosis, hepatic fibrosis, cardiac fibrosis after myocardial infarction, idiopathic cardiomyopathy, pancreatic sclerosis, pancreatic fibrosis, pancreatolithiasis, Takayasu's arteritis, chronic thyroiditis, dermatomyositis, multiple myositis, myelofibrosis, Banti disease, retroperitoneal fibrosis, various radiation injuries and the like.

Further, the medicament comprising the compounds of the present invention represented by the general formula (1) as active ingredients can be used for the aforementioned conditions or diseases of mammals, preferably humans, pets or companion animals such as dogs and cats or farm animals together with or in combination with one or more kinds of other prophylactic or therapeutic drugs. Examples of the drugs that can be used together or in combination include, for example, the following drugs: immunomodulation-type anti-rheumatic drugs and antimetabolite used as therapeutic drugs for rheumatoid arthritis, specifically, gold preparations, bucillamine, lobenzarit, hydroxychlorokin, D-penicillamine, salazosulfapyridine, methotrexate, azathiopurin, mizoribine, leflunomide, tacrolimus, cyclosporin and the like and preparations containing the same; anti-cytokine antibody preparations directed to cytokines such as interleukin (IL) 1, IL-6, and tumor necrosis factor (TNF)-α or preparations of soluble receptors for those cytokines, which are biological preparations, specifically, infliximab, etanercept and the like and preparations containing the same; steroid preparations, specifically, dexamethasone, betamethasone, prednisolone, fluticasone, beclometasone and the like and preparations containing the same; bronchodilators used as therapeutic agents for chronic bronchial asthma, specifically, salmeterol and salbutamol, which are adrenalin β2 stimulants, ipratropium, which is an anticholinergic drug, and the like and preparations containing the same; therapeutic drugs for allergic diseases, for example, theophyline, which is a xanthine analogue drug, and the like, fexoquinadine, epinastatine, cetirizine, ketotifen, disodium cromoglycate, pemirolast and the like, which are antiallergic agents, and preparations containing the same; irinotecan, 5-fluorouracil and the like, which are antitumor agents, and preparations containing the same. Further, the medicament comprising the compounds of the present invention represented by the general formula (1) as active ingredients are used, for example, together with or in combination with radiotherapy.

The method for using the compounds of the present invention represented by the general formula (1) or pharmaceutically acceptable salts thereof as the medicaments described above is not particularly limited, and an effective amount of the compounds of the present invention represented by the general formula (1) or pharmaceutically acceptable salts thereof per se may be used, or they may be mixed with a pharmaceutically acceptable carrier to form a pharmaceutical composition, and used. The carrier may be, for example, a suspending agent such as carboxymethylcellulose, or purified water, physiological saline or the like, if desired. Other known carriers can also be used. An example include a method of dispersing or dissolving the compounds of the present invention represented by the general formula (1) or a pharmaceutically acceptable salt thereof in purified water containing 0.5% carboxymethylcellulose and using the dispersion or solution.

Examples of formulations for preparing the aforementioned pharmaceutical composition include tablet, powder, granule, syrup, suspension, capsule, injection, and the like. For the manufacture of these formulations, various carriers suitable for these preparations are used. For example, examples of the carrier for oral preparations include excipients, binders, lubricants, fluid accelerators, and colorants.

When the compounds of the present invention are formulated as a parenteral preparation such as an injection, water for injection, physiological saline, glucose aqueous solution, vegetable oil for injection, propylene glycol, polyethylene glycol and the like can generally be used as a diluent. Disinfectants, antiseptics, stabilizers, isotonic agents, soothing agents and the like may be further added, as required.

When the compounds of the present invention are administered to mammals, e.g., humans, they can be administered in the form of a tablet, a powder, a granule, a suspension, a capsule or the like. They can also be parenterally administered in the form of an injection including drip infusion, a suppository, a gel, a lotion, an ointment, a cream, or a spray. A dose thereof varies depending on a disease to be applied, an administration route, the age, weight, degree of symptom of a patient and the like. Examples of the dose include generally an administration at a dose of 1 to 1,000 mg per day for an adult once to three times a day as divided portions. In general, an administration period may be every day for several days to two months. Both of the daily dose and the administration period may be increased or decreased depending on symptoms of a patient.

Fibrosis, which is a disease characterized by fibrosing of tissues, is known as a severe disease which is often mortal. Fibrosing of tissues is caused by proliferation of interstitial cells, which represented by fibroblasts, and production of extracellular matrix such as collagen. Fibrosing is considered a repair mechanism against tissue affections in organs. Excessive fibrosing causes fibrosing diseases of organs, and further progression of fibrosing causes sclerotic diseases. Many of such sclerotic diseases are intractable, progressive and irreversible. Although fibrosing varies in various organs, etiological hypotheses of fibrosing have many similarities. More specifically, a certain inflammatory lesion precedes, and in its healing process, various kinds of cytokines and growth factors are produced mainly from immunocompetent cells and platelets as well as interstitial cells such as fibroblasts themselves involved in the healing, and activated to cause deposition of extracellular matrix (Takehara, Molecular Medicine, 2001, vol. 38, p. 854).

Among fibroses, pulmonary fibrosis is one of the representative diseases. Pulmonary fibrosis is a disease in which disruption of alveolar structure is caused by chronic inflammation and increase of collagenic fibers in alveolar walls, and which eventually leads to respiratory failure and death. For example, pulmonary fibrosis occurs following infectious pneumonia and the like. Examples of the infectious pneumonia include severe acute respiratory syndrome (SARS) and influenzal pneumonia. It has been reported that, in SARS, in particular, severe inflammation is caused in pulmonary stroma, and as a result, it highly likely to develop into pulmonary fibrosis (Antonino et al., Radiology, 2003). In addition, pulmonary fibrosis is also caused by various medicaments.

In recent years, with increase of medicaments used for diagnosis, prophylactic and therapeutic treatments of various kinds of diseases, drug-induced pulmonary fibrosis caused by such drugs is increasing. Drug-induced pulmonary fibrosis is a severe disease that eventually leads to death, and it causes serious problems in therapeutic treatments of various diseases. Therefore, prophylactic and therapeutic treatments of drug-induced pulmonary fibrosis constitute a particularly important subject of concern.

Against drug-induced pulmonary fibrosis, steroid therapy is currently used. However, effective rate of the steroid therapy is low and the effect is only partial and transient, and thus lesions often remain [Igaku no Ayumi, 2001, vol. 197, p. 313]. Further, side effect of steroid agents and acute aggravation due to decrease of doses or termination of their administrations are also often observed, which remains clinically far unsatisfactory level.

As a recent finding, it was reported that administration of pirfenidone was effective against pulmonary fibrosis in clinical tests in the United States (Raghu et al., American Journal of Respiratory and Critical Care Medicine, 1999, vol. 159, p. 1061) and Japan (Nagai et al., Internal Medicine, 2002, vol. 41, p. 1118). However, development of novel prophylactic and/or therapeutic agents highly effective for these diseases is desired at all events.

The medicament provided by the present invention can be used as a medicament comprising a type 4 $PLA_2$ inhibitor as an active ingredient for prophylactic and/or therapeutic treatment of fibrosis, preferably pulmonary fibrosis, further preferably drug-induced pulmonary fibrosis.

As described above, fibrosis, in particular, pulmonary fibrosis, is a severe disease and is an important object of prophylactic and/or therapeutic treatment. As for pulmonary fibrosis, more than 100 kinds of factors including toxic gases and various medicaments have been elucidated as the causes of early alveolopathy. As described above, with the increase of medicaments used for diagnosis, prophylactic and therapeutic treatments of various kinds of diseases, drug-induced pulmonary fibrosis caused by such drugs is increasing.

As for drug-induced pulmonary fibrosis, causality between expression of pathological conditions such as coughing, difficulty of breathing, or fervescence and the administration of medicaments is suspected, and it is considered that a diffuse interstitial shadow appears on a thoracic X-ray photograph simultaneously with or slightly after the administration of medicaments.

As medicaments reported to cause drug-induced pulmonary fibrosis, anticancer agents, anti-rheumatic agents, immunosuppressants, antibiotics, chemotherapeutants, antihypertensive agents, diuretics, anti-inflammatory/analgesic agents, biologics, Chinese medicines, and the like are known (Inooka et al., Therapeutics, 1995, vol. 29, p. 1295). Typical medicaments are shown in Table 1.

TABLE 1

| Classification | Examples of agent |
| --- | --- |
| 1) Anticancer agent, immunosuppressant | Peplomycin, bleomycin, cychlophosphamide, nitrosourea, busulfan, methotrexate, azathioprine, mitomycin-C, tegafur, carmofur, tegafur/uracil preparation, cisplatin, doxorubicin, 6-mercaptopurine, daunomycin, vincristine, vinblastine, vindesine, procarbazine, neocarzinostatin, melphalan, thiotepa, nimustine, cytarabine, zinostatin stimalamer, chlorambucil, carmustine, lomustine, semustine, teniposide, etoposide, Taxol, taxotere, irinotecan, gefitinib, tamoxifen and the like |
| 2) Antihypertensive agent, diuretic | α-Methyldopa, trichlormethiazide, hydrochlorothiazide, enalapril, hexamethonium, mecamylamine, pentolinium, practolol, pindolol, propranolol, acebutolol, hydralazine and the like |

TABLE 1-continued

| Classification | Examples of agent |
| --- | --- |
| 3) Antibiotic, chemotherapeutant | Cephem antibiotics (cephaloridine, cephalothin, cephalexin, cefradine, cefazolin, cefaclor, cefmenoxime, cefmetazole, cefoperazone, cefotiam, cefroxadin, ceftizoxime, latamoxef and the like), tetracyclines (minocycline, oxycycline), antituberculous agents (isoniazid, paraaminosalicylic acid, rifampicin, streptomycin), penicillin antibiotics (ampicillin, piperacillin, vastcillin, pentcillin, amoxicillin), aminoglycoside antibiotics (streptomycin), macrolide antibiotics (midecamycin), phosphomycin, aminoglycosides (tobramycin, Micromycin), new quinolone drugs (enoxacin, ofloxacin, norfloxacin), antifungal agents (amphotericin) and the like |
| 4) Others | Inhalants (cromoglicic acid and the like), gold preparations (aurothiomalic acid and the like), psychotropic agents and nervines (aminotriptyline, diphenylhydantoin, carbamazepine, phenobarbital, valproate salt, imipramine, mephenesin, meprobamate), antiphlogistic and analgesics (naproxen, acetaminophen, acetylsalicylic acid, phenacetin, diclofenac, loxoprofen, fenbufen, nabumetone, aluminoprophen and the like), antiarrhythmic agents (amiodarone, procainamide, aprindine), antidiabetic agents (chlorpropamide), antithyroid agents (thiouracil), proteolytic enzymes (serrapeptidase), antiparkinsonic agents (levodopa, bromocriptine), antirheumatic agents (bucillamine, auranofin, actarit), sho-saiko-to, chai-ling-tang, rikkunshi-to, interferon, warfarin, salazosulfapyridine, dichloroferamide, fominoben, D-penicillamine, propylthiouracil, corticosteroid, flavoxate, allopurinol, ethoxysclerol and the like |

In therapeutic treatment of rheumatoid arthritis, for example, agents that cause pulmonary fibrosis at high frequency such as methotrexate and sodium aurothiomalate are used as disease-modifying antirheumatic drugs. Further, disease-modifying antirheumatic drugs that may cause pulmonary fibrosis at a relatively low frequency, such as actarit, bucillamine, auranofin, salazosulfapyridine, and D-penicillamine are also used. Although these disease-modifying antirheumatic drugs are useful agents in the rheumatoid arthritis treatment system, pulmonary fibrosis caused as a side effect is a factor of restricting use of these drugs. In recent years, methotrexate, in particular, has come to be used as an antirheumatic agent, and onset of pulmonary fibrosis that is also histopathologically called interstitial pneumonia as the side effect of methotrexate becomes a problem in the rheumatoid arthritis treatment system.

Further, in cancer therapy, cychlophosphamide, Taxol, etoposide, cisplatin, vincristine, vinblastine, irinotecan, gefitinib, and bleomycin are useful as anticancer agents. However, because all of these anticancer agents cause pulmonary fibrosis that is also histopathologically called as interstitial pneumonia as a side effect at a high frequency, they have a problem in the therapeutic treatment system. Bleomycin, gefitinib, irinotecan, and cisplatin are used for therapeutic treatment of lung cancer. However, if patients with lung cancer develop pulmonary fibrosis, the condition is most likely for the patients to be fatal. Among these drugs, bleomycin suffers from a problem that it causes pulmonary fibrosis at a high frequency.

More specifically, in the present invention, drug-induced pulmonary fibroses caused by the aforementioned drugs are preferred as objects of application of the prophylactic and/or therapeutic agent of present invention.

When a compound represented by the aforementioned formula (1) or a pharmacologically acceptable salt thereof is used as a type 4 $PLA_2$ inhibitor, various combinations of the compounds represented by the formula (1) and pharmacologically acceptable salts thereof described in the specification can also be arbitrarily chosen.

When a medicament comprising a compound represented by the general formula (1) or a pharmacologically acceptable salt thereof according to the present invention is used as a type 4 $PLA_2$ inhibitor as a prophylactic and/or therapeutic agent for fibrosis, for example, an effective amount of a compound represented by the general formula (1) or a pharmacologically acceptable salt thereof, per se, may be used, or the substance may be used after preparation of a pharmaceutical composition in the form of solid, liquid or gel by mixing the substance with a pharmaceutically acceptable carrier. As for the pharmaceutically acceptable carrier, known information and the information about carriers described in this specification can be referred to. When the medicament of the present invention is used in combination with known a type 4 $PLA_2$ inhibitor, the known type 4 $PLA_2$ inhibitor or a pharmaceutically acceptable salt thereof, per se, may be used in an effective amount, or as mentioned above, the inhibitors may be used after preparation of a pharmaceutical composition by mixing the inhibitor with a pharmaceutically acceptable carrier. As the medicament of the present invention, a pharmaceutical composition comprising a compound represented by the general formula (1) or a pharmacologically acceptable salt thereof together with a known type 4 $PLA_2$ inhibitor as active ingredients may be prepared and used.

It would be readily understood by those skilled in the art that progression-preventing agents, that is used for preventing progression of pathological conditions, occasionally fall within the scope of the agent for prophylactic and/or therapeutic treatment of the present invention.

Examples of the dosage form for preparation of the aforementioned pharmaceutical composition include tablet, powder, granule, syrup, suspension, capsule, inhalant, injection, and the like, and in order to prepare the compositions, various carriers are used depending on the type of the composition. Examples of the carrier for oral agents include, for example, excipients, binders, lubricants, flowability improvers, and colorants. When an inhalant is prepared (examples of administration method include a method of inhaling powder of the pharmaceutical composition or a solution or dispersion obtained by dissolving or suspending the pharmaceutical composition in a solvent, per se, a method of inhaling mist of the composition prepared by using a sprayer called atomizer or nebulizer), the preparation of the aforementioned pharmaceutical composition in the form of solid can be referred to for preparation of a powder for the inhalation, and a powder obtained is preferably further made into micropowder. When the composition is inhaled as a liquid, preferred examples of the preparation method include a method of dissolving a solid pharmaceutical composition, which is prepared by referring to the above explanation, in distilled water or a suitable solvent to obtain a solution of medicament upon use, and a method of preparing a liquid pharmaceutical composition prepared by referring the above explanation to obtain a solution of medicament. When an injection and the like are prepared, distilled water for injection, physiological saline, glucose solution, vegetable oil for injection, propylene glycol, polyethylene glycols and the like can generally be used as diluents. Further, antimicrobial agents, antiseptics, stabilizers, isotonic agents, soothing agents, and the like may be added, as required.

When the aforementioned prophylactic and/or therapeutic agent is administered, a suitable dosage form can be chosen and administered via a suitable route. For example, the agent can be orally administered in the form of a tablet, a powder, a granule, a syrup, a suspension, or a capsule. The agent can also be administered via transairway route in the form of an inhalant. Further, the agent can be administered subcutaneously, intradermally, intravascularly, intramuscularly or intraperitoneally in the form of injection including a drip infusion. Furthermore, the agent can be transmucosally administered in the form of a sublingual agent or a suppository, and can be transdermally administered in the form of a gel, a lotion, an ointment, a cream, or a spray.

A dose thereof varies depending on the dosage form, and the age, weight, degree of symptoms of a patient and the like. Examples of the daily dose include generally an administration at a dose of 1 to 1,000 mg per day for an adult once to three times a day as divided portions. As for administration period, every day administration for a period of several days to two months is commonly applied. The daily dose and the administration period may be increased or decreased depending on symptoms of a patient.

As for the application of the aforementioned prophylactic and/or therapeutic agent, the agent may be administered to patients with pulmonary fibrosis as explained above. In addition, the prophylactic and/or therapeutic agent of the present invention may preferably be administered after the administration of, most preferably immediately after the administration of an agent, which may possibly induces pulmonary fibrosis as an adverse reaction. Furthermore, as for the administration time, the prophylactic and/or therapeutic agent of the present invention may be administered simultaneously with an agent which may possibly induces pulmonary fibrosis as an adverse reaction, or the agent of the present invention may be administered beforehand.

Furthermore, the compounds of the present invention and salts thereof as well as derivatives thereof useful as prodrugs are excellent in safety (various toxicities and safety pharmacology), pharmacokinetic performance, and the like, and thus usefulness thereof as active ingredients of medicaments can be confirmed.

Examples of tests concerning safety include, for example, those listed below. However, they are not limited to these examples. Examples include cytotoxic tests (tests using HL60 cells, hepatocytes and the like), genotoxicity tests (Ames test, mouse lymphoma TK test, chromosomal aberration test, micronucleus test and the like), skin sensitization tests (Buehler method, GPMT method, APT method, LLNA test and the like), skin photosensitization tests (adjuvant and strip method and the like), eye irritation tests (single instillation, short-term continuation instillation, repetitive instillation and the like), safety pharmacology tests for the cardiovascular system (telemetry method, APD method, hERG inhibition assay and the like), safety pharmacology tests for the central nervous system (FOB method, modified version of Irwin method and the like), safety pharmacology tests for the respiratory system (measurement method utilizing a respiratory function measuring apparatus, measurement method utilizing a blood gas analyzer and the like), general toxicity tests, reproductive and developmental toxicity tests, and the like.

Examples tests concerning pharmacokinetic performance include, for example, those listed below. However, they are not limited to these examples. Examples include cytochrome P450 enzyme inhibition or induction tests, cell permeability tests (tests using CaCO-2 cells, MDCK cells and the like), drug transporter ATPase assay, oral absorption tests, blood concentration transition measurement tests, metabolism tests (stability test, metabolite molecular species test, reactivity test and the like), solubility tests (solubility test based on turbidity method and the like), and the like.

Usefulness of the compounds of the present invention represented by the aforementioned formula (1) and salts thereof as well as derivatives thereof useful as prodrugs as active ingredients of medicaments can be confirmed by performing, for example, a cytotoxic test. Examples of the cytotoxic test include methods utilizing various cultured cells, for example, HL-60 cells, which are human preleukemia cells, primary isolated cultured cells of hepatocytes, a neutrophil fraction prepared from human peripheral blood, and the like. Although the test can be carried out by the method described below, the method is not limited only to the following description. Cells are prepared as a suspension of $10^5$ to $10^7$ cells/ml, and the suspension is added to microtubes or microplate in a volume of 0.01 to 1 mL. To the suspension, a solution dissolving a compound is added in a volume of 1/100 to 1 fold volume of the cell suspension, and the cells were cultured in a cell culture medium having a final concentration of the compound of 0.001 to 1000 µM for 30 minutes to several days at 37° C. under 5% $CO_2$. After terminating the culture, survival rate of the cells is evaluated by using the MTT method, WST-1 method (Ishiyama, M., et al., In Vitro Toxicology, 8, p. 187, 1995), or the like. By measuring cytotoxicity of the compound to cells, usefulness as active ingredients of medicaments can be confirmed.

Usefulness of the compounds of the present invention represented by the aforementioned formula (1) and salts thereof as well as derivatives thereof useful as prodrugs as active ingredients of medicaments can be confirmed by performing, for example, a genotoxicity test. Examples of the genotoxicity test include, the Ames test, mouse lymphoma TK test, chromosomal aberration test, micronucleus test, and the like. The Ames test is a method of determining reverse mutation by culturing *Salmonella* or *Escherichia* bacteria of designated species on a culture dish or the like added with a compound (refer to IYAKUSHIN (Notification by the chief of Evaluation and Licensing Division, Pharmaceutical and Medical Safety Bureau, Ministry of Health, Labor and Welfare, Japan), No. 1604, 1999, "Guideline for Genotoxicity Test", II-1. Genotoxicity Test, and the like). The mouse lymphoma TK test is a genetic mutation ability detection test targeting the thymidine kinase gene of the mouse lymphoma L5178Y cell (refer to IYAKUSHIN No. 1604, 1999, "Guideline for Genotoxicity Test", II-3. Mouse Lymphoma TK Test; Clive, D. et al., Mutat. Res., 31, pp. 17-29, 1975; Cole, J., et al., Mutat. Res., 111, pp. 371-386, 1983, and the like). The chromosomal aberration test is a method for determining activity of causing chromosomal aberration by culturing mammalian cultured cells in the presence of a compound, then after fixation of the cells, staining and observing chromosomes of the cells (refer to IYAKUSHIN No. 1604, 1999, "Guideline for Genotoxicity Test", II-2. Chromosomal Aberration Test Utilizing Mammalian Cultured Cells, and the like). The micronucleus test is a method of evaluating micronucleus forming ability caused by chromosomal aberration, and a method of using a rodent (in vivo test) (IYAKUSHIN No. 1604, 1999, "Guideline for Genotoxicity Test", II-4. Micronucleus Test Using Rodent; Hayashi M. et al., Mutat. Res., 312, pp. 293-304, 1994; Hayashi, M. et al., Environ. Mol. Mutagen., 35, pp. 234-252, 2000), a method of using cultured cells (in vitro test) (Fenech M., et al., Mutat. Res., 147, pp. 29-36, 1985; Miller, B., et al., Mutat. Res., 392, pp. 45-59, 1997, and the like) are available. By elucidating genotoxicity of the compounds based on one or more of these methods, usefulness of the compounds as active ingredients of medicaments can be confirmed.

Usefulness of the compounds of the present invention represented by the aforementioned formula (1) and salts thereof as well as derivatives thereof useful as prodrugs as active ingredients of medicaments can be confirmed by performing, for example, a skin sensitization test. As the skin sensitization test using guinea pig, the Buehler method (Buehler, E. V., Arch. Dermatol., 91, pp. 171-177, 1965), GPMT method (maximization method, Magnusson B., et al., J. Invest. Dermatol., 52, pp. 268-276, 1969), APT method (adjuvant and patching method (Sato, Y. et al., Contact Dermatitis, 7, pp. 225-237, 1981)) and the like are available. Further, as the skin sensitization test using mouse, the LLNA (local lymph node assay) method (OECD Guideline for the testing of chemicals 429, skin sensitization 2002; Takeyoshi, M. et al., Toxicol. Lett., 119 (3), pp. 203-8, 2001; Takeyoshi, M. et al., J. Appl. Toxicol., 25 (2), pp. 129-34, 2005) and the like are available. By elucidating skin sensitization property of the compounds based on one or more of these methods, usefulness of the compounds as active ingredients of medicaments can be confirmed.

Usefulness of the compounds of the present invention represented by the aforementioned formula (1) and salts thereof as well as derivatives thereof useful as prodrugs as active ingredients of medicaments can be confirmed by performing, for example, a skin photosensitization test. Examples of the skin photosensitization test include a skin photosensitization test using guinea pig (refer to "Drug Nonclinical Test Guideline Commentary 2002", Yakuji Nippo, published on 2002, 1-9: Skin Photosensitization Test, and the like), and the like, and examples of the method include the adjuvant and strip method (Ichikawa, H. et al., J. Invest. Dermatol., 76, pp. 498-501, 1981), Harber method (Harber, L. C., Arch. Dermatol., 96, pp. 646-653, 1967), Horio method (Horio, T., J. Invest. Dermatol., 67, pp. 591-593, 1976), Jordan method (Jordan, W. P., Contact Dermatitis, 8, pp. 109-116, 1982), Kochever method (Kochever, I. E. et al., J. Invest. Dermatol., 73, pp. 144-146, 1979), Maurer method (Maurer, T. et al., Br. J. Dermatol., 63, pp. 593-605, 1980), Morikawa method (Morikawa, F. et al., "Sunlight and Man", Tokyo Univ. Press, Tokyo, pp. 529-557, 1974), Vinson method (Vinson, L. J., J. Soc. Cosm. Chem., 17, pp. 123-130, 1966), and the like. By elucidating skin photosensitization property of the compounds based on one or more of these methods, usefulness of the compounds as active ingredients of medicaments can be confirmed.

Usefulness of the compounds of the present invention represented by the aforementioned formula (1) and salts thereof as well as derivatives thereof useful as prodrugs as active ingredients of medicaments can be confirmed by performing, for example, an eye irritation test. Examples of the eye irritation test include the single instillation test method using rabbit eyes, monkey eyes, and the like (instillation of one time), short term continuous instillation test method (instillation of multiple times in a short period of time with equal intervals), repetitive instillation test method (repetitive intermittent instillation over several days to 10 days), and the like, and a method of evaluating eye irritation symptoms during a certain period of time after instillation according to the improved Draize scores (Fukui, N. et al., Gendai no Rinsho, 4 (7), pp. 277-289, 1970) and the like are available. By elucidating eye irritation of the compounds based on one or more of these methods, usefulness of the compounds as active ingredients of medicaments can be confirmed.

Usefulness of the compounds of the present invention represented by the aforementioned formula (1) and salts thereof as well as derivatives thereof useful as prodrugs as active ingredients of medicaments can be confirmed by performing, for example, a safety pharmacology test for the cardiovascular system. Examples of the safety pharmacology test for the cardiovascular system include the telemetry method (method for measuring influence of administration of a compound under no anesthetization on electrocardiogram, heart rate, blood pressure, blood stream, and the like (Electrocardiographic, Echocardiographic, Blood Pressure and Pathological Tests of Animals for Fundamental and Clinical Medicine, edited by Sugano S., Tsubone H., Nakada Y., published on 2003, Maruzen), APD method (method for measuring cardiac muscle cell action potential retention time (Muraki, K. et al., AM. J. Physiol., 269, H524-532, 1995; Ducic, I. et al., J. Cardiovasc. Pharmacol., 30 (1), pp. 42-54, 1997)), hERG inhibition evaluation method (patch clamping method (Chachin, M. et al., Nippon Yakurigaku Zasshi, 119, pp. 345-351, 2002), binding assay method (Gilbert, J. D. et al., J. Pharm. Tox. Methods, 50, pp. 187-199, 2004), Rb+ efflux assay method (Cheng, C. S. et al., Drug Develop. Indust. Pharm., 28, pp. 177-191, 2002), membrane potential assay method (Dorn, A. et al., J. Biomol. Screen., 10, pp. 339-347, 2005), and the like. By elucidating influence on the cardiovascular system of the compounds based on one or more of these methods, usefulness of the compounds as active ingredients of medicaments can be confirmed.

Usefulness of the compounds of the present invention represented by the aforementioned formula (1) and salts thereof as well as derivatives thereof useful as prodrugs as active ingredients of medicaments can be confirmed by performing, for example, a safety pharmacology test for the central nervous system. Examples of the safety pharmacology test for the central nervous system include the FOB method (Functional Observational Battery, Mattson, J. L. et al., J. American College of Technology, 15 (3), pp. 239-254, 1996)), modified version of Irwin method (method for evaluating observation of general symptoms and behavior (Irwin, S., Comprehensive Observational Assessment (Berl.) 13, pp. 222-257, 1968)), and the like. By elucidating action on the central nervous system of the compounds based on one or more of these methods, usefulness of the compounds as active ingredients of medicaments can be confirmed.

Usefulness of the compounds of the present invention represented by the aforementioned formula (1) and salts thereof as well as derivatives thereof useful as prodrugs as active ingredients of medicaments can be confirmed by performing, for example, a safety pharmacology test for the respiratory system. Examples of the safety pharmacology test for the respiratory system include the measurement method using a respiratory function measuring apparatus (method of measuring respiration rate, single ventilation volume, minute ventilation and the like, Drorbaugh, J. E. et al., Pediatrics, 16, pp. 81-87, 1955; Epstein, M. A. et al., Respir. Physiol., 32, pp. 105-120, 1978), measurement method of using a blood gas analyzer (method of measuring blood gas, hemoglobin oxygen saturation and the like, Matsuo, S., Medicina, 40, pp. 188-, 2003), and the like. By elucidating action on the respiratory system of the compounds based on one or more of these methods, usefulness of the compounds as active ingredients of medicaments can be confirmed.

Usefulness of the compounds of the present invention represented by the aforementioned formula (1) and salts thereof as well as derivatives thereof useful as prodrugs as active ingredients of medicaments can be confirmed by performing, for example, a general toxicity test. The general toxicity test is a method of orally or intravenously administering a compound dissolved or suspended in an appropriate solvent once or repetitively (over several days) to a rodent such as rat and mouse or non-rodent such as monkey and dog, and evaluating observation of general conditions, clinicochemical changes, pathohistological changes, and the like of the administered animal. By elucidating general toxicity of the compounds based on these methods, usefulness of the compounds as an active ingredient of medicament can be confirmed.

Usefulness of the compounds of the present invention represented by the aforementioned formula (1) and salts thereof as well as derivatives thereof useful as prodrugs as active ingredients of medicaments can be confirmed by performing, for example, a reproductive and developmental toxicity test. The reproductive and developmental toxicity test is a test for examining induction of harmful effect by a compound on the reproductive and developmental processes by using a rodent such as rat and mouse or non-rodent such as monkey and dog (refer to "Drug Nonclinical Test Guideline Commentary 2002", Yakuji Nippo, published on 2002, 1-6: Reproductive and Developmental Toxicity Test, and the like). Examples of the reproductive and developmental toxicity test include tests concerning fertility and early embryogenesis up to nidation, tests concerning development and maternal functions before and after birth, tests concerning embryogenesis and fetal development (refer to IYAKUSHIN No. 1834, 2000, Appendix, "Guideline for Drug Toxicity Test", [3] Reproductive and Developmental Toxicity Test, and the like), and the like. By elucidating reproductive and developmental toxicity of the compounds based on these methods, usefulness of the compounds as an active ingredient of medicament can be confirmed.

Usefulness of the compounds of the present invention represented by the aforementioned formula (1) and salts thereof as well as derivatives thereof useful as prodrugs as active ingredients of medicaments can be confirmed by performing, for example, a cytochrome P450 enzyme inhibition or induction test (Gomez-Lechon, M. J. et al., Curr. Drug Metab., 5 (5), pp. 443-462, 2004). Examples of the cytochrome P450 enzyme inhibition or induction test include, for example, the method of determining in vitro whether a compound inhibits activity of a cytochrome P450 enzyme by using a cytochrome P450 enzyme of each molecular species purified from cells or prepared by using a genetic recombinant, or a human P450 expression system microsome (Miller, V. P. et al., Ann. N.Y. Acad. Sci., 919, pp. 26-32, 2000), method of measuring changes of expression of cytochrome P450 enzyme of each molecular species and enzyme activity by using human liver microsomes or disrupted cell suspension (Hengstler, J. G. et al., Drug Metab. Rev., 32, pp. 81-118, 2000), method of extracting RNA from human hepatocytes exposed to a compound, and comparing mRNA expression amount with that of a control to investigate enzyme induction ability of the compound (Kato, M. et al., Drug Metab. Pharmacokinet., 20 (4), pp. 236-243, 2005), and the like. By elucidating action of the compounds on inhibition or induction of cytochrome P450 enzyme based on one or more of these methods, usefulness of the compounds as active ingredients of medicaments can be confirmed.

Usefulness of the compounds of the present invention represented by the aforementioned formula (1) and salts thereof as well as derivatives thereof useful as prodrugs as active ingredients of medicaments can be confirmed by performing, for example, a cell permeability test. Examples of the cell permeability test include, for example, the method of measuring cell membrane permeability of a compound in an in vitro cell culture system using CaCO-2 cells (Belie, F. et al., Crit. Rev. Ther. Drug Carrier Syst., 14, pp. 221-286, 1997; Yamashita, S. et al., Eur. J. Pharm. Sci., 10, pp. 195-204, 2000; Ingels, F. M. et al., J. Pharm. Sci., 92, pp. 1545-1558, 2003), method of measuring cell membrane permeability of a compound in an in vitro cell culture system using MDCK cells (Irvine, J. D. et al., J. Pharm. Sci., 88, pp. 28-33, 1999), and the like. By elucidating cell permeability of the compounds based on one or more of these methods, usefulness of the compounds as active ingredients of medicaments can be confirmed.

Usefulness of the compounds of the present invention represented by the aforementioned formula (1) and salts thereof as well as derivatives thereof useful as prodrugs as active ingredients of medicaments can be confirmed by performing, for example, a drug transporter ATPase assay as ATP-binding cassette (ABC) transporter. Examples of the drug transporter ATPase assay include the method of examining whether a compound is a substrate of P-glycoprotein (P-gp) by using a P-gp baculovirus expression system (Germann, U. A., Methods Enzymol., 292, pp. 427-41, 1998), and the like. Moreover, the usefulness can be confirmed by performing, for example, a transportation test as a solute carrier (SLC) transporter using oocytes extracted from platanna (*Xenopus laevis*). Examples of the transportation test include the method of examining whether a compound is a substrate of ATP2 or not by using OATP2-expressing oocytes (Tamai I. et. al., Pharm Res., 2001 Sep., 18(9):1262-1269). By elucidating action of the compounds on the ABC transporter or SLC transporter based on these methods, usefulness of the compounds as active ingredients of medicaments can be confirmed.

Usefulness of the compounds of the present invention represented by the aforementioned formula (1) and salts thereof as well as derivatives thereof useful as prodrugs as active ingredients of medicaments can be confirmed by performing, for example, an oral absorption test. Examples of the oral absorption test include a method of orally administering a compound of a certain amount dissolved or suspended in an appropriate solvent to a rodent, monkey, dog or the like, and measuring blood level of the compound after the oral administration over time to evaluate blood transition of the compound by oral administration using the LC-MS/MS method ("Newest Mass Spectrometry for Life Science", Kodansha Scientific, 2002, edited by Harada K. et al, and the like), and the like. By elucidating oral absorption of the compounds based on these methods, usefulness of the compounds as active ingredients of medicaments can be confirmed.

Usefulness of the compounds of the present invention represented by the aforementioned formula (1) and salts thereof as well as derivatives thereof useful as prodrugs as active ingredients of medicaments can be confirmed by performing, for example, a blood concentration transition measurement test. Examples of the blood concentration transition measurement test include a method of orally or parenterally (e.g., intravenously, intramuscularly, intraperitoneally, subcutaneously, transdermally, by instillation, transnasally, and the like) administering a compound to a rodent, monkey, dog or the like, and measuring change of the blood level of the compound over time after the administration using the LC-MS/MS method ("Newest Mass Spectrometry for Life Science", Kodansha Scientific, 2002, edited by Harada K. et al, and the like), and the like. By elucidating blood concentration transition of the compounds based on these methods, usefulness of the compounds as active ingredients of medicaments can be confirmed.

Usefulness of the compounds of the present invention represented by the aforementioned formula (1) and salts thereof as well as derivatives thereof useful as prodrugs as active ingredients of medicaments can be confirmed by performing, for example, a metabolic test. Examples of the metabolic test include the blood stability test method (method of predicting metabolic clearance in vivo based on metabolic rate of a compound in hepatic microsomes of human or other animal species (refer to Shou, W. Z. et al., J. Mass Spectrom., 40 (10) pp. 1347-1356, 2005; L1, C. et al., Drug Metab. Dispos., 34 (6), 901-905, 2006, and the like), metabolite molecular species test method, reactive metabolite test method, and the like. By elucidating metabolic profile of the compounds based on one or more of these methods, usefulness of the compounds as active ingredients of medicaments can be confirmed.

Usefulness of the compounds of the present invention represented by the aforementioned formula (1) and salts thereof as well as derivatives thereof useful as prodrugs as active ingredients of medicaments can be confirmed by performing, for example, a solubility test. Examples of method for evaluating solubility in water include methods of confirming solubility under an acidic condition, neutral condition, or basic condition, and also include confirming change of solubility in the presence of bile acid. Examples of the solubility test include the solubility test based on the turbidity method (Lipinski, C. A. et al., Adv. Drug Deliv. Rev., 23, pp. 3-26, 1997; Bevan, C. D. et al., Anal. Chem., 72, pp. 1781-1787, 2000), and the like. By elucidating solubility of the compounds based on these methods, usefulness of the compounds as active ingredients of medicaments can be confirmed.

Usefulness of the compounds of the present invention represented by the aforementioned formula (1) and salts thereof as well as derivatives thereof useful as prodrugs as active ingredients of medicaments can be confirmed by examining, for example, upper gastrointestinal injury, renal dysfunction, and the like. As a pharmacological test for the upper gastrointestinal tract, actions on gastric mucosa can be investigated by using a starved rat gastric mucosa injury model. Examples of pharmacological test for kidney functions include renal blood flow and glomerular filtration rate measuring method [Physiology, 18th edition, Bunkodo, 1986, Chapter 17], and the like. By elucidating actions of the compounds on the upper gastrointestinal tract and renal functions using two or more of these methods, usefulness of the compounds as active ingredients of medicaments can be confirmed.

EXAMPLES

Hereafter, the present invention will be further specifically explained with reference to examples. However, the scope of the present invention is not limited to the following examples.

In the examples, for thin layer chromatography (TLC), Precoated Silica Gel 60 F254 (produced by Merck, product number: 5715-1M)) was used. After development with chloroform:methanol (1:0 to 1:1), acetonitrile:acetic acid:water (200:1:1 to 100:4:4) or ethyl acetate:hexane (1:0 to 0:1), spots were observed by UV irradiation (254 nm or 365 nm) or coloration with iodine solution, aqueous potassium permanganate, phosphomolybdic acid (ethanol solution), ninhydrine or dinitrophenylhydrazine solution in hydrochloric acid. For drying organic solvent, anhydrous magnesium sulfate or anhydrous sodium sulfate was used. As for column chromatography, the indication of "Quad" means use of Quad 1 preparative chromatography system (produced by Biotage), and one or several columns selected from cartridge columns KP-Sil-12M, 40S and 40M produced by the same manufacturer were used depending on the amount of sample. The indication of "Yamazen" means use of Multi Prep YFLC (produced by Yamazen Corporation), and any of the columns of same manufacturer, Ultra Pack Si-40A, 40B and 40D was used as the column. The indication of "MORITEX" means use of 2-ch parallel purification apparatus "Purif-α 2(50F)" produced by MORITEX Corporation, and a column of Purif-Pac k-Si series produced by same manufacturer was used as the column. For flash column chromatography, Silica gel 60N (spherical shape, neutral, 40 to 100 μm, produced by Kanto Chemicals) was used. Preparative thin layer chromatography (hereinafter abbreviated as "PTLC") was performed by using one or several plates of PLC Plate Silica Gel 60 F254 (20×20 cm, thickness: 2 mm, concentration zone: 4 cm, produced by Merck, product number: 13793-1M) were used depending on the amount of sample. For HPLC purification, LC-10A (Shimadzu Corporation) was used, Develosil C-30-UG-5 (Nomura Chemical Co., Ltd.) was used as a column, and water/acetonitrile solvent containing 0.1% acetic acid was used as the eluent. As the liquid chromatography device used in the "preparation of chiral compounds", Shimadzu LC6A system (Shimadzu Corporation) was used. As the separation column, Chiralcel OJ-RH (20 mm (I.D.)×250 mm, Daicel Chemical Industries, Ltd.) was used. Elution was performed under conditions of a flow rate of 10 ml/minute with a solvent consisting of 70% Solution B in Solution A, wherein Solution A is water, and Solution B is acetonitrile. When purification was performed by HPLC, the solvent was removed by lyophilization to obtain the object compound, unless particularly indicated. For the measurement of nuclear magnetic resonance (NMR) spectra, the measurement was performed by using Gemini-300 (FT-NMR, produced by Varian) or AL-300 (FT-NMR, JEOL Co., Ltd.). As the solvent, deuterated chloroform ($CDCl_3$) was used unless specifically indicated, and chemical shifts were measured by using tetramethylsilane (TMS) as an internal standard, and indicated with δ (ppm). Binding constant was indicated with J (Hz).

For "LCMS", mass spectrum was measured by liquid chromatography-mass spectrometry (LC-MS). For the analysis, either of the apparatuses of the following (A) and (B) was used.

(A) A Platform-LC type mass spectrometry apparatus (produced by Micromass) was used as the mass spectrometer, and the measurement was performed by the electrospray ionization (ESI) method. As the liquid chromatography apparatus, an apparatus produced by GILSON was used. As the separation column, Develosil C30-UG-5 (50×4.6 mm, produced by Nomura Chemical Co., Ltd.) was used. Elution was generally performed at a flow rate of 2 ml/minute using a linear gradient of 5 to 98% (v/v) Solution B [acetonitrile containing 0.1% (v/v) acetic acid] in Solution A [water containing 0.1% (v/v) acetic acid] as the solvent from 0 minute to 4 minutes, and then 98% Solution B up to 6 minutes.

(B) A single quadrupole type mass spectrometry apparatus, HPLC/SQD System (produced by Waters) was used as the mass spectrometer, and the measurement was performed by the electrospray ionization (ESI) method. As the liquid chromatography apparatus, Acquity Ultra Performance LC produced by Waters was used. As the separation column, ACQUITY HPLC BEH C18 (2.1×50 mm, 1.7 μm, produced by Waters) was used. Elution was generally performed at a flow rate of 0.6 ml/minute using a linear gradient of 5 to 90% (v/v) Solution B [acetonitrile containing 0.1% (v/v) acetic acid] in Solution A [water containing 0.1% (v/v) acetic acid] from 0 minute to 2.0 minutes, and then a linear gradient of 90 to 98% Solution B from 2.0 to 2.5 minutes.

In the following examples, the indications "Example Compound x-y-z" refers to the final product in "Example x-y-z". For example, "Example Compound 1-1-2" refers to "the final product of Example 1-1-2", i.e., 3-(2-hydroxy-4-methoxy-5-(1-methyl-1H-indazol-5-yl)phenyl)propanoic acid. Further, meanings of the abbreviations and the like used in the text are as described later.

Reference Example 1-1

Synthesis of 7-hydroxychroman-2-one (Intermediate 1)

A solution of hydroxycoumarin (2.0 g, TCI) in anhydrous THF (50 ml) was added with 10% palladium hydroxide/activated carbon (1.0 g, WAKO), and stirred at room temperature for 2 hours under hydrogen atmosphere. The atmosphere was replaced with nitrogen gas, and then the insoluble matters were removed by filtration through Celite. The solvent was evaporated under reduced pressure to obtain the title compound (2.0 g).

(LCMS: 163.0 (MH$^-$), Retention time: 3.03 minutes, LCMS condition: A)

Example 1-1-2

Synthesis of 3-(2-hydroxy-4-methoxy-5-(1-methyl-1H-indazol-5-yl)phenyl)propanoic acid

[Step A] Synthesis of 6-bromo-7-hydroxychroman-2-one (Intermediate 2)

A solution of Intermediate 1 (20 g) in acetonitrile (50 ml) was added with N-bromosuccinimide (20 g, WAKO) under ice cooling, and stirred for 10 minutes under ice cooling, and then stirred at room temperature for 1 hour. The reaction mixture was concentrated under reduced pressure, and then recrystallized from acetonitrile to obtain the title compound (15 g).

(Intermediate 2, LCMS: 240.9 (MH$^-$), Retention time: 3.25 minutes, LCMS condition: B)

[Step B] Synthesis of 6-bromo-7-methoxychroman-2-one (Intermediate 3)

A solution of Intermediate 2 (5.0 g) in THF (20 ml) was added with diethyl azodicarboxylate (4.1 g, Ald), triphenylphosphine (8.0 g, WAKO), and methanol (990 μl, KANTO), and stirred for 4 hours. The reaction mixture was added with water (100 ml) and dichloromethane (20 ml×2) and extracted, the organic layer was successively washed with saturated aqueous sodium hydrogencarbonate, saturated aqueous ammonium chloride, and saturated brine, and dried, and the solvent was evaporated under reduced pressure. The residue was purified by column chromatography (Yamazen, n-hexane:ethyl acetate=3:1) to obtain the title compound (3.0 g).

(Intermediate 3, LCMS: 254.9 (MH$^-$), Retention time: 3.64 minutes, LCMS condition: A)

[Step C] Synthesis of 3-(2-hydroxy-4-methoxy-5-(1-methyl-1H-indazol-5-yl)phenyl)propanoic acid A solution of Intermediate 3 (4.2 g) in dimethoxyethane (50 ml) was added with 1-methyl-1H-indazol-5-ylboronic acid (rgt1, 4.3 g), potassium carbonate (4.5 g), water (50 ml), and tetrakistriphenylphosphinepalladium(0) [henceforth abbreviated as Pd(PPh$_3$)$_4$] (2.7 g, Nacarai), and stirred at 90° C. for 14 hours. This reaction mixture was added with 2 N aqueous sodium hydroxide (5 ml), and further stirred at 80° C. for 0.5 hour. The reaction mixture was added with 1 N aqueous hydrochloric acid (10 ml), and extracted with diethyl ether (30 ml×2), and then the aqueous layer was neutralized with 5 N aqueous hydrochloric acid, and extracted with ethyl acetate. The reaction mixture was washed with saturated aqueous sodium hydrogencarbonate, the organic layer was dried, and then the solvent was evaporated under reduced pressure to obtain the title compound (3.3 g).

Example 1-1-1

Synthesis of methyl 3-(2-hydroxy-4-methoxy-5-(1-methyl-1H-indazol-5-yl)phenyl)propanoate A solution of Example Compound 1-1-2 (3.3 g) in methanol (50 ml) was added with TsOH (200 mg, WAKO), and stirred at 60° C. for 1 hour under nitrogen atmosphere. The reaction mixture was added with water (30 ml), and ethyl acetate (30 ml×2) for extraction, and then washed with saturated aqueous sodium hydrogencarbonate, the organic layer was dried, and then the solvent was evaporated under reduced pressure. The residue was purified by column chromatography (Yamazen, n-hexane:ethyl acetate=3:1), and the solvent was evaporated under reduced pressure by using a rotary evaporator to obtain the title compound (3.3 g).

Example 2-1-1

Synthesis of methyl 3-(4-methoxy-2-methyl-5-(1-methyl-1H-indazol-5-yl)phenyl)propanoate

[Step D] Synthesis of methyl 3-(4-methoxy-5-(1-methyl-1H-indazol-5-yl)-2-(trifluoromethylsulfonyloxy)phenyl)propanoate (Intermediate 4)

A solution of Example Compound 1-1-1 (3.3 g) in dichloromethane (20 ml) was added with pyridine (4.0 ml, WAKO), then added with Tf$_2$O (2.0 ml, TCI) under ice cooling, and stirred at room temperature for 3 hours under nitrogen atmosphere. The reaction mixture was added with methanol (2 ml), and the solvent was evaporated under reduced pressure. The residue was purified by column chromatography (Yamazen, n-hexane:ethyl acetate=3:1), and the solvent was evaporated under reduced pressure by using a rotary evaporator to obtain the title compound (yield: 2.0 g).

(Intermediate 4, LCMS: 473.2 (MH+), Retention time: 5.09 minutes, LCMS condition: A)

[Step E] Synthesis of methyl 3-(4-methoxy-2-methyl-5-(1-methyl-1H-indazol-5-yl)-phenyl)propanoate A solution of Intermediate 4 (23 mg) in DMF (1.0 ml) was added with methyl boronic acid (18 mg, Ald), sodium carbonate (30 mg), and PdCl$_2$dppf.CH$_2$Cl$_2$ (8.0 mg, Ald), and stirred at 120° C. for 8 hours. The reaction mixture was added with water (30 ml), and ethyl acetate (30 ml×2) for extraction, and then successively washed with saturated aqueous sodium hydrogencarbonate, saturated aqueous ammonium chloride, and saturated brine, the organic layer was dried, and then the solvent was evaporated under reduced pressure. The residue was purified by column chromatography (Yamazen, n-hexane:ethyl acetate=3:1), and the solvent was evaporated under reduced pressure by using a rotary evaporator to obtain the title compound (yield: 15 mg).

Example 2-1-2

Synthesis of 3-(4-methoxy-2-methyl-5-(1-methyl-1H-indazol-5-yl)phenyl)propanoic acid A solution of Example Compound 2-1-1 (30 mg) in methanol (500 µl) was added with 2 N aqueous sodium hydroxide (500 µl), and stirred at 60° C. for 2 hours. The reaction mixture was concentrated under reduced pressure, neutralized with 1 N aqueous hydrochloric acid under ice cooling, and then extracted with methylene chloride (2 ml×3). The organic layer was washed with saturated brine, and dried, and then the solvent was evaporated under reduced pressure to obtain the title compound (25 mg).

Example 2-2-1

Synthesis of methyl 3-(4-hydroxy-2-methyl-5-(1-methyl-1H-indazol-5-yl)phenyl)propanoate A solution of Example Compound 2-1-1 (700 mg) in dichloromethane (5.0 ml) was added with a solution of boron tribromide in dichloromethane (1.0 M, 4.0 ml, Ald) at −78° C., stirred at for 30 minutes, and then stirred at room temperature for 2 hours. The reaction mixture was added with methanol (1.0 ml), then added with water (30 ml) and ethyl acetate (30 ml×2) for extraction, and successively washed with saturated aqueous sodium hydrogencarbonate, saturated aqueous ammonium chloride, and saturated brine, the organic layer was dried, and then the solvent was evaporated under reduced pressure. The residue was purified by column chromatography (Yamazen, n-hexane:ethyl acetate=3:1), and the solvent was evaporated under reduced pressure by using a rotary evaporator to obtain the title compound (yield: 690 mg).

Example 2-2-2

Synthesis of 3-(4-hydroxy-2-methyl-5-(1-methyl-1H-indazol-5-yl)-phenyl)propanoic acid A solution of Example Compound 2-2-1 (30 mg) in methanol (500 µl) was added with 2 N aqueous sodium hydroxide (500 µl), and stirred fort hours. The reaction mixture was neutralized with 1 N aqueous hydrochloric acid under ice cooling, concentrated under reduced pressure, and filtered to obtain the title compound (30 mg).

Example 2-3-2

Synthesis of methyl 3-(4-(4-fluorobenzyloxy)-2-methyl-5-(1-methyl-1H-indazol-5-yl)phenyl)propanoate A solution of Example Compound 2-2-1 (15 mg) in DMF (1 ml) was added with potassium carbonate (16 mg, WAKO) and 4-fluorobenzyl bromide (18.8 mg, TCI), and stirred at room temperature for 12 hours. The reaction mixture was concentrated, then added with THF (500 µl) and 2 N aqueous sodium hydroxide (500 µl), and stirred at 60° C. for 2 hours. The reaction mixture was concentrated under reduced pressure, then neutralized with 1 N aqueous hydrochloric acid under ice cooling, and then extracted with methylene chloride (2 ml×3). The organic layer was washed with saturated brine, and dried, and then the solvent was evaporated under reduced pressure to obtain the title compound (yield: 10 mg).

Example 2-4-2

Synthesis of methyl 3-(4-(3-fluorobenzyloxy)-2-methyl-5-(1-methyl-1H-indazol-5-yl)phenyl)propanoate The title compound was obtained (yield: 10 mg) from Example Compound 2-2-1 (15 mg) and 3-fluorobenzyl bromide (18.8 mg, TCI) according to the method of Example 2-3-2.

Example 1-5-2

Synthesis of 3-(4-(2,3-dihydro-1H-inden-2-yloxy)-2-hydroxy-5-(1-methyl-1H-indazol-5-yl)phenyl)propanoic acid 6-Bromo-7-(2,3-dihydro-1H-inden-2-yloxy)chroman-2-one (1.25 g, Intermediate 5) can be obtained from Intermediate 2 (1.0 g) and 2-hydroxyindane (henceforth abbreviated as "sm5", 830 mg, LANC) according to the method of Example 1-1-2, Step B. The title compound was obtained (yield: 690 mg) from Intermediate 5 (500 mg) according to the method of Example 1-1-2, Step C.

(Intermediate 5, LCMS: N.D. (MH+), Retention time: 5.31 minutes, LCMS condition: A)

Example 1-5-1

Synthesis of methyl 3-(4-(2,3-dihydro-1H-inden-2-yloxy)-2-hydroxy-5-(1-methyl-1H-indazol-5-yl)phenyl)propanoate The title compound was obtained (yield: 300 mg) from Example Compound 1-5-2 (300 mg) according to the method of Example 1-1-1.

Example 2-5-1

Synthesis of methyl 3-(4-(2,3-dihydro-1H-inden-2-yloxy)-2-methyl-5-(1-methyl-1H-indazol-5-yl)phenyl)propanoate Methyl 3-(4-(2,3-dihydro-1H-inden-2-yloxy)-5-(1-methyl-1H-indazol-5-yl)-2-(trifluoromethylsulfonyloxy)phenyl)propanoate (Intermediate 6) can be obtained (yield: 110 mg) from Example Compound 1-5-1 (100 mg) according to the method of Example 2-1-1, Step D. The title compound was obtained (yield: 80 mg) from Intermediate 6 (100 mg) according to the method of Example 2-1-1, Step E.

Intermediate 6: (LCMS: 575 (MH+), Retention time: 6.11 minutes, LCMS condition: A)

Example 3-5-1

Synthesis of methyl 3-(4-(2,3-dihydro-1H-inden-2-yloxy)-5-(1-methyl-1H-indazol-5-yl)-2-vinylphenyl)propanoate The title compound was obtained (yield: 80 mg) from Intermediate 6 (100 mg) and 2,4,6-trivinylcyclotriboroxane-pyridine complex (99 mg, Acros) according to the method of Example 2-1-1, Step E.

Example 4-5-1

Synthesis of methyl 3-(4-(2,3-dihydro-1H-inden-2-yloxy)-2-methoxy-5-(1-methyl-1H-indazol-5-yl)phenyl)propanoate The title compound (42 mg) was obtained from Example Compound 1-5-1 (40 mg) and methyl iodide (42 mg, TCI) according to the method of the first half of Example 2-3-2.

Example 5-5-1

Synthesis of methyl 3-(4-(2,3-dihydro-1H-inden-2-yloxy)-2-ethyl-5-(1-methyl-1H-indazol-5-yl)phenyl)propanoate A solution of Example Compound 3-5-1 (29 mg) in dimethoxyethane (1.0 ml) was added with p-toluenesulfone hydrazide (71 mg, KANTO) and an aqueous solution (0.5 ml) of sodium acetate (47 mg, WAKO), and stirred at 80° C. for 15 hours. The reaction mixture was added with water (3 ml), and added with ethyl acetate (3 ml×2) for extraction, and then successively washed with saturated aqueous sodium hydrogencarbonate, saturated aqueous ammonium chloride, and saturated brine, the organic layer was dried, and then the solvent was evaporated under reduced pressure. The residue was purified by column chromatography (Yamazen, n-hexane:ethyl acetate=3:1), and the solvent was evaporated under reduced pressure by using a rotary evaporator to obtain the title compound (yield: 25 mg).

Example 6-5-1

Synthesis of methyl 3-(4-(2,3-dihydro-1H-inden-2-yloxy)-2-cyano-5-(1-methyl-1H-indazol-5-yl)phenyl)propanoate A solution of Intermediate 6 (30 mg) in N,N-dimethylacetamide (1 ml) was added with $K_4[Fe(CN)_6] \cdot 3H_2O$ (6.6 mg, Ald), sodium carbonate (5.5 mg), and palladium acetate (1.1 mg, WAKO), and stirred at 120° C. for 5 hours. The reaction mixture was added with water (3 ml), and ethyl acetate (3 ml×2) for extraction, and then successively washed with saturated aqueous sodium hydrogencarbonate, saturated aqueous ammonium chloride, and saturated brine, the organic layer was dried, and then the solvent was evaporated under reduced pressure. The residue was purified by column chromatography (Yamazen, n-hexane:ethyl acetate=3:1), and the solvent was evaporated under reduced pressure by using a rotary evaporator to obtain the title compound (yield: 10 mg).

Synthesis by Preparation Method 2

Example 2-N1-1

Synthesis of methyl 3-(4-amino-2-methyl-5-(1-methyl-1H-indazol-5-yl)phenyl)propanoate

[Step a] Synthesis of (E)-methyl 3-(4-amino-2-methylphenyl)acrylate (Intermediate 7)

A solution of 4-bromo-3-methylaniline (5 g, TCI) in triethylamine (50 ml) was added with methyl acrylate (3.6 ml, TCI), tris(2-methylphenyl)phosphine (2.5 g, TCI), and palladium acetate (606 mg, WAKO), and stirred at 90° C. for 18 hours. The reaction mixture was added with water (30 ml) and ethyl acetate (30 ml×2) for extraction, and then successively washed with saturated aqueous sodium hydrogencarbonate, saturated aqueous ammonium chloride, and saturated brine, the organic layer was dried, and the solvent was evaporated under reduced pressure. The residue was purified by column chromatography (Yamazen, n-hexane:ethyl acetate=3:1), and the solvent was evaporated under reduced pressure by using a rotary evaporator to obtain the title compound (yield: 4.0 g).

(Intermediate 7, LCMS: 192.4 (MH+), Retention time: 1.25 minutes, LCMS condition: B)

[Step b] Synthesis of methyl 3-(4-amino-2-methylphenyl)propanoate (Intermediate 8)

A reaction was performed according to the synthesis method of Intermediate 1 by using Intermediate 7 (2.0 g) and 10% palladium hydroxide/activated carbon (1.5 g). The reaction mixture was filtered through Celite, and the solvent of the filtrate was evaporated under reduced pressure. The residue was purified by column chromatography (Yamazen, n-hexane:ethyl acetate=3:1), and the solvent was evaporated under reduced pressure by using a rotary evaporator to obtain the title compound (1.5 g) (the reaction was performed in THF solvent (20 ml) for 20 hours).

(Intermediate 8, LCMS: 194.3 (MH+), Retention time: 2.13 minutes, LCMS condition: A)

[Step c] Synthesis of methyl 3-(4-amino-5-bromo-2-methylphenyl)propanoate (Intermediate 9)

A solution of Intermediate 8 (1.4 g) in acetonitrile (20 ml) was added with N-bromosuccinimide (1.4 g, WAKO) under ice cooling, stirred for 10 minutes under ice cooling, and then stirred at room temperature for 3 hours. The reaction mixture was concentrated under reduced pressure, then added with ethyl acetate (10 ml), and successively washed with saturated aqueous ammonium chloride, 5% aqueous sodium sulfite, saturated aqueous sodium hydrogencarbonate and saturated brine, the organic layer was dried, and then the solvent was evaporated under reduced pressure. The residue was purified by column chromatography (Yamazen, n-hexane:ethyl acetate=3:1) to obtain the title compound (1.0 g).

(Intermediate 9, LCMS: 272.2 (MH+), Retention time: 1.51 minutes, LCMS condition: B)

[Step d] Synthesis of methyl 3-(4-amino-2-methyl-5-(1-methyl-1H-indazol-5-yl)-phenyl)propanoate A solution of Intermediate 9 (460 mg) in 1,4-dioxane (5 ml, KANTO) was added with 1-methyl-1H-indazol-5-ylboronic acid (rgt1, 350 mg), cesium carbonate (410 mg, KANTO), and PdCl$_2$dppf.CH$_2$Cl$_2$ (115 mg, Ald), and stirred at 90° C. for 18 hours. The reaction mixture was cooled to room temperature, and then added with water (30 ml) and ethyl acetate (30 ml×2) to perform extraction. The reaction mixture was successively washed with saturated aqueous sodium hydrogencarbonate, saturated aqueous ammonium chloride, and saturated brine, the organic layer was dried, and then the solvent was evaporated under reduced pressure. The residue was purified by column chromatography (Yamazen, n-hexane:ethyl acetate=3:1), and the solvent was evaporated under reduced pressure by using a rotary evaporator to obtain the title compound (400 mg).

Example 7-N1-1

Synthesis of methyl 3-(4-amino-2-chloro-5-(1-methyl-1H-indazol-5-yl)phenyl)propanoate (E)-Methyl 3-(4-amino-2-chlorophenyl)acrylate (Intermediate 10) was obtained from 3-chloro-4-iodoaniline (6.8 g, TCI) according to the method of Example 2-N1-1, Step a (yield: 5.2 g). From this Intermediate 10 (2.5 g) and 10% Pd/carbon powder (N.E. Chemcat), methyl 3-(4-amino-2-chlorophenyl)propanoate (Intermediate 11) was obtained (yield: 2.5 g) according to the method of Example 2-N1-1, Step b. From this Intermediate 11 (1.0 g), methyl 3-(4-amino-5-bromo-2-chlorophenyl)propanoate (Intermediate 12) was obtained (yield: 800 mg) according to the method of Example 2-N1-1, Step c. From this Intermediate 12 (1.0 g), the title compound was obtained (yield: 900 mg) according to the method of Example 2-N1-1, Step d.

(Intermediate 10, LCMS: 212.0 (MH+), Retention time: 1.38 minutes, LCMS condition: B)

(Intermediate 11, LCMS: 214.1 (MH+), Retention time: 3.54 minutes, LCMS condition: A)

(Intermediate 12, LCMS: 291.9 (MH+), Retention time: 1.62 minutes, LCMS condition: B)

Example 8-N1-1

Synthesis of methyl 3-(4-amino-5-(1-methyl-1H-indazol-5-yl)-2-(trifluoromethyl)phenyl)propanoate From 4-bromo-3-trifluoromethylaniline (6.5 g, WAKO), (E)-methyl 3-(4-amino-2-(trifluoromethyl)phenyl)acrylate (Intermediate 13) can be obtained (yield: 4.0 g) according to the method of Example 2-N1-1, Step a. From this Intermediate 13 (100 mg) and 10% Pd/carbon powder (N.E. Chemcat), methyl 3-(4-amino-2-(trifluoromethyl)phenyl)propanoate (Intermediate 14) was obtained (yield: 100 mg) according to the method of Example 2-N1-1, Step b.

From this Intermediate 14 (3.5 g), methyl 3-(4-amino-5-bromo-2-(trifluoromethyl)phenyl)propanoate (Intermediate 15) was obtained (yield: 2.1 g) according to the method of Example 2-N1-1, Step c. From this Intermediate 15 (100 mg), the title compound was obtained (yield: 80 mg) according to the method of Example 2-N1-1, Step d.

(Intermediate 13, LCMS: 246.0 (MH+), Retention time: 1.58 minutes, LCMS condition: B)

(Intermediate 14, LCMS: 248.2 (MH+), Retention time: 3.74 minutes, LCMS condition: A)

(Intermediate 15, LCMS: 367.1 (MH+), Retention time: 4.44 minutes, LCMS condition: A)

Example 2-N2-1

Synthesis of methyl 3-(2-methyl-5-(1-methyl-1H-indazol-5-yl)-4-(4-(trifluoromethyl)phenylsulfoneamido)phenyl)propanoate [Step e1]

A solution of Example Compound 2-N1-1 (20 mg) and 4-(trifluoromethyl)benzenesulfonyl chloride (24 mg, TCI) in methylene chloride (0.5 ml) was added with pyridine (0.5 ml, WAKO) at 0° C., and stirred at the same temperature for 30 minutes, and then at room temperature for further 5 hours. The reaction mixture was washed with saturated brine (10 ml), and then dried over anhydrous magnesium sulfate. The solvent was evaporated under reduced pressure, and then the residue was purified by silica gel column chromatography (Yamazen, n-hexane:ethyl acetate=1:1) to obtain the title compound (15 mg).

Example 2-N2-1

Synthesis of methyl 3-(2-methyl-5-(1-methyl-1H-indazol-5-yl)-4-(4-(trifluoromethyl)phenylsulfonamido)phenyl)propanoate [Step e2]

A solution of Example Compound 2-N1-1 (20 mg) in methylene chloride (0.45 ml) was added with a solution of 4-(trifluoromethyl)benzenesulfonyl chloride (44 mg, TCI) in methylene chloride (0.4 ml), and pyridine (0.15 ml, KANTO) at room temperature, and stirred for 18 hours by vibration. The reaction mixture was added with PS-trisamine resin (tris-(2-aminoethyl)amine polystyrene, 100 mg, Argonaut), and stirred at room temperature for 1 hour with stirring by vibration. The reaction mixture was filtered, then added with a solution of tetrafluorophthalic anhydride (26 mg, Ald) in THF, and stirred for 2 hours by vibration. The reaction mixture was added with the PS-trisamine resin (300 mg, Argonaut), and stirred at room temperature for 2 hours by vibration. The reaction mixture was filtered, and the solvent was evaporated to obtain the title compound (15 mg).

Example 2-N101-1

Synthesis of methyl 3-(2-methyl-5-(1-methyl-1H-indazol-5-yl)-4-(4-(trifluoromethyl)benzamido)phenyl)propanoate [Step e3]

A solution of Example Compound 2-N1-1 (20 mg) in methylene chloride (0.20 ml) was added with a solution of 4-(trifluoromethyl)benzenecarbonyl chloride (25 mg, TCI) in methylene chloride (0.2 ml) and triethylamine (0.40 ml, WAKO) at room temperature, and stirred for 17 hours by vibration. The reaction mixture was added with PS-trisamine resin (75 mg, Argonaut), and stirred at room temperature for 2 hours by vibration. The reaction mixture was further added with the PS-trisamine resin (75 mg, Argonaut), MP-carbonate (150 mg), and methylene chloride, and stirred at room temperature for 3 hours by vibration. The reaction mixture was filtered, and then further added with the PS-trisamine resin (75 mg, Argonaut) and MP-carbonate (150 mg, Argonaut), and stirred at room temperature for 17 hours by vibration. The reaction mixture was filtered, and the solvent was evaporated to obtain the title compound (21 mg).

Example 2-N301-1

Synthesis of methyl 3-(4-(isopropylamino)-2-methyl-5-(1-methyl-1H-indazol-5-yl)phenyl)propanoate [Step f1]

A solution of Example Compound 2-N1-1 (32 mg) in methanol (1 ml) was added with acetic acid (6 mg, WAKO)

and acetone (8.7 mg, KANTO), stirred at room temperature for 30 minutes, then added with a solution of sodium cyanotrihydroborate in THF (1 M, 0.2 ml, Ald), and further stirred at room temperature for 4 hours. The reaction mixture was added with saturated aqueous sodium hydrogencarbonate (15 ml) and ethyl acetate to extract the organic layer, and washed saturated brine (30 ml), and then the solvent was evaporated. The residue was purified by silica gel column chromatography (Yamazen, n-hexane:ethyl acetate=1:1) to obtain the title compound (49 mg).

Example 2-N302-1

Synthesis of methyl 3-(4-(isopropyl(methyl)amino)-2-methyl-5-(1-methyl-1H-indazol-5-yl)phenyl)propanoate [Step f2]

The title compound was obtained (yield: 22 mg) by reacting Example Compound 2-N301-1 (30 mg) and formaldehyde (30% aqueous solution, 0.1 ml, WAKO) and treating the resultant according to the synthesis method of Example Compound 2-N301-1.

Example 2-C1-1

Synthesis of (E)-methyl 3-(2-methyl-5-(1-methyl-1H-indazol-5-yl)-4-(4-(trifluoromethyl)styryl)phenyl)propanoate Example Compound 2-N1-1 (324 mg) was dissolved in a 50% aqueous solution of HBF$_4$ (0.5 ml), and this solution was added dropwise with an aqueous solution (0.5 ml) of sodium nitrite (83 mg) under ice cooling. The reaction mixture was stirred for 30 minutes, and then the precipitates were collected by filtration to obtain 4-(2-methoxycarbonylethyl)-5-methyl-2-(1-methyl-1H-indazol-5-yl)benzene diazonium tetrafluoroborate (Intermediate 16, yield: 200 mg). A solution of this Intermediate 16 (200 mg) in 1,4-dioxane (1 ml) was successively added with water (1 ml), (E)-4-(trifluoromethyl)styrylboronic acid (200 mg, Ald), and Pd(OAc)$_2$ (20 mg, Ald), and stirred at room temperature for 3 hours. The reaction mixture was added with saturated aqueous sodium hydrogencarbonate (15 ml) and ethyl acetate to extract the organic layer, and washed with saturated brine (30 ml), and then solvent was evaporated. The residue was purified by silica gel column chromatography (Yamazen, n-hexane:ethyl acetate=3:1) to obtain the title compound (30 mg).

Example 7-N304-1

Synthesis of methyl 3-(2-chloro-4-(isobutylamino)-5-(1-methyl-1H-indazol-5-yl)phenyl)propanoate A solution of Example Compound 7-N1-1 (34 mg) in methanol (2.0 ml) was added with acetic acid (6 μL, WAKO), isobutylaldehyde (9 μL, TCI), stirred at room temperature for about 30 minutes, then added with a solution of sodium cyanotrihydroborate in THF (1 M, 0.2 ml, Ald), and stirred overnight at room temperature. The reaction mixture was added with saturated aqueous sodium hydrogencarbonate (1 ml) and ethyl acetate, then the organic layer was extracted, and the solvent was evaporated. The residue was purified by using a silica gel column to obtain the title compound (46 mg).

Example 7-N304-2

Synthesis of 3-(2-chloro-4-(isobutylamino)-5-(1-methyl-1H-indazol-5-yl)phenyl)propanoic acid A solution of Example Compound 7-N304-1 (10 mg) in methanol (1 ml) was added with 2 N aqueous sodium hydroxide (1 ml), and stirred for 3 hours. The reaction mixture was concentrated under reduced pressure, neutralized with 1 N aqueous hydrochloric acid under ice cooling, and then extracted with ethyl acetate. The solvent was evaporated under reduced pressure to obtain the title compound (8 mg).

Example 7-N305-1

Synthesis of methyl 3-(2-chloro-4-(isobutyl(methyl)amino)-5-(1-methyl-1H-indazol-5-yl)phenyl)propanoate The title compound was obtained (yield: 30 mg) by reacting Example Compound 7-N304-1 (40 mg) and formaldehyde (35% aqueous solution, 0.5 ml, KANTO) and treating the resultant according to the synthesis method of Example Compound 7-N304-1.

Example 7-N305-2

Synthesis of 3-(2-chloro-4-(isobutyl(methyl)amino)-5-(1-methyl-1H-indazol-5-yl)phenyl)propanoic acid A solution of Example Compound 7-N305-1 (10 mg) in methanol (1 ml) was added with 2 N aqueous sodium hydroxide (1 ml), and stirred for 3 hours. The reaction mixture was concentrated under reduced pressure, neutralized with 1 N aqueous hydrochloric acid under ice cooling, and then extracted with ethyl acetate. The solvent was evaporated under reduced pressure to obtain the title compound (8 mg).

Example 2-N316-1

Synthesis of methyl 3-(4-(cyclopentylamino)-2-methyl-5-(1-methyl-1H-indazol-5-yl)phenyl)propanoate A solution of Example Compound 2-N1-1 (32 mg) in methanol (1 ml) was added with acetic acid (7 μL, WAKO) and cyclopentanone (8.0 mg, Aldrich), stirred at room temperature for 60 minutes, then added with a solution of sodium cyanotrihydroborate in THF (1 M, 0.2 ml, Ald), and stirred overnight at room temperature. The reaction mixture was added with saturated aqueous sodium hydrogencarbonate (0.25 ml), then filtered, and washed (dichloromethane), the organic layer was extracted, and then solvent was evaporated. The residue was purified to obtain the title compound (17 mg).

Example 2-N338-1

Synthesis of methyl 3-(4-(cyclopentyl(methyl)amino)-2-methyl-5-(1-methyl-1H-indazol-5-yl)phenyl)propanoate The title compound was obtained (yield: 15 mg) by reacting Example Compound 2-N316-1 (30 mg) and formaldehyde (35% aqueous solution, 0.05 ml, KANTO), and treating the resultant according to the synthesis method of Example Compound 2-N316-1.

Data measured by the apparatuses in all the examples are shown in the tables mentioned below. Meanings of the symbols used in the tables are as follows.

"Exp.": Example numbers are indicated,

"G": Substituents corresponding to G in the general formula (1) are indicated. The abbreviations used in the tables correspond to the abbreviations for the groups explained below.

"SM1" and "SM2": Example numbers or intermediate numbers of starting materials are indicated (example numbers are indicated in the form of "Exp. —example number", and intermediate numbers are indicated in the form of "IM—intermediate number". For example, "IM-2" represents Intermediate 2). The abbreviations used for "SM2" represent the groups of the abbreviations used in the drawing mentioned below. For example, the starting materials described in the columns of "SM1" and "SM2" for Example 1-5-2 in Table 2-4 correspond to "Intermediate 5 (=IM-5)" and "sm5" mentioned in Example 1-5-2, respectively.

"X": The groups X in the general formula (1) are indicated.

"Y": The groups Y in the general formula (1) are indicated.

"Z": The groups Z in the general formula (1) are indicated.

"LCMS"; The data of liquid chromatography mass spectrometry spectra are indicated (m/z). Specifically, the data include those of "method", "RTime", and "mass" mentioned below.

"method": The LCMS conditions are indicated. When the condition is indicated as "A", it means that that the method (A) was used in the "LCMS" apparatus described above. When the condition is indicated as "B", it means that that the method (B) was used in the "LCMS" apparatus described above. When the condition is indicated as "C" in the columns of the condition, mass spectrum data measured by fast atom bombardment mass spectrometry (FAB-MS) using JEOL-JMS-SX102 (made by JEOL Co., Ltd.) are indicated.

"RTime": The retention times (minute) observed in LCMS are indicated.

"mass": The mass spectrum data (MH+ or MH−) are indicated (the indication "N.D." means that no molecular ion peak could be detected). The values of m/z in the columns of "mass" represent the values for the protonated molecular ions (MH+), unless particularly indicated.

"Ref.": The preparation methods for corresponding example compounds are indicated. The symbols mentioned in the columns of Ref. represent the preparation method for reference. For example, "Exp. 1-1-1" means the preparation method described in Example 1-1-1, and means that the compound can be synthesized in the same manner as that of the example. Further, "Exp. A" means the preparation method described in Example 1-1-1, step A. When an oblique line is indicated, it means that that example per se is described in the specification.

"Str.": The structures of "G" are indicated. When an arrow is indicated in the columns of Str., it indicates the bonding position to the compound of the general formula (1).

"Spl.": The manufacturers of the reagents used are indicated. The manufacturers of the reagents used may be indicated with the following abbreviations: "TCI": Tokyo Chemicals, "Ald": Aldrich, "sAld": Sigma Aldrich, "KANTO": Kanto Kagaku, "WAKO": Wako Pure Chemical Industries, "LANC": Lancaster, "MAYB": Maybridge, "Acros": Acros, "nakarai": Nakarai Tesque, "AAesar": Alfa Aesar, "Avocado": Avocado, "Fchem": FluoroChem, "Argonaut": Argonaut, "ABCR": ABCR, "Matrix": Matrix, "Array": Array BioPharma, "Oak": Oakwood, "MP Biomedicals": MP Biomedicals, "APOLLO": APOLLO, and "APIN": APIN.

The other abbreviations used in the text and the tables have the following meanings: n—: normal, i: iso, s: secondary, t: tertiary, c: cyclo, Me: methyl, Et: ethyl, Pr: propyl, Bu: butyl, Pen: pentyl, Hex: hexyl, Hep: heptyl, Ph: phenyl, Bn: benzyl, Py: pyridyl, Indan: indanyl, Ac: acetyl, CHO: formyl, COOH: carboxyl, NO2: nitro, DMA: dimethylamino, NH2: Amino, CF3: trifluoromethyl, F: fluoro, Cl: chloro, Br: bromo, CF3: trifluoromethyl, OMe: methoxy, OH: hydroxy, TFA: trifluoroacetyl, SO2: sulfonyl, CO: carbonyl, Nap: naphthyl, Ind: 1H-indolyl, 1HIdz: 1H-indazolyl, 2HIdz: 2H-indazolyl, Bzt: benzothiazole, 2ABzt: 2-aminobenzothiazole, BF: benzofuranyl, BT: benzo[b]thienyl, Qu: quinolyl, IQ: Isoquinolyl, THF: tetrahydrofuran, TsOH: p-toluenesulfonic acid, Tf2O: trifluoromethanesulfonic anhydride, and rgt1: 1-methyl-1H-indazol-5-ylboronic acid.

The numbers indicated before the substituents represent substitution positions. The numbers indicated before the abbreviations of aromatic rings with hyphens indicate the substitution positions on the aromatic rings. (S) mentioned in the compound names and structural formulas means that the corresponding asymmetric carbon is in the S-configuration, and (R) means that the corresponding asymmetric carbon is in the R-configuration. Further, when (R) or (S) is not indicated for a compound having an asymmetric carbon, it means that the compound was obtained as a racemic mixture of (R)-isomer and (S)-isomer at an arbitrary ratio.

When a hydrolysis reaction is performed in the synthesis process of the example compounds mentioned in the following tables, methanol, THF, or a mixed solvent thereof were appropriately used as the organic solvent used for the reaction. As for the synthesis of sm312, it is well known to those skilled in the art that said compound can be synthesized from the known compound: 2-bromothiazole-5-carboxualdehyde [known from, for example, WO2004/37818A1 (May 6, 2004), and the like] according to the methods described in the literature [Pereira, R. et al., Bioorganic & Medicinal Chemistry Letters, 2006, vol. 16, p. 49], or the references cited in the literature.

[Formula 8]

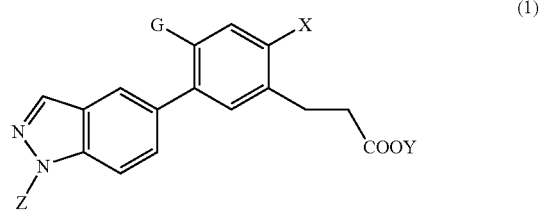

(1)

TABLE 2-1

| | | | | | | | LCMS | | |
| Exp. | SM1 | SM2 | G | X | Y | Z | method | RTime | mass | Ref. |
|---|---|---|---|---|---|---|---|---|---|---|
| 1-1-1 | | Exp. 1-1-2 | g1 | OH | Me | Me | B | 1.40 | 341.3 | |
| 1-1-2 | IM-3 | rgt1 | g1 | OH | H | Me | A | 3.16 | 327.3 | |
| 2-1-1 | | IM-4 | g1 | Me | Me | Me | A | 4.70 | 339.3 | |

TABLE 2-1-continued

| Exp. | SM1 | SM2 | G | X | Y | Z | LCMS method | RTime | mass | Ref. |
|---|---|---|---|---|---|---|---|---|---|---|
| 2-1-2 | Exp. 2-1-1 | | g1 | Me | H | Me | A | 3.84 | 325.3 | |
| 2-2-1 | Exp. 2-1-1 | | g2 | Me | Me | Me | B | 1.45 | 325.3 | |
| 2-2-2 | Exp. 2-2-1 | | g2 | Me | H | Me | A | 3.20 | 311.3 | |
| 2-3-2 | Exp. 2-2-1 | sm3 | g3 | Me | H | Me | A | 4.72 | 417.2 (MH−) | |
| 2-4-2 | Exp. 2-2-1 | sm4 | g4 | Me | H | Me | A | 4.77 | 417.2 (MH−) | Exp. 2-3-2 |
| 2-6-2 | Exp. 2-2-1 | sm6 | g6 | Me | H | Me | A | 4.72 | 417.2 (MH−) | Exp. 2-3-2 |
| 2-7-2 | Exp. 2-2-1 | sm7 | g7 | Me | H | Me | A | 5.27 | 497.1 (MH−) | Exp. 2-3-2 |
| 2-8-2 | Exp. 2-2-1 | sm8 | g8 | Me | H | Me | A | 5.41 | 467.2 (MH−) | Exp. 2-3-2 |
| 2-10-2 | Exp. 2-2-1 | sm10 | g10 | Me | H | Me | A | 4.94 | 415.3 (MH−) | Exp. 2-3-2 |
| 2-11-2 | Exp. 2-2-1 | sm11 | g11 | Me | H | Me | A | 4.82 | 435.2 (MH−) | Exp. 2-3-2 |
| 2-17-2 | Exp. 2-2-1 | sm17 | g17 | Me | H | Me | A | 5.03 | 433.2 (MH−) | Exp. 2-3-2 |
| 2-19-2 | Exp. 2-2-1 | sm19 | g19 | Me | H | Me | A | 4.85 | 435.2 (MH−) | Exp. 2-3-2 |
| 2-20-2 | Exp. 2-2-1 | sm20 | g20 | Me | H | Me | A | 5.00 | 467.1 (MH−) | Exp. 2-3-2 |
| 2-21-2 | Exp. 2-2-1 | sm21 | g21 | Me | H | Me | A | 4.96 | 415.3 | Exp. 2-3-2 |

TABLE 2-2

| Exp. | SM1 | SM2 | G | X | Y | Z | LCMS method | RTime | mass | Ref. |
|---|---|---|---|---|---|---|---|---|---|---|
| 2-25-2 | Exp. 2-2-1 | sm25 | g25 | Me | H | Me | A | 4.30 | 351.2 (MH−) | Exp. 2-3-2 |
| 2-26-2 | Exp. 2-2-1 | sm26 | g26 | Me | H | Me | A | 4.76 | 365.0 (MH−) | Exp. 2-3-2 |
| 2-27-2 | Exp. 2-2-1 | sm27 | g27 | Me | H | Me | A | 5.50 | 367.3 | Exp. 2-3-2 |
| 2-28-2 | Exp. 2-2-1 | sm28 | g28 | Me | H | Me | A | 5.07 | 381.3 | Exp. 2-3-2 |
| 1-3-2 | IM-5 | sm-o3 | g3 | OH | H | Me | B | 1.48 | 419.3 (MH−) | Exp. 1-5-2 |
| 1-9-2 | IM-5 | sm-o9 | g9 | OH | H | Me | B | 1.43 | 431.3 (MH−) | Exp. 1-5-2 |
| 1-12-2 | IM-5 | sm-o12 | g12 | OH | H | Me | B | 1.43 | 469.3 (MH−) | Exp. 1-5-2 |
| 1-13-2 | IM-5 | sm-o13 | g13 | OH | H | Me | B | 1.55 | 415.3 (MH−) | Exp. 1-5-2 |
| 1-14-2 | IM-5 | sm-o14 | g14 | OH | H | Me | B | 1.52 | 415.3 (MH−) | Exp. 1-5-2 |
| 1-15-2 | IM-5 | sm-o15 | g15 | OH | H | Me | B | 1.52 | 415.3 (MH−) | Exp. 1-5-2 |
| 1-16-2 | IM-5 | sm-o16 | g16 | OH | H | Me | B | 1.63 | 469.3 (MH−) | Exp. 1-5-2 |
| 1-17-2 | IM-5 | sm-o17 | g17 | OH | H | Me | B | 1.57 | 437.3 (MH−) | Exp. 1-5-2 |
| 1-18-2 | IM-5 | sm-o18 | g18 | OH | H | Me | B | 1.61 | 429.4 (MH−) | Exp. 1-5-2 |
| 1-22-2 | IM-5 | sm-o22 | g22 | OH | H | Me | B | 1.53 | 433.3 (MH−) | Exp. 1-5-2 |
| 1-23-2 | IM-5 | sm-o23 | g23 | OH | H | Me | B | 1.64 | 483.3 (MH−) | Exp. 1-5-2 |

TABLE 2-3

| Exp. | SM1 | SM2 | G | X | Y | Z | LCMS method | RTime | mass | Ref. |
|---|---|---|---|---|---|---|---|---|---|---|
| 1-24-2 | IM-5 | sm-o24 | g24 | OH | H | Me | B | 1.80 | 421.4 (MH−) | Exp. 1-5-2 |
| 1-26-2 | IM-5 | sm-o26 | g26 | OH | H | Me | B | 1.47 | 367.3 (MH−) | Exp. 1-5-2 |
| 1-27-2 | IM-5 | sm-o27 | g27 | OH | H | Me | B | 1.48 | 367.3 (MH−) | Exp. 1-5-2 |
| 1-28-2 | IM-5 | sm-o28 | g28 | OH | H | Me | B | 1.56 | 381.3 (MH−) | Exp. 1-5-2 |
| 1-29-2 | IM-5 | sm-o29 | g29 | OH | H | Me | B | 1.89 | 423.4 (MH−) | Exp. 1-5-2 |
| 1-30-2 | IM-5 | sm-o30 | g30 | OH | H | Me | B | 1.47 | 379.3 (MH−) | Exp. 1-5-2 |
| 1-31-2 | IM-5 | sm-o31 | g31 | OH | H | Me | B | 1.57 | 393.3 (MH−) | Exp. 1-5-2 |
| 1-32-2 | IM-5 | sm-o32 | g32 | OH | H | Me | B | 1.64 | 479.4 (MH−) | Exp. 1-5-2 |

TABLE 2-4

| Exp. | SM1 | SM2 | G | X | Y | Z | LCMS method | RTime | mass | Ref. |
|---|---|---|---|---|---|---|---|---|---|---|
| 1-5-1 | | 1-5-2 | g5 | OH | Me | Me | B | 4.83 | 443.0 | |
| 1-5-2 | IM-5 | sm5 | g5 | OH | H | Me | A | 4.20 | 429.2 | |
| 2-5-1 | | IM-6 | g5 | Me | Me | Me | A | 5.80 | 441.2 | Exp. 2-1-1 |
| 2-5-2 | | Exp. 2-5-1 | g5 | Me | H | Me | A | 5.02 | 427.1 | Exp. 2-1-2 |
| 3-5-1 | | IM-6 | g5 | Vinyl | Me | Me | A | 5.81 | 453.0 | Exp. 2-1-1 |
| 3-5-2 | | Exp. 3-5-1 | g5 | Vinyl | H | Me | A | 5.08 | 439.2 | Exp. 2-1-2 |
| 4-5-1 | Exp. 1-5-1 | sm1 | g5 | MeO | Me | Me | A | 5.59 | 457.2 | Exp. 2-3-1 |
| 4-5-2 | | Exp. 4-5-1 | g5 | MeO | H | Me | B | 4.89 | 442.9 | Exp. 2-1-2 |
| 5-5-1 | | Exp. 3-5-1 | g5 | Et | Me | Me | A | 5.88 | 455.3 | |
| 5-5-2 | | Exp. 5-5-1 | g5 | Et | H | Me | A | 5.14 | 441.3 | Exp. 2-1-2 |
| 6-5-1 | | IM-6 | g5 | CN | Me | Me | A | 5.54 | 452.2 | |
| 6-5-2 | | Exp. 6-5-1 | g5 | CN | H | Me | A | 5.04 | 438.2 | Exp. 2-1-2 |

TABLE 3-1

| Exp. | SM1 | SM2 | G | X | Y | Z | LCMS method | RTime | mass | Ref. |
|---|---|---|---|---|---|---|---|---|---|---|
| 2-N1-1 | | IM-9 | gn1 | Me | Me | Me | A | 3.64 | 324.3 | |
| 2-N1-2 | | Exp. 2-N1-1 | gn1 | Me | H | Me | A | 3.04 | 351.2 | Exp. 2-1-2 |
| 7-N1-1 | | IM-12 | gn1 | Cl | Me | Me | A | 4.36 | 344.2 | Exp. 2-N1-1 |
| 7-N1-2 | | Exp. 7-N1-1 | gn1 | Cl | H | Me | A | 3.52 | 330.1 | Exp. 2-1-2 |
| 8-N1-1 | | IM-15 | gn1 | CF3 | Me | Me | A | 4.47 | 378.2 | Exp. 2-N1-1 |
| 2-N2-1 | Exp. 2-N1-1 | sm-n2 | gn2 | Me | Me | Me | A | 4.54 | 532.4 | |
| 2-N2-2 | | Exp. 2-N2-1 | gn2 | Me | H | Me | A | 4.02 | 518.4 | Exp. 2-1-2 |
| 2-N3-1 | Exp. 2-N1-1 | sm-n3 | gn3 | Me | Me | Me | B | 1.79 | 532.2 | Exp. 2-N2-1 |
| 2-N3-2 | | Exp. 2-N3-1 | gn3 | Me | H | Me | A | 3.90 | 518.4 | Exp. 2-1-2 |
| 2-N4-1 | Exp. 2-N1-1 | sm-n4 | gn4 | Me | Me | Me | B | 1.73 | 532.2 | Exp. 2-N2-1 |
| 2-N4-2 | | Exp. 2-N4-1 | gn4 | Me | H | Me | A | 3.82 | 518.4 | Exp. 2-1-2 |
| 2-N5-1 | Exp. 2-N1-1 | sm-n5 | gn5 | Me | Me | Me | A | 4.58 | 566.4 | Exp. 2-N2-1 |
| 2-N5-2 | | Exp. 2-N5-1 | gn5 | Me | H | Me | A | 4.06 | 552.4 | Exp. 2-1-2 |
| 2-N9-1 | Exp. 2-N1-1 | sm-n9 | gn9 | Me | Me | Me | B | 1.66 | 464.2 | Exp. 2-N2-1 |
| 2-N9-2 | | Exp. 2-N9-1 | gn9 | Me | H | Me | A | 3.62 | 450.4 | Exp. 2-1-2 |
| 2-N10-1 | Exp. 2-N1-1 | sm-n10 | gn10 | Me | Me | Me | B | 1.73 | 478.2 | Exp. 2-N2-1 |
| 2-N10-2 | | Exp. 2-N10-1 | gn10 | Me | H | Me | A | 3.78 | 464.4 | Exp. 2-1-2 |
| 2-N11-1 | Exp. 2-N1-1 | sm-n11 | gn11 | Me | Me | Me | B | 1.73 | 478.2 | Exp. 2-N2-1 |
| 2-N11-2 | | Exp. 2-N11-1 | gn11 | Me | H | Me | A | 3.74 | 464.4 | Exp. 2-1-2 |

TABLE 3-2

| Exp. | SM1 | SM2 | G | X | Y | Z | LCMS method | RTime | mass | Ref. |
|---|---|---|---|---|---|---|---|---|---|---|
| 2-N12-1 | Exp. 2-N1-1 | sm-n12 | gn12 | Me | Me | Me | B | 1.72 | 478.2 | Exp. 2-N2-1 |
| 2-N12-2 | | Exp. 2-N12-1 | gn12 | Me | H | Me | A | 3.76 | 464.4 | Exp. 2-1-2 |
| 2-N13-1 | Exp. 2-N1-1 | sm-n13 | gn13 | Me | Me | Me | B | 1.78 | 548.2 | Exp. 2-N2-1 |
| 2-N13-2 | | Exp. 2-N13-1 | gn13 | Me | H | Me | A | 3.96 | 534.4 | Exp. 2-1-2 |
| 2-N14-1 | Exp. 2-N1-1 | sm-n14 | gn14 | Me | Me | Me | B | 1.67 | 494.2 | Exp. 2-N2-1 |
| 2-N14-2 | | Exp. 2-N14-1 | gn14 | Me | H | Me | A | 3.65 | 480.4 | Exp. 2-1-2 |
| 2-N15-1 | Exp. 2-N1-1 | sm-n15 | gn15 | Me | Me | Me | B | 1.75 | 498.2 | Exp. 2-N2-1 |
| 2-N15-2 | | Exp. 2-N15-1 | gn15 | Me | H | Me | A | 3.87 | 484.4 | Exp. 2-1-2 |
| 2-N16-1 | Exp. 2-N1-1 | sm-n16 | gn16 | Me | Me | Me | B | 1.68 | 482.2 | Exp. 2-N2-1 |
| 2-N16-2 | | Exp. 2-N16-1 | gn16 | Me | H | Me | A | 3.66 | 468.4 | Exp. 2-1-2 |
| 2-N17-1 | Exp. 2-N1-1 | sm-n17 | gn17 | Me | Me | Me | B | 1.68 | 482.2 | Exp. 2-N2-1 |

TABLE 3-2-continued

| Exp. | SM1 | SM2 | G | X | Y | Z | LCMS method | RTime | mass | Ref. |
|---|---|---|---|---|---|---|---|---|---|---|
| 2-N17-2 | Exp. 2-N17-1 | | gn17 | Me | H | Me | A | 3.68 | 468.4 | Exp. 2-1-2 |
| 2-N18-1 | Exp. 2-N1-1 | sm-n18 | gn18 | Me | Me | Me | B | 1.91 | 540.3 | Exp. 2-N2-1 |
| 2-N18-2 | Exp. 2-N18-1 | | gn18 | Me | H | Me | A | 4.28 | 526.5 | Exp. 2-1-2 |
| 2-N19-1 | Exp. 2-N1-1 | sm-n19 | gn19-1 | Me | Me | Me | B | 1.58 | 489.2 | Exp. 2-N2-1 |
| 2-N19-2 | Exp. 2-N19-1 | | gn19-2 | Me | H | Me | A | 3.22 | 494.4 | Exp. 2-1-2 |
| 2-N20-1 | Exp. 2-N1-1 | sm-n20 | gn20 | Me | Me | Me | B | 1.92 | 556.3 | Exp. 2-N2-1 |
| 2-N20-2 | Exp. 2-N20-1 | | gn20 | Me | H | Me | A | 4.38 | 542.5 | Exp. 2-1-2 |

TABLE 3-3

| Exp. | SM1 | SM2 | G | X | Y | Z | LCMS method | RTime | mass | Ref. |
|---|---|---|---|---|---|---|---|---|---|---|
| 2-N21-1 | Exp. 2-N1-1 | sm-n21 | gn21 | Me | Me | Me | B | 1.54 | 531.2 | Exp. 2-N2-1 |
| 2-N21-2 | Exp. 2-N21-1 | | gn21 | Me | H | Me | B | 1.31 | 517.1 | Exp. 2-1-2 |
| 2-N22-1 | Exp. 2-N1-1 | sm-n22 | gn22 | Me | Me | Me | B | 1.84 | 561.2 | Exp. 2-N2-1 |
| 2-N22-2 | Exp. 2-N22-1 | | gn22 | Me | H | Me | B | 1.58 | 547.1 | Exp. 2-1-2 |
| 2-N23-1 | Exp. 2-N1-1 | sm-n23 | gn23 | Me | Me | Me | B | 1.53 | 499.1 | Exp. 2-N2-1 |
| 2-N23-2 | Exp. 2-N23-1 | | gn23 | Me | H | Me | B | 1.29 | 485.1 | Exp. 2-1-2 |
| 2-N24-1 | Exp. 2-N1-1 | sm-n24 | gn24 | Me | Me | Me | B | 1.61 | 483.2 | Exp. 2-N2-1 |
| 2-N24-2 | Exp. 2-N24-1 | | gn24 | Me | H | Me | B | 1.35 | 469.1 | Exp. 2-1-2 |
| 2-N25-1 | Exp. 2-N1-1 | sm-n25 | gn25 | Me | Me | Me | B | 1.62 | 470.1 | Exp. 2-N2-1 |
| 2-N25-2 | Exp. 2-N25-1 | | gn25 | Me | H | Me | B | 1.36 | 456.1 | Exp. 2-1-2 |
| 2-N26-1 | Exp. 2-N1-1 | sm-n26 | gn26 | Me | Me | Me | B | 1.72 | 490.2 | Exp. 2-N2-1 |
| 2-N26-2 | Exp. 2-N26-1 | | gn26 | Me | H | Me | B | 1.47 | 476.1 | Exp. 2-1-2 |
| 2-N27-1 | Exp. 2-N1-1 | sm-n27 | gn27 | Me | Me | Me | B | 1.87 | 542.2 | Exp. 2-N2-1 |
| 2-N27-2 | Exp. 2-N27-1 | | gn27 | Me | H | Me | B | 1.63 | 528.2 | Exp. 2-1-2 |
| 2-N28-1 | Exp. 2-N1-1 | sm-n28 | gn28 | Me | Me | Me | B | 1.83 | 536.1 | Exp. 2-N2-1 |
| 2-N28-2 | Exp. 2-N28-1 | | gn28 | Me | H | Me | B | 1.58 | 522.1 | Exp. 2-1-2 |

TABLE 3-4

| Exp. | SM1 | SM2 | G | X | Y | Z | LCMS method | RTime | mass | Ref. |
|---|---|---|---|---|---|---|---|---|---|---|
| 2-N29-1 | Exp. 2-N1-1 | sm-n29 | gn29 | Me | Me | Me | B | 1.32 | 482.2 | Exp. 2-N2-1 |
| 2-N29-2 | Exp. 2-N29-1 | | gn29 | Me | H | Me | B | 1.08 | 486.1 | Exp. 2-1-2 |
| 2-N30-1 | Exp. 2-N1-1 | sm-n30 | gn30 | Me | Me | Me | B | 1.90 | 540.2 | Exp. 2-N2-1 |
| 2-N30-2 | Exp. 2-N30-1 | | gn30 | Me | H | Me | B | 1.65 | 526.2 | Exp. 2-1-2 |
| 2-N31-1 | Exp. 2-N1-1 | sm-n31 | gn31 | Me | Me | Me | B | 1.52 | 428.2 | Exp. 2-N2-1 |
| 2-N31-2 | Exp. 2-N31-1 | | gn31 | Me | H | Me | B | 1.26 | 414.1 | Exp. 2-1-2 |
| 2-N32-1 | Exp. 2-N1-1 | sm-n32 | gn32 | Me | Me | Me | B | 1.42 | 402.2 | Exp. 2-N2-1 |
| 2-N32-2 | Exp. 2-N32-1 | | gn32 | Me | H | Me | B | 1.16 | 388.1 | Exp. 2-1-2 |
| 2-N33-1 | Exp. 2-N1-1 | sm-n33 | gn33 | Me | Me | Me | B | 1.49 | 416.2 | Exp. 2-N2-1 |
| 2-N33-2 | Exp. 2-N33-1 | | gn33 | Me | H | Me | B | 1.23 | 402.2 | Exp. 2-1-2 |
| 2-N34-1 | Exp. 2-N1-1 | sm-n34 | gn34 | Me | Me | Me | B | 1.60 | 470.1 | Exp. 2-N2-1 |
| 2-N34-2 | Exp. 2-N34-1 | | gn34 | Me | H | Me | B | 1.36 | 456.1 | Exp. 2-1-2 |
| 2-N35-1 | Exp. 2-N1-1 | sm-n35 | gn35 | Me | Me | Me | B | 1.86 | 506.2 | Exp. 2-N2-1 |

TABLE 3-4-continued

| | | | | | | | LCMS | | |
|---|---|---|---|---|---|---|---|---|---|
| Exp. | SM1 | SM2 | G | X | Y | Z | method | RTime | mass Ref. |
| 2-N35-2 | Exp. 2-N35-1 | | gn35 | Me | H | Me | B | 1.60 | 492.2 Exp. 2-1-2 |
| 2-N36-1 | Exp. 2-N1-1 | sm-n36 | gn36 | Me | Me | Me | B | 1.92 | 568.1 Exp. 2-N2-1 |
| 2-N36-2 | Exp. 2-N36-1 | | gn36 | Me | H | Me | B | 1.67 | 554.1 Exp. 2-1-2 |

TABLE 3-5

| | | | | | | | LCMS | | |
|---|---|---|---|---|---|---|---|---|---|
| Exp. | SM1 | SM2 | G | X | Y | Z | method | RTime | mass Ref. |
| 2-N37-1 | Exp. 2-N1-1 | sm-n37 | gn37 | Me | Me | Me | B | 1.74 | 514.2 Exp. 2-N2-1 |
| 2-N37-2 | Exp. 2-N37-1 | | gn37 | Me | H | Me | B | 1.49 | 500.1 Exp. 2-1-2 |
| 2-N38-1 | Exp. 2-N1-1 | sm-n38 | gn38 | Me | Me | Me | B | 1.78 | 514.2 Exp. 2-N2-1 |
| 2-N38-2 | Exp. 2-N38-1 | | gn38 | Me | H | Me | B | 1.53 | 500.1 Exp. 2-1-2 |
| 2-N39-1 | Exp. 2-N1-1 | sm-n39 | gn39 | Me | Me | Me | B | 1.92 | 556.2 Exp. 2-N2-1 |
| 2-N39-2 | Exp. 2-N39-1 | | gn39 | Me | H | Me | B | 1.68 | 542.1 Exp. 2-1-2 |
| 2-N40-1 | Exp. 2-N1-1 | sm-n40 | gn40 | Me | Me | Me | B | 1.38 | 479.2 Exp. 2-N2-1 |
| 2-N40-2 | Exp. 2-N40-1 | | gn40 | Me | H | Me | B | 1.14 | 465.1 Exp. 2-1-2 |

TABLE 3-6

| | | | | | | | LCMS | | |
|---|---|---|---|---|---|---|---|---|---|
| Exp. | SM1 | SM2 | G | X | Y | Z | method | RTime | mass Ref. |
| 2-N101-1 | Exp. 2-N1-1 | sm-n101 | gn101 | Me | Me | Me | B | 1.82 | 496.0 |
| 2-N101-2 | Exp. 2-N101-1 | | gn101 | Me | H | Me | B | 1.66 | 482.0 Exp. 2-1-2 |
| 2-N102-1 | Exp. 2-N1-1 | sm-n102 | gn102 | Me | Me | Me | B | 1.91 | 514.0 Exp. 2-N101-1 |
| 2-N102-2 | Exp. 2-N102-1 | | gn102 | Me | H | Me | B | 1.73 | 500.0 Exp. 2-1-2 |
| 2-N103-1 | Exp. 2-N1-1 | sm-n103 | gn103 | Me | Me | Me | B | 1.91 | 532.0 Exp. 2-N101-1 |
| 2-N103-2 | Exp. 2-N103-1 | | gn103 | Me | H | Me | B | 1.69 | 518.0 Exp. 2-1-2 |
| 2-N104-1 | Exp. 2-N1-1 | sm-n104 | gn104 | Me | Me | Me | B | 1.84 | 554.0 Exp. 2-N101-1 |
| 2-N104-2 | Exp. 2-N104-1 | | gn104 | Me | H | Me | B | 1.61 | 539.9 Exp. 2-1-2 |
| 2-N105-1 | Exp. 2-N1-1 | sm-n105 | gn105 | Me | Me | Me | B | 1.84 | 514.1 Exp. 2-N101-1 |
| 2-N105-2 | Exp. 2-N105-1 | | gn105 | Me | H | Me | B | 1.63 | 500.0 Exp. 2-1-2 |
| 2-N110-1 | Exp. 2-N1-1 | sm-n110 | gn110 | Me | Me | Me | B | 1.84 | 510.0 Exp. 2-N101-1 |
| 2-N110-2 | Exp. 2-N110-1 | | gn110 | Me | H | Me | B | 1.68 | 496.0 Exp. 2-1-2 |
| 2-N111-1 | Exp. 2-N1-1 | sm-n111 | gn111 | Me | Me | Me | B | 1.95 | 530.0 Exp. 2-N101-1 |
| 2-N111-2 | Exp. 2-N111-1 | | gn111 | Me | H | Me | B | 1.75 | 516.0 Exp. 2-1-2 |
| 2-N112-1 | Exp. 2-N1-1 | sm-n112 | gn112 | Me | Me | Me | B | 1.92 | 530.0 Exp. 2-N101-1 |
| 2-N112-2 | Exp. 2-N112-1 | | gn112 | Me | H | Me | B | 1.78 | 515.9 Exp. 2-1-2 |
| 2-N113-1 | Exp. 2-N1-1 | sm-n113 | gn113 | Me | Me | Me | B | 1.80 | 512.0 Exp. 2-N101-1 |
| 2-N113-2 | Exp. 2-N113-1 | | gn113 | Me | H | Me | B | 1.61 | 498.0 Exp. 2-1-2 |

TABLE 3-7

| | | | | | | | LCMS | | |
|---|---|---|---|---|---|---|---|---|---|
| Exp. | SM1 | SM2 | G | X | Y | Z | method | RTime | mass Ref. |
| 2-N114-1 | Exp. 2-N1-1 | sm-n114 | gn114 | Me | Me | Me | B | 1.83 | 496.0 Exp. 2-N101-1 |
| 2-N114-2 | Exp. 2-N114-1 | | gn114 | Me | H | Me | B | 1.65 | 481.9 Exp. 2-1-2 |
| 2-N115-1 | Exp. 2-N1-1 | sm-n115 | gn115 | Me | Me | Me | B | 1.90 | 496.0 Exp. 2-N101-1 |

TABLE 3-7-continued

| Exp. | SM1 | SM2 | G | X | Y | Z | LCMS method | RTime | mass | Ref. |
|---|---|---|---|---|---|---|---|---|---|---|
| 2-N115-2 | Exp. 2-N115-1 | | gn115 | Me | H | Me | B | 1.75 | 481.9 | Exp. 2-1-2 |
| 2-N116-1 | Exp. 2-N1-1 | sm-n116 | gn116 | Me | Me | Me | B | 1.69 | 506.0 | Exp. 2-N101-1 |
| 2-N116-2 | Exp. 2-N116-1 | | gn116 | Me | H | Me | B | 1.49 | 491.9 | Exp. 2-1-2 |
| 2-N117-1 | Exp. 2-N1-1 | sm-n117 | gn117 | Me | Me | Me | B | 1.77 | 507.0 | Exp. 2-N101-1 |
| 2-N117-2 | Exp. 2-N117-1 | | gn117 | Me | H | Me | B | 1.62 | 492.9 | Exp. 2-1-2 |
| 2-N118-1 | Exp. 2-N1-1 | sm-n118 | gn118 | Me | Me | Me | B | 1.60 | 453.0 | Exp. 2-N101-1 |
| 2-N118-2 | Exp. 2-N118-1 | | gn118 | Me | H | Me | B | 1.39 | 439.0 | Exp. 2-1-2 |
| 2-N119-1 | Exp. 2-N1-1 | sm-n119 | gn119 | Me | Me | Me | B | 2.04 | 484.0 | Exp. 2-N101-1 |
| 2-N119-2 | Exp. 2-N119-1 | | gn119 | Me | H | Me | B | 1.88 | 470.1 | Exp. 2-1-2 |
| 2-N120-1 | Exp. 2-N1-1 | sm-n120 | gn120 | Me | Me | Me | B | 1.90 | 520.0 | Exp. 2-N101-1 |
| 2-N120-2 | Exp. 2-N120-1 | | gn120 | Me | H | Me | B | 1.73 | 505.9 | Exp. 2-1-2 |
| 2-N121-1 | Exp. 2-N1-1 | sm-n121 | gn121 | Me | Me | Me | B | 1.97 | 484.0 | Exp. 2-N101-1 |
| 2-N121-2 | Exp. 2-N121-1 | | gn121 | Me | H | Me | B | 1.82 | 470.0 | Exp. 2-1-2 |
| 2-N122-1 | Exp. 2-N1-1 | sm-n122 | gn122 | Me | Me | Me | B | 1.69 | 480.0 | Exp. 2-N101-1 |
| 2-N122-2 | Exp. 2-N122-1 | | gn122 | Me | H | Me | B | 1.47 | 465.9 | Exp. 2-1-2 |

TABLE 3-8

| Exp. | SM1 | SM2 | G | X | Y | Z | LCMS method | RTime | mass | Ref. |
|---|---|---|---|---|---|---|---|---|---|---|
| 2-N123-1 | Exp. 2-N1-1 | sm-n123 | gn123 | Me | Me | Me | B | 1.78 | 462.0 | Exp. 2-N101-1 |
| 2-N123-2 | Exp. 2-N123-1 | | gn123 | Me | H | Me | B | 1.60 | 448.0 | Exp. 2-1-2 |
| 2-N124-1 | Exp. 2-N1-1 | sm-n124 | gn124 | Me | Me | Me | B | 1.97 | 500.0 | Exp. 2-N101-1 |
| 2-N124-2 | Exp. 2-N124-1 | | gn124 | Me | H | Me | B | 1.81 | 486.0 | Exp. 2-1-2 |
| 2-N125-1 | Exp. 2-N1-1 | sm-n125 | gn125 | Me | Me | Me | B | 1.99 | 495.0 | Exp. 2-N101-1 |
| 2-N125-2 | Exp. 2-N125-1 | | gn125 | Me | H | Me | B | 1.76 | 481.0 | Exp. 2-1-2 |
| 2-N126-1 | Exp. 2-N1-1 | sm-n126 | gn126 | Me | Me | Me | B | 2.08 | 511.0 | Exp. 2-N101-1 |
| 2-N126-2 | Exp. 2-N126-1 | | gn126 | Me | H | Me | B | 1.86 | 497.0 | Exp. 2-1-2 |
| 2-N127-1 | Exp. 2-N1-1 | sm-n127 | gn127 | Me | Me | Me | B | 1.62 | 506.0 | Exp. 2-N101-1 |
| 2-N127-2 | Exp. 2-N127-1 | | gn127 | Me | H | Me | B | 1.40 | 492.0 | Exp. 2-1-2 |
| 2-N128-1 | Exp. 2-N1-1 | sm-n128 | gn128 | Me | Me | Me | B | 1.98 | 525.0 | Exp. 2-N101-1 |
| 2-N128-2 | Exp. 2-N128-1 | | gn128 | Me | H | Me | B | 1.78 | 511.0 | Exp. 2-1-2 |
| 2-N129-1 | Exp. 2-N1-1 | sm-n129 | gn129 | Me | Me | Me | B | 2.08 | 553.0 | Exp. 2-N101-1 |
| 2-N129-2 | Exp. 2-N129-1 | | gn129 | Me | H | Me | B | 1.82 | 539.0 | Exp. 2-1-2 |
| 2-N130-1 | Exp. 2-N1-1 | sm-n130 | gn130 | Me | Me | Me | B | 1.69 | 468.0 | Exp. 2-N101-1 |
| 2-N130-2 | Exp. 2-N130-1 | | gn130 | Me | H | Me | B | 1.49 | 454.0 | Exp. 2-1-2 |

TABLE 3-9

| Exp. | SM1 | SM2 | G | X | Y | Z | LCMS method | RTime | mass | Ref. |
|---|---|---|---|---|---|---|---|---|---|---|
| 2-N131-1 | Exp. 2-N1-1 | sm-n131 | gn131 | Me | Me | Me | B | 2.02 | 485.0 | Exp. 2-N101-1 |
| 2-N131-2 | Exp. 2-N131-1 | | gn131 | Me | H | Me | B | 1.81 | 471.0 | Exp. 2-1-2 |
| 2-N132-1 | Exp. 2-N1-1 | sm-n132 | gn132 | Me | Me | Me | B | 1.93 | 525.0 | Exp. 2-N101-1 |
| 2-N132-2 | Exp. 2-N132-1 | | gn132 | Me | H | Me | B | 1.74 | 511.0 | Exp. 2-1-2 |
| 2-N133-1 | Exp. 2-N1-1 | sm-n133 | gn133 | Me | Me | Me | B | 2.21 | 538.0 | Exp. 2-N101-1 |
| 2-N133-2 | Exp. 2-N133-1 | | gn133 | Me | H | Me | B | 2.05 | 524.1 | Exp. 2-1-2 |
| 2-N134-1 | Exp. 2-N1-1 | sm-n134 | gn134 | Me | Me | Me | B | 1.65 | 527.0 | Exp. 2-N101-1 |

TABLE 3-9-continued

|  |  |  |  |  |  |  | LCMS |  |  |  |
|---|---|---|---|---|---|---|---|---|---|---|
| Exp. | SM1 | SM2 | G | X | Y | Z | method | RTime | mass | Ref. |
| 2-N134-2 | Exp. 2-N134-1 |  | gn134 | Me | H | Me | B | 1.44 | 513.0 | Exp. 2-1-2 |
| 2-N135-1 | Exp. 2-N1-1 | sm-n135 | gn135 | Me | Me | Me | B | 1.76 | 525.0 | Exp. 2-N101-1 |
| 2-N135-2 | Exp. 2-N135-1 |  | gn135 | Me | H | Me | B | 1.57 | 511.0 | Exp. 2-1-2 |
| 2-N136-1 | Exp. 2-N1-1 | sm-n136 | gn136 | Me | Me | Me | B | 2.11 | 593.0 | Exp. 2-N101-1 |
| 2-N136-2 | Exp. 2-N136-1 |  | gn136 | Me | H | Me | B | 1.95 | 579.0 | Exp. 2-1-2 |

TABLE 3-10

|  |  |  |  |  |  |  | LCMS |  |  |  |
|---|---|---|---|---|---|---|---|---|---|---|
| Exp. | SM1 | SM2 | G | X | Y | Z | method | RTime | mass | Ref. |
| 7-N119-1 | Exp. 7-N2-1 | sm-n119 | gn119 | Cl | Me | Me | A | 5.98 | 504.1 | Exp. 2-N101-1 |
| 7-N119-2 | Exp. 7-N120-1 |  | gn119 | Cl | H | Me | A | 5.26 | 490.1 | Exp. 2-1-2 |
| 7-N124-1 | Exp. 7-N2-1 | sm-n124 | gn124 | Cl | Me | Me | A | 5.89 | 520.2 | Exp. 2-N101-1 |
| 7-N124-2 | Exp. 7-N124-1 |  | gn124 | Cl | H | Me | A | 5.16 | 506.1 | Exp. 2-1-2 |
| 8-N101-1 | Exp. 8-N2-1 | sm-n101 | gn101 | CF3 | Me | Me | B | 1.97 | 550.0 | Exp. 2-N101-1 |
| 8-N101-2 | Exp. 8-N101-1 |  | gn101 | CF3 | H | Me | B | 1.82 | 536.0 | Exp. 2-1-2 |
| 8-N102-1 | Exp. 8-N2-1 | sm-n102 | gn102 | CF3 | Me | Me | B | 2.06 | 568.0 | Exp. 2-N101-1 |
| 8-N102-2 | Exp. 8-N102-1 |  | gn102 | CF3 | H | Me | B | 1.88 | 554.0 | Exp. 2-1-2 |
| 8-N103-1 | Exp. 8-N2-1 | sm-n103 | gn103 | CF3 | Me | Me | B | 2.04 | 586.0 | Exp. 2-N101-1 |
| 8-N103-2 | Exp. 8-N103-1 |  | gn103 | CF3 | H | Me | B | 1.82 | 571.9 | Exp. 2-1-2 |
| 8-N104-1 | Exp. 8-N2-1 | sm-n104 | gn104 | CF3 | Me | Me | B | 2.00 | 608.0 | Exp. 2-N101-1 |
| 8-N104-2 | Exp. 8-N104-1 |  | gn104 | CF3 | H | Me | B | 1.78 | 593.9 | Exp. 2-1-2 |
| 8-N105-1 | Exp. 8-N2-1 | sm-n105 | gn105 | CF3 | Me | Me | B | 1.99 | 568.0 | Exp. 2-N101-1 |
| 8-N105-2 | Exp. 8-N105-1 |  | gn105 | CF3 | H | Me | B | 1.77 | 554.0 | Exp. 2-1-2 |

TABLE 3-11

|  |  |  |  |  |  |  | LCMS |  |  |  |
|---|---|---|---|---|---|---|---|---|---|---|
| Exp. | SM1 | SM2 | G | X | Y | Z | method | RTime | mass | Ref. |
| 8-N110-1 | Exp. 8-N2-1 | sm-n110 | gn110 | CF3 | Me | Me | B | 1.99 | 564.0 | Exp. 2-N101-1 |
| 8-N110-2 | Exp. 8-N110-1 |  | gn110 | CF3 | H | Me | B | 1.83 | 550.0 | Exp. 2-1-2 |
| 8-N111-1 | Exp. 8-N2-1 | sm-n111 | gn111 | CF3 | Me | Me | B | 2.10 | 584.0 | Exp. 2-N101-1 |
| 8-N111-2 | Exp. 8-N111-1 |  | gn111 | CF3 | H | Me | B | 1.91 | 569.9 | Exp. 2-1-2 |
| 8-N112-1 | Exp. 8-N2-1 | sm-n112 | gn112 | CF3 | Me | Me | B | 2.07 | 584.0 | Exp. 2-N101-1 |
| 8-N112-2 | Exp. 8-N112-1 |  | gn112 | CF3 | H | Me | B | 1.91 | 569.9 | Exp. 2-1-2 |
| 8-N113-1 | Exp. 8-N2-1 | sm-n113 | gn113 | CF3 | Me | Me | B | 1.95 | 566.0 | Exp. 2-N101-1 |
| 8-N113-2 | Exp. 8-N113-1 |  | gn113 | CF3 | H | Me | B | 1.76 | 552.0 | Exp. 2-1-2 |
| 8-N114-1 | Exp. 8-N2-1 | sm-n114 | gn114 | CF3 | Me | Me | B | 1.99 | 550.0 | Exp. 2-N101-1 |
| 8-N114-2 | Exp. 8-N114-1 |  | gn114 | CF3 | H | Me | B | 1.82 | 535.9 | Exp. 2-1-2 |
| 8-N115-1 | Exp. 8-N2-1 | sm-n115 | gn115 | CF3 | Me | Me | B | 2.06 | 550.0 | Exp. 2-N101-1 |
| 8-N115-2 | Exp. 8-N115-1 |  | gn115 | CF3 | H | Me | B | 1.90 | 535.9 | Exp. 2-1-2 |
| 8-N116-1 | Exp. 8-N2-1 | sm-n116 | gn116 | CF3 | Me | Me | B | 1.86 | 560.0 | Exp. 2-N101-1 |
| 8-N116-2 | Exp. 8-N116-1 |  | gn116 | CF3 | H | Me | B | 1.67 | 545.9 | Exp. 2-1-2 |
| 8-N117-1 | Exp. 8-N2-1 | sm-n117 | gn117 | CF3 | Me | Me | B | 1.96 | 561.0 | Exp. 2-N101-1 |
| 8-N117-2 | Exp. 8-N117-1 |  | gn117 | CF3 | H | Me | B | 1.76 | 546.9 | Exp. 2-1-2 |

TABLE 3-12

| Exp. | SM1 | SM2 | G | X | Y | Z | LCMS method | RTime | mass | Ref. |
|---|---|---|---|---|---|---|---|---|---|---|
| 8-N118-1 | Exp. 8-N2-1 | sm-n118 | gn118 | CF3 | Me | Me | B | 1.76 | 507.0 | Exp. 2-N101-1 |
| 8-N118-2 | Exp. 8-N118-1 | | gn118 | CF3 | H | Me | B | 1.57 | 493.0 | Exp. 2-1-2 |
| 8-N119-1 | Exp. 8-N2-1 | sm-n119 | gn119 | CF3 | Me | Me | B | 2.19 | 538.0 | Exp. 2-N101-1 |
| 8-N119-2 | Exp. 8-N119-1 | | gn119 | CF3 | H | Me | B | 2.03 | 524.0 | Exp. 2-1-2 |
| 8-N120-1 | Exp. 8-N2-1 | sm-n120 | gn120 | CF3 | Me | Me | B | 2.07 | 574.0 | Exp. 2-N101-1 |
| 8-N120-2 | Exp. 8-N120-1 | | gn120 | CF3 | H | Me | B | 1.90 | 559.9 | Exp. 2-1-2 |
| 8-N121-1 | Exp. 8-N2-1 | sm-n121 | gn121 | CF3 | Me | Me | B | 2.13 | 538.0 | Exp. 2-N101-1 |
| 8-N121-2 | Exp. 8-N121-1 | | gn121 | CF3 | H | Me | B | 1.97 | 524.0 | Exp. 2-1-2 |
| 8-N122-1 | Exp. 8-N2-1 | sm-n122 | gn122 | CF3 | Me | Me | B | 1.86 | 534.0 | Exp. 2-N101-1 |
| 8-N122-2 | Exp. 8-N122-1 | | gn122 | CF3 | H | Me | B | 1.66 | 519.9 | Exp. 2-1-2 |
| 8-N123-1 | Exp. 8-N2-1 | sm-n123 | gn123 | CF3 | Me | Me | B | 1.94 | 516.0 | Exp. 2-N101-1 |
| 8-N123-2 | Exp. 8-N123-1 | | gn123 | CF3 | H | Me | B | 1.78 | 501.9 | Exp. 2-1-2 |
| 8-N124-1 | Exp. 8-N2-1 | sm-n124 | gn124 | CF3 | Me | Me | B | 2.12 | 554.0 | Exp. 2-N101-1 |
| 8-N124-2 | Exp. 8-N124-1 | | gn124 | CF3 | H | Me | B | 1.97 | 540.0 | Exp. 2-1-2 |
| 8-N125-1 | Exp. 8-N2-1 | sm-n125 | gn125 | CF3 | Me | Me | B | 2.15 | 549.0 | Exp. 2-N101-1 |
| 8-N125-2 | Exp. 8-N125-1 | | gn125 | CF3 | H | Me | B | 1.95 | 535.0 | Exp. 2-1-2 |

TABLE 3-13

| Exp. | SM1 | SM2 | G | X | Y | Z | LCMS method | RTime | mass | Ref. |
|---|---|---|---|---|---|---|---|---|---|---|
| 8-N126-1 | Exp. 8-N2-1 | sm-n126 | gn126 | CF3 | Me | Me | B | 2.23 | 565.0 | Exp. 2-N101-1 |
| 8-N126-2 | Exp. 8-N126-1 | | gn126 | CF3 | H | Me | B | 2.02 | 550.9 | Exp. 2-1-2 |
| 8-N127-1 | Exp. 8-N2-1 | sm-n127 | gn127 | CF3 | Me | Me | B | 1.80 | 560.0 | Exp. 2-N101-1 |
| 8-N127-2 | Exp. 8-N127-1 | | gn127 | CF3 | H | Me | B | 1.60 | 546.0 | Exp. 2-1-2 |
| 8-N128-1 | Exp. 8-N2-1 | sm-n128 | gn128 | CF3 | Me | Me | B | 2.14 | 579.0 | Exp. 2-N101-1 |
| 8-N128-2 | Exp. 8-N128-1 | | gn128 | CF3 | H | Me | B | 1.95 | 565.0 | Exp. 2-1-2 |
| 8-N129-1 | Exp. 8-N2-1 | sm-n129 | gn129 | CF3 | Me | Me | B | 2.24 | 607.0 | Exp. 2-N101-1 |
| 8-N129-2 | Exp. 8-N129-1 | | gn129 | CF3 | H | Me | B | 2.03 | 593.0 | Exp. 2-1-2 |
| 8-N130-1 | Exp. 8-N2-1 | sm-n130 | gn130 | CF3 | Me | Me | B | 1.86 | 522.0 | Exp. 2-N101-1 |
| 8-N130-2 | Exp. 8-N130-1 | | gn130 | CF3 | H | Me | B | 1.68 | 507.9 | Exp. 2-1-2 |
| 8-N131-1 | Exp. 8-N2-1 | sm-n131 | gn131 | CF3 | Me | Me | B | 2.17 | 539.0 | Exp. 2-N101-1 |
| 8-N131-2 | Exp. 8-N131-1 | | gn131 | CF3 | H | Me | B | 1.98 | 524.9 | Exp. 2-1-2 |
| 8-N132-1 | Exp. 8-N2-1 | sm-n132 | gn132 | CF3 | Me | Me | B | 2.10 | 579.0 | Exp. 2-N101-1 |
| 8-N132-2 | Exp. 8-N132-1 | | gn132 | CF3 | H | Me | B | 1.92 | 565.0 | Exp. 2-1-2 |
| 8-N133-1 | Exp. 8-N2-1 | sm-n133 | gn133 | CF3 | Me | Me | B | 2.34 | 592.0 | Exp. 2-N101-1 |
| 8-N133-2 | Exp. 8-N133-1 | | gn133 | CF3 | H | Me | B | 2.19 | 578.1 | Exp. 2-1-2 |

TABLE 3-14

| Exp. | SM1 | SM2 | G | X | Y | Z | LCMS method | RTime | mass | Ref. |
|---|---|---|---|---|---|---|---|---|---|---|
| 8-N134-1 | Exp. 8-N2-1 | sm-n134 | gn134 | CF3 | Me | Me | B | 1.83 | 581.0 | Exp. 2-N101-1 |
| 8-N134-2 | Exp. 8-N134-1 | | gn134 | CF3 | H | Me | B | 1.63 | 567.0 | Exp. 2-1-2 |
| 8-N135-1 | Exp. 8-N2-1 | sm-n135 | gn135 | CF3 | Me | Me | B | 1.93 | 579.0 | Exp. 2-N101-1 |
| 8-N135-2 | Exp. 8-N135-1 | | gn135 | CF3 | H | Me | B | 1.77 | 565.0 | Exp. 2-1-2 |

TABLE 3-14-continued

| Exp. | SM1 | SM2 | G | X | Y | Z | LCMS method | RTime | mass | Ref. |
|---|---|---|---|---|---|---|---|---|---|---|
| 8-N136-1 | Exp. 8-N2-1 | sm-n136 | gn136 | CF3 | Me | Me | B | 2.24 | 647.0 | Exp. 2-N101-1 |
| 8-N136-2 | Exp. 8-N136-1 | | gn136 | CF3 | H | Me | B | 2.10 | 633.0 | Exp. 2-1-2 |

TABLE 3-15

| Exp. | SM1 | SM2 | G | X | Y | Z | LCMS method | RTime | mass | Ref. |
|---|---|---|---|---|---|---|---|---|---|---|
| 2-N301-1 | Exp. 2-N1-1 | sm-n301 | gn301 | Me | Me | Me | B | 1.90 | 366.1 | |
| 2-N301-2 | Exp. 2-N301-1 | | gn301 | Me | H | Me | B | 1.53 | 352.4 | Exp. 2-1-2 |
| 2-N302-1 | Exp. 2-N301-1 | sm-n300 | gn302 | Me | Me | Me | B | 1.56 | 380.1 | |
| 2-N302-2 | Exp. 2-N302-1 | | gn302 | Me | H | Me | A | 3.13 | 366.5 | Exp. 2-1-2 |
| 2-N303-1 | Exp. 2-N1-1 | sm-n303 | gn303 | Me | Me | Me | B | 1.97 | 366.1 | Exp. 2-N301-1 |
| 2-N303-2 | Exp. 2-N303-1 | | gn303 | Me | H | Me | B | 1.64 | 352.4 | Exp. 2-1-2 |
| 2-N304-1 | Exp. 2-N1-1 | sm-n304 | gn304 | Me | Me | Me | B | 2.09 | 380.1 | Exp. 2-N301-1 |
| 2-N304-2 | Exp. 2-N304-1 | | gn304 | Me | H | Me | B | 1.78 | 366.5 | Exp. 2-1-2 |
| 2-N305-1 | Exp. 2-N304-1 | sm-n300 | gn305 | Me | Me | Me | B | 2.04 | 393.9 | Exp. 2-N302-1 |
| 2-N305-2 | Exp. 2-N305-1 | | gn305 | Me | H | Me | A | 1.72 | 380.2 | Exp. 2-1-2 |
| 2-N306-1 | Exp. 2-N1-1 | sm-n306 | gn306 | Me | Me | Me | B | 2.19 | 406.2 | Exp. 2-N301-1 |
| 2-N306-2 | Exp. 2-N306-1 | | gn306 | Me | H | Me | A | 4.62 | 392.2 | Exp. 2-1-2 |
| 2-N307-1 | Exp. 2-N1-1 | sm-n307 | gn307 | Me | Me | Me | B | 2.00 | 414.0 | Exp. 2-N301-1 |
| 2-N307-2 | Exp. 2-N307-1 | | gn307 | Me | H | Me | B | 1.72 | 400.5 | Exp. 2-1-2 |
| 2-N308-1 | Exp. 2-N1-1 | sm-n308 | gn308 | Me | Me | Me | B | 1.97 | 432.3 | Exp. 2-N301-1 |
| 2-N308-2 | Exp. 2-N308-1 | | gn308 | Me | H | Me | A | 4.36 | 418.4 | Exp. 2-1-2 |
| 2-N309-1 | Exp. 2-N308-1 | sm-n300 | gn309 | Me | Me | Me | B | 2.09 | 446.3 | Exp. 2-N302-1 |
| 2-N309-2 | Exp. 2-N309-1 | | gn309 | Me | H | Me | A | 4.51 | 432.5 | Exp. 2-1-2 |

TABLE 3-16

| Exp. | SM1 | SM2 | G | X | Y | Z | LCMS method | RTime | mass | Ref. |
|---|---|---|---|---|---|---|---|---|---|---|
| 2-N310-1 | Exp. 2-N1-1 | sm-n310 | gn310 | Me | Me | Me | A | 5.32 | 482.4 | Exp. 2-N301-1 |
| 2-N310-2 | Exp. 2-N310-1 | | gn310 | Me | H | Me | B | 1.86 | 468.5 | Exp. 2-1-2 |
| 2-N311-1 | Exp. 2-N310-1 | sm-n300 | gn311 | Me | Me | Me | B | 2.22 | 496.3 | Exp. 2-N302-1 |
| 2-N311-2 | Exp. 2-N311-1 | | gn311 | Me | H | Me | A | 5.06 | 482.4 | Exp. 2-1-2 |
| 2-N312-1 | Exp. 2-N1-1 | sm-n312 | gn312 | Me | Me | Me | A | 5.96 | 565.4 | Exp. 2-N301-1 |
| 2-N312-2 | Exp. 2-N312-1 | | gn312 | Me | H | Me | A | 5.25 | 551.4 | Exp. 2-1-2 |
| 2-N313-1 | Exp. 2-N312-1 | sm-n300 | gn313 | Me | Me | Me | B | 2.32 | 579.3 | Exp. 2-N302-1 |
| 2-N313-2 | Exp. 2-N313-1 | | gn313 | Me | H | Me | A | 5.51 | 565.4 | Exp. 2-1-2 |
| 2-N314-1 | Exp. 2-N1-1 | sm-n314 | gn314 | Me | Me | Me | B | 2.48 | 490.3 | Exp. 2-N301-1 |
| 2-N314-2 | Exp. 2-N314-1 | | gn314 | Me | H | Me | B | 1.95 | 476.5 | Exp. 2-1-2 |
| 2-N315-1 | Exp. 2-N314-1 | sm-n300 | gn315 | Me | Me | Me | A | 5.93 | 504.5 | Exp. 2-N302-1 |
| 2-N315-2 | Exp. 2-N315-1 | | gn315 | Me | H | Me | A | 5.22 | 490.5 | Exp. 2-1-2 |
| 7-N304-1 | Exp. 7-N1-1 | sm-n304 | gn304 | Cl | Me | Me | A | 5.72 | 400.2 | Exp. 2-N301-1 |
| 7-N304-2 | Exp. 7-N304-1 | | gn304 | Cl | H | Me | A | 4.93 | 386.2 | Exp. 2-1-2 |
| 7-N305-1 | Exp. 7-N304-1 | sm-n300 | gn305 | Cl | Me | Me | A | 6.08 | 414.2 | Exp. 2-N302-1 |

TABLE 3-16-continued

| Exp. | SM1 | SM2 | G | X | Y | Z | LCMS method | RTime | mass | Ref. |
|---|---|---|---|---|---|---|---|---|---|---|
| 7-N305-2 | Exp. 7-N305-1 | | gn305 | Cl | H | Me | A | 5.27 | 400.2 | Exp. 2-1-2 |
| 2-C1-1 | IM-16 | sm-c1 | gc1 | Me | Me | Me | B | 2.25 | 479 | |
| 2-C1-2 | | 2-C1-1 | gc2 | Me | H | Me | B | 1.97 | 465 | Exp. 2-1-2 |

TABLE 3-17

| Exp. | SM1 | SM2 | G | X | Y | Z | LCMS method | RTime | mass | Ref. |
|---|---|---|---|---|---|---|---|---|---|---|
| 2-N316-1 | Exp. 2-N1-1 | sm-n316 | gn316 | Me | Me | Me | B | 2.11 | 392 | Exp. 2-N301-1 |
| 2-N316-2 | | Exp. 2-N316-1 | gn316 | Me | H | Me | B | 1.78 | 378 | Exp. 2-1-2 |
| 2-N317-1 | Exp. 2-N1-1 | sm-n317 | gn317 | Me | Me | Me | B | 2.18 | 394 | Exp. 2-N316-1 |
| 2-N317-2 | | Exp. 2-N317-1 | gn317 | Me | H | Me | B | 1.88 | 380 | Exp. 2-1-2 |
| 2-N318-1 | Exp. 2-N1-1 | sm-n318 | gn318 | Me | Me | Me | B | 2.05 | 380 | Exp. 2-N316-1 |
| 2-N318-2 | | Exp. 2-N318-1 | gn318 | Me | H | Me | B | 1.72 | 366 | Exp. 2-1-2 |
| 2-N319-1 | Exp. 2-N1-1 | sm-n319 | gn319 | Me | Me | Me | B | 2.19 | 394 | Exp. 2-N316-1 |
| 2-N319-2 | | Exp. 2-N319-1 | gn319 | Me | H | Me | B | 1.89 | 380 | Exp. 2-1-2 |
| 2-N320-1 | Exp. 2-N1-1 | sm-n320 | gn320 | Me | Me | Me | B | 2.16 | 394 | Exp. 2-N316-1 |
| 2-N320-2 | | Exp. 2-N320-1 | gn320 | Me | H | Me | B | 1.86 | 380 | Exp. 2-1-2 |
| 2-N321-1 | Exp. 2-N1-1 | sm-n321 | gn321 | Me | Me | Me | B | 1.80 | 352 | Exp. 2-N316-1 |
| 2-N321-2 | | Exp. 2-N321-1 | gn321 | Me | H | Me | B | 1.44 | 338 | Exp. 2-1-2 |
| 2-N322-1 | Exp. 2-N1-1 | sm-n322 | gn322 | Me | Me | Me | B | 2.08 | 380 | Exp. 2-N316-1 |
| 2-N322-2 | | Exp. 2-N322-1 | gn322 | Me | H | Me | B | 1.76 | 366 | Exp. 2-1-2 |
| 2-N323-1 | Exp. 2-N1-1 | sm-n323 | gn323 | Me | Me | Me | B | 2.18 | 394 | Exp. 2-N316-1 |
| 2-N323-2 | | Exp. 2-N323-1 | gn323 | Me | H | Me | B | 1.87 | 380 | Exp. 2-1-2 |

TABLE 3-18

| Exp. | SM1 | SM2 | G | X | Y | Z | LCMS method | RTime | mass | Ref. |
|---|---|---|---|---|---|---|---|---|---|---|
| 2-N324-1 | Exp. 2-N1-1 | sm-n324 | gn324 | Me | Me | Me | B | 2.19 | 394 | Exp. 2-N316-1 |
| 2-N324-2 | | Exp. 2-N324-1 | gn324 | Me | H | Me | B | 1.89 | 380 | Exp. 2-1-2 |
| 2-N325-1 | Exp. 2-N1-1 | sm-n325 | gn325 | Me | Me | Me | B | 2.05 | 392 | Exp. 2-N316-1 |
| 2-N325-2 | | Exp. 2-N325-1 | gn325 | Me | H | Me | B | 1.73 | 378 | Exp. 2-1-2 |
| 2-N326-1 | Exp. 2-N1-1 | sm-n326 | gn326 | Me | Me | Me | B | 2.27 | 408 | Exp. 2-N316-1 |
| 2-N326-2 | | Exp. 2-N326-1 | gn326 | Me | H | Me | B | 1.97 | 394 | Exp. 2-1-2 |
| 2-N327-1 | Exp. 2-N1-1 | sm-n327 | gn327 | Me | Me | Me | B | 2.17 | 394 | Exp. 2-N316-1 |
| 2-N327-2 | | Exp. 2-N327-1 | gn327 | Me | H | Me | B | 1.85 | 380 | Exp. 2-1-2 |
| 2-N328-1 | Exp. 2-N1-1 | sm-n328 | gn328 | Me | Me | Me | B | 2.07 | 428 | Exp. 2-N316-1 |
| 2-N328-2 | | Exp. 2-N328-1 | gn328 | Me | H | Me | B | 1.79 | 414 | Exp. 2-1-2 |
| 2-N329-1 | Exp. 2-N1-1 | sm-n329 | gn329 | Me | Me | Me | B | 2.15 | 442 | Exp. 2-N316-1 |
| 2-N329-2 | | Exp. 2-N329-1 | gn329 | Me | H | Me | B | 1.87 | 428 | Exp. 2-1-2 |
| 2-N330-1 | Exp. 2-N1-1 | sm-n330 | gn330 | Me | Me | Me | B | 2.00 | 432 | Exp. 2-N316-1 |
| 2-N330-2 | | Exp. 2-N330-1 | gn330 | Me | H | Me | B | 1.73 | 418 | Exp. 2-1-2 |
| 2-N331-1 | Exp. 2-N1-1 | sm-n331 | gn331 | Me | Me | Me | B | 1.99 | 432 | Exp. 2-N316-1 |
| 2-N331-2 | | Exp. 2-N331-1 | gn331 | Me | H | Me | B | 1.73 | 418 | Exp. 2-1-2 |

TABLE 3-19

| Exp. | SM1 | SM2 | G | X | Y | Z | LCMS method | RTime | mass | Ref. |
|---|---|---|---|---|---|---|---|---|---|---|
| 2-N332-1 | Exp. 2-N1-1 | sm-n332 | gn332 | Me | Me | Me | B | 1.98 | 444 | Exp. 2-N316-1 |
| 2-N332-2 | | Exp. 2-N332-1 | gn332 | Me | H | Me | B | 1.70 | 430 | Exp. 2-1-2 |
| 2-N333-1 | Exp. 2-N1-1 | sm-n333 | gn333 | Me | Me | Me | B | 1.76 | 444 | Exp. 2-N316-1 |
| 2-N333-2 | | Exp. 2-N333-1 | gn333 | Me | H | Me | B | 1.69 | 430 | Exp. 2-1-2 |
| 2-N334-1 | Exp. 2-N1-1 | sm-n334 | gn334 | Me | Me | Me | B | 1.96 | 444 | Exp. 2-N316-1 |
| 2-N334-2 | | Exp. 2-N334-1 | gn334 | Me | H | Me | B | 1.68 | 430 | Exp. 2-1-2 |
| 2-N335-1 | Exp. 2-N1-1 | sm-n335 | gn335 | Me | Me | Me | B | 2.27 | 486 | Exp. 2-N316-1 |
| 2-N335-2 | | Exp. 2-N335-1 | gn335 | Me | H | Me | B | 2.03 | 472 | Exp. 2-1-2 |
| 2-N336-1 | Exp. 2-N1-1 | sm-n336 | gn336 | Me | Me | Me | B | 2.37 | 470 | Exp. 2-N316-1 |
| 2-N336-2 | | Exp. 2-N336-1 | gn336 | Me | H | Me | B | 2.13 | 456 | Exp. 2-1-2 |
| 2-N337-1 | Exp. 2-N306-1 | sm-n300 | gn337 | Me | Me | Me | B | 1.89 | 420 | Exp. 2-N302-1 |
| 2-N337-2 | | Exp. 2-N337-1 | gn337 | Me | H | Me | B | 1.45 | 406 | Exp. 2-1-2 |

TABLE 3-19-continued

| | | | | | | | LCMS | | |
|---|---|---|---|---|---|---|---|---|---|
| Exp. | SM1 | SM2 | G | X | Y | Z | method | RTime | mass Ref. |
| 2-N338-1 | Exp. 2-N316-1 | sm-n300 | gn338 | Me | Me | Me | B | 1.80 | 406 Exp. 2-N302-1 |
| 2-N338-2 | Exp. 2-N338-1 | | gn338 | Me | H | Me | B | 1.35 | 392 Exp. 2-1-2 |
| 2-N339-1 | Exp. 2-N317-1 | sm-n300 | gn339 | Me | Me | Me | B | 2.22 | 408 Exp. 2-N338-1 |
| 2-N339-2 | Exp. 2-N339-1 | | gn339 | Me | H | Me | B | 1.85 | 394 Exp. 2-1-2 |

TABLE 3-20

| | | | | | | | LCMS | | |
|---|---|---|---|---|---|---|---|---|---|
| Exp. | SM1 | SM2 | G | X | Y | Z | method | RTime | mass Ref. |
| 2-N340-1 | Exp. 2-N318-1 | sm-n300 | gn340 | Me | Me | Me | B | 1.95 | 394 Exp. 2-N338-1 |
| 2-N340-2 | Exp. 2-N340-1 | | gn340 | Me | H | Me | B | 1.53 | 380 Exp. 2-1-2 |
| 2-N341-1 | Exp. 2-N319-1 | sm-n300 | gn341 | Me | Me | Me | B | 2.23 | 408 Exp. 2-N338-1 |
| 2-N341-2 | Exp. 2-N341-1 | | gn341 | Me | H | Me | B | 1.87 | 394 Exp. 2-1-2 |
| 2-N342-1 | Exp. 2-N320-1 | sm-n300 | gn342 | Me | Me | Me | B | 2.14 | 408 Exp. 2-N338-1 |
| 2-N342-2 | Exp. 2-N342-1 | | gn342 | Me | H | Me | B | 1.72 | 394 Exp. 2-1-2 |
| 2-N343-1 | Exp. 2-N321-1 | sm-n300 | gn343 | Me | Me | Me | B | 1.30 | 366 Exp. 2-N338-1 |
| 2-N343-2 | Exp. 2-N343-1 | | gn343 | Me | H | Me | B | 0.99 | 352 Exp. 2-1-2 |
| 2-N344-1 | Exp. 2-N303-1 | sm-n300 | gn344 | Me | Me | Me | B | 1.56 | 380 Exp. 2-N338-1 |
| 2-N344-2 | Exp. 2-N344-1 | | gn344 | Me | H | Me | B | 1.18 | 366 Exp. 2-1-2 |
| 2-N345-1 | Exp. 2-N322-1 | sm-n300 | gn345 | Me | Me | Me | B | 1.73 | 394 Exp. 2-N338-1 |
| 2-N345-2 | Exp. 2-N345-1 | | gn345 | Me | H | Me | B | 1.31 | 380 Exp. 2-1-2 |
| 2-N346-1 | Exp. 2-N323-1 | sm-n300 | gn346 | Me | Me | Me | B | 1.90 | 408 Exp. 2-N338-1 |
| 2-N346-2 | Exp. 2-N346-1 | | gn346 | Me | H | Me | B | 1.78 | 394 Exp. 2-1-2 |

TABLE 3-21

| | | | | | | | LCMS | | |
|---|---|---|---|---|---|---|---|---|---|
| Exp. | SM1 | SM2 | G | X | Y | Z | method | RTime | mass Ref. |
| 2-N348-1 | Exp. 2-N326-1 | sm-n300 | gn348 | Me | Me | Me | B | 2.26 | 422 Exp. 2-N338-1 |
| 2-N348-2 | Exp. 2-N348-1 | | gn348 | Me | H | Me | B | 1.89 | 408 Exp. 2-1-2 |
| 2-N349-1 | Exp. 2-N327-1 | sm-n300 | gn349 | Me | Me | Me | B | 2.12 | 408 Exp. 2-N338-1 |
| 2-N349-2 | Exp. 2-N349-1 | | gn349 | Me | H | Me | B | 1.76 | 394 Exp. 2-1-2 |
| 2-N350-1 | Exp. 2-N328-1 | sm-n300 | gn350 | Me | Me | Me | B | 2.12 | 442 Exp. 2-N338-1 |
| 2-N350-2 | Exp. 2-N350-1 | | gn350 | Me | H | Me | B | 1.74 | 428 Exp. 2-1-2 |
| 2-N351-1 | Exp. 2-N329-1 | sm-n300 | gn351 | Me | Me | Me | B | 2.24 | 456 Exp. 2-N338-1 |
| 2-N351-2 | Exp. 2-N351-1 | | gn351 | Me | H | Me | B | 1.91 | 442 Exp. 2-1-2 |
| 2-N352-1 | Exp. 2-N331-1 | sm-n300 | gn352 | Me | Me | Me | B | 2.13 | 446 Exp. 2-N338-1 |
| 2-N352-2 | Exp. 2-N352-1 | | gn352 | Me | H | Me | B | 1.83 | 432 Exp. 2-1-2 |

TABLE 3-22

| | | | | | | | LCMS | | |
|---|---|---|---|---|---|---|---|---|---|
| Exp. | SM1 | SM2 | G | X | Y | Z | method | RTime | mass Ref. |
| 2-N356-1 | Exp. 2-N330-1 | sm-n300 | gn356 | Me | Me | Me | B | 2.13 | 446 Exp. 2-N338-1 |
| 2-N356-2 | Exp. 2-N356-1 | | gn356 | Me | H | Me | B | 1.85 | 432 Exp. 2-1-2 |
| 2-N357-1 | Exp. 2-N332-1 | sm-n300 | gn357 | Me | Me | Me | B | 1.81 | 458 Exp. 2-N338-1 |
| 2-N357-2 | Exp. 2-N357-1 | | gn357 | Me | H | Me | B | 1.44 | 444 Exp. 2-1-2 |
| 2-N358-1 | Exp. 2-N333-1 | sm-n300 | gn358 | Me | Me | Me | B | 2.05 | 458 Exp. 2-N338-1 |
| 2-N358-2 | Exp. 2-N358-1 | | gn358 | Me | H | Me | B | 1.73 | 444 Exp. 2-1-2 |
| 2-N359-1 | Exp. 2-N334-1 | sm-n300 | gn359 | Me | Me | Me | B | 1.95 | 458 Exp. 2-N338-1 |
| 2-N359-2 | Exp. 2-N359-1 | | gn359 | Me | H | Me | B | 1.58 | 444 Exp. 2-1-2 |
| 2-N360-1 | Exp. 2-N335-1 | sm-n300 | gn360 | Me | Me | Me | B | 2.34 | 500 Exp. 2-N338-1 |
| 2-N360-2 | Exp. 2-N360-1 | | gn360 | Me | H | Me | B | 2.02 | 486 Exp. 2-1-2 |
| 2-N361-1 | Exp. 2-N336-1 | sm-n300 | gn361 | Me | Me | Me | B | 2.47 | 484 Exp. 2-N338-1 |
| 2-N361-2 | Exp. 2-N361-1 | | gn361 | Me | H | Me | B | 2.19 | 470 Exp. 2-1-2 |
| 2-N362-1 | Exp. 2-N307-1 | sm-n300 | gn362 | Me | Me | Me | B | 2.08 | 428 Exp. 2-N338-1 |
| 2-N362-2 | Exp. 2-N362-1 | | gn362 | Me | H | Me | B | 1.75 | 414 Exp. 2-1-2 |
| 2-N363-1 | Exp. 2-N1-1 | sm-n363 | gn363 | Me | Me | Me | B | 2.02 | 462 Exp. 2-N316-1 |
| 2-N363-2 | Exp. 2-N363-1 | | gn363 | Me | H | Me | B | 1.77 | 448 Exp. 2-1-2 |

TABLE 3-23

| Exp. | SM1 | SM2 | G | X | Y | Z | LCMS method | RTime | mass | Ref. |
|---|---|---|---|---|---|---|---|---|---|---|
| 2-N364-1 | Exp. 2-N1-1 | sm-n364 | gn364 | Me | Me | Me | B | 2.02 | 462 | Exp. 2-N316-1 |
| 2-N364-2 | Exp. 2-N364-1 | | gn364 | Me | H | Me | B | 1.75 | 448 | Exp. 2-1-2 |
| 2-N365-1 | Exp. 2-N1-1 | sm-n365 | gn365 | Me | Me | Me | B | 1.92 | 492 | Exp. 2-N316-1 |
| 2-N365-2 | Exp. 2-N365-1 | | gn365 | Me | H | Me | B | 1.66 | 478 | Exp. 2-1-2 |
| 2-N366-1 | Exp. 2-N1-1 | sm-n366 | gn366 | Me | Me | Me | B | 2.02 | 462 | Exp. 2-N316-1 |
| 2-N366-2 | Exp. 2-N366-1 | | gn366 | Me | H | Me | B | 1.76 | 448 | Exp. 2-1-2 |
| 2-N367-1 | Exp. 2-N1-1 | sm-n367 | gn367 | Me | Me | Me | B | 2.15 | 498 | Exp. 2-N316-1 |
| 2-N367-2 | Exp. 2-N367-1 | | gn367 | Me | H | Me | B | 1.91 | 484 | Exp. 2-1-2 |
| 2-N368-1 | Exp. 2-N363-1 | sm-n300 | gn368 | Me | Me | Me | B | 2.13 | 476 | Exp. 2-N338-1 |
| 2-N368-2 | Exp. 2-N368-1 | | gn368 | Me | H | Me | B | 1.84 | 462 | Exp. 2-1-2 |
| 2-N369-1 | Exp. 2-N364-1 | sm-n300 | gn369 | Me | Me | Me | B | 2.14 | 476 | Exp. 2-N338-1 |
| 2-N369-2 | Exp. 2-N369-1 | | gn369 | Me | H | Me | B | 1.87 | 462 | Exp. 2-1-2 |
| 2-N370-1 | Exp. 2-N365-1 | sm-n300 | gn370 | Me | Me | Me | B | 2.02 | 506 | Exp. 2-N338-1 |
| 2-N370-2 | Exp. 2-N370-1 | | gn370 | Me | H | Me | B | 1.73 | 492 | Exp. 2-1-2 |
| 2-N371-1 | Exp. 2-N366-1 | sm-n300 | gn371 | Me | Me | Me | B | 2.10 | 476 | Exp. 2-N338-1 |
| 2-N371-2 | Exp. 2-N371-1 | | gn371 | Me | H | Me | B | 1.77 | 462 | Exp. 2-1-2 |

TABLE 3-24

| Exp. | SM1 | SM2 | G | X | Y | Z | LCMS method | RTime | mass | Ref. |
|---|---|---|---|---|---|---|---|---|---|---|
| 2-N372-1 | Exp. 2-N367-1 | sm-n300 | gn372 | Me | Me | Me | B | 2.28 | 512 | Exp. 2-N338-1 |
| 2-N372-2 | Exp. 2-N372-1 | | gn372 | Me | H | Me | B | 2.04 | 498 | Exp. 2-1-2 |
| 2-N373-1 | Exp. 2-N1-1 | sm-n373 | gn373 | Me | Me | Me | B | 1.83 | 472 | Exp. 2-N316-1 |
| 2-N373-2 | Exp. 2-N373-1 | | gn373 | Me | H | Me | B | 1.91 | 458 | Exp. 2-1-2 |
| 2-N374-1 | Exp. 2-N1-1 | sm-n374 | gn374 | Me | Me | Me | B | 2.04 | 498 | Exp. 2-N316-1 |
| 2-N374-2 | Exp. 2-N374-1 | | gn374 | Me | H | Me | B | 1.92 | 484 | Exp. 2-1-2 |
| 2-N375-1 | Exp. 2-N1-1 | sm-n375 | gn375 | Me | Me | Me | B | 1.76 | 462 | Exp. 2-N316-1 |
| 2-N375-2 | Exp. 2-N375-1 | | gn375 | Me | H | Me | B | 1.77 | 448 | Exp. 2-1-2 |
| 2-N376-1 | Exp. 2-N1-1 | sm-n376 | gn376 | Me | Me | Me | B | 1.98 | 466 | Exp. 2-N316-1 |
| 2-N376-2 | Exp. 2-N376-1 | | gn376 | Me | H | Me | B | 1.85 | 452 | Exp. 2-1-2 |
| 2-N377-1 | Exp. 2-N373-1 | sm-n300 | gn377 | Me | Me | Me | A | 5.44 | 486 | Exp. 2-N338-1 |
| 2-N377-2 | Exp. 2-N377-1 | | gn377 | Me | H | Me | B | 1.68 | 472 | Exp. 2-1-2 |
| 2-N378-1 | Exp. 2-N374-1 | sm-n300 | gn378 | Me | Me | Me | A | 6.03 | 512 | Exp. 2-N338-1 |
| 2-N378-2 | Exp. 2-N378-1 | | gn378 | Me | H | Me | B | 2.00 | 498 | Exp. 2-1-2 |
| 2-N379-1 | Exp. 2-N375-1 | sm-n300 | gn379 | Me | Me | Me | A | 5.20 | 476 | Exp. 2-N338-1 |
| 2-N379-2 | Exp. 2-N379-1 | | gn379 | Me | H | Me | B | 1.62 | 462 | Exp. 2-1-2 |

TABLE 3-25

| Exp. | SM1 | SM2 | G | X | Y | Z | LCMS method | RTime | mass | Ref. |
|---|---|---|---|---|---|---|---|---|---|---|
| 2-N380-1 | Exp. 2-N376-1 | sm-n300 | gn380 | Me | Me | Me | A | 5.85 | 480 | Exp. 2-N338-1 |
| 2-N380-2 | Exp. 2-N380-1 | | gn380 | Me | H | Me | B | 1.94 | 466 | Exp. 2-1-2 |
| 2-N382-1 | Exp. 2-N1-1 | sm-n382 | gn382 | Me | Me | Me | B | 2.11 | 428 | Exp. 2-N316-1 |
| 2-N382-2 | Exp. 2-N382-1 | | gn382 | Me | H | Me | B | 1.85 | 414 | Exp. 2-1-2 |
| 2-N383-1 | Exp. 2-N1-1 | sm-n383 | gn383 | Me | Me | Me | B | 2.11 | 428 | Exp. 2-N316-1 |
| 2-N383-2 | Exp. 2-N383-1 | | gn383 | Me | H | Me | B | 1.85 | 414 | Exp. 2-1-2 |
| 2-N384-1 | Exp. 2-N1-1 | sm-n384 | gn384 | Me | Me | Me | B | 2.20 | 442 | Exp. 2-N316-1 |
| 2-N384-2 | Exp. 2-N384-1 | | gn384 | Me | H | Me | B | 1.95 | 428 | Exp. 2-1-2 |
| 2-N385-1 | Exp. 2-N1-1 | sm-n385 | gn385 | Me | Me | Me | B | 2.29 | 456 | Exp. 2-N316-1 |
| 2-N385-2 | Exp. 2-N385-1 | | gn385 | Me | H | Me | B | 2.05 | 442 | Exp. 2-1-2 |
| 2-N386-1 | Exp. 2-N1-1 | sm-n386 | gn386 | Me | Me | Me | B | 2.27 | 456 | Exp. 2-N316-1 |
| 2-N386-2 | Exp. 2-N386-1 | | gn386 | Me | H | Me | B | 2.02 | 442 | Exp. 2-1-2 |
| 2-N387-1 | Exp. 2-N1-1 | sm-n387 | gn387 | Me | Me | Me | B | 2.37 | 470 | Exp. 2-N316-1 |
| 2-N387-2 | Exp. 2-N387-1 | | gn387 | Me | H | Me | B | 2.14 | 456 | Exp. 2-1-2 |

TABLE 3-26

| Exp. | SM1 | SM2 | G | X | Y | Z | LCMS method | RTime | mass | Ref. |
|---|---|---|---|---|---|---|---|---|---|---|
| 2-N388-1 | Exp. 2-N1-1 | sm-n388 | gn388 | Me | Me | Me | B | 2.08 | 458 | Exp. 2-N316-1 |
| 2-N388-2 | Exp. 2-N388-1 | | gn388 | Me | H | Me | B | 1.83 | 444 | Exp. 2-1-2 |

TABLE 3-26-continued

| Exp. | SM1 | SM2 | G | X | Y | Z | LCMS method | RTime | mass | Ref. |
|---|---|---|---|---|---|---|---|---|---|---|
| 2-N389-1 | Exp. 2-N1-1 | sm-n389 | gn389 | Me | Me | Me | B | 2.20 | 472 | Exp. 2-N316-1 |
| 2-N389-2 | Exp. 2-N389-1 | | gn389 | Me | H | Me | B | 1.95 | 458 | Exp. 2-1-2 |
| 2-N390-1 | Exp. 2-N1-1 | sm-n390 | gn390 | Me | Me | Me | B | 2.37 | 500 | Exp. 2-N316-1 |
| 2-N390-2 | Exp. 2-N390-1 | | gn390 | Me | H | Me | B | 2.15 | 486 | Exp. 2-1-2 |
| 2-N391-1 | Exp. 2-N1-1 | sm-n391 | gn391 | Me | Me | Me | B | 2.45 | 514 | Exp. 2-N316-1 |
| 2-N391-2 | Exp. 2-N391-1 | | gn391 | Me | H | Me | B | 2.24 | 500 | Exp. 2-1-2 |
| 2-N392-1 | Exp. 2-N1-1 | sm-n392 | gn392 | Me | Me | Me | B | 2.10 | 458 | Exp. 2-N316-1 |
| 2-N392-2 | Exp. 2-N392-1 | | gn392 | Me | H | Me | B | 1.83 | 444 | Exp. 2-1-2 |
| 2-N393-1 | Exp. 2-N1-1 | sm-n393 | gn393 | Me | Me | Me | B | 2.15 | 472 | Exp. 2-N316-1 |
| 2-N393-2 | Exp. 2-N393-1 | | gn393 | Me | H | Me | B | 1.90 | 458 | Exp. 2-1-2 |
| 2-N395-1 | Exp. 2-N1-1 | sm-n395 | gn395 | Me | Me | Me | B | 2.16 | 498 | Exp. 2-N316-1 |
| 2-N395-2 | Exp. 2-N395-1 | | gn395 | Me | H | Me | B | 1.93 | 484 | Exp. 2-1-2 |

TABLE 3-27

| Exp. | SM1 | SM2 | G | X | Y | Z | LCMS method | RTime | mass | Ref. |
|---|---|---|---|---|---|---|---|---|---|---|
| 2-N396-1 | Exp. 2-N1-1 | sm-n396 | gn396 | Me | Me | Me | B | 2.17 | 498 | Exp. 2-N316-1 |
| 2-N396-2 | Exp. 2-N396-1 | | gn396 | Me | H | Me | B | 1.92 | 484 | Exp. 2-1-2 |
| 2-N397-1 | Exp. 2-N1-1 | sm-n397 | gn397 | Me | Me | Me | B | 2.23 | 506 | Exp. 2-N316-1 |
| 2-N397-2 | Exp. 2-N397-1 | | gn397 | Me | H | Me | B | 2.00 | 492 | Exp. 2-1-2 |
| 2-N399-1 | Exp. 2-N382-1 | sm-n300 | gn399 | Me | Me | Me | B | 2.20 | 442 | Exp. 2-N338-1 |
| 2-N399-2 | Exp. 2-N399-1 | | gn399 | Me | H | Me | B | 1.92 | 428 | Exp. 2-1-2 |
| 2-N400-1 | Exp. 2-N383-1 | sm-n300 | gn400 | Me | Me | Me | B | 2.19 | 442 | Exp. 2-N338-1 |
| 2-N400-2 | Exp. 2-N400-1 | | gn400 | Me | H | Me | B | 1.89 | 428 | Exp. 2-1-2 |
| 2-N401-1 | Exp. 2-N384-1 | sm-n300 | gn401 | Me | Me | Me | B | 2.27 | 456 | Exp. 2-N338-1 |
| 2-N401-2 | Exp. 2-N401-1 | | gn401 | Me | H | Me | B | 1.97 | 442 | Exp. 2-1-2 |
| 2-N402-1 | Exp. 2-N385-1 | sm-n300 | gn402 | Me | Me | Me | B | 2.37 | 470 | Exp. 2-N338-1 |
| 2-N402-2 | Exp. 2-N402-1 | | gn402 | Me | H | Me | B | 2.10 | 456 | Exp. 2-1-2 |
| 2-N403-1 | Exp. 2-N386-1 | sm-n300 | gn403 | Me | Me | Me | B | 2.34 | 470 | Exp. 2-N338-1 |
| 2-N403-2 | Exp. 2-N403-1 | | gn403 | Me | H | Me | B | 2.04 | 456 | Exp. 2-1-2 |

TABLE 3-28

| Exp. | SM1 | SM2 | G | X | Y | Z | LCMS method | RTime | mass | Ref. |
|---|---|---|---|---|---|---|---|---|---|---|
| 2-N404-1 | Exp. 2-N387-1 | sm-n300 | gn404 | Me | Me | Me | B | 2.46 | 484 | Exp. 2-N338-1 |
| 2-N404-2 | Exp. 2-N404-1 | | gn404 | Me | H | Me | B | 2.20 | 470 | Exp. 2-1-2 |
| 2-N405-1 | Exp. 2-N388-1 | sm-n300 | gn405 | Me | Me | Me | B | 2.10 | 472 | Exp. 2-N338-1 |
| 2-N405-2 | Exp. 2-N405-1 | | gn405 | Me | H | Me | B | 1.77 | 458 | Exp. 2-1-2 |
| 2-N406-1 | Exp. 2-N389-1 | sm-n300 | gn406 | Me | Me | Me | B | 2.23 | 486 | Exp. 2-N338-1 |
| 2-N406-2 | Exp. 2-N406-1 | | gn406 | Me | H | Me | B | 1.92 | 472 | Exp. 2-1-2 |
| 2-N407-1 | Exp. 2-N390-1 | sm-n300 | gn407 | Me | Me | Me | B | 2.44 | 514 | Exp. 2-N338-1 |
| 2-N407-2 | Exp. 2-N407-1 | | gn407 | Me | H | Me | B | 2.18 | 500 | Exp. 2-1-2 |
| 2-N408-1 | Exp. 2-N391-1 | sm-n300 | gn408 | Me | Me | Me | B | 2.54 | 528 | Exp. 2-N338-1 |
| 2-N408-2 | Exp. 2-N408-1 | | gn408 | Me | H | Me | B | 2.29 | 514 | Exp. 2-1-2 |
| 2-N409-1 | Exp. 2-N392-1 | sm-n300 | gn409 | Me | Me | Me | B | 2.00 | 472 | Exp. 2-N338-1 |
| 2-N409-2 | Exp. 2-N409-1 | | gn409 | Me | H | Me | B | 1.64 | 458 | Exp. 2-1-2 |
| 2-N410-1 | Exp. 2-N393-1 | sm-n300 | gn410 | Me | Me | Me | B | 2.17 | 486 | Exp. 2-N338-1 |
| 2-N410-2 | Exp. 2-N410-1 | | gn410 | Me | H | Me | B | 1.85 | 472 | Exp. 2-1-2 |
| 2-N412-1 | Exp. 2-N395-1 | sm-n300 | gn412 | Me | Me | Me | B | 2.28 | 512 | Exp. 2-N338-1 |
| 2-N412-2 | Exp. 2-N412-1 | | gn412 | Me | H | Me | B | 2.04 | 498 | Exp. 2-1-2 |
| 2-N413-1 | Exp. 2-N396-1 | sm-n300 | gn413 | Me | Me | Me | B | 2.28 | 512 | Exp. 2-N338-1 |
| 2-N413-2 | Exp. 2-N413-1 | | gn413 | Me | H | Me | B | 2.04 | 498 | Exp. 2-1-2 |
| 2-N414-1 | Exp. 2-N397-1 | sm-n300 | gn414 | Me | Me | Me | B | 2.32 | 520 | Exp. 2-N338-1 |
| 2-N414-2 | Exp. 2-N414-1 | | gn414 | Me | H | Me | B | 2.06 | 506 | Exp. 2-1-2 |

TABLE 3-29

| Exp. | SM1 | SM2 | G | X | Y | Z | LCMS method | RTime | mass | Ref. |
|---|---|---|---|---|---|---|---|---|---|---|
| 2-N137-1 | Exp. 2-N1-1 | sm-n137 | gn137 | Me | Me | Me | B | 2.32 | 512 | Exp. 2-N101-1 |
| 2-N137-2 | Exp. 2-N137-1 | | gn137 | Me | H | Me | B | 2.05 | 498 | Exp. 2-1-2 |

TABLE 3-29-continued

| Exp. | SM1 | SM2 | G | X | Y | Z | LCMS method | RTime | mass | Ref. |
|---|---|---|---|---|---|---|---|---|---|---|
| 2-N138-1 | Exp. 2-N1-1 | sm-n138 | gn138 | Me | Me | Me | B | 2.08 | 514 | Exp. 2-N101-1 |
| 2-N138-2 | Exp. 2-N138-1 | | gn138 | Me | H | Me | B | 1.87 | 500 | Exp. 2-1-2 |
| 2-N139-1 | Exp. 2-N1-1 | sm-n139 | gn139 | Me | Me | Me | B | 1.76 | 472 | Exp. 2-N101-1 |
| 2-N139-2 | Exp. 2-N139-1 | | gn139 | Me | H | Me | B | 1.53 | 458 | Exp. 2-1-2 |
| 2-N140-1 | Exp. 2-N1-1 | sm-n140 | gn140 | Me | Me | Me | B | 1.74 | 472 | Exp. 2-N101-1 |
| 2-N140-2 | Exp. 2-N140-1 | | gn140 | Me | H | Me | B | 1.51 | 458 | Exp. 2-1-2 |
| 2-N141-1 | Exp. 2-N1-1 | sm-n141 | gn141 | Me | Me | Me | B | 1.86 | 486 | Exp. 2-N101-1 |
| 2-N141-2 | Exp. 2-N141-1 | | gn141 | Me | H | Me | B | 1.64 | 472 | Exp. 2-1-2 |
| 2-N142-1 | Exp. 2-N1-1 | sm-n142 | gn142 | Me | Me | Me | B | 2.27 | 542 | Exp. 2-N101-1 |
| 2-N142-2 | Exp. 2-N142-1 | | gn142 | Me | H | Me | B | 2.09 | 528 | Exp. 2-1-2 |
| 2-N143-1 | Exp. 2-N1-1 | sm-n143 | gn143 | Me | Me | Me | B | 2.37 | 556 | Exp. 2-N101-1 |
| 2-N143-2 | Exp. 2-N143-1 | | gn143 | Me | H | Me | B | 2.20 | 542 | Exp. 2-1-2 |
| 2-N144-1 | Exp. 2-N1-1 | sm-n144 | gn144 | Me | Me | Me | B | 1.86 | 512 | Exp. 2-N101-1 |
| 2-N144-2 | Exp. 2-N144-1 | | gn144 | Me | H | Me | B | 1.64 | 498 | Exp. 2-1-2 |
| 2-N145-1 | Exp. 2-N1-1 | sm-n145 | gn145 | Me | Me | Me | B | 1.97 | 546 | Exp. 2-N101-1 |
| 2-N145-2 | Exp. 2-N145-1 | | gn145 | Me | H | Me | B | 1.76 | 532 | Exp. 2-1-2 |
| 2-N146-1 | Exp. 2-N1-1 | sm-n146 | gn146 | Me | Me | Me | B | 1.72 | 494 | Exp. 2-N101-1 |
| 2-N146-2 | Exp. 2-N146-1 | | gn146 | Me | H | Me | B | 1.50 | 480 | Exp. 2-1-2 |
| 2-N147-1 | Exp. 2-N1-1 | sm-n147 | gn147 | Me | Me | Me | B | 2.18 | 528 | Exp. 2-N101-1 |
| 2-N147-2 | Exp. 2-N147-1 | | gn147 | Me | H | Me | B | 1.98 | 514 | Exp. 2-1-2 |

TABLE 3-30

| Exp. | SM1 | SM2 | G | X | Y | Z | LCMS method | RTime | mass | Ref. |
|---|---|---|---|---|---|---|---|---|---|---|
| 7-N382-1 | Exp. 7-N1-1 | sm-n382 | gn382 | Cl | Me | Me | B | 2.19 | 448 | Exp. 7-N304-1 |
| 7-N382-2 | Exp. 7-N382-1 | | gn382 | Cl | H | Me | B | 1.92 | 434 | Exp. 7-N304-2 |
| 7-N383-1 | Exp. 7-N1-1 | sm-n383 | gn383 | Cl | Me | Me | B | 2.19 | 448 | Exp. 7-N304-1 |
| 7-N383-2 | Exp. 7-N383-1 | | gn383 | Cl | H | Me | B | 1.92 | 434 | Exp. 7-N304-2 |
| 7-N384-1 | Exp. 7-N1-1 | sm-n384 | gn384 | Cl | Me | Me | B | 2.27 | 462 | Exp. 7-N304-1 |
| 7-N384-2 | Exp. 7-N384-1 | | gn384 | Cl | H | Me | B | 2.01 | 448 | Exp. 7-N304-2 |
| 7-N385-1 | Exp. 7-N1-1 | sm-n385 | gn385 | Cl | Me | Me | B | 2.36 | 476 | Exp. 7-N304-1 |
| 7-N385-2 | Exp. 7-N385-1 | | gn385 | Cl | H | Me | B | 2.11 | 462 | Exp. 7-N304-2 |
| 7-N386-1 | Exp. 7-N1-1 | sm-n386 | gn386 | Cl | Me | Me | B | 2.33 | 476 | Exp. 7-N304-1 |
| 7-N386-2 | Exp. 7-N386-1 | | gn386 | Cl | H | Me | B | 2.09 | 462 | Exp. 7-N304-2 |
| 7-N387-1 | Exp. 7-N1-1 | sm-n387 | gn387 | Cl | Me | Me | B | 2.42 | 490 | Exp. 7-N304-1 |
| 7-N387-2 | Exp. 7-N387-1 | | gn387 | Cl | H | Me | B | 2.19 | 476 | Exp. 7-N304-2 |
| 7-N388-1 | Exp. 7-N1-1 | sm-n388 | gn388 | Cl | Me | Me | B | 2.16 | 478 | Exp. 7-N304-1 |
| 7-N388-2 | Exp. 7-N388-1 | | gn388 | Cl | H | Me | B | 1.90 | 464 | Exp. 7-N304-2 |
| 7-N389-1 | Exp. 7-N1-1 | sm-n389 | gn389 | Cl | Me | Me | B | 2.27 | 492 | Exp. 7-N304-1 |
| 7-N389-2 | Exp. 7-N389-1 | | gn389 | Cl | H | Me | B | 2.01 | 478 | Exp. 7-N304-2 |

TABLE 3-31

| Exp. | SM1 | SM2 | G | X | Y | Z | LCMS method | RTime | mass | Ref. |
|---|---|---|---|---|---|---|---|---|---|---|
| 7-N390-1 | Exp. 7-N1-1 | sm-n390 | gn390 | Cl | Me | Me | B | 2.43 | 520 | Exp. 7-N304-1 |
| 7-N390-2 | Exp. 7-N390-1 | | gn390 | Cl | H | Me | B | 2.21 | 506 | Exp. 7-N304-2 |
| 7-N391-1 | Exp. 7-N1-1 | sm-n391 | gn391 | Cl | Me | Me | B | 2.51 | 534 | Exp. 7-N304-1 |
| 7-N391-2 | Exp. 7-N391-1 | | gn391 | Cl | H | Me | B | 2.30 | 520 | Exp. 7-N304-2 |
| 7-N392-1 | Exp. 7-N1-1 | sm-n392 | gn392 | Cl | Me | Me | B | 2.20 | 478 | Exp. 7-N304-1 |
| 7-N392-2 | Exp. 7-N392-1 | | gn392 | Cl | H | Me | B | 1.94 | 464 | Exp. 7-N304-2 |
| 7-N393-1 | Exp. 7-N1-1 | sm-n393 | gn393 | Cl | Me | Me | B | 2.23 | 492 | Exp. 7-N304-1 |
| 7-N393-2 | Exp. 7-N393-1 | | gn393 | Cl | H | Me | B | 1.97 | 478 | Exp. 7-N304-2 |
| 7-N395-1 | Exp. 7-N1-1 | sm-n395 | gn395 | Cl | Me | Me | B | 2.22 | 518 | Exp. 7-N304-1 |
| 7-N395-2 | Exp. 7-N395-1 | | gn395 | Cl | H | Me | B | 1.98 | 504 | Exp. 7-N304-2 |
| 7-N396-1 | Exp. 7-N1-1 | sm-n396 | gn396 | Cl | Me | Me | B | 2.23 | 518 | Exp. 7-N304-1 |
| 7-N396-2 | Exp. 7-N396-1 | | gn396 | Cl | H | Me | B | 1.97 | 504 | Exp. 7-N304-2 |
| 7-N397-1 | Exp. 7-N1-1 | sm-n397 | gn397 | Cl | Me | Me | B | 2.29 | 526 | Exp. 7-N304-1 |
| 7-N397-2 | Exp. 7-N397-1 | | gn397 | Cl | H | Me | B | 2.05 | 512 | Exp. 7-N304-2 |

TABLE 3-32

| Exp. | SM1 | SM2 | G | X | Y | Z | LCMS method | RTime | mass | Ref. |
|---|---|---|---|---|---|---|---|---|---|---|
| 7-N399-1 | Exp. 7-N382-1 | sm-n300 | gn399 | Cl | Me | Me | B | 2.31 | 462 | Exp. 7-N305-1 |
| 7-N399-2 | Exp. 7-N399-1 | | gn399 | Cl | H | Me | B | 2.04 | 448 | Exp. 7-N305-2 |
| 7-N400-1 | Exp. 7-N383-1 | sm-n300 | gn400 | Cl | Me | Me | B | 2.33 | 462 | Exp. 7-N305-1 |
| 7-N400-2 | Exp. 7-N400-1 | | gn400 | Cl | H | Me | B | 2.07 | 448 | Exp. 7-N305-2 |
| 7-N401-1 | Exp. 7-N384-1 | sm-n300 | gn401 | Cl | Me | Me | B | 2.41 | 476 | Exp. 7-N305-1 |
| 7-N401-2 | Exp. 7-N401-1 | | gn401 | Cl | H | Me | B | 2.16 | 462 | Exp. 7-N305-2 |
| 7-N402-1 | Exp. 7-N385-1 | sm-n300 | gn402 | Cl | Me | Me | B | 2.49 | 490 | Exp. 7-N305-1 |
| 7-N402-2 | Exp. 7-N402-1 | | gn402 | Cl | H | Me | B | 2.26 | 476 | Exp. 7-N305-2 |
| 7-N403-1 | Exp. 7-N386-1 | sm-n300 | gn403 | Cl | Me | Me | B | 2.46 | 490 | Exp. 7-N305-1 |
| 7-N403-2 | Exp. 7-N403-1 | | gn403 | Cl | H | Me | B | 2.23 | 476 | Exp. 7-N305-2 |
| 7-N404-1 | Exp. 7-N387-1 | sm-n300 | gn404 | Cl | Me | Me | B | 2.57 | 504 | Exp. 7-N305-1 |
| 7-N404-2 | Exp. 7-N404-1 | | gn404 | Cl | H | Me | B | 2.34 | 490 | Exp. 7-N305-2 |
| 7-N405-1 | Exp. 7-N388-1 | sm-n300 | gn405 | Cl | Me | Me | B | 2.30 | 492 | Exp. 7-N305-1 |
| 7-N405-2 | Exp. 7-N405-1 | | gn405 | Cl | H | Me | B | 2.03 | 478 | Exp. 7-N305-2 |
| 7-N406-1 | Exp. 7-N389-1 | sm-n300 | gn406 | Cl | Me | Me | B | 2.39 | 506 | Exp. 7-N305-1 |
| 7-N406-2 | Exp. 7-N406-1 | | gn406 | Cl | H | Me | B | 2.15 | 492 | Exp. 7-N305-2 |

TABLE 3-33

| Exp. | SM1 | SM2 | G | X | Y | Z | LCMS method | RTime | mass | Ref. |
|---|---|---|---|---|---|---|---|---|---|---|
| 7-N407-1 | Exp. 7-N390-1 | sm-n300 | gn407 | Cl | Me | Me | B | 2.57 | 534 | Exp. 7-N305-1 |
| 7-N407-2 | Exp. 7-N407-1 | | gn407 | Cl | H | Me | B | 2.34 | 520 | Exp. 7-N305-2 |
| 7-N408-1 | Exp. 7-N391-1 | sm-n300 | gn408 | Cl | Me | Me | B | 2.66 | — | Exp. 7-N305-1 |
| 7-N408-2 | Exp. 7-N408-1 | | gn408 | Cl | H | Me | B | 2.43 | 534 | Exp. 7-N305-2 |
| 7-N409-1 | Exp. 7-N392-1 | sm-n300 | gn409 | Cl | Me | Me | B | 2.34 | 492 | Exp. 7-N305-1 |
| 7-N409-2 | Exp. 7-N409-1 | | gn409 | Cl | H | Me | B | 2.07 | 478 | Exp. 7-N305-2 |
| 7-N410-1 | Exp. 7-N393-1 | sm-n300 | gn410 | Cl | Me | Me | B | 2.36 | 506 | Exp. 7-N305-1 |
| 7-N410-2 | Exp. 7-N410-1 | | gn410 | Cl | H | Me | B | 2.10 | 492 | Exp. 7-N305-2 |
| 7-N412-1 | Exp. 7-N395-1 | sm-n300 | gn412 | Cl | Me | Me | B | 2.35 | 532 | Exp. 7-N305-1 |
| 7-N412-2 | Exp. 7-N412-1 | | gn412 | Cl | H | Me | B | 2.12 | 518 | Exp. 7-N305-2 |
| 7-N413-1 | Exp. 7-N396-1 | sm-n300 | gn413 | Cl | Me | Me | B | 2.34 | 532 | Exp. 7-N305-1 |
| 7-N413-2 | Exp. 7-N413-1 | | gn413 | Cl | H | Me | B | 2.10 | 518 | Exp. 7-N305-2 |
| 7-N414-1 | Exp. 7-N397-1 | sm-n300 | gn414 | Cl | Me | Me | B | 2.42 | 540 | Exp. 7-N305-1 |
| 7-N414-2 | Exp. 7-N414-1 | | gn414 | Cl | H | Me | B | 2.19 | 526 | Exp. 7-N305-2 |

TABLE 4-1

| G | Str. |
|---|---|
| g1 | H$_3$C—O— |
| g2 | HO— |
| g3 | 4-fluorobenzyloxy |
| g4 | 3-fluorobenzyloxy |
| g5 | indan-2-yloxy |
| g6 | 2-fluorobenzyloxy |
| g7 | 4-bromo-2-fluorobenzyloxy |
| g8 | 3,4-dichlorobenzyloxy |
| g9 | 4-methoxybenzyloxy |

TABLE 4-1-continued

| G | Str. |
|---|---|
| g10 | 2-methylbenzyloxy |
| g11 | 2,4-difluorobenzyloxy |
| g12 | 3,5-dichlorobenzyloxy |
| g13 | 4-methylbenzyloxy |
| g14 | (R)-1-phenylethoxy |
| g15 | (S)-1-phenylethoxy |
| g16 | 4-(trifluoromethyl)benzyloxy |
| g17 | 3-chlorobenzyloxy |
| g18 | 1-phenylpropoxy |
| g19 | 3,4-difluorobenzyloxy |
| g20 | 2,6-dichlorobenzyloxy |
| g21 | 3-methylbenzyloxy |
| g22 | 2-(4-fluorophenyl)ethoxy |
| g23 | 2-(2-(trifluoromethyl)phenyl)ethoxy |
| g24 | 3-cyclopentylpropoxy |
| g25 | isopropoxy |
| g26 | n-butoxy |
| g27 | isobutoxy |
| g28 | isopentyloxy |
| g29 | n-heptyloxy |
| g30 | cyclopentyloxy |
| g31 | 3-methylcyclopentyloxy |
| g32 | diphenylmethoxy |

TABLE 4-2

| G | Str. |
|---|---|
| gn1 | H₂N→ |
| gn2 | 4-(CF₃)C₆H₄-SO₂-NH→ |
| gn3 | 3-(CF₃)C₆H₄-SO₂-NH→ |
| gn4 | 2-(CF₃)C₆H₄-SO₂-NH→ |
| gn5 | 2-Cl-4-(CF₃)C₆H₃-SO₂-NH→ |
| gn9 | C₆H₅-SO₂-NH→ |
| gn10 | 4-CH₃-C₆H₄-SO₂-NH→ |
| gn11 | 3-CH₃-C₆H₄-SO₂-NH→ |
| gn12 | 2-CH₃-C₆H₄-SO₂-NH→ |
| gn13 | 2-(OCF₃)C₆H₄-SO₂-NH→ |
| gn14 | 3-MeO-C₆H₄-SO₂-NH→ |

TABLE 4-2-continued

| G | Str. |
|---|---|
| gn15 | 3-Cl-C₆H₄-SO₂-NH→ |
| gn16 | 4-F-C₆H₄-SO₂-NH→ |
| gn17 | 3-F-C₆H₄-SO₂-NH→ |
| gn18 | 4-biphenyl-SO₂-NH→ |
| gn19-1 | 3-CN-C₆H₄-SO₂-NH→ |
| gn19-2 | 3-HOOC-C₆H₄-SO₂-NH→ |
| gn20 | 4-(PhO)-C₆H₄-SO₂-NH→ |
| gn21 | 4-(oxazol-5-yl)-C₆H₄-SO₂-NH→ |
| gn22 | 2-phenyl-4-methyl-thiazol-5-yl-SO₂-NH→ |

TABLE 4-2-continued
| G | Str. |
|---|---|
| gn23 | 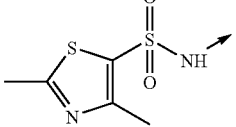 |
| gn24 | 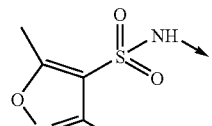 |
| gn25 | 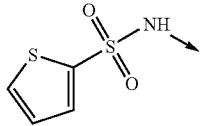 |
| gn26 | 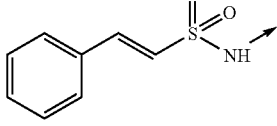 |
| gn27 | 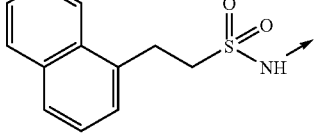 |
| gn28 | 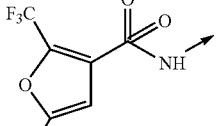 |
| gn29 | 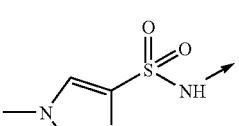 |
| gn30 | 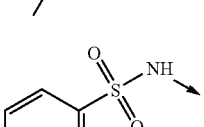 |
| gn31 | 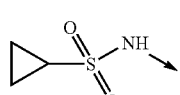 |
| gn32 | 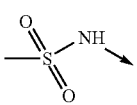 |
TABLE 4-2-continued
| G | Str. |
|---|---|
| gn33 | 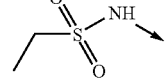 |
| gn34 | 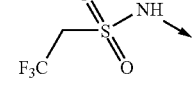 |
| gn35 | 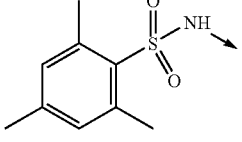 |
| gn36 | 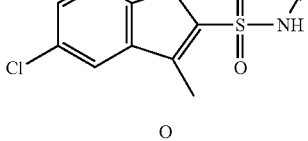 |
| gn37 | 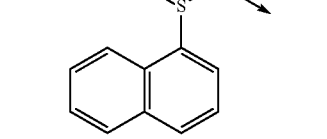 |
| gn38 | 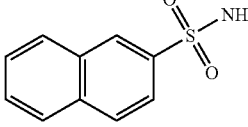 |
| gn39 | 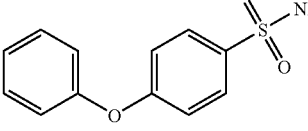 |
| gn40 | 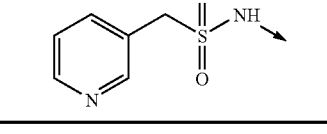 |
TABLE 4-3
| G | Str. |
|---|---|
| gn101 | 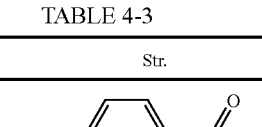 |
| gn102 | 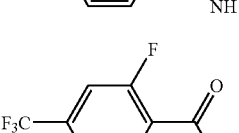 |

TABLE 4-3-continued
| G | Str. |
|---|---|
| gn103 | 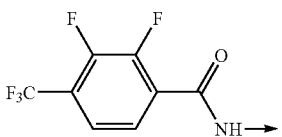 |
| gn104 | 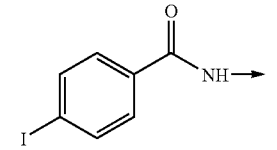 |
| gn105 | 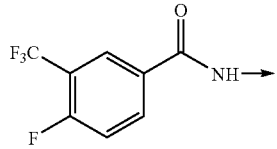 |
| gn110 | 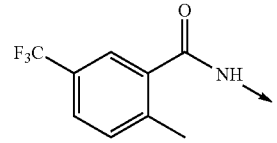 |
| gn111 | 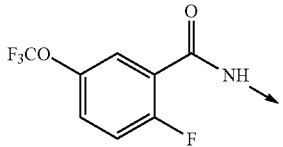 |
| gn112 | 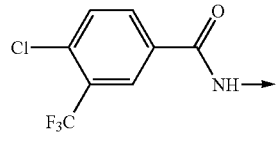 |
| gn113 | 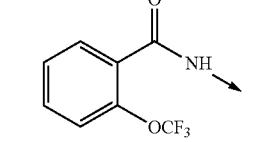 |
| gn114 | 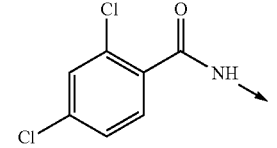 |
| gn115 | 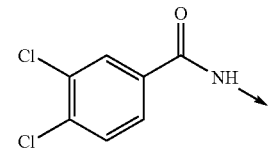 |
| gn116 | 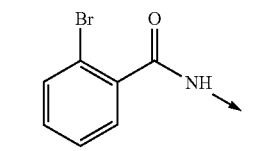 |
| gn117 |  |
| gn118 | 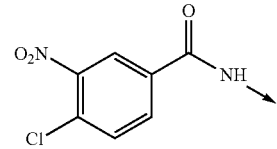 |
| gn119 | 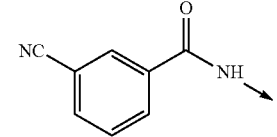 |
| gn120 | 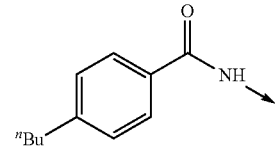 |
| gn121 | 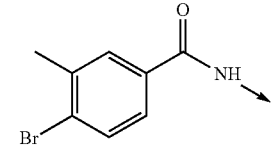 |
| gn122 | 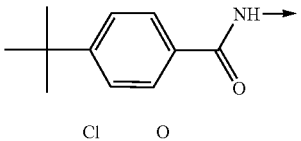 |
| gn123 | 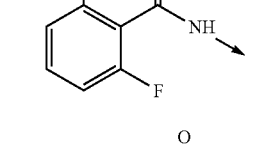 |
| gn124 | 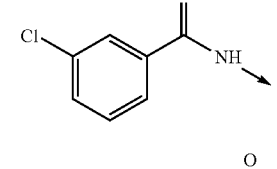 |
| gn125 | 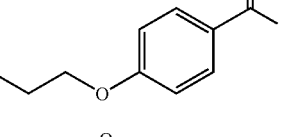 |
| gn126 | 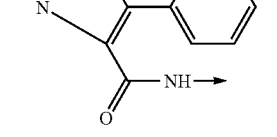 |

TABLE 4-3-continued
| G | Str. |
|---|---|
| gn127 | 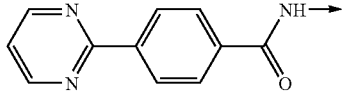 |
| gn128 | 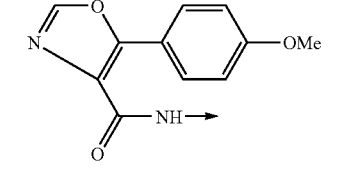 |
| gn129 | 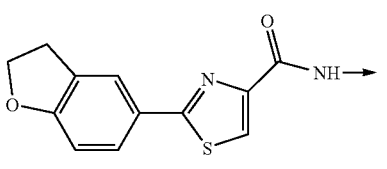 |
| gn130 | 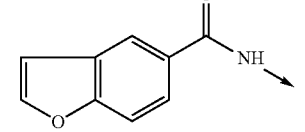 |
| gn131 | 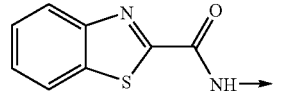 |
| gn132 | 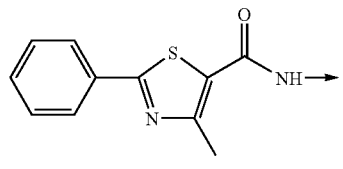 |
| gn133 | 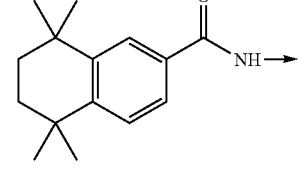 |
| gn134 | 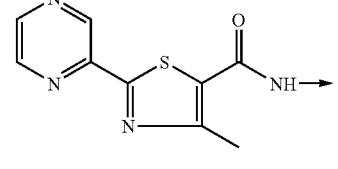 |
| gn135 | 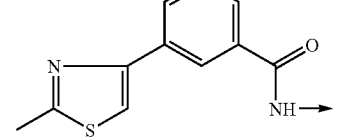 |
| gn136 | 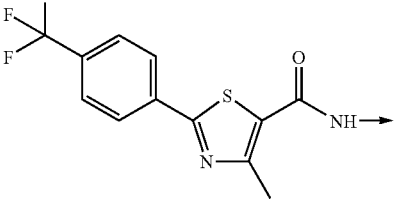 |
TABLE 4-4
| G | Str. |
|---|---|
| gn301 | 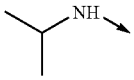 |
| gn302 | 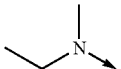 |
| gn303 | 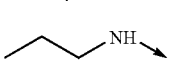 |
| gn304 | 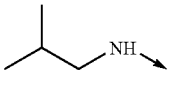 |
| gn305 | 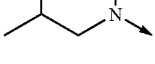 |
| gn306 | 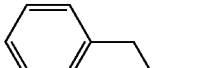 |
| gn307 | 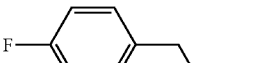 |
| gn308 | 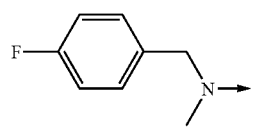 |
| gn309 | 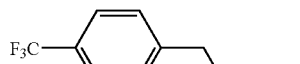 |
| gn310 | 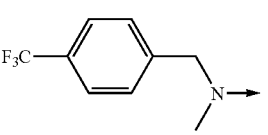 |
| gn311 | |

TABLE 4-4-continued

| G | Str. |
|---|---|
| gn312 | 3-(trifluoromethyl)phenyl-thiazol-5-yl-CH2-NH- |
| gn313 | 3-(trifluoromethyl)phenyl-thiazol-5-yl-CH2-N(CH3)- |
| gn314 | 2-biphenyl-CH2-NH- |
| gn315 | 2-biphenyl-CH2-N(CH3)- |

TABLE 4-5

| G | Str. |
|---|---|
| gc-1 | 4-(trifluoromethyl)phenyl-CH=CH- |

TABLE 4-6

| G | Str. |
|---|---|
| gn316 | cyclopentyl-NH- |
| gn317 | (3-pentyl)-NH- |
| gn318 | (sec-butyl)-NH- |
| gn319 | neopentyl-NH- |
| gn320 | (3-methyl-2-butyl)-NH- |
| gn321 | ethyl-NH- |
| gn322 | n-butyl-NH- |
| gn323 | isobutyl-NH- (isopentyl) |
| gn324 | (2-methylbutyl)-NH- |
| gn325 | (3-methyl-2-butenyl)-NH- |
| gn326 | (2-hexyl)-NH- |
| gn327 | (2-pentyl)-NH- |
| gn328 | (2-phenylethyl)-NH- |
| gn329 | (1-methyl-2-phenylethyl)-NH- |
| gn330 | 2-fluorobenzyl-NH- |

TABLE 4-6-continued
| G | Str. |
|---|---|
| gn331 | 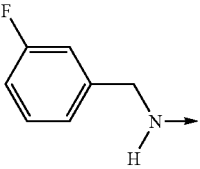 |
| gn332 | 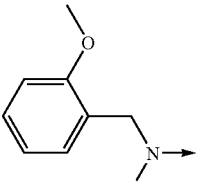 |
| gn333 | 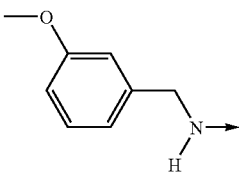 |
| gn334 | 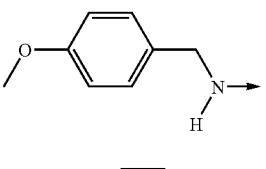 |
| gn335 | 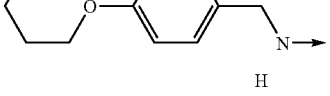 |
| gn336 | 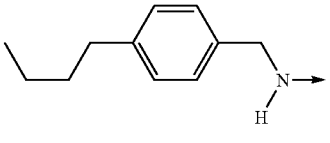 |
| gn337 | 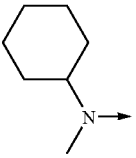 |
| gn338 | 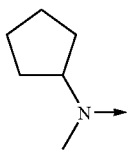 |
| gn339 | 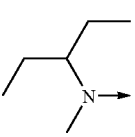 |
TABLE 4-6-continued
| G | Str. |
|---|---|
| gn340 | 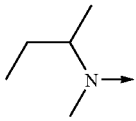 |
| gn341 | 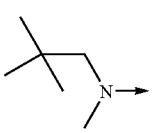 |
| gn342 | 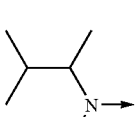 |
| gn343 | 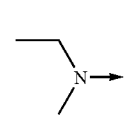 |
| gn344 | 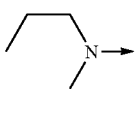 |
| gn345 | 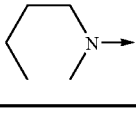 |
TABLE 4-7
| G | Str. |
|---|---|
| gn346 | 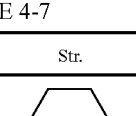 |
| gn348 | 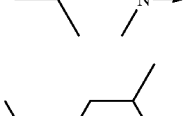 |
| gn349 | 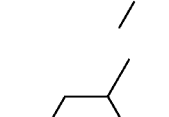 |
| gn350 | 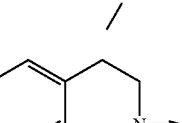 |
| gn351 | 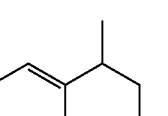 |

TABLE 4-7-continued
| G | Str. |
|---|---|
| gn352 | 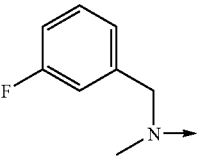 |
| gn356 | 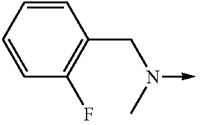 |
| gn357 | 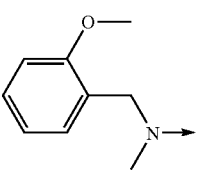 |
| gn358 | 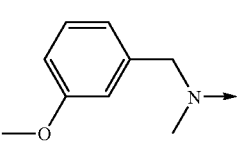 |
| gn359 | 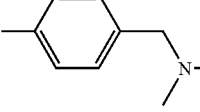 |
| gn360 | 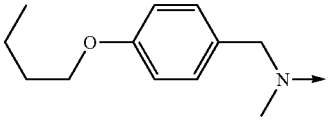 |
| gn361 | 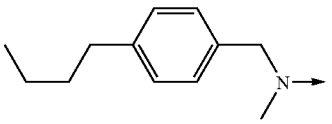 |
| gn362 | 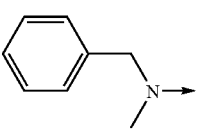 |
| gn363 | 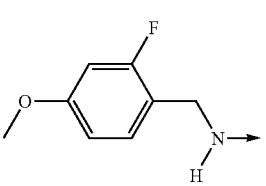 |
| gn364 | 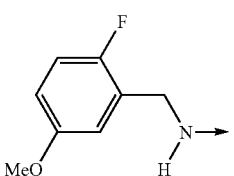 |
| gn365 | 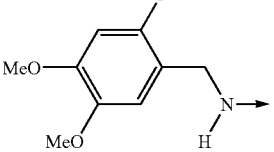 |
| gn366 | 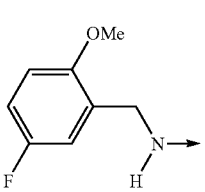 |
| gn367 | 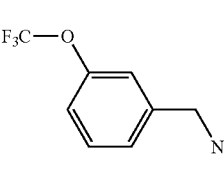 |
| gn368 | 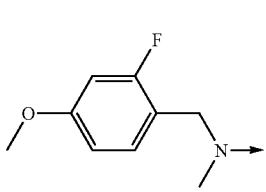 |
| gn369 | 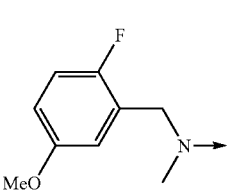 |
| gn370 | 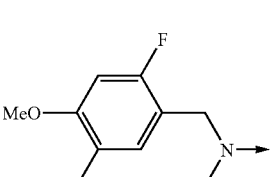 |
| gn371 | 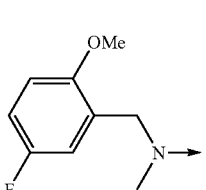 |
| gn372 | 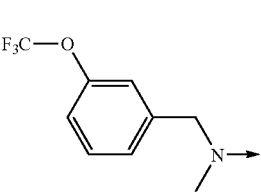 |

TABLE 4-7-continued
| G | Str. |
|---|---|
| gn373 | 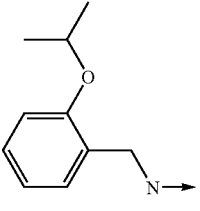 |
| gn374 | 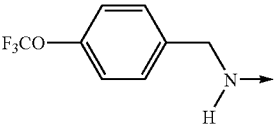 |
| gn375 | 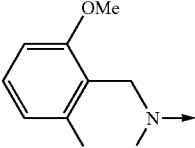 |
| gn376 | 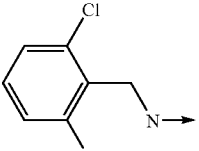 |
| gn377 | 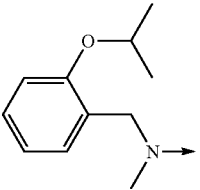 |
| gn378 | 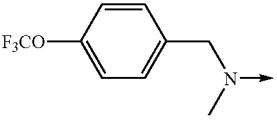 |
TABLE 4-8
| G | Str. |
|---|---|
| gn379 | 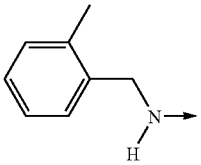 |
| gn380 | 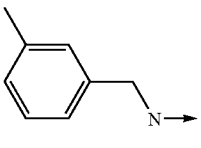 |
TABLE 4-8-continued
| G | Str. |
|---|---|
| gn382 | 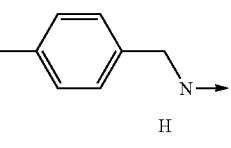 |
| gn383 | 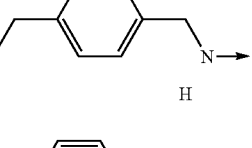 |
| gn384 | 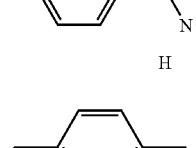 |
| gn385 | 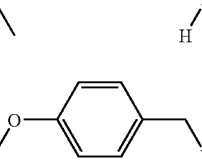 |
| gn386 | 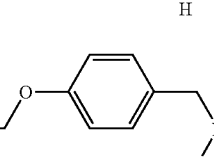 |
| gn387 | 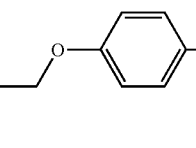 |
| gn388 | 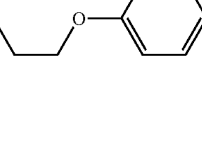 |
| gn389 | 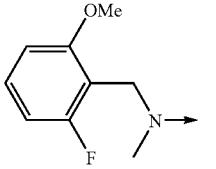 |
| gn390 | 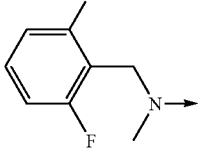 |
| gn391 | 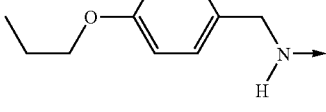 |

TABLE 4-8-continued
| G | Str. |
|---|---|
| gn392 | 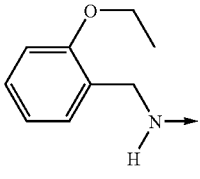 |
| gn393 | 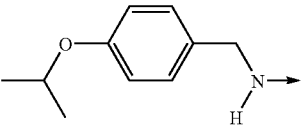 |
| gn395 | 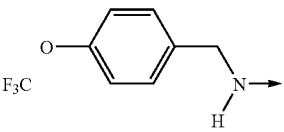 |
| gn396 | 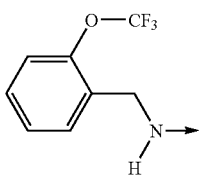 |
| gn397 | 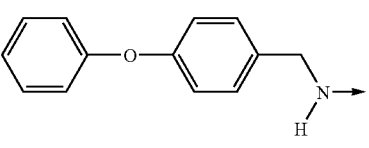 |
| gn399 | 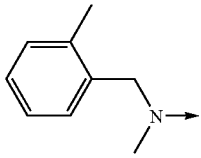 |
| gn400 | 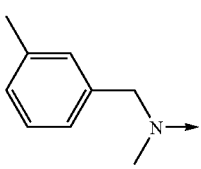 |
| gn401 | 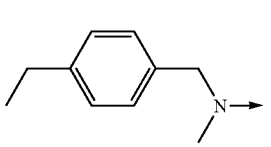 |
| gn402 | 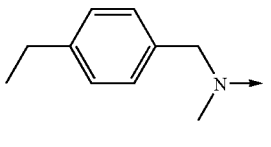 |
| gn403 | 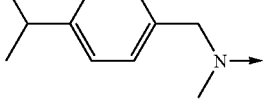 |
| gn404 | 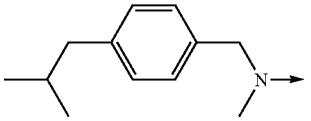 |
| gn405 | 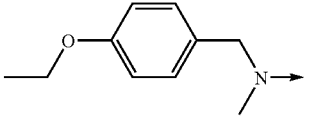 |
| gn406 | 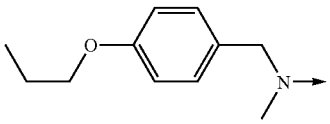 |
| gn407 | 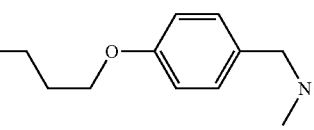 |
| gn408 | 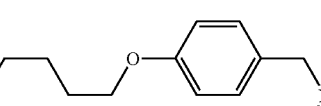 |
| gn409 | 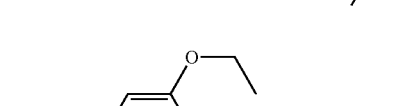 |
| gn410 | 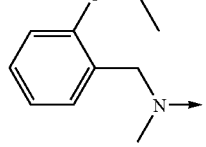 |
| gn412 | 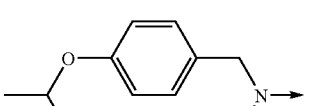 |
| gn413 | 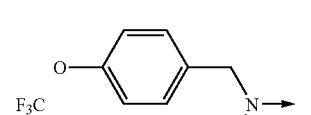 |
| gn414 | 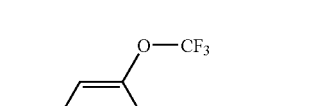 |

TABLE 4-9
| G | Str. |
|---|---|
| gn137 | 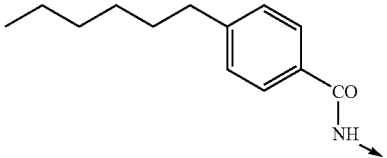 |
| gn138 | 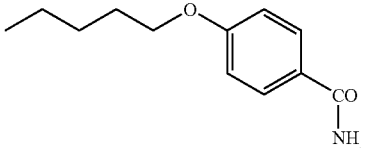 |
| gn139 | 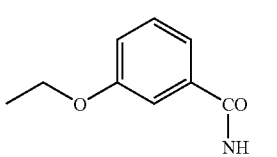 |
| gn140 | 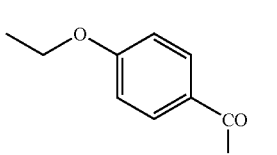 |
| gn141 | 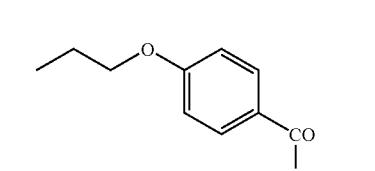 |
| gn142 | 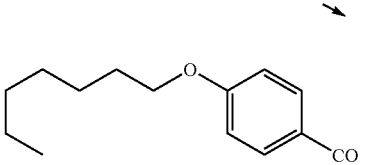 |
| gn143 | 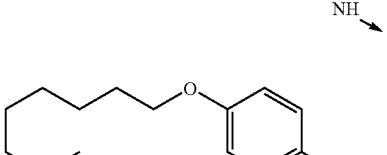 |
| gn144 | 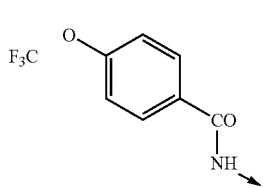 |
TABLE 4-9-continued
| G | Str. |
|---|---|
| gn145 | 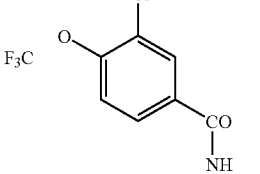 |
| gn146 | 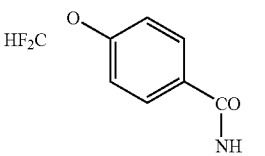 |
| gn147 | 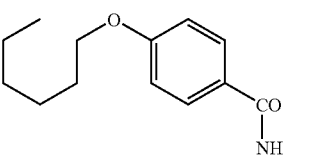 |
TABLE 5-1
| SM2 | Str. | Spl. |
|---|---|---|
| sm3 | 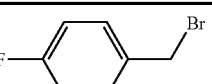 | TCl |
| sm4 | 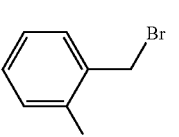 | TCl |
| sm6 | 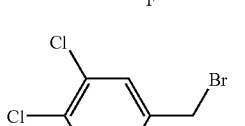 | TCl |
| sm7 | 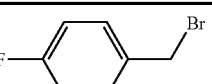 | FChem |
| sm8 | 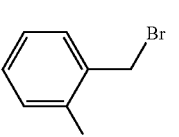 | WAKO |
|  |  | Ald |
| sm10 | 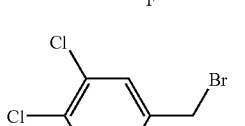 | TCl |

TABLE 5-1-continued

| SM2 | Str. | Spl. |
|---|---|---|
| sm11 | 2,4-difluorobenzyl bromide | TCl |
| sm17 | 3-chlorobenzyl bromide | Ald |
| sm19 | 3,4-difluorobenzyl bromide | TCl |
| sm20 | 2,6-dichlorobenzyl bromide | TCl |
| sm21 | 3-methylbenzyl bromide | TCl |
| sm25 | isopropyl iodide | TCl |
| sm26 | n-butyl iodide | KANTO |
| sm27 | isobutyl bromide | TCl |
| sm28 | isopentyl bromide | TCl |

TABLE 5-2

| SM2 | Str. | Spl. |
|---|---|---|
| sm-o3 | 4-fluorobenzyl alcohol | TCl |
| sm-o9 | 4-methoxybenzyl alcohol | TCl |
| sm-o12 | 3,5-dichlorobenzyl alcohol | Avocado |
| sm-o13 | 4-methylbenzyl alcohol | TCl |
| sm-o14 | (S)-1-phenylethanol | TCl |
| sm-o15 | (R)-1-phenylethanol | TCl |
| sm-o16 | 4-(trifluoromethyl)benzyl alcohol | TCl |
| sm-o17 | 3-chlorobenzyl alcohol | TCl |
| sm-o18 | 1-phenyl-1-propanol | TCl |
| sm-o22 | 2-(4-fluorophenyl)ethanol | Ald |
| sm-o23 | 2-(2-(trifluoromethyl)phenyl)ethanol | Ald |
| sm-o24 | 3-cyclopentyl-1-propanol | Ald |
| sm-o26 | 1-butanol | TCl |
| sm-o27 | isobutanol | TCl |
| sm-o28 | isopentanol | TCl |
| sm-o29 | 1-octanol | TCl |

TABLE 5-2-continued

| SM2 | Str. | Spl. |
|---|---|---|
| sm-o30 | cyclopentanol | KANTO |
| sm-o31 | 3-methylcyclopentanol | Ald |
| sm-o32 | diphenylmethanol | TCl |

TABLE 5-3

| SM2 | Str. | Spl. |
|---|---|---|
| sm-n2 | 4-(trifluoromethyl)benzenesulfonyl chloride | TCl |
| sm-n3 | 3-(trifluoromethyl)benzenesulfonyl chloride | Ald |
| sm-n4 | 2-(trifluoromethyl)benzenesulfonyl chloride | Ald |
| sm-n5 | 2-chloro-4-(trifluoromethyl)benzenesulfonyl chloride | TCl |
| sm-n9 | benzenesulfonyl chloride | TCl |
| sm-n10 | 4-methylbenzenesulfonyl chloride | TCl |
| sm-n11 | 3-methylbenzenesulfonyl chloride | Ald |
| sm-n12 | 2-methylbenzenesulfonyl chloride | Ald |

TABLE 5-3-continued

| SM2 | Str. | Spl. |
|---|---|---|
| sm-n13 | 2-(trifluoromethoxy)benzenesulfonyl chloride | FChem |
| sm-n14 | 3-methoxybenzenesulfonyl chloride | Ald |
| sm-n15 | 3-chlorobenzenesulfonyl chloride | Ald |
| sm-n16 | 4-fluorobenzenesulfonyl chloride | Ald |
| sm-n17 | 3-fluorobenzenesulfonyl chloride | Ald |
| sm-n18 | biphenyl-4-sulfonyl chloride | Avocado |
| sm-n19 | 3-cyanobenzenesulfonyl chloride | MAYB |
| sm-n20 | 4-phenoxybenzenesulfonyl chloride | AAesar |

TABLE 5-4

| SM2 | Str. | Spl. |
|---|---|---|
| sm-n21 | 4-(oxazol-5-yl)benzenesulfonyl chloride | MAYB |

TABLE 5-4-continued

| SM2 | Str. | Spl. |
|---|---|---|
| sm-n22 | 2-phenyl-4-methyl-thiazole-5-sulfonyl chloride | MAYB |
| sm-n23 | 2,4-dimethyl-thiazole-5-sulfonyl chloride | MAYB |
| sm-n24 | 3,5-dimethyl-isoxazole-4-sulfonyl chloride | AAesar |
| sm-n25 | thiophene-2-sulfonyl chloride | MAYB |
| sm-n26 | (E)-2-phenylethenesulfonyl chloride | Ald |
| sm-n27 | 2-(naphthalen-1-yl)ethanesulfonyl chloride | TCl |
| sm-n28 | 2-trifluoromethyl-5-methyl-furan-3-sulfonyl chloride | MAYB |
| sm-n29 | 1,2-dimethyl-imidazole-4-sulfonyl chloride | MAYB |
| sm-n30 | biphenyl-2-sulfonyl chloride | Oak |
| sm-n31 | cyclopropanesulfonyl chloride | Ald |
| sm-n32 | methanesulfonyl chloride | TCl |
| sm-n33 | ethanesulfonyl chloride | TCl |
| sm-n34 | 2,2,2-trifluoroethanesulfonyl chloride | Acros |

TABLE 5-4-continued

| SM2 | Str. | Spl. |
|---|---|---|
| sm-n35 | 2,4,6-trimethylbenzenesulfonyl chloride | Ald |
| sm-n36 | 5-chloro-3-methyl-benzothiophene-2-sulfonyl chloride | Matrix |
| sm-n37 | naphthalene-1-sulfonyl chloride | TCl |
| sm-n38 | naphthalene-2-sulfonyl chloride | Ald |
| sm-n39 | 4-phenoxybenzenesulfonyl chloride | AAesar |
| sm-n40 | pyridin-3-ylmethanesulfonyl chloride | Array |

TABLE 5-5

| SM2 | Str. | Spl. |
|---|---|---|
| sm-n101 | 4-(trifluoromethyl)benzoyl chloride | TCl |
| sm-n102 | 2-fluoro-4-(trifluoromethyl)benzoyl chloride | Ald |
| sm-n103 | 2,3-difluoro-4-(trifluoromethyl)benzoyl chloride | Matrix |
| sm-n104 | 4-iodobenzoyl chloride | TCl |

TABLE 5-5-continued
| SM2 | Str. | Spl. |
|---|---|---|
| sm-n105 | 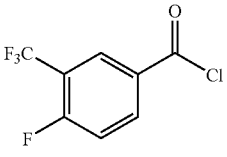 | WAKO |
| sm-n110 | 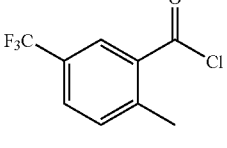 | ABCR |
| sm-n111 | 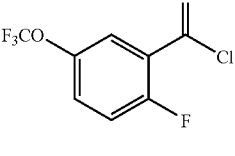 | FChem |
| sm-n112 | 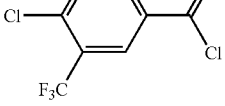 | ABCR |
| sm-n113 | 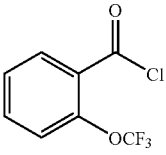 | Matrix |
| sm-n114 | 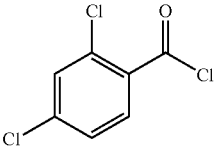 | Ald |
| sm-n115 | 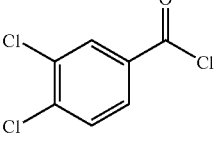 | TCl |
| sm-n116 | 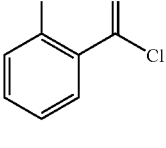 | Ald |
| sm-n117 | 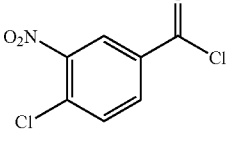 | Ald |
| sm-n118 | 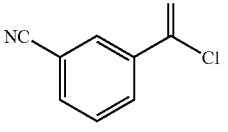 | Ald |
| sm-n119 | 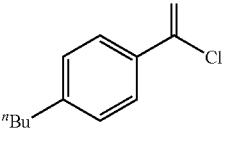 | TCl |
| sm-n120 | 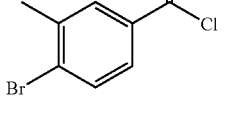 | LANC |
| sm-n121 | 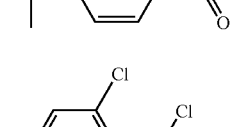 | Ald |
| sm-n122 | 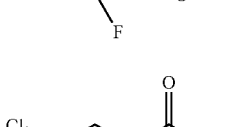 | WAKO |
| sm-n123 | 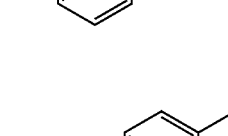 | TCl |
| sm-n124 | 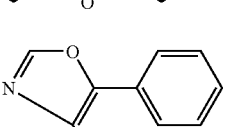 | Ald |
| sm-n125 | 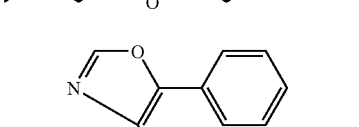 | MAYB |
| sm-n126 | 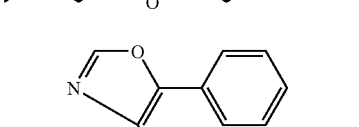 | MAYB |
| sm-n127 | 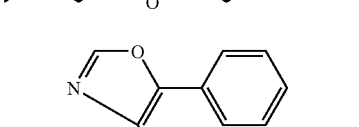 | MAYB |

TABLE 5-5-continued

| SM2 | Str. | Spl. |
|---|---|---|
| sm-n128 | 5-(4-methoxyphenyl)oxazole-4-carbonyl chloride | MAYB |
| sm-n129 | 2-(2,3-dihydrobenzofuran-5-yl)thiazole-4-carbonyl chloride | MAYB |
| sm-n130 | benzofuran-5-carbonyl chloride | MAYB |
| sm-n131 | benzo[d]thiazole-2-carbonyl chloride | LANC |
| sm-n132 | 4-methyl-2-phenylthiazole-5-carbonyl chloride | MAYB |
| sm-n133 | 5,5,8,8-tetramethyl-5,6,7,8-tetrahydronaphthalene-2-carbonyl chloride | MAYB |
| sm-n134 | 4-methyl-2-(pyrazin-2-yl)thiazole-5-carbonyl chloride | MAYB |
| sm-n135 | 3-(2-methylthiazol-4-yl)benzoyl chloride | MAYB |
| sm-n136 | 4-methyl-2-(4-(trifluoromethyl)phenyl)thiazole-5-carbonyl chloride | MAYB |

TABLE 5-6

| SM2 | Str. | Spl. |
|---|---|---|
| sm-n300 | formaldehyde | WAKO |
| sm-n301 | acetone | KANTO |
| sm-n303 | propanal | TCI |
| sm-n304 | isobutyraldehyde | TCI |
| sm-n306 | cyclohexanone | TCI |
| sm-n307 | benzaldehyde | nacalai |
| sm-n308 | 4-fluorobenzaldehyde | TCI |
| sm-n310 | 4-(trifluoromethyl)benzaldehyde | TCI |
| sm-n312 | 2-(3-(trifluoromethyl)phenyl)thiazole-5-carbaldehyde | |
| sm-n314 | biphenyl-2-carbaldehyde | Array |

TABLE 5-7

| SM2 | Str. | Spl. |
|---|---|---|
| sm-c1 | (E)-2-(4-(trifluoromethyl)phenyl)vinylboronic acid | Ald |

TABLE 5-8

| SM2 | Str. | Spl. |
|---|---|---|
| sm-316 | cyclopentanone | Ald |
| sm-317 | 3-pentanone | TCl |
| sm-318 | 2-butanone | TCl |
| sm-319 | 3,3-dimethyl-2-butanone | TCl |
| sm-320 | 3-methyl-2-butanone | WAKO |
| sm-321 | propanal | WAKO |
| sm-322 | butanal | TCl |
| sm-323 | 3-methylbutanal | Ald |
| sm-324 | 2-methylbutanal | TCl |
| sm-325 | 3-methyl-2-butenal | TCl |
| sm-326 | 2-hexanone | TCl |
| sm-327 | 2-pentanone | TCl |
| sm-328 | phenylacetaldehyde | MP Biomedicals |
| sm-329 | 2-phenylpropanal | WAKO |

TABLE 5-8-continued

| SM2 | Str. | Spl. |
|---|---|---|
| sm-330 | 2-fluorobenzaldehyde | TCl |
| sm-331 | 3-fluorobenzaldehyde | TCl |
| sm-332 | 2-methoxybenzaldehyde | TCl |
| sm-333 | 3-methoxybenzaldehyde | TCl |
| sm-334 | 4-methoxybenzaldehyde | TCl |
| sm-335 | 4-butoxybenzaldehyde | TCl |
| sm-336 | 4-butylbenzaldehyde | TCl |
| sm-363 | 2-fluoro-4-methoxybenzaldehyde | ABCR |
| sm-364 | 2-fluoro-5-methoxybenzaldehyde | TCl |
| sm-365 | 2-fluoro-4,5-dimethoxybenzaldehyde | TCl |

TABLE 5-8-continued
| SM2 | Str. | Spl. |
|---|---|---|
| sm-366 | 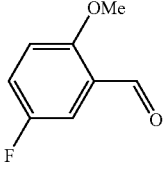 | TCl |
| sm-367 | 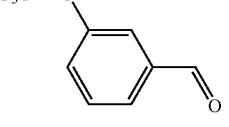 | TCl |
| sm-373 | 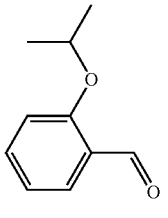 | AAesar |
| sm-374 |  | TCl |
| sm-375 | 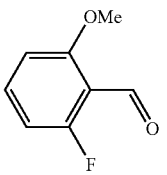 | Ald |
| sm-376 | 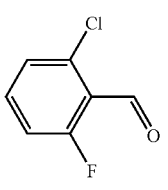 | LANC |
| sm-382 | 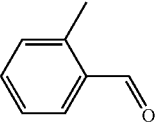 | TCl |
| sm-383 | 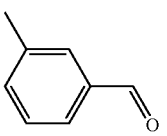 | TCl |
| sm-384 | 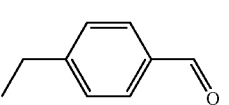 | Ald |
| sm-385 | 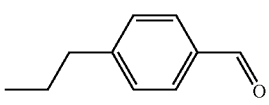 | Ald |
| sm-386 | 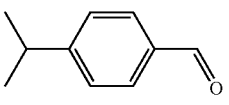 | TCl |
| sm-387 | 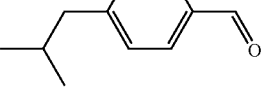 | TCl |
| sm-388 | 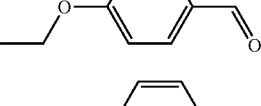 | TCl |
| sm-389 | 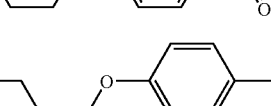 | TCl |
| sm-390 | 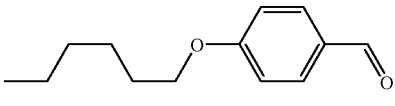 | TCl |
| sm-391 | 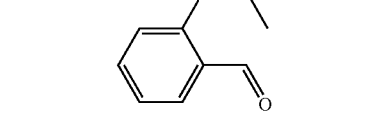 | TCl |
| sm-392 | 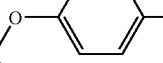 | TCl |
| sm-393 | 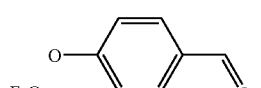 | LANC |
| sm-395 | 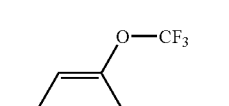 | TCl |
| sm-396 |  | LANC |
| sm-397 | 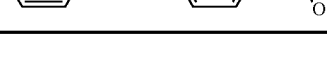 | TCl |
TABLE 5-9
| SM2 | Str. | Spl. |
|---|---|---|
| sm-n137 | 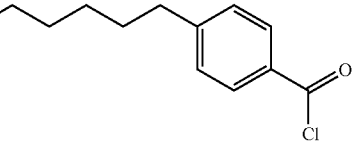 | Ald |

TABLE 5-9-continued

| SM2 | Str. | Spl. |
|---|---|---|
| sm-n138 | | LANC |
| sm-n139 | | APIN |
| sm-n140 | | Ald |
| sm-n141 | | WAKO |
| sm-n142 | | Ald |
| sm-n143 | | WAKO |
| sm-n144 | | Ald |
| sm-n145 | | ABCR |
| sm-n146 | | APOLLO |
| sm-n147 | | Acros |

PHARMACOLOGICAL EXAMPLES

1. Suppressing Action on PGE₂ Production from IL-1 β-Stimulated MG-63 Cells (1) Method for Measurement An action of suppressing $PGE_2$ production caused by interleukin (IL) 1β as an inflammatory stimulant was studied by the following method. Cells of MG-63, which is a human osteosarcoma cell line (purchased from Dainippon Pharmaceutical), were suspended in MEM medium (GIBCO) containing 10% fetal bovine serum (BioWest), and then inoculated to each well of 96-well culture plate at a density of $1 \times 10^4$ cells/well and cultured overnight. The medium was changed to MEM medium containing 0.5% fetal bovine serum, and then a test compound was added to each well. Human interleukin-1β (ENDOGEN) was further added as an inflammatory stimulant at a final concentration of 0.5 ng/ml. The cells were further cultured for 18 hours. Then, the culture supernatant was collected, and the $PGE_2$ concentration in the culture supernatant was measured by using EIA kit (CAYMAN). By using a well which was not added with the stimulant as a negative control and a well which was added only with the stimulant as a positive control, suppression ratio on $PGE_2$ production can be calculated from produced amount of $PGE_2$ in the well added with the test compound using the following equation.

$$PGE_2 \text{ production suppression ratio} = [1-(C-B)/(A-B)] \times 100 \quad \text{[Equation 1]}$$

A: $PGE_2$ production amount of positive control
B: $PGE_2$ production amount of negative control
C: $PGE_2$ production amount in well added with test compound Further, cytotoxicity of the compounds was studied by using the cells after the collection of the supernatant with Cell Counting Kit-8 (Dojindo Laboratories). Specifically, Cell Counting Kit-8 was added to the cells remained after the collection of the supernatant, and then absorbance was measured at 670 nm. The absorbance of the well of the aforementioned positive control was taken as 100%, and a test compound that gave absorbance in well of less than 80% was judged to be positive in cytotoxicity.

(2) Measurement Results

The test compounds (Example Compound Nos. 1-1-2, 1-3-2, 1-12-2, 1-13-2, 1-14-2, 1-15-2, 1-16-2, 1-18-2, 1-22-2, 1-23-2, 1-24-2, 1-26-2, 1-27-2, 1-28-2, 1-29-2, 1-30-2, 1-31-2, 1-32-2, 2-1-2, 2-2-2, 2-3-2, 2-4-2, 2-6-2, 2-7-2, 2-8-2, 2-10-2, 2-11-2, 2-17-2, 2-19-2, 2-20-2, 2-21-2, 2-25-2, 2-26-2, 2-27-2, 2-28-2, 1-5-2, 2-5-2, 3-5-2, 4-5-2, 5-5-2, 6-5-2, 2-N-1-2, 2-N2-2, 2-N3-2, 2-N-5-2, 2-N9-2, 2-N10-2, 2-N11-2, 2-N12-2, 2-N13-2, 2-N14-2, 2-N15-2, 2-N16-2, 2-N17-2, 2-N18-2, 2-N20-2, 7-N119-2, 7-N124-2, 2-N301-2, 2-N302-2, 2-N303-2, 2-N304-2, 2-N305-2, 2-N306-2, 2-N307-2, 2-N308-2, 2-N309-2, 2-N310-2, 2-N311-2, 2-N312-2, 2-N313-2, 2-N314-2, 2-N315-2, 7-N304-2, 7-N305-2) suppressed the PGE$_2$ production caused by IL-1β by 50% or more at 0.4 μM. Moreover, all the test compounds did not exhibit cytotoxicity at that concentration.

The test compounds (Compound Nos. 2-N316-2, 2-N317-2, 2-N318-2, 2-N319-2, 2-N320-2, 2-N321-2, 2-N322-2, 2-N323-2, 2-N324-2, 2-N325-2, 2-N326-2, 2-N327-2, 2-N328-2, 2-N329-2, 2-N330-2, 2-N331-2, 2-N332-2, 2-N333-2, 2-N334-2, 2-N335-2, 2-N336-2, 2-N337-2, 2-N338-2, 2-N339-2, 2-N340-2, 2-N341-2, 2-N342-2, 2-N343-2, 2-N344-2, 2-N345-2, 2-N346-2, 2-N348-2, 2-N349-2, 2-N350-2, 2-N351-2, 2-N352-2, 2-N353-2, 2-N354-2, 2-N355-2, 2-N356-2, 2-N357-2, 2-N358-2, 2-N359-2, 2-N360-2, 2-N361-2, 2-N362-2, 2-N363-2, 2-N364-2, 2-N366-2, 2-N368-2, 2-N369-2, 2-N371-2, 2-N373-2, 2-N375-2, 2-N376-2, 2-N377-2, 2-N379-2, 2-N380-2, 2-N382-2, 2-N386-2, 2-N387-2, 2-N388-2, 2-N392-2, 2-N393-2, 2-N403-2, 2-N404-2, 2-N405-2, 2-N137-2, 2-N138-2, 2-N141-2, 2-N142-2, 2-N143-2, 2-N144-2, 2-N145-2, 2-N146-2, 2-N147-2, 2-N148-2, 7-N382-2) suppressed the PGE$_2$ production caused by IL-1β by 50% or more at 0.4 μM. Moreover, all the test compounds did not exhibit cytotoxicity at that concentration.

Therefore, the compounds and salts thereof of the present invention are useful as agents for suppressing inflammatory prostaglandin production.

2. Inhibitory Action Against Type 4 PLA$_2$ Activity (1) Method for Measurement

The inhibitory action against type 4 PLA$_2$ activity was investigated by the following method. On liposome membranes prepared by ultrasonication of 1,2-dioleoyl-sn-glycero-3-phospho-L-serine (DOPS), γ-linolenoyl ester of 7-hydroxycoumarin (GLU) is dispersed. Type 4 PLA$_2$ is added to the liposome membranes, and fluorescence of hydroxycoumarin excised by the enzymatic activity of type 4 PLA$_2$ is measured over time. For the measurement, a 96-well plate for fluorometry and a fluorescence plate reader (wavelength: Ex. 355 nm, Em. 460 nm) were used. After the measurement, the maximum reaction rate was calculated by plotting time in abscissa and fluorescence intensity in ordinate. The inhibitory ratio against type 4 PLA$_2$ activity can be calculated from the reaction rate observed in a well to which a test compound is added, based on the results observed for a well not added with type 4 PLA$_2$ as a negative control, and a well to which only type 4 PLA$_2$ is added as a positive control, in accordance with the following equation.

Type 4 PLA$_2$ activity inhibition ratio (%)=[1−(C−B)/(A−B)]×100 [Equation 2]

A: Maximum reaction rate of positive control
B: Maximum reaction rate of negative control
C: Maximum reaction rate in well added with test compound (2) Measurement Results The test compounds (Example Compound Nos. 1-13-2, 1-15-2, 1-18-2, 1-22-2, 1-23-2, 1-24-2, 1-25-2, 1-27-2, 1-28-2, 1-29-2, 1-30-2, 1-31-2, 1-32-2, 2-1-2, 2-2-2, 2-3-2, 2-4-2, 2-6-2, 2-7-2, 2-8-2, 2-10-2, 2-11-2, 2-17-2, 2-19-2, 2-20-2, 2-21-2, 2-25-2, 2-26-2, 2-27-2, 2-28-2, 1-5-2, 2-5-2, 3-5-2, 4-5-2, 5-5-2, 2-N3-2, 2-N12-2, 2-N18-2, 2-N20-2, 2-N101-2, 2-N102-2, 2-N112-2, 2-N115-2, 2-N119-2, 2-N124-2, 2-N125-2, 2-N128-2, 2-N133-2, 2-N136-2, 7-N119-2, 7-N124-2, 8-N119-2, 8-N124-2, 8-N125-2, 8-N128-2, 2-N301-2, 2-N302-2, 2-N303-2, 2-N304-2, 2-N305-2, 2-N306-2, 2-N307-2, 2-N308-2, 2-N309-2, 2-N310-2, 2-N311-2, 2-N312-2, 2-N313-2, 2-N314-2, 2-N315-2, 7-N304-2, 7-N305-2, 2-C1-2) suppressed the type 4 PLA$_2$ activity by 50% or more at 0.4 μM.

Other test compounds (Example Compound Nos. 2-N316-2, 2-N317-2, 2-N318-2, 2-N319-2, 2-N320-2, 2-N321-2, 2-N322-2, 2-N323-2, 2-N324-2, 2-N325-2, 2-N326-2, 2-N327-2, 2-N328-2, 2-N329-2, 2-N330-2, 2-N331-2, 2-N332-2, 2-N333-2, 2-N334-2, 2-N335-2, 2-N336-2, 2-N337-2, 2-N338-2, 2-N340-2, 2-N341-2, 2-N342-2, 2-N343-2, 2-N344-2, 2-N345-2, 2-N346-2, 2-N348-2, 2-N349-2, 2-N350-2, 2-N351-2, 2-N352-2, 2-N353-2, 2-N354-2, 2-N355-2, 2-N356-2, 2-N357-2, 2-N358-2, 2-N359-2, 2-N362-2, 2-N363-2, 2-N364-2, 2-N366-2, 2-N368-2, 2-N369-2, 2-N371-2, 2-N373-2, 2-N376-2, 2-N377-2, 2-N380-2, 2-N382-2, 2-N386-2, 2-N387-2, 2-N388-2, 2-N392-2, 2-N393-2, 2-N403-2, 2-N404-2, 2-N405-2, 2-N137-2, 2-N138-2, 2-N142-2, 2-N143-2, 2-N147-2, 7-N382-2) suppressed the type 4 PLA$_2$ activity by 50% or more at 0.4 μM.

Therefore, the compounds and salts thereof of the present invention are useful as agents for suppressing type 4 PLA$_2$ activity.

3. Suppressing Action on PGD$_2$ and LTB$_4$ Production from IgE-Stimulated RBL-2H3 Cells (1) Method for Measurement Suppressing action on PGD$_2$ and LTB$_4$ production caused by IgE antibodies as an allergic stimulant can be investigated by the following method. Cells of RBL-2H3, which is a rat mastocytoma cell line (purchased from ATCC), are suspended in DMEM medium (GIBCO) containing 10% fetal bovine serum (BioFluid), inoculated to each well of 48-well culture plate at a density of 2×10$^4$ cells/well and cultured overnight. Then, IgE antiserum directed to dinitrophenylated BSA (henceforth DNP-BSA) is further added to each well, and the cells are cultured for 30 minutes. Then, the medium is changed to DMEM medium containing 0.5% fetal bovine serum, a test compound is added with each well, and DNP-BSA is further added at a final concentration of 100 ng/ml as a stimulant. Ten minutes after the stimulant is added, the culture supernatant is collected, and the PGD$_2$ concentration and LTB$_4$ concentration in the culture supernatant are measured by using EIA kit (CAYMAN). By using a well which is not added with the stimulant as a negative control and a well which is added only with the stimulant as a positive control, suppressing ratio on mediator production can be calculated from the production amount of the mediator in the well added with the test compound using the following equation.

PGD$_2$ or LTB$_4$ production suppression ratio=[1−(C−B)/(A−B)]×100 [Equation 3]

A: PGD$_2$ or LTB$_4$ production amount of positive control
B: PGD$_2$ or LTB$_4$ production amount of negative control
C: PGD$_2$ or LTB$_4$ production amount in well added with test compound Cytotoxicity of the compounds can be studied in the same manner as those described above by using the cells after the collection of the supernatant with Cell Counting Kit-8.

Further, activities can be similarly measured by using, as control compounds for comparison, reference compound (1), 3-(2-cyclohexylmethyloxy-1,1'-biphenyl-5-yl)propionic acid described in WO99/19291, reference compounds (2) and (3), [2-(5,6,7,8-tetrahydro-5,5,8,8-tetramethyl-2-naphthalenyl)methyloxy-1,1'-biphenyl-5-yl]carboxylic acid [reference compound (2)] and 3-[3'-carboxy-2-(5,6,7,8-tetrahydro-5,5,8,8-tetramethyl-2-naphthalenyl)methyloxy-1,1'-biphenyl-6-yl]propionic acid [reference compound (3)] described in U.S. Pat. No. 5,391,817 and Japanese Patent Unexamined Publication (Kokai) No. 7-22399.

4. Suppressing Action on PGE$_2$ and LTB$_4$ Production in Zymosan-Stimulated Rat Air Pouch Suppressing action on PGE$_2$ and LTB$_4$ production in zymosan-stimulated rat air pouch can be investigated by the following method. Air in a volume of 20 mL is subcutaneously injected into a Lewis female rat on its back to form an air pouch, and after three days, 10 mL of air is additionally injected. After six days from the first air injection, 3 mg of zymosan (Sigma) is injected into the air pouch to induce PGE$_2$ and LTB$_4$ production in the rat air pouch. A test compound suspended or dissolved in purified water containing 1.0% methylcellulose is orally administered to the test animals at a does of 0.1 to 500 mg/5 ml/kg 1 hour before the zymosan injection. To control rats, purified water containing 1.0% methylcellulose and no test compound is administered in the same manner. After 3 hours from the zymosan infusion, inside of the air pouch is washed with 10 mL of physiological saline, and the washing solution is collected. PGE$_2$ and LTB$_4$ concentrations in the collected solution can be measured by using EIA kit (CAYMAN). PGE$_2$ and LTB$_4$ production-suppressing ratios can be calculated by using the following equation.

PGE$_2$ or LTB$_4$ production-suppressing ratio (%)=[1−B/A]×100     [Equation 4]

A: PGE$_2$ or LTB$_4$ production amount in positive control group
B: PGE$_2$ or LTB$_4$ production amount in test compound-administered group

5. Prophylactic and Therapeutic Effects for Rat Adjuvant Arthritis (1) Method for Measurement A suppressing effect on footpad edema observed in rat adjuvant arthritis, which is a disease model of rheumatoid arthritis as being one of autoimmune diseases and also a chronic inflammatory disease, can be studied by the following method. Groups of Lewis female rats each consisting of six mice are used for the test. The test animals are immunized by subcutaneously administering, to right hind leg footpads, 50 μl of liquid paraffin containing 10 mg/ml of *M. tuberculosis* H37 RA (DIFCO) as an adjuvant. A test compound is suspended or dissolved in purified water containing 0.5% methylcellulose and orally administered to the test animals at 0.1 to 500 mg/5 ml/kg. When the therapeutic effect is investigated, the test compound is administered once a day for 14 days, from the 13th day after the immunization. When the prophylactic effect is investigated, the test compound is administered once a day for 33 days, from the 1st day after the immunization. To the control group, purified water containing 1.0% methylcellulose is administered in a similar manner, which is not added with a test compound. Every 2 or 3 days after the administration of adjuvant, volume of left hind leg footpad, which is not administered with the adjuvant, is measured by using an apparatus for measuring a volume of edema of a rat hind leg footpad (UGO BASILE). A suppression ratio on edema can be obtained by calculation using the following equation. The representative compounds of the present invention showed favorable suppression ratios on edema.

Edema suppression ratio (%)={1−[(D−C)/C]/[(B−A)/A]}×100     [Equation 5]

A: Left hind leg footpad volume of positive control immediately before administration of adjuvant
B: Left hind leg footpad volume of positive control on each measurement day
C: Left hind leg footpad volume of test compound administered group immediately before administration of adjuvant
D: Left hind leg footpad volume of test compound administered group on each measurement day Usefulness of the compounds can be evaluated on the basis of a dose (mg/kg) which provides 50% of the edema suppressing ratio based on the control group, i.e., ID$_{50}$ (mg/kg). A graph is prepared by plotting logarithmic values (X) of dose of test compound in abscissa and edema suppressing ratio (Y) in ordinate. Linear regression of Y to X is performed by using values of two points on both sides of the average of the edema suppressing ratio of 50%. The value of X can be calculated as ID$_{50}$ by substituting 50% for Y in the linear regression equation.

The representative compounds of the present invention showed favorable ID$_{50}$ values.

6. Effect on Rat Pulmonary Fibrosis (1) Method for Measurement

Prophylactic and therapeutic effects on pulmonary fibrosing in a bleomycin-induced rat pulmonary fibrosis model, which is a pathological model of pulmonary fibrosis, can be studied by the following method. Groups of Lewis female rats each consisting of seven rats are used for the test.

The test animals are anesthetized with ketamine and xylazine, and a 25 or 50 g/100 μl solution of bleomycin (Nippon Kayaku) dissolved in physiological saline (Ohtsuka Pharmaceutical Factory) is injected into the tracheae by spraying using a syringe. The negative control group is administered with 100 μl of saline into the tracheae. Each test compound is suspended or dissolved in purified water containing 1.0% methylcellulose, and orally administered to the test animals at doses of 10, 30, 100 and 300 mg/5 ml/kg. When the prophylactic effect on pulmonary fibrosing is investigated, the administration of the test compounds is started before the bleomycin administration and performed once or twice a day for consecutive 21 days. When the therapeutic effect on pulmonary fibrosing is investigated, the administration of the test compounds is started after the bleomycin administration and performed once or twice a day for consecutive 21 days. The positive control group is administered with purified water containing 1.0% methylcellulose not added with any test compound in a similar manner. On the 21st day after the administration of bleomycin, the rats are sacrificed, and lungs are fixed with neutral buffered formalin to prepare histopathological samples. Staining of the histopathological samples is performed by the Azan method or the Masson trichrome method. The histopathological samples of lungs are examined, and degree of fibrosing is represented with the following scores on the basis of invasion of inflammatory cells, formation of granulation tissues and proliferation of collagen fibers as indicators, i.e., −: no abnormality, ±: extremely mild change, +: mild change, ++: moderate change, and +++: significant change.

INDUSTRIAL APPLICABILITY

The compounds of the present invention have superior inhibitory activity against type 4 PLA$_2$, and as a result, exhibit suppressing action on prostaglandin production and/or suppressing action on leukotriene production. Therefore, the compounds of the present invention are useful as active ingredients of medicaments for prophylactic and/or therapeutic treatment of various inflammatory diseases, autoimmune diseases, allergic diseases, pain and the like caused by these lipid mediators.

What is claimed is:

1. A compound represented by the following general formula (1) or a salt thereof:

[Formula 1]

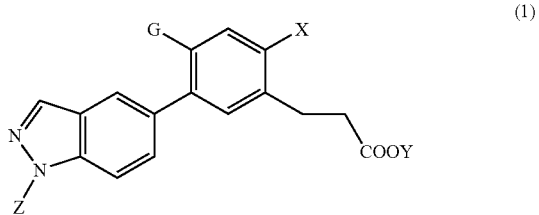

wherein, in the general formula (1),
X represents a methyl group or a chlorine atom
Y represents a hydrogen atom;
Z represents a methyl group; and
G is the following formula $G^2$:

$$R^4\text{-}A^2\text{-}D\text{-} \qquad (G^2)$$

wherein, in the general formulas ($G^2$)
$R^4$ represents an alkyl group having 1 to 6 carbon atoms;
D represents —NH; and
$A^2$ represents a single bond.

2. A medicament comprising the compound according to claim 1 or a pharmaceutically acceptable salt thereof as an active ingredient.

3. A prostaglandin and/or leucotriene production suppressing agent comprising the compound according to claim 1 or a pharmaceutically acceptable salt thereof as an active ingredient.

4. The medicament according to claim 2, which is for therapeutic treatment of a disease for which suppression of prostaglandin and/or leucotriene production is effective.

5. A type 4 phospholipase $A_2$ enzyme activity inhibitor comprising the compound according to claim 1 or a pharmaceutically acceptable salt thereof as an active ingredient.

6. The medicament according to claim 2, which is for therapeutic treatment of a disease induced by expression of type 4 phospholipase $A_2$ enzyme activity.

7. The medicament according to claim 2, which is for therapeutic treatment of an inflammatory disease of a mammal.

8. The medicament according to claim 2, which is for therapeutic treatment of an autoimmune disease of a mammal.

9. The medicament according to claim 2, which is for therapeutic treatment of an allergic disease of a mammal.

10. The medicament according to claim 2, which is for defervescence and/or analgesia of a mammal, wherein the defervescence and/or analgesia is through suppression of prostaglandin and/or leukotriene production.

11. A pharmaceutical composition for therapeutic treatment of a condition in living body of a mammal in which an acute or chronic inflammatory reaction is observed, which comprises the compound according to claim 1 or a pharmaceutically acceptable salt thereof in an amount effective for the therapeutic treatment, and a pharmaceutically acceptable carrier.

12. The compound or a salt thereof according to claim 1, wherein X is a methyl group or a chlorine atom, Y is a hydrogen atom, Z is a methyl group, G is the general formula ($G^2$) which has the same meaning as that defined above provided that D is —NH—, and $R^4$ is an alkyl group having 3 to 6 carbon atoms, and $A^2$ is a single bond.

13. The compound or a salt thereof according to claim 1, wherein X is a methyl group, Y is a hydrogen atom, Z is a methyl group, G is the general formula ($G^2$) which has the same meaning as that defined above provided that D is —NH—, and $R^4$ is an alkyl group having 3 to 6 carbon atoms, and $A^2$ is a single bond.

14. The compound or a salt thereof according to claim 1, wherein X is a chlorine atom, Y is a hydrogen atom, Z is a methyl group, G is the general formula ($G^2$) which has the same meaning as that defined above provided that D is —NH—, and $R^4$ is an alkyl group having 3 to 6 carbon atoms, and $A^2$ is a single bond.

15. A compound or a salt thereof selected from the group consisting of the following compounds:

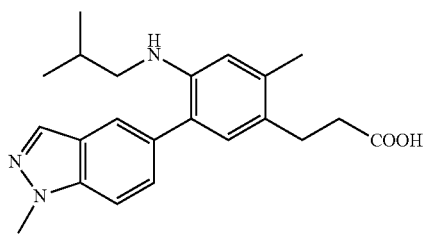

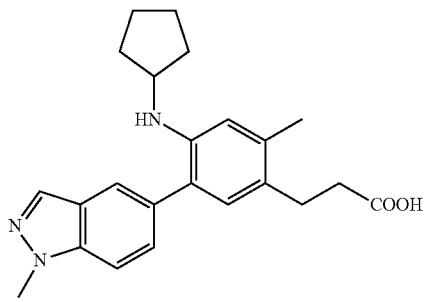

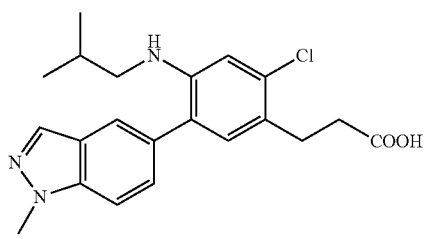

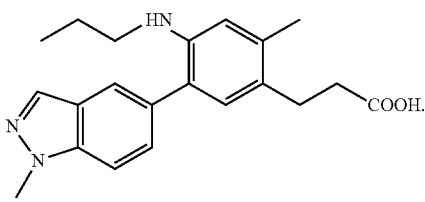

16. The compound defined below or a salt thereof:

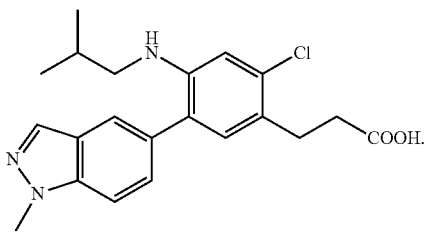

17. The compound defined below or a salt thereof:

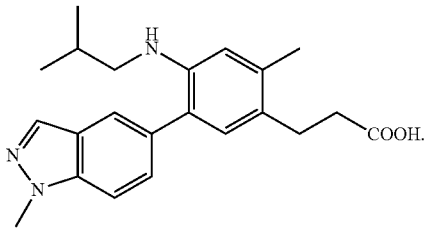

18. A medicament comprising the compound according to any one of claims 15-17 or a pharmaceutically acceptable salt thereof as an active ingredient.

19. A prostaglandin and/or leucotriene production suppressing agent comprising the compound according to any one of claims 15-17 or a pharmaceutically acceptable salt thereof as an active ingredient.

20. The medicament according to claim 18, which is for therapeutic treatment of a disease for which suppression of prostaglandin and/or leucotriene production is effective.

21. A type 4 phospholipase $A_2$ enzyme activity inhibitor comprising the compound according to any one of claims 15-17 or a pharmaceutically acceptable salt thereof as an active ingredient.

22. The medicament according to claim 18, which is for therapeutic treatment of a disease induced by expression of type 4 phospholipase $A_2$ enzyme activity.

23. The medicament according to claim 18, which is for therapeutic treatment of an inflammatory disease of a mammal.

24. The medicament according to claim 18, which is for therapeutic treatment of an autoimmune disease of a mammal.

25. The medicament according to claim 18, which is for therapeutic treatment of an allergic disease of a mammal.

26. The medicament according to claim 18, which is for defervescence and/or analgesia of a mammal, wherein the defervescence and/or analgesia is through suppression of prostaglandin and/or leukotriene production.

27. A pharmaceutical composition for therapeutic treatment of a condition in living body of a mammal in which an acute or chronic inflammatory reaction is observed, which comprises the compound according to claim 18 or a pharmaceutically acceptable salt thereof in an amount effective for the therapeutic treatment, and a pharmaceutically acceptable carrier.

* * * * *